US007345091B2

(12) United States Patent
Lockwood et al.

(10) Patent No.: US 7,345,091 B2
(45) Date of Patent: Mar. 18, 2008

(54) CAROTENOID ETHER ANALOGS OR DERIVATIVES FOR THE INHIBITION AND AMELIORATION OF DISEASE

(75) Inventors: Samuel Fournier Lockwood, Lake Linden, MI (US); Sean O'Malley, Honolulu, HI (US); David G. Watumull, Honolulu, HI (US); Laura M. Hix, San Francisco, CA (US); Henry Jackson, Honolulu, HI (US); Geoff Nadolski, Kaaawa, HI (US)

(73) Assignee: Cardax Pharmaceuticals, Inc., Aiea, HI (US)

( * ) Notice: Subject to any disclaimer, the term of this patent is extended or adjusted under 35 U.S.C. 154(b) by 0 days.

(21) Appl. No.: 10/793,671

(22) Filed: Mar. 4, 2004

(65) Prior Publication Data
US 2005/0009758 A1 Jan. 13, 2005

Related U.S. Application Data

(63) Continuation-in-part of application No. 10/629,538, filed on Jul. 29, 2003, now Pat. No. 7,145,025.

(60) Provisional application No. 60/485,304, filed on Jul. 3, 2003, provisional application No. 60/473,741, filed on May 28, 2003, provisional application No. 60/472,831, filed on May 22, 2003, provisional application No. 60/467,973, filed on May 5, 2003, provisional application No. 60/399,194, filed on Jul. 29, 2002.

(51) Int. Cl.
*A61K 31/341* (2006.01)
*A61K 31/351* (2006.01)
(52) U.S. Cl. ..................... 514/460; 514/473
(58) Field of Classification Search ........... 549/315, 549/316, 415; 568/10, 11; 514/460, 473
See application file for complete search history.

(56) References Cited

U.S. PATENT DOCUMENTS

| 2,768,198 | A | 10/1956 | Marbet |
|---|---|---|---|
| 3,206,316 | A | 9/1965 | Klaui et al. |
| 3,354,218 | A | 11/1967 | Surmatis |
| 3,755,422 | A | 8/1973 | Morel |
| 3,788,468 | A | 1/1974 | Gainer |
| 3,853,993 | A | 12/1974 | Gainer |
| 3,965,261 | A | 6/1976 | Gainer |
| 3,975,445 | A | 8/1976 | Kienzle et al. |
| 3,975,519 | A | 8/1976 | Gainer |
| 3,989,757 | A | 11/1976 | Surmatis |
| 4,009,270 | A | 2/1977 | Gainer |
| 4,038,144 | A | 7/1977 | Gainer |
| 4,046,880 | A | 9/1977 | Gainer |
| 4,070,460 | A | 1/1978 | Gainer |
| 4,156,090 | A | 5/1979 | Kienzle |
| 4,176,179 | A | 11/1979 | Gainer |
| 4,304,784 | A | 12/1981 | Fujimura et al. |
| 4,435,427 | A | 3/1984 | Hoppe et al. |
| 4,491,574 | A | 1/1985 | Seifter et al. |
| 4,851,339 | A | 7/1989 | Hills |
| 5,057,494 | A | 10/1991 | Sheffield |
| 5,153,001 | A | 10/1992 | Ismail |
| 5,221,668 | A | 6/1993 | Henningfield et al. |
| 5,278,189 | A | 1/1994 | Rath et al. |
| 5,310,554 | A | 5/1994 | Haigh |
| 5,326,757 | A | 7/1994 | Demopoulos |
| 5,328,845 | A | 7/1994 | Finkelstein et al. |
| 5,346,488 | A | 9/1994 | Prince et al. |
| 5,364,563 | A | 11/1994 | Cathrein et al. |
| 5,422,247 | A | 6/1995 | Finkelstein et al. |
| 5,455,362 | A | 10/1995 | Ernst et al. |
| 5,457,135 | A | 10/1995 | Baranowitz et al. |
| 5,492,701 | A | 2/1996 | Cervos et al. |

(Continued)

FOREIGN PATENT DOCUMENTS

DE 0204987 12/1986

(Continued)

OTHER PUBLICATIONS

Buchwald, M. and W.P. Jencks. "Optical properties of astaxanthin solutions and aggregates." *Biochemistry* 1968, vol. 7, pp. 834-843.

(Continued)

*Primary Examiner*—Taofiq Solola
(74) *Attorney, Agent, or Firm*—Meyertons, Hood, Kivlin, Kowert & Goetzel, P.C.; Eric B. Meyertons

(57) ABSTRACT

A method for inhibiting and/or ameliorating the occurrence of diseases associated with reactive oxygen species, reactive nitrogen species, radicals and/or non-radicals in a subject whereby a subject is administered a carotenoid analog or derivative, either alone or in combination with another carotenoid analog or derivative, or co-antioxidant formulation. The analog or derivative is administered such that the subject's risk of experiencing diseases associated with reactive oxygen species, reactive nitrogen species, radicals and/ or non-radicals may be thereby reduced. In some embodiments, the invention may include a chemical compound including an at least partially water soluble carotenoid analog or derivative. The carotenoid analog may include a conjugated polyene with between 7 to 14 double bonds. The conjugated polyene may include a cyclic ring including at least one substituent. The substituent may be coupled to the cyclic ring with an ether functionality.

16 Claims, 38 Drawing Sheets

U.S. PATENT DOCUMENTS

| | | | |
|---|---|---|---|
| 5,527,533 A | 6/1996 | Tso et al. |
| 5,536,504 A | 7/1996 | Eugster et al. |
| 5,589,468 A | 12/1996 | Lin et al. |
| 5,605,699 A | 2/1997 | Bernhard et al. |
| 5,607,707 A | 3/1997 | Ford et al. |
| 5,607,839 A | 3/1997 | Tsubokura et al. |
| 5,612,485 A | 3/1997 | Schlipalius |
| 5,643,943 A | 7/1997 | Gamache et al. |
| 5,668,183 A | 9/1997 | Leuenberger |
| 5,705,180 A | 1/1998 | Schlipalius |
| 5,744,502 A | 4/1998 | Lignell et al. |
| 5,773,026 A | 6/1998 | Schlipalius |
| 5,801,159 A | 9/1998 | Miller et al. |
| 5,811,446 A | 9/1998 | Thomas |
| 5,837,224 A | 11/1998 | Voorhees et al. |
| 5,849,345 A | 12/1998 | Giger et al. |
| 5,854,015 A | 12/1998 | Garnett et al. |
| 5,858,700 A | 1/1999 | Ausich et al. |
| 5,863,953 A | 1/1999 | Luddecke et al. |
| 5,871,766 A | 2/1999 | Hennekens |
| 5,876,782 A | 3/1999 | Sas et al. |
| 5,886,053 A | 3/1999 | Schmutzler et al. |
| 5,891,907 A | 4/1999 | Kolter et al. |
| 5,895,659 A | 4/1999 | Luddecke et al. |
| 5,897,871 A | 4/1999 | Schlipalius |
| 5,925,684 A | 7/1999 | Schweikert et al. |
| 5,959,138 A | 9/1999 | Torres-Cardona et al. |
| 5,968,251 A | 10/1999 | Auweter et al. |
| 5,976,575 A | 11/1999 | Gellenbeck |
| 6,020,003 A | 2/2000 | Stroh et al. |
| 6,040,147 A | 3/2000 | Ridker et al. |
| 6,043,259 A | 3/2000 | Dhalla et al. |
| 6,046,181 A | 4/2000 | Oonishi et al. |
| 6,051,587 A | 4/2000 | Dakashinamurti et al. |
| 6,054,491 A | 4/2000 | Lignell et al. |
| 6,060,511 A | 5/2000 | Gainer |
| 6,075,058 A | 6/2000 | Handelman |
| 6,083,520 A | 7/2000 | Toneby |
| 6,093,348 A | 7/2000 | Kowalski et al. |
| 6,132,790 A | 10/2000 | Schlipalius |
| 6,218,436 B1 | 4/2001 | Howard et al. |
| 6,232,060 B1 | 5/2001 | Miller et al. |
| 6,245,818 B1 | 6/2001 | Lignell |
| 6,258,855 B1 | 7/2001 | Lorenz et al. |
| 6,265,450 B1 | 7/2001 | Asami et al. |
| 6,271,408 B1 | 8/2001 | Pfander et al. |
| 6,313,169 B1 | 11/2001 | Bowen et al. |
| 6,331,537 B1 | 12/2001 | Hamilton et al. |
| 6,335,015 B1 | 1/2002 | Lignell et al. |
| 6,344,214 B1 | 2/2002 | Lorenz |
| 6,399,105 B1 | 6/2002 | Collin |
| 6,426,362 B1 | 7/2002 | Miller et al. |
| 6,428,816 B1 | 8/2002 | Schlipalius et al. |
| 6,540,654 B2 | 4/2003 | Levy et al. |
| 6,541,519 B2 | 4/2003 | Collin et al. |
| 6,579,544 B1 | 6/2003 | Rosenberg et al. |
| 6,827,941 B1 | 12/2004 | Luddecke et al. |
| 2002/0032176 A1 | 3/2002 | Maoka et al. |
| 2002/0051998 A1 | 5/2002 | Schmidt-Dannert et al. |
| 2002/0110604 A1 | 8/2002 | Babish et al. |
| 2002/0169334 A1 | 11/2002 | Levy et al. |
| 2003/0035821 A1 | 2/2003 | Heaton et al. |
| 2003/0100045 A1 | 5/2003 | Cheng et al. |
| 2003/0180406 A1 | 9/2003 | Sies |
| 2003/0182687 A1 | 9/2003 | Cheng et al. |
| 2004/0110849 A1 | 6/2004 | Zelkha et al. |
| 2004/0162329 A1 | 8/2004 | Lockwood et al. |
| 2005/0004235 A1 | 1/2005 | Lockwood et al. |
| 2005/0009758 A1 | 1/2005 | Lockwood et al. |
| 2005/0009788 A1 | 1/2005 | Lockwood et al. |
| 2005/0009930 A1 | 1/2005 | Lockwood et al. |
| 2005/0026874 A1 | 2/2005 | Lockwood et al. |
| 2005/0037995 A1 | 2/2005 | Lockwood et al. |
| 2005/0049248 A1 | 3/2005 | Lockwood et al. |
| 2005/0059635 A1 | 3/2005 | Lockwood et al. |
| 2005/0059659 A1 | 3/2005 | Lockwood et al. |
| 2005/0065096 A1 | 3/2005 | Lockwood et al. |
| 2005/0065097 A1 | 3/2005 | Lockwood et al. |
| 2005/0075316 A1 | 4/2005 | Lockwood et al. |
| 2005/0075337 A1 | 4/2005 | Lockwood et al. |
| 2005/0090469 A1 | 4/2005 | Lockwood et al. |
| 2005/0113372 A1 | 5/2005 | Lockwood et al. |
| 2005/0143475 A1 | 6/2005 | Lockwood et al. |
| 2005/0148517 A1 | 7/2005 | Lockwood et al. |
| 2005/0261254 A1 | 11/2005 | Lockwood et al. |
| 2006/0058269 A1 | 3/2006 | Lockwood et al. |
| 2006/0088904 A1 | 4/2006 | Lockwood et al. |
| 2006/0088905 A1 | 4/2006 | Lockwood et al. |
| 2006/0111580 A1 | 5/2006 | Lockwood et al. |
| 2006/0155150 A1 | 7/2006 | Lockwood et al. |
| 2006/0167319 A1 | 7/2006 | Lockwood et al. |
| 2006/0178538 A1 | 8/2006 | Lockwood et al. |
| 2006/0183185 A1 | 8/2006 | Lockwood et al. |
| 2006/0183947 A1 | 8/2006 | Lockwood et al. |

FOREIGN PATENT DOCUMENTS

| | | |
|---|---|---|
| JP | 07300421 | 11/1995 |
| JP | 08073312 | 3/1996 |
| JP | 08337592 | 12/1996 |
| JP | 09084591 | 3/1997 |
| JP | 09202730 | 8/1997 |
| JP | 10155459 | 6/1998 |
| JP | 10327865 | 12/1998 |
| JP | 2000-143688 | 5/2000 |
| JP | 2001114673 | 4/2001 |
| WO | WO 90/10440 | 9/1990 |
| WO | WO 92/05780 | 4/1992 |
| WO | WO 96/40092 | 12/1996 |
| WO | WO 98/29111 | 7/1998 |
| WO | WO 98/37874 | 9/1998 |
| WO | WO 99/11251 | 3/1999 |
| WO | WO 99/30701 | 6/1999 |
| WO | WO 02/47680 | 6/2002 |
| WO | WO 02/068385 | 9/2002 |
| WO | WO 03/066583 | 8/2003 |

OTHER PUBLICATIONS

Reznikoff et al "Quantitative and Qualitative Studies of Chemical Transformation of Cloned C3H Mouse Embryo Cells Sensitive to Postconfluence Inhibition of Cell Division." *Cancer Research*, 1973, vol. 33 pp. 2339-2349.

Andrewes et al. "Animal carotenoids. 9. On the absolute configuration of astaxanthin and actinioerythrin." *Acta Chem. Scand.* 1974, vol. B28, pp. 730-736.

Salares et al. "Resonance Raman spectra of lobster shell carotenoproteins and a model astaxanthin aggregate. A possible photobiological function for the yellow protein." *Biochemistry* 1977, vol. 16, pp. 4751-4756.

Salares et al. ,,Excited state (exciton) interactions in polyene aggregates. *J. Raman Spectr.* 1977, vol. 6, pp. 282-288.

Halliwell, B. "Superoxide-dependent formation of hydroxyl radicals in the presence of iron chelates. Is it a mechanism for hydroxyl radical production in biological systems?" *FEBS Lett* 1978, vol. 92, pp. 321-326.

Harada et al. "Circular dichroic power due to chiral exciton coupling between two polyacene chromophores." *J. Am. Chem. Soc.* 1978, vol. 100, pp. 4029-4036.

Stuber et al. "A new synthesis of L-*threo*-hex-2-enaro-1,4-lactone ("saccharoascorbic" acid): a method for the protection of the enediol of ascorbic acid." *Carbohydrate Research* 1978, vol. 60, pp. 251-258.

Bock et al. "Preparation of some bromodeoxyaldonic acids." *Carbohydrate Research* 1979, vol. 68 pp. 313-319.

Merriman and Bertram "Reversible inhibition by retinoids of 3-methylcholanthrene- induced neoplastic transformation in C3H10T1/2 cells." *Cancer Research* 1979, vol. 39, pp. 1661-1666.

Noack and Thomson "Conformation and optical-activity of all-*trans*, mono-*cis*, and di-*cis* carotenoids- temperature-dependent circular-dichroism." *Helvetica Chimica Acta* 1979, vol. 62, pp. 1902-1921.

Müller et al. "Contribution to the analytical separation and the synthesis of 3-hydroxy-4-oxocarotenoids." *Helvetica Chimica Acta* 1980, vol. 63, pp. 1654-1664. German, Abstract Engl.

Sturzenegger et al. "Classification of the CD spectra of cartenoids." *Helvetica Chimica Acta* 1980, vol. 63, pp. 1074-1092.

Bernhard et al. "Synthesis of optically-active natural carotenoids and structurally related-compounds. 9. Synthesis of (3R)-hydroxyechinenone, (3R,3'R)-adonixanthin and (3R,3'S)-adonixanthin, (3R)-adonirubin, their optical antipodes and related-compounds." *Helvetica Chimica Acta* 1981, vol. 64, pp. 2469-2484. German, Abstract Engl.

Noack and Thomson "Temperature and concentration dependent circular-dichroism of mono-*cis* and di-*cis* isomers of (3R,3'S)-astaxanthin diacetate." *Helvetica Chimica Acta* 1981, vol. 64, pp. 2383-2392.

Braunwald and Kloner "The stunned myocardium-prolonged post-ischemic ventricular dysfunction." *Circulation* 1982, vol. 66, pp. 1146-1149.

Harada and Nakanishi "Circular Dichroic Spectroscopy—Exciton Coupling in Organic Stereochemistry", 1983, University Science Books, Mill Valley (CA).

Goodman "Mechanisms of disease: Vitamin A and retinoids in health and disease." *New England Journal Medicine* 1984, vol. 310, pp. 1023-1031.

Bertram. "Neoplastic Transformation in Cell Cultures: In Vitro/In-Vivo Correlations." *IARC Sci.Pub.* 1985, vol. 67, pp. 77-91.

Myers et al. "Enhancement of recovery of myocardial function by oxygen free radical scavengers after reversible myocardial ischemia." *Circulation* 1985, vol. 72, pp. 915-921.

Ambrosio et al. "Reduction in experimental infarct size by recombinant human superoxide dismutase: insights into the pathophysiology of reperfusion injury." *Circulation* 1986, vol. 74, pp. 1424-1433.

Blaustein et al. "Influence of exogenously generated oxidant species on myocardial function." *American Journal of Physiology* 1986, vol. 250, pp. H595-H599.

Gey, K. F. "On the antioxidant hypothesis with regard to atherosclerosis." *Bibliotheca Nutritio et Dieta*, 1986, vol. 37, pp. 53-91.

Bolli et al., "The iron chelator desferioxamine attenuates postischemic ventricular dysfunction." *American Journal of Physiology* 1988, vol. 7253, pp. H1372-H1380.

Bolli et al., "Attenuation of dysfunction in the postischemic 'stunned' myocardium by dimethylurea." *Circulation* 1987, vol. 76, pp. 458-468.

Gross et al. "Beneficial actions of superoxide dismutase and catalase in stunned myocardium of dogs." *American Journal of Physiology* 1986, vol. 250, pp. H372-H377.

Hearse et al: "Xanthine oxidase: a critical mediator of myocardial injury during ischemia and reperfusion." *Acta Physiololica Scandanavica* 1986, vol. 548, pp. 65-74.

Such et al. "Beneficial effects of N-acetylcysteine on acute myocardial infarction in open chest dogs." *Archives of Pharmacology and Toxicology* 1986, vol. 12, pp. 7-40.

Bolli et al. "The iron chelator desferioxamine attenuates postischemic ventricular dysfunction." *American Journal of Physiology* 1987, vol. 253, pp. H1372-H1380.

Bolli, R. "Oxygen-derived free radicals and post-ischemic myocardial dysfunction ('stunned myocardium')." *Journal of the American College of Cardiology* 1988, vol. 12, pp. 239-249.

Cross et al. "Oxygen radicals and human disease." *Annals of Internal Medicine* 1987, vol. 107, pp. 526-545.

Simpson et al. "Free radicals and myocardial ischemia and reperfusion injury." *Journal of Laboratory and Clinical Medicine* 1987, vol. 110, pp. 13-30.

Mehta et al.. "Neutrophils as potential participants in acute myocardial ischemia: relevance to reperfusion." *Journal of the American College of Cardiology* 1988, vol. 11, pp. 1309-1316.

Liao et al. "Synthesis of L-ascorbate and 6-phosphate." *Carbohydrate Research*, 1988, vol. 176, pp. 73-77.

Hearse and Tosaki "Free radicals and calcium: simultaneous interacting triggers as determinants of vulnerability to reperfusion-arrhytmias in the rat heart". *Journal of Molecular and Cellular Cardiology* 1988, vol. 20, pp. 213-223.

Mashovsky, M. D. Tocopherol acetate (Tocopheroli acetas) 6-Acetoxy-2-methyl-2-(4,8,12-trimethyltridecyl)-chromane. pp. 37-38. Aevit (Aevitum). p. 41. Acetysalicyclic acid (Acidum acetylsalicylicum). p. 190. 1988, In *Medicinal Substances*, Part 2, 1988. (Russian, abstracts in English).

Pung et al. "β-Carotene and canthaxanthin inhibit chemically- and physically-induced neoplastic transformation in 10T1/2 cells." *Carcinogenesis*, 1998, vol. 9, pp. 533-1539.

Bertram, et al. "Development of in vitro systems for chemoprevention research". *Preventative Medicine* 1989, vol. 18, pp. 562-575.

Bolli et al. "Direct evidence that oxygen-derived free radicals contribute to post-ischemic myocardial dysfunction in the intact dog." *Proceeding of the National Academy of Sciences*, U.S.A. 1989, vol. 86, pp. 4695-4699.

Opie, L. H. "Reperfusion injury and its pharmacologic modification." *Circulation* 1989, vol. 80, pp. 1049-1092.

Steinberg et al. "Beyond cholesterol: modifications of low-density lipoprotein that increase its atherogenicity." *New England Journal of Medicine* 1989, vol. 320, pp. 915-924.

Terao, J. "Antioxidant activity of beta-carotene-related carotenoids in solution." *Lipids* 1989, vol. 24, pp. 659-661.

In *Drug Facts and Comparisons*. 1990 Ed. Sewester, C. S., Olin, B. R., Hebel, S. K., Eds. Facts and Comparisons Division, J. B. Lippincott Co., St. Louis, MO. pp. 6, 7, 13, 14, 60, 62, 997, 998.

Chopra et al. "Free radical scavenging: potentially beneficial action of thiol-containing angiotensin-converting enzyme inhibitors." *Biochem Soc Trans* 1990, 18:1184-1185.

Davies et al. "Lipid peroxidation associated with successful thrombolysis." *Lancet* 1990, 335:741-743.

Di Mascio et al. "Carotenoids, tocopherols, and thiols and biological singlet molecular oxygen quenchers." *Biochemical Society Transactions* 1990, vol. 18, pp. 1054-1056.

Fedan, J. S. 1990 "Anticoagulant, antiplatelet, and fibrinolytic (thrombolytic) drugs." In *Modern Pharmacology*. Third Ed, Little, Brown and Co., Boston, MA.

Johansson et al. "Recombinant human extracellular superoxixe dismutase reduced concentration of oxygen free radicals in the reperfused rat heart." *Cardiovascular Research* 1990, vol. 24, pp. 500-503.

Kurashige et al. "Inhibition of oxidative injury of biological membranes by astaxanthin." *Physiological Chemistry and Physics and Medical NMR* 1990, vol. 22, pp. 27-38.

Rogers et al. "Retinoid-enhanced gap junctional communication is achieved by increased levels of *connexin 43* mRNA and protein" *Molecular Carcinogenesis* 1990, vol. 3, pp. 335-343.

Shuter et al. "Studies on the effects of antioxidants and inhibitors of radical generation on free radical production in the reperfused rat heart using electron spin resonance spectroscopy." *Free Radical Research Communications* 1990, vol. 9, pp. 223-232.

Williams et al. "The relationship between neutrophils and increased microvascular permeability in a model of myocardial ischemia and reperfusion in the rabbit." *British Journal of* Pharmacology, 1990, vol. 100, pp. 729-734.

Bertram et al. "Diverse carotenoids protect against chemically induced neoplastic transformation." *Carcinogenesis*, 1991, vol. 12: 671-678.

Di Mascio et al. "Antioxidant defense systems: the role of carotenoids, tocopherols, and thiols." *Am J Clin Nutr* 1991, 53: 194S-200S.

Axford-Gatley and Wilson "Reduction of experimental myocardial infarct size by oral administration of alpha-tocopherol." *Cardiovascular Research*, 1991, vol. 25, pp. 89-92.

Conorev et al. "Improvement of contractile recovery of isolated rat heart after cardioplegic ischemic arrest with endogenous phosphocreatine: involvement of antiperoxidative effect?" *Cardiovascular Research* 1991, vol. 25, pp. 164-171.

Esterbauer et al. "Effect of antioxidants on oxidative modification of LDL." *Annals of Medicine* 1991, vol. 23, pp. 573-581.

McMurray and Chopra "Influence of ACE inhibitors on free radicals and reperfusion injury: pharmacological curiosity or therapeutic hope?" *British Journal of Pharmacology* 1991, vol. 31, pp. 373-379.

Petty et al. "Effect of a cardioselective alpha-tocopherol analogue on reperfusion injury in rats induced by myocardial ischemia." *European Journal of Pharmacology* 1991, vol. 192, pp. 383-388.

Miki. "Biological functions and activities of animal carotenoids." *Pure and Applied Chemistry* 1991, vol. 63, pp. 141-146.

Welbourn et al. "Pathophysiology of ischemic reperfusion injury: central role of the neutrophil." *British Journal of Surgery* 1991, vol. 78, pp. 651-655.

Gabrielson et al. "Measurement of neutrophil activation and epidermal cell toxicity by palytoxin and 12-O-tetradecanoylphorbol-13-acetate." *Carcinogenesis* 1992, 13 1671-1674.

Hearse and Bolli. "Reperfusion induced injury: manifestations, mechanisms, and clinical relevance." *Cardiovascular Research* 1992, vol. 26, pp. 101-108.

Kimura et al. "Moderation of myocardial ischemia reperfusion injury by calcium channel and calmodulin receptor inhibition." *Heart Vessels*, 1992, vol. 7, pp. 189-195.

Lim et al. "Antioxidant activity of xanthophylls on peroxyl radical-mediated phospholipid peroxidation." *Biochmica Biophysica Acta* 1992, vol. 1126, pp. 178-184.

Palozza and Krinsky. "Astaxanthin and canthaxanthin are potent antioxidants in a membrane model." *Arch. Biochem. Biophys.* 1992, vol. 297, pp. 291-295.

Zhang et al. "Carotenoids up-regulate connexin 43 gene expression independent of their pro-vitamin A or antioxidant properties." *Cancer Research*, 1992, vol. 52, pp. 5707-5712.

Ames et al. "Oxidants, antioxidants, and the degenerative diseases of aging." *Proceedings of the National Academy of Sciences, U.S.A.* 1993, vol. 90, pp. 7915-7922.

Baxter and Yellon. "Attenuation of reperfusion-induced ventricular fibrillation in the rat isolated hypertrophied heart by preischemic diltiazem treatment." *Cardiovascular Drugs Therapy* 1993, vol. 7, pp. 225-231.

Clevidence and Bieri. "Association of carotenoids with human plasma lipoproteins." *Methods in Enzymology*, 1993, vol. 214, pp. 33-46.

Grech et al. "Free-radical generation during angioplasty reperfusion for acute myocardial infarction." *Lancet* 1993, vol. 341, pp. 990-991.

Grech et al. "Differential free-radical activity after successful and unsuccessful thrombolytic reperfusion in acute myocardial infarction." *Coronary Artery Disease*, 1993, vol. 4, pp. 769-774.

Hossain et al. "Retinoids and carotenoids upregulate gap junctional communication: correlation with enhanced growth control and cancer prevention." In *Progess in Cell Research vol. 3: Gap Junctions*. (1993) Elsiever, Amsterdam, pp. 301-309.

Jimenez and Pick. "Differential reactivity of beta-carotene isomers from *Dunaliella bardawil* toward oxygen radicals." *Plant Physiology*, 1993, vol. 101, pp. 385-390.

Oshima et al. "Inhibitory effect of beta-carotene and astaxanthin on photosensitized oxidation of phospholipid bilayers." *Journal of Nutritional Science and Vitaminology*, 1993, vol. 39, pp. 607-615.

Bertram and Zhang. Assays for the regulation of gap junctional communication and connexin expression by carotenoids. 1994, *Methods in Enzymology*, vol. 234, pp. 235-244.

MacIsaac et al. "Toward the quiescent coronary plaque." *Journal of the American College of Cardiology*, 1993, vol. 22, pp. 1228-1241.

Oliveros et al. Quenching of singlet oxygen by carotenoid derivatives: kinetic analysis by near-infrared luminescence *New Journal of Chemistry*, 1994, vol. 18, pp. 535-539.

Singh et al. "Plasma levels of antioxidant vitamins and oxidative stress in patients with acute myocardial infarction." *Acta Cardiologica*, 1994, vol. XLIX, pp. 441-452.

Tinkler et al. "Dietary carotenoids protect human cells from damage." *Journal of Photochemistry and Photobiology*, 1994, vol. 26, pp. 283-285.

Britton. "Structure and properties of carotenoids in relation to function." *The FASEB Journal*, 1995, vol. 9, pp. 1551-1558.

Leist et al. "Tumor necrosis factor-induced hepatocyte apoptosis precedes liver failure in experimental murine shock models." *American Journal of Pathology*, 1995, vol. 146, pp. 1220-1234.

Navab et al. "Pathogenesis of atherosclerosis." *American Journal of Cardiology*, 1995, vol. 76, pp. 18C-23C.

Peters. "Myocardial gap junction organization in ischemia and infarction." *Microscopy Research Techniques*, 1995, vol. 31, pp. 375-386.

Singh et al. "Plasma levels of antioxidant vitamins and oxidative stress in patients with acute myocardial infarction." *Acta Cardiologica*, 1994, vol. XLIX 5, pp. 441-452.

Singh et al. "Effect of antioxidant-rich foods on plasma ascorbic acid, cardiac enzymes, and lipid peroxide levels in patients hospitalized with acute myocardial infarction." *Journal of the American Dietetic Association*, 1995, vol. 95, pp. 775-780.

Torrissen and Christiansen. "Requirements for carotenoids in fish diets." *Journal of Applied Ichthyology*, 1995, vol. 11, pp. 225-230.

Aviram. "Interaction of oxidized low density lipoprotein with macrophages in atherosclerosis, and the antiatherogenicity of antioxidants." *European Journal of Clinical Chemistry and Clinical Biochemistry*, 1996, vol. 34, pp. 599-608.

Ben-Amotz and Levy. "Bioavailability of a natural isomer mixture compared with synthetic all-*trans*beta-carotene inhuman serum." *American Journal of Clinical Nutrition*, 1996, vol. 63, pp. 729-734.

Mayne. "Beta-carotene, carotenoids, and disease prevention in humans." *The FASEB Journal*, 1996, vol. 10, pp. 690-701.

Moore and Papas. "Biochemistry and health significance of Vitamin E." *Journal of Advanced Medicine*, 1996, vol. 9, pp. 11-29.

Parker. Absorption, metabolism, and transport of carotenoids. *The FASEB Journal*, 1996, vol. 10, pp. 542-551.

Peters. "Ligand binding by albumin." In *All About Albumin*, Academic Press, San Diego (CA), 1996. pp. 76-128.

Schaer et al. "Beneficial effects of RheothRx injection in patients receiving thrombolytic therapy for acute myocardial infarction. Results of a randomized, double-blind, placebo-controlled trial." *Circulation*, 1996, vol. 94, pp. 298-307.

Shimidzu et al. "Carotenoids as singlet oxygen quenchers in marine organisms." *Fisheries Science*, 1996, vol. 62, pp. 134-137.

Serrano et al. "Superoxide and hydrogen perodixe induce CD18-mediated adhesion in the postischemic heart." *Biochimica Biophysica Acta*, 1996, vol. 1316, pp. 191-202.

Singh et al. "Usefulness of antioxidant vitamins in suspected acute myocardial infarction (the Indian experiment of infarct survival-3." *American Journal of Cardiology*, 1996, vol. 77, pp. 232-236.

Stephens et al. "Randomised controlled trial of vitamin E in patients with coronary disease: Cambridge Heart Antioxidant Study (CHAOS)." *Lancet*, 1996, vol. 347, pp. 781-786.

Goulinet and Chapman. "Plasma LDL and HDL subspecies are heterogeneous in particle content of tocopherols and oxygenated and hydrocarbon carotenoids: relevance to oxidative resistance and atherogenesis." *Arteriosclerosis, Thrombosis, and Vascular Biology*, 1997, vol. 17, pp. 786-796.

Kim et al. "Zeaxanthin dipalmitate from *Lycium chinense* has hepatoprotective activity." *Research Communications in Molecular Pathology and Pharmacology*, 1997, vol. 97, pp. 301-314.

Maxwell and Lip "Reperfusion injury: a review of the pathophysiology, clinical manifestations and therapeutic options." *International Journal of Cardiology*, 1997, vol. 58, pp. 95-117.

Mortensen et al. "Comparative mechanisms and rates of free radical scavenging by carotenoid antioxidants." *FEBS Letters*, 1997, vol. 418, pp. 91-97.

Oshima et al. "Accumulation and clearance of capsanthin in blood plasma after the ingestion of paprika juice in men." *Journal of Nutrition*, 1997, vol. 127, pp. 1475-1479.

Perkins et al. "Three-dimensional structure of the gap junction connexon." *Biophysical Journal*, 1997, vol. 72, pp. 533-544.

Turujman et al. "Rapid liquid chromatographic method to distinguish wild salmon from aquacultured salmon fed synthetic astaxanthin." *Journal of AOAC International*, 1997, vol. 80, pp. 622-632.

Holvoet et al. "Oxidized LDL and malondialdehyde-modified LDL in patients with acute coronary syndromes and stable coronary artery disease." *Circulation*, 1998, vol. 98, pp. 1487-1494.

Kaprielian et al. "Downregulation of immunodetectable connexin 43 and decreased gap junction size in the pathogenesis of chronic hibernation in the human left ventricle." *Circulation*, 1998, vol. 97, pp. 651-660.

Levy et al. "Plasma antioxidants and lipid peroxidation in acute myocardial infarction and thrombolysis." *Journal of the American College of Nutrition*, 1998, vol. 17, pp. 337-341.

Saez et al. "Regulation of gap junctions by protein phosphorylation." *Brazilian Journal of Medical Biology Research*, 1998, vol. 31, pp. 593-600.

Saffitz and Yamada. "Do alterations in intercellular coupling play a role in cardiac contractile dysfunction?" *Circulation*, 1998, vol. 97, pp. 630-632.

Singh et al. "Randomized, double-blind placebo-controlled trial of coenzyme Q10 in patients with acute myocardial infarction." *Cardiovascular Drugs and Therapy*, 1998, vol. 12, pp. 347-353.

Bertram, J. S. "Carotenoids and gene regulation." *Nutrition Reviews*, 1999, vol. 57, pp. 182-191.

Boileau et al. "Carotenoids and vitamin A", In *Antioxidant status, diet, nutrition, and health*. CRC Press, (1999). Boca Raton, FL, pp. 133-158.

Boileau et al. "*Cis*-lycopene is more bioavailable than *trans*-lycopene in vitro and in vivo in lymph-cannulated ferrets." *Journal of Nutrition*, 1999, vol. 129, pp. 1176-1181.

Buffon et al. "Preprocedural serum levels of C-reactive protein predict early complications and late restenosis after coronary angioplasty." *Journal of the American College of Cardiology*, 1999, vol. 34, pp. 1512-1521.

Curry et al. "Fatty acid binding to human serum albumin: new insights from crystallographic studies". *Biochimical Biophysica Acta*, 1999, vol. 1441, pp. 131-140.

Fernandez-Cobo et al. "Downregulation of connexin 43 gene expression in rat heart during inflammation: The role of tumor necrosis factor", *Cytokine*, 1999, vol. 11, pp. 216-224.

Hennekens. "Antioxidant vitamins and cardiovascular disease" In *Antioxidant status, diet, nutrition and health*. CRC press, 1999, Boca Raton, FL pp. 463-477.

Horwitz et al. "Timing of treatment for myocardial reperfusion injury." *Journal of Cardiovascular Pharmacology*, 1999, vol. 33, pp. 19-29.

Huang et al. "Heterogeneous loss of connexin 43 protein in ischemic dog hearts." *Journal of Cardiovascular Electrophysiology*, 1999, vol. 10, pp. 79-91.

Jewell and O'Brien. "Effect of dietary supplementation with carotenoids on xenobiotic metabolizing enzymes in the liver, lung, kidney and small intestine of the rat." *British Journal of Nutrition*, 1999, vol. 81, pp. 235-242.

Lagrand et al. "C-reactive protein as a cardiovascular risk factor: more than an epiphenomenon?" *Circulation*, 1999, vol. 100, pp. 96-102.

Lowe et al. "Carotenoid composition and antioxidant potential in subfractions of human low-density lipoprotein." *Annals of Clinical Biochemistry*, 1999, vol. 36, pp. 323-332.

Mahaffey et al. "Adenosine as an adjunct to thrombolytic therapy for acute myocardial infarction." *Journal of the American College of Cardiology* (1999). 34(6): 1711-1720.

Papas. "Antioxidant status: diet, health and disease; Part I: Factors affecting antioxidant status and its role." *Mature Medicine* (1999) 315-319.

Sajkowska et al. "Fibrinolytic therapy and n-acetylcysteine in the treatment of patients with acute myocardial infarction: its influence on authentic plasma hydroperoxide levels and polymorphonuclear neutrophil oxygen metabolism." *Cardiology* (1999). 91: 60-65.

Arab and Steck "Lycopene and cardiovascular disease." *American Journal of Clinical Nutrition*, 2000, vol. 71 (supp), pp. 1691S-1695S.

Bhattacharya et al. Crystallographic analysis reveals common modes of binding of medium and long-chain fatty acids to human serum albumin. *J. Mol. Biol.* (2000) 303: 721-732.

Ding and Hu. "The synthesis of vicinal halohydrin phosphates via highly regioselective ring opening of epoxides with dialkyl halophophate." *J. Chem. Chem. Soc., Perkin Trans.* 2000 1:1651-1655.

Devaraj and Jialal "Alpha tocopherol supplementation decreases serum C-reactive protein and monocyte interleukin-6 levels in normal volunteers and type 2 diabetic patients." *Free Radical Biology Medicine* (2000). 29(8): 790-2.

Iwamoto et al. "Inhibition of low-density lipoprotein oxidation by astaxanthin." *Journal of Atherosclerosis and Thrombosis* (2000). 7: 216-222.

Jollis and Romano. "Volume-outcome relationship in acute myocardial infarction." *Journal of the American Medical Society*, 2000, vol. 284, pp. 3169-3171.

Jyonouchi et al. "Antitumor activity of astaxanthin and its mode of action." *Nutrition and Cancer* 2000, vol. 36, pp. 59-65.

Lee et al. "Biphasic regulation of leukocyte superoxide generation by nitric oxide and peroxynitrite." *Journal of Biological Chemistry*, 2000, vol. 275, pp. 38965-38972.

Magid et al. "Relation between hospital primary angioplasty volume and mortality for patients with acute MI treated with primary angioplasty vs thrombolytic therapy." *Journal of the American Medical Association*, 2000, vol. 284, pp. 3169-3171.

Mycek et al. *Lippincott's Illustrated Reviews: Pharmacology.*, 2000, Lippincott, Williams & Wilkins, pp. 201-204.

Orset and Young "Exposure to low irradiances favors the synthesis of 9-cis beta,beta carotene in *Dunaliella salina* (Teod.)." *Plant Physiology*, 2000, vol. 122, pp. 609-617.

Osterlie et al. "Plasma appearance and distribution of astaxanthin E/Z and R/S isomers in plasma lipoproteins of men after single dose administration of astaxanthin." *Journal of Nutritional Biochemistry*, 2000, vol. 11, pp. 482-490.

Ounpuu et al. "The global burden of cardiovascular disease." *Medscape Cardiology*, 2000, vol. 4, pp. 1-5.

Peters and Wit "Gap junction remodeling in infarction: does it play a role in arrhythmogenesis?" *Journal of Cardiovascular Electrophysiology*, 2000, vol. 11, pp. 488-490.

Sethi et al. "Beneficial effects of vitamin E treatment in acute myocardial infarction." *Journal Cardiovascular Pharmacology and Therapeutics*, 2000, vol. 5, pp. 51-58.

Upritchard et al. "Effect of supplementation with tomato juice, vitamin E, and vitamin C on LDL oxidation and products of inflammatory activity in type 2 diabetes." *Diabetes Care*, 2000, vol. 23, pp. 733-738.

Watanabe et al. "Role of Arg-410 and Tyr-411 in human serum albumin for ligand binding and esterase-like activity." *Biochemical Journal*, 2000, vol. 349, pp. 813-819.

Di Napoli et al. "C-reactive protein in ischemic stroke: an independent prognostic factor." *Stroke* 2001, vol. 32, pp. 917-924.

Duilio et al. "Neutrophils are primary source of $O_2$ radicals during reperfusion after prolonged myocardial ischemia." *American Journal of Physiology: Heart and Circulatory Physiology*, 2001, vol. 280 H2649-H2657.

Goto et al. "Efficient radical trapping at the surface and inside the phospholipids membrane is responsible for highly potent antiperoxidative activity of the acrotenoid astaxanthin." *Biochimica Biophysica Acta*, 2001, vol. 1512, pp. 251-258.

Jialal et al. "Is there a vitamin E paradox?" *Current Opinions in Lipidology*, 2001, vol. 12, pp. 49-53.

Kang et al. "Effect of astaxanthin on the hepatotoxicity, lipid peroxidation and antioxidative enzymes in the liver of CC14-treated rats." *Methods Find Exp Clin Pharmacol.*, 2001, vol. 23, pp. 79-84.

Petitpas et al. "Crystal structures of human serum albumin complexed with monounsaturated and polyunsaturated fatty acids." *The Journal of Molecular Biology*, 2001, vol. 314, pp. 955-960.

Lutnaes et al. "Is (9Z)- 'meso'-zeaxanthin optically active?" *Chirality*, 2001, vol. 13, pp. 224-229.

Roe et al. "Shifting the open-artery hypothesis downstream: the quest for optimal reperfusion." *Journal of the American College of Cardiology*, 2001, vol. 37, pp. 9-18.

Zsila et al. "Chiral detection of carotenoid assemblies." *Chirality*, 2001, vol. 13, pp. 446-453.

Zsila et al. "Investigation of the self-organization of lutein and lutein diacetate by electronic absorption, circular dichroism spectroscopy, and atomic force microscopy." *Journal of Physical Chemistry*, 2001, vol. 105, pp. 9413-9421.

Zsila et al. "Induced chirality upon crocetin binding to human serum albumin: origin and nature." *Tetrahedron: Assymmetry*, 2001, vol. 12, pp. 3125-3137.

Zsila et al.. "Supramolecular assemblies of carotenoids." *Chirality*, 2001, vol. 13, pp. 739-744.

Barrett et al. "C-reactive protein associated increase in myocardial infarct size after ischemia/reperfusion." *Journal of Pharmacology and Experimental Therapeutics*, 2002, vol. 303, pp. 1007-1013.

Bikádi et al. "The supramolecular structure of self-assmebly formed by capsanthin derivatives." *Enantiomer*, 2002, vol. 7, pp. 67-76.

Choi et al. "Interactions of very long-chain saturated fatty acids with serum albumin." *Journal of Lipid Research*, 2002, vol. 43, pp. 1000-1010.

Kistler et al. "Metabolism and CYP-inducer properties of astaxanthin in man and primary human hepatocytes." *Archives of Toxicology*, 2002, vol. 75, pp. 665-676.

Kragh-Hansen et al. "Practical aspects of the ligand-binding and enzymatic properties of human serum albumin." *Biolological & Pharmaceutical Bulletin*, 2002, vol. 25, pp. 695-704.

Kurihara et al. "Contribution of the antioxidative property of astaxanthin to its protective effect on the promotion of cancer metastasis in mice treated with restraint stress." *Life Science*, 2002, vol. 21, pp. 2509-2520.

Rao and Agarwal "Bioavailability and in vivo antioxidant properties of lycopene from tomato products and their possible role in the prevention of cancer." *Nutrition and Cancer* 1998, vol. 31, pp. 199-203.

Kim et al. "Electronic absorption and Raman studies of the radical anion and dianion of a polyene molecule (19,19',20,20'-tetranor-b,b-carotene)." *Chemical Physical Letters* 1997, vol. 276, pp. 418-422.

Duhamel et al., "Terminally substituted linear conjugated polyenes: precursors of molecular wires." *Tetrahedron Letters* 1993, vol. 34, pp. 7399-7400.

Xu et al. "TXA2-PGI2 balance disorder in rat brain with incomplete cerebral ischemia and reperfusion, and the correction of this imbabance by carthamic xanthophyll." *Jinan Daxue Xuebao, Ziran Kexue Yu Yixueban*, 1993, vol. 14, pp. 34-38 (Abstract only).

Engster, "Beilstein Institut zur Foerderung der chemischen Wissenschaft, Tnaxanthin, Database accession No. 2313964." Carotenoid Chemistry and Biochemistry, Proceedings of the 6th International Symposium on Carotenoids, 1981, pp. 1-9 (Abstract only).

Co-Pending U.S. Appl. No. 11/357,897 entitled, "Structural Carotenoid Analogs for the Inhibition and Amelioration of Disease" to Lockwood et al. filed Feb. 17, 2006; available in private PAIR.

Co-Pending U.S. Appl. No. 11/214,478 entitled, "Carotenoid Analogs or Derivatives for the Inhibition and Amelioration of Inflammation" to Lockwood et al. filed Aug. 29, 2005; available in private PAIR.

Co-Pending U.S. Appl. No. 11/242,641 entitled, "Methods for the Synthesis of Chiral Dihydroxy Intermediates Useful for the Chiral Synthesis of Carotenoids" to Lockwood et al. filed Oct. 3, 2005; available in private PAIR.

Co-Pending U.S. Appl. No. 11/242,643 entitled, "Methods for the Synthesis of Astaxanthin" to Lockwood et al. filed Oct. 3, 2005; available in private PAIR.

Co-Pending U.S. Appl. No. 11/242,615 entitled, "Methods for the Synthesis of Lutein" to Lockwood et al. filed Oct. 3, 2005; available in private PAIR.

Co-Pending U.S. Appl. No. 11/242,639 entitled, "Methods for the Synthesis of Zeaxanthin" to Lockwood et al. filed Oct. 3, 2005; available in private PAIR.

Co-Pending U.S. Appl. No. 11/242,609 entitled, "Methods for the Synthesis of Unsaturated Ketone Intermediates Useful for the Synthesis of Carotenoids" to Lockwood et al. filed Oct. 3, 2005; available in private PAIR.

Co-Pending U.S. Appl. No. 11/242,645 entitled, "Methods for the Synthesis of Astaxanthin" to Lockwood et al. filed Oct. 3, 2005; available in private PAIR.

Co-Pending U.S. Appl. No. 11/242,627 entitled, "Methods for the Synthesis of Chiral Dihydroxy Ketone Intermediates Useful for the Chiral Synthesis of Carotenoids" to Lockwood et al. filed Oct. 3, 2005; available in private PAIR.

Co-Pending U.S. Appl. No. 11/242,591 entitled, "Methods for the Synthesis of Astaxanthin" to Lockwood et al. filed Oct. 3, 2005; available in private PAIR.

Co-Pending U.S. Appl. No. 11/359,984 entitled, "Carotenoids, Carotenoid Analogs, or Carotenoid Derivatives for the Stabilization or Improvement of Visual Acuity" to Lockwood et al. filed Feb. 22, 2006; available in private PAIR.

Co-Pending U.S. Appl. No. 11/372,353 entitled, "Carotenoids, Carotenoid Analogs, or Carotenoid Derivatives for the Treatment of Proliferative Disorders" to Lockwood et al. filed Mar. 9, 2006; available in private PAIR.

Co-Pending U.S. Appl. No. 11/392,470 entitled, "Reduction in Complement Activation and Inflammation During Tissue Injury by Carotenoids, Carotenoid Analogs, or Derivatives Thereof" to Lockwood et al. filed Mar. 29, 2006; available in private PAIR.

Co-Pending U.S. Appl. No. 11/388,237 entitled, "Water-Dispersible Carotenoids, Including Analogs and Derivatives" to Lockwood et al. filed Mar. 23, 2006; available in private PAIR.

Co-Pending U.S. Appl. No. 11/417,307 entitled, "Use of Carotenoids and/orCarotenoid Derivatives/Analogs for Reduction/ Inhibition of Certain Negative Effects of Cox Inhibitors" to Lockwood et al. filed May 2, 2006; available in private PAIR.

Co-Pending U.S. Appl. No. 11/415,375 entitled, "Methods for Synthesis of Carotenoids, Including Analogs, Derivatives, and Synthetic and Biological Intermediates" to Lockwood et al. filed May 1, 2006; available in private PAIR.

International Preliminary Examination Report PCT/US 03/23706, Oct. 27, 2004.

Hertzberg, S., Liaaen-Jensen, S., 1985. Carotenoid sulfates. 4. syntheses and properties of carotenoid sulfates. Acta Chemica Scandinavica B 39, 629-638.

Zsila, F., et al, "Color and chirality: carotenoid self-assemblies in flower petals," Planta 213, (2001), pp. 937-942.

Britton, G., et al., "Carotenoids: Isolation and Analysis," Birkhauser:Basel, vol. 1a, (1995), p. 82.

Boileau et al. "Bioavailabiltiy of all-Trans and cis-Isomers of Lycopene" Exp. Biol. Med. (Maywood) (2002) 227, 914-919.

Jyonouchi et al. "Studies of Immunomodulating Actions of Carotenoids. I. Effects of beta-Carotene and Astaxanthin on Murine Lymphocyte Functions and Cell Surface Marker Expression in in vitro Culture System" Nutr. Cancer (1991) 16: 93-105.

Subczynski, W., et al., "Effect of polar carotenoids on the oxygen diffusion-concentration product in lipid bilayers; An EPR spin label study," Biochim Biophys Acta, 1068, (1991), pp. 68-72.

Kjosen et al. "Carotenoids of Higher Plants 6. Total Synthesis of Lycoxanthin and Lycophyll" Acta. Chem. Scand. 26 (1972) 10 4121-4129.

Huang, D., et al., "Development and Validation of Oxygen Radical Absorbance Capacity Assay for Lipophilic Antioxidants Using Randomly Methylated beta-Cyclodextrin as the Solubility Enhancer" J Agric Food Chem.(2002) 50, 1815-1821.

Jensen, S., et al., "All-rac-alpha-tocopherol acetate is a better vitamin E source thasn all-rac-alpha-tocopherol succinate for broilers," J Nutr, 129: (1999), pp. 1355-1360.

International Search Report for PCT Application No. PCT/US2005/ 012811, mailed Oct. 10, 2005.

International Preliminary Report on Patentability for PCT Application No. PCT Application No. PCT/US2005/012811, mailed Oct. 10, 2005.

International Search Report for PCT Application No. PCT/US2006/ 010726, mailed Aug. 16, 2006.

International Preliminary Report on Patentability for PCT Application No. PCT/US2006/010726, mailed Aug. 16, 2006.

Hara et al. "Stabilization of Liposomal Membranes by Thermozeaxanthins: Carotenoid-Glucoside Esters" Biochim. Biophys. Abst. (1999) 1461, 147-154.

International Search Report for PCT Application No. PCT/US2006/08363, mailed Jul. 28, 2006.
Bowen et al. "Esterification Does Not Impair Lutein Bioavailability in Humans" J. Nutr. (2002) 32, 3668-3673.
International Search Report for PCT Application No. PCT/US03/23706 mailed Mar. 9, 2004.
International Search Report for PCT Application No. PCT/US06/16487, mailed Oct. 30, 2006.
International Preliminary Report on Patentability for No. PCT Application No. PCT/US06/16487, mailed Oct. 30, 2006.
Co-Pending U.S. Appl. No. 11/415,375 entitled, "Structural Carotenoid Analogs or Derivatives for the Modulation of Systemic and/or Target Organ Redox Status" to Lockwood et al. filed Dec. 7, 2006; available in private PAIR.
Foss et al. "Natural Occurrence of Enantiomeric and Meso Astaxanthin. 7. Crustaceans Including Zooplankton" Comp. Biochem. Physiol. B Comp. Biochem. (1987) 86: 313-314.
Fuhrhop et al. "Bolaform Amphiphiles with a Rigid Hydrophobic Bixin Core in Surface Monolayers and Lipid Membranes" Langmuir (1990) 6, 497-505.
Gabrielska et al. "Zeaxanthin (dihydroxy-B-carotene) but not B-Carotene Rigidifies Lipid Membranres: a 1H-NMR Study of Carotenoid-Egg Phosphatidylcholine Liposomes" Biochim. Biophys. Acta (1996) 1285, 167.
Gartner et al. "Preferential Increase in Chylomicron Levels of the Xanthophylls Lutein and Zeaxanthin Compared to B-Carotene in the Human" Int. J. Vitam. Nutr. Res. (1996) 66, 119.
Furr et al. "Intestinal Absorption and Tissue Distribution of Carotenoids" Nutritional Biochemistry (1997) 8, 364.
Gartner et al. "Lycopene is More Bioavailable from Tomato Paste than from Fresh Tomatoes" Am. J. Clin. Nutr. (1997) 66: 116-122.
Clark et al. "A Comparison of Lycopene and Astaxanthin Absorption From Corn Oil and Olive Oil Emulsions" Lipids (2000) 35(7), 803-806.
Frank et al. "Effect of the Solvent Environment on the Spectroscopic Properties and Dynamics of the Lowest Excited States of Carotenoids" J. Phys. Chem. B (2000) 104, 4569-4577.
Bodor et al. "Drug Targeting by Retrometabolic Design: Soft Drugs and Chemical Delivery Systems" J. Recept: Signal Transduct. Res. (2001) 21: 287-310.
Buchwald et al. "Physicochemical Aspects of the Enzymatic Hydrolysis of Carboxylic Esters" Pharmazie (2002) 57 (2), 87-93.
Zechmeister "Cis-Trans Isomerization and Stereochemistry of Carotenoids and Diphenylpolyenes" Chem. Rev. 34 (1944) 267-344.
Karrer et al. in "Carotenoids, Special Part: XIII. Carotenoid Carboxylic Acids 1. Bixin" Elsevier, New York—Amsterdam—London—Brussels (1950) 256-271.
Robinson "Lysolecithin" Pharm. Pharmacol. (1961) 13, 321.
Markham et al. "Carotenoids of Higher Plants I. The Structures of Lycoxanthin and Lycophyll" Phytochemistry (1968) 7, 839.
Isler in "Carotenoids" Isler, O., Ed.; Birkhäuser: Basel, 1971; 11-28.
Kelly et al. "Carotenoids of Higher Plants. 4. The Stereochemistry of Lycoxanthin and Lycophyll" Chem. Scand., Ser. A (1971) 25, 1607.
Weedon In Carotenoids; Isler, O., Ed.; Birkhäuser: Basel, 1971; pp. 29-59.
Pfander et al. "Synthese von neuen Carotinoid-Glycosylestern" Chimia (1980) 34, 20.
Lindig et al. "Rate Parameters for the Quenching of Singlet Oxygen by Water-Soluble and Lipid-Soluble Substrates in Aqueous and Micellar Systems" Photochem. Photobiol. (1981) 33, 627.
Meyer vol. 1A: Isolation and Analysis; Britton, G.; Liaaen-Jensen, S.; Pfander, H., Eds.; Birkhäuser: Basel, (1995) pp. 277-282.
Milon et al. "Organization of Carotenoid-Phospholipid Bilayer Systems. Incorporation of Zeaxanthin, Astaxanthin, and their C50 Homologues into Dimyristoylphosphatidylcholine Vesicles" Helv. Chim. Acta. (1986) 69:12-24.
Di Mascio et al. "Lycopene as the Most Efficient Biological Carotenoid Singlet Oxygen Quencher" Arch. Biochem. Biophys. (1989) 274 , 532.

Torrissen et al. "Pigmentation of Salmonids—Carotenoid Deposition and Metabolism" CRC Crit. Rev. Aquat. Sci. (1989) 1: 209-225.
Lee et al. "Effects, Quenching Mechanisms, and Kinetics of Carotenoids in Chlorophyll-Sensitized Photooxidation of Soybean Oil" J. Agric. Food Chem. (1990) 38, 1630.
Speranza et al. "Interaction Between Singlet Oxygen and Biologically Active Compounds in Aqueous Solution. III. Physical and Chemical Singlet Oxygen Quenching Rate Constants of 6,6-diapocarotenoids." (1990) J. Photochem. Photobiol. B8, 51-61.
Mathews-Roth "Recent Progress in the Medical Applications of Carotenoids" Pure Appl. Chem. (1991) 63, 147-156.
Beecher et al. "Qualitative Relationship of Dietary and Plasma Carotenoids in Human Beings" Ann NY Acad Sci (1992) 669: 320-321.
Devasagayam et al. "Synthetic Carotenoids, Novel Polyene Polyketones and New Capsorubin Isomers as Efficient Quenchers of Singlet Molecular Oxygen" Photochem. Photobiol. (1992) 55:511-514.
Khachik et al. "Separation and Quantification of Carotenoids in Human Plasma" in "Carotenoids. Part A. Chemistry, separation, quantitation, and antioxidation" Packer L , editor.; San Diego: Academic Press, Inc., (1992) 205-219.
Ames et al. "DNA Lesions, Inducible DNA Repair, and Cell Division: Three Key Factors in Mutagenesis and Carcinogenesis" Environ Health Perspect (1993) 101 (Suppl. 5): 35-44.
Blanchard-Desce et al. "Caroviologens. Synthesis and Optical Properties of A, O-bis-Pyridine and A-O-bis-Pyridinium Polyenes" Bull. Soc. Chim. Fr. (1993) 130, 266-272.
Jyonouchi et al. "Studies of Immunomodulating Actions of Carotenoids. II. Astaxanthin Enhances in vitro Antibody Production to T-dependent Antigens without Facilitating Polyclonal B-cell Activation" Nutr. Cancer (1993) 19, 269-280.
Hirayama et al. "Singlet Oxygen Quenchiing Ability of Naturally Occurring Carotenes" Lipids (1994) 29, 149.
Koga et al. "Synthesis of Phosphatidyl Derivative of Vitamin E and its Antioxidant Activity in Phospholipid Bilayers" Lipids (1994) 29, 83.
Olson "Absorption, Transport, and Metabolism of Carotenoids in Humans" Pure & Applied Chemistry (1994) 66, 1011.
Jyonouchi et al. "Astaxanthin, a Carotenoid without Vitamin A Activity, Augments Antibody Responses in Cultures Including T-Helper Cell Clones and Suboptimal Doses of Antigen" J. Nutr. (1995) 125, 2483-2492.
Frank et al. "Carotenoids in Photosynthesis" Photochem. Photobiol. (1996) 63: 257-264.
Kelly et al. "NMR, MS, and X-Ray Crystal Structure Determination of the Bixin Family of Apocarotenoids" J. Chem. Res. (M) (1996) 2637-2645.
Koepke et al. "The Crystal Structure of the Light-Harvesting Complex II (B800-850) from Rhodospirillum Molischianum" Structure (1996) 4, 581-597.
Mori et al. "Bistable Aggregate of all-Trans-Astaxanthin in an Aqueous Solution" Chem. Phys. Lett. (1996) 254, 84-88.
Olson "Beneftis and Liabilities of Vitamin A and Carotenoids" J. Nutr. (1996) 126: 1208S-1212S.
Partali et al. "Stable, Highly Unsaturated Glycerides—Enzymatic Synthesis with a Carotenoic Acid" Angew. Chem. Int. Ed. (1996) 35, 329-330.
Van Vliet "Absorption of B-Carotene and other Carotenoids in Humans and Animal Models" Eur. J. Clin. Nutr. (1996) 50 Suppl 3, S32.
Halliwell "Antioxidants and Human Disease: A general Introduction" Nutr. Rev. (1997) 55, 544-552.
Levy et al. "Plasma Antioxidants and Lipid Peroxidation in Acute Myocardial Infarction and Thrombolysis" Analyst (1997) 122 977-980.
Pfander et al. "Carotenoid Synthesis: A Progress Report" Pure Appl. Chem. (1997) 69, 2047.
Beckman et al. "The Free Radical Theory of Aging Matures" Physiol Rev. (1998) 78, 547-581.

Koga et al. "Protective Effect of a Vitamin E Analogue, Phophatidylchromanol, Against Oxidative Hemolysis of Human Erythrocytes" J. Lipids (1998) 33, 589.

Krinsky "The Antioxidant and Biological Properties of the Carotenoids" Ann. N. Y. Acad. Sci. (1998) 854, 443.

Russell "Pysiological and Clinical Significance of Carotenoids" Int. J. Vitam. Nutr. Res. (1998) 68, 349.

Mercadante, A. "New carotenoids: Recent Progress" Pure Appl. Chem., (1999) vol. 71, No. 12, 2263-2272.

Olson "Bioavailability of Carotenoids" Arch. Latinoam. Nutr. (1999) 49, 21S-25S.

Ruttimann "Dienolether Condensations—a Powerful Tool in Carotenoid Synthesis" Pure Appl. Chem. (1999) 71, 2285.

Yuan et al. "Hydrolysis Kinetics of Astaxanthin Esters and Stability of Astaxanthin of Haematococcus Pluvialis During Saponification" J. Agric. Food Chem. (1999) 47, 31.

Yuan et al. "Isomerization of trans-Astaxanthin to cis-Isomers in Organic Solvents" J. Agric. Food Chem. (1999) 47, 3656.

Baroli et al. "Molecular Genetics of Xanthophylidependent Photoprotection in Green Algae and Plants" Philos. Trans. R. Soc. Lond. B Biol. Sci. (2000) 355, 1385-1394.

Bell et al. "Depletion of alpha-Tocopherol and Astaxanthin in Atlantic Salmon (*Salmo salar*) Affects Autoxidative Defense and Fatty Acid Metabolism" J. Nutr. (2000) 130, 1800-1808.

Neveu et al. "Gap Junctions and Neoplasia" in: E.L. Hertzberg, E.E. Bittar (Eds.), Gap Junctions, JAI Press, Greenwich, CT, (2000) pp. 221-262.

Tahir et al. "Regio- and Chemoselective Alkylation of L-Ascorbic Acid under Mitsunobu Conditions" J. Org. Chem. (2000) 65(3), 911-913.

Beutner et al. "Quantitative Assessment of Antioxidant Properties of Natural Colorants and Phytochemicals: Carotenoids, Avonoids, Phenols and Indigoids. The Role of b-Carotene in Antioxidant Functions" J Sci Food Agric. (2001) 81, 559-568.

Hakimelahi et al. "Synthesis and Biological Evaluation of Purine-Containing Butenolides" J. Med. Chem. (2001) 44 (11) 1749-1757.

Horn et al. "Organic Nanoparticles in the Aqueous Phase-Theory, Experiment, and Use" Angew. Chem., Int. Ed. Engl: (2001) 40, 4330-4361.

Kiefer et al. "Identification and Characterization of a Mammalian Enzyme Catalyzing the Asymmetric Oxidative Cleavage of Provitamin" A. J. Biol. Chem. (2001) 276: 14110-14116.

Mortensen et al. "The Interaction of Dietary Carotenoids with Radical Species" Arch Biochem Biophys (2001) 385:13-19.

Shibata et al. "Molecular Characteristics of Astaxanthin and B-Carotene in the Phospholipid Monolayer and Their Distributions in the Phospholipid Bilayer" Chem. Phys. Lipids (2001) 113, 11-22.

Sugarawa et al. "Lysophosphatidylcholine Enhances Carotenoid Uptake from Mixed Micelles by Caco-2 Human Intestinal Cells" J. Nutr. (2001) 131, 2921.

Yanishlieva et al. "B-Apo-8'-Caroteonic Acid and its Derivatives" J. Am. Oil Chem. Soc. (2001) 78, 641-644.

Wang et al. "A Quantum Chemistry Study of Binding Carotenoids in the Bacterial Light-Harvesting Complexes" J. Am. Chem. Soc. (2002) 124, 8445-8451.

Zaripheh et al. "Factors That Influence the Bioavailability of Xanthophylls" J. Nutr. (2002) 132, 531S.

Cholnoky et al. "The Structure of Lycoxanthin and Lycophyll" Tetrahedron Lett. (1968) 16, 1931.

Davis et al. "Reconstitution of the Bacterial Core Light-Harvesting Complexes of Rhodobacter sphaeroides and Rhodospirillumrubrum with Isolated a- and b-Polypeptides, Bacteriochlorophyll a, and Carotenoid" J. Biol. Chem. (1995) 270, 5793-5804.

Froescheis et al. "Determination of Lycopene in Tissues and Plasma of Rats by Normal-Phase High-Performance Liquid Chromatography With Photometric Detection" J. Chromatogr. B Biomed. Sci. Appl. (2000) 739, 291.

CAROTENOID ETHER ANALOGS OR DERIVATIVES FOR THE INHIBITION AND AMELIORATION OF DISEASE

PRIORITY CLAIM

This application is a continuation in part of patent application Ser. No. 10/629,538 entitled "Structural Carotenoid Analogs for the Inhibition and Amelioration of Disease" filed on Jul. 29, 2003, now U.S. Pat. No. 7,145,025, which claims priority to Provisional Patent Application No. 60/399,194 entitled "Structural Carotenoid Analogs for the Inhibition and Amelioration of Reperfusion Injury" filed on Jul. 29, 2002; Provisional Patent Application No. 60/467,973 entitled "Structural Carotenoid Analogs for the Inhibition and Amelioration of Disease" filed on May 5, 2003; Provisional Patent Application No. 60/472,831 entitled "Structural Carotenoid Analogs for the Inhibition and Amelioration of Disease" filed on May 22, 2003; Provisional Patent Application No. 60/473,741 entitled "Structural Carotenoid Analogs for the Inhibition and Amelioration of Disease" filed on May 28, 2003; and Provisional Patent Application No. 60/485,304 entitled "Structural Carotenoid Analogs for the Inhibition and Amelioration of Disease" filed on Jul. 3, 2003.

BACKGROUND OF THE INVENTION

1. Field of the Invention

The invention generally relates to the fields of medicinal and synthetic chemistry. More specifically, the invention relates to the synthesis and use of carotenoid analogs or derivatives.

2. Description of the Relevant Art

Cardiovascular disease (CVD), and specifically coronary artery disease (CAD), remains the leading cause of death in the United States and worldwide. CVD is a leading cause of mortality and morbidity in the world. Small to moderate reductions in cardiovascular risk, which lead to decreased emergency department visits and hospitalizations for acute coronary syndromes, can yield substantial clinical and public health benefits.

Extensive research with antioxidants has shown that they are effective therapeutic agents in the primary and secondary prevention of cardiovascular disease. CVD remains the leading cause of death for all races in the U.S.; now, approximately 60 million Americans have some form of CVD. Life expectancy in the U.S. would increase by almost 7 years if CVD could be eliminated. The absolute number of deaths due to CVD has fallen since 1996; however, it remains the single largest cause of death in the United States, with a total annual healthcare burden of greater than $300 billion (including heart attack and stroke).

Ischemia is the lack of an adequate oxygenated blood supply to a particular tissue. Ischemia underlies many acute and chronic disease states including, but not limited to:
  Myocardial infarction, or MI
  Unstable angina
  Stable angina pectoris
  Abrupt reclosure following percutaneous transluminal coronary angioplasty (PTCA)
  Thrombotic stroke (85% of the total number of strokes)
  Embolic vascular occlusion
  Peripheral vascular insufficiency
  Organ transplantation
  Deep venous thrombosis, or DVT
  Indwelling catheter occlusion Ischemia may also become a problem in elective procedures such as: scheduled organ transplantation; scheduled coronary artery bypass graft surgery (CABG); and scheduled percutaneous transluminal coronary angioplasty (PTCA). Common to each of these settings is the phenomenon of reperfusion injury: the production of reactive oxygen species (ROS) upon reintroduction of oxygenated blood flow to a previously ischemic area, with subsequent paradoxical additional tissue damage. In particular, the use(s) of thrombolytic therapy in acute myocardial infarction (AMI) and acute thrombotic stroke—as well as surgical revascularization with PTCA—are typically associated with the reperfusion of ischemic myocardium and/or brain. Clinical outcome is improved with the achievement of early patency after acute thrombosis, however, not without cost (i.e., "reperfusion injury").

Current therapy allows for reperfusion with pharmacologic agents, including recombinant tissue-type plasminogen activator (r-TPA), Anistreplase (APSAC), streptokinase, and urokinase. Recent studies have shown the best clinical outcome after AMI occurs with early surgical reperfusion. However, surgical reperfusion is available at only 15 to 20 percent of care centers in the United States, and much fewer worldwide. It is likely, therefore, that pharmacologic reperfusion will remain clinically relevant and important for the foreseeable future. Thrombolytic therapy is unsuccessful in reperfusion of about 20% of infarcted arteries. Of the arteries that are successfully reperfused, approximately 15% abruptly reclose (within 24 hours). Measures of systemic inflammation (e.g., serum levels of C-reactive protein or CRP) correlate strongly with clinical reclosure in these patients. Myocardial salvage appears to be maximal in a 2 to 6 hour "therapeutic window" subsequent to acute plaque rupture and thrombosis. In acute thrombotic or thromboembolic stroke, this therapeutic window is even narrower, generally less than 3 hours post-thrombosis. Recombinant tissue-type plasminogen activator administered within 3 hours of ischemic stroke significantly improves clinical outcome, but increases the risk of hemorrhage.

During a period of ischemia, many cells undergo the biochemical and pathological changes associated with anoxia but remain potentially viable. These potentially viable cells are therefore the "battleground" in the reperfusion period. Ischemia creates changes in the affected tissue, with the potential final result of contraction band and/or coagulation necrosis of at-risk myocardium. Pathologic changes in ischemic myocardium include, but are not limited to:
  Free radical and ROS production
  ATP loss and defective ATP resynthesis
  Creatine phosphate loss
  Extracellular potassium loss
  Active tension-generating capacity loss of myocardium
  Cellular swelling
  Acidosis
  Loss of ionic homeostasis
  Structural disorganization
  Electrical instability and arrhythmogenesis
  Lipid membrane peroxidation
  Glutathione and other endogenous/exogenous antioxidant depletion (including vitamins C and E and carotenoids)

Rescue of ischemic myocardium that has not irreversibly reached the threshold of necrosis is the focus of intervention in ischemia-reperfusion injury.

Gap junctions are a unique type of intercellular junction found in most animal cell types. They form aqueous channels that interconnect the cytoplasms of adjacent cells and enable the direct intercellular exchange of small (less than approximately 1 kiloDalton) cytoplasmic components. Gap junctions are created across the intervening extracellular space by the docking of two hemichannels ("connexons") contributed by each adjacent cell. Each hemichannel of is an oligomer of six connexin molecules.

Connexin 43 was the second connexin gene discovered and it encodes one of the most widely expressed connexins in established cell lines and tissues. Gap junctions formed by connexin 43 have been implicated in development, cardiac function, and growth control.

One common manifestation of CVD is cardiac arrhythmia. Cardiac arrhythmia is generally considered a disturbance of the electrical activity of the heart that manifests as an abnormality in heart rate or heart rhythm. Patients with a cardiac arrhythmia may experience a wide variety of symptoms ranging from palpitations, to fainting ("syncope"), and sudden cardiac death.

The major connexin in the cardiovascular system is connexin 43. Gap junctional coordination of cellular responses among cells of the vascular wall, in particular the endothelial cells, is thought to be critical for the local modulation of vasomotor tone and for the maintenance of circulatory homeostasis. Controlling the upregulation of connexin 43 may also assist in the maintenance of electrical stability in cardiac tissue. Maintaining electrical stability in cardiac tissue may benefit the health of hundreds of thousands of people a year with some types of cardiovascular disease [e.g., ischemic heart disease (IHD) and arrhythmia], and may prevent the occurrence of sudden cardiac death in patients at high risk for arrhythmia.

Cancer is generally considered to be characterized by the uncontrolled, abnormal growth of cells. Connexin 43, as previously mentioned, is also associated with cellular growth control. Growth control by connexin 43 is likely due to connexin 43's association with gap junctional communication. Maintenance, restoration, or increases of functional gap junctional communication inhibits the proliferation of transformed cells. Therefore, upregulation and/or control of the availability of connexin 43 may potentially inhibit and/or ameliorate the spread of cancerous cells.

Chronic liver injury, regardless of etiology, may lead to a progressive spectrum of pathology from acute and chronic inflammation, to early stage fibrosis, and finally to cirrhosis, end-stage liver disease (ESRD), and hepatocellular carcinoma (HCC). A cascade of inflammatory events secondary to the initiating injury, including the release of cytokines and the formation of reactive oxygen species (ROS), activates hepatic stellate cells (HSC). HSC produce extracellular matrix components (ECM), including collagen, and are critical in the process which generates hepatic fibrosis.

End-stage liver disease [manifested as either cirrhosis or hepatocellular carcinoma (HCC)] is the eighth leading cause of disease-related death in the United States. Chronic inflammation in the liver resulting from viral infection, alcohol abuse, drug-induced toxicity, iron and copper overload, and many other factors can initiate hepatic fibrosis. By-products of hepatocellular damage activate Kupffer cells, which then release a number of cytokines, ROS (including in particular superoxide anion), and other paracrine and autocrine factors which in turn act upon hepatic stellate cells (HSC). It is now believed that the lynchpin cell in the fibrogenetic cascade is the HSC, the cell type responsible for the production of ECM. In vitro evidence demonstrates that ROS can induce HSC cells. Elevated levels of indirect markers of oxidative stress (e.g., thiobarbituric acid reactive species or TBARS) are observed in all patients with chronic liver disease. In addition, levels of gluthathione, glutathione peroxidase, superoxide dismutase, carotenoids, and α-tocopherol (vitamin E) are significantly lower in patients with chronic liver disease. Supplying these endogenous and/or exogenous antioxidants reverses many of the signs of chronic liver disease, including both surrogate markers for the disease process, as well as direct measurements of hepatic fibrosis. Therefore, they are likely potent agents for therapeutic intervention in liver disease.

SUMMARY

In some embodiments, the administration of structural analogs or derivatives of carotenoids may inhibit and/or ameliorate the occurrence of diseases in subjects. Maladies which may be treated with structural analogs or derivatives of carotenoids may include any disease that involves production of reactive oxygen species and/or other radical and non-radical species (for example singlet oxygen, a reactive oxygen species but not a radical). In some embodiments, water-soluble analogs of carotenoids may be used to treat a disease that involves production of reactive oxygen species. Oxidation of DNA, proteins, and lipids by reactive oxygen species and other radical and non-radical species has been implicated in a host of human diseases. Radicals may be the primary cause for the following conditions, may make the body more susceptible to other disease-initiating factors, may inhibit endogenous defenses and repair processes, and/or may enhance the progression of incipient disease(s). The administration of structural analogs or derivatives of carotenoids by one skilled in the art—including consideration of the pharmacokinetics and pharmacodynamics of therapeutic drug delivery—is expected to inhibit and/or ameliorate said disease conditions. In the first category are those disease conditions in which a single organ is primarily affected, and for which evidence exists that radicals and/or non-radicals are involved in the pathology of the disease. These examples are not to be seen as limiting, and additional disease conditions will be obvious to those skilled in the art.

Head, Eyes, Ears, Nose, and Throat: age-related macular degeneration (ARMD), retinal detachment, hypertensive retinal disease, uveitis, choroiditis, vitreitis, ocular hemorrhage, degenerative retinal damage, cataractogenesis and cataracts, retinopathy of prematurity, Meuniere's disease, drug-induced ototoxicity (including aminoglycoside and furosemide toxicity), infectious and idiopathic otitis, otitis media, infectious and allergic sinusitis, head and neck cancer;

Central Nervous System (brain and spinal cord): senile dementia (including Alzheimer's dementia), Neuman-Pick's disease, neurotoxin reactions, hyperbaric oxygen effects, Parkinson's disease, cerebral and spinal cord trauma, hypertensive cerebrovascular injury, stroke (thromboembolic, thrombotic, and hemorrhagic), infectious encephalitis and meningitis, allergic encephalomyelitis and other demyelinating diseases, amyotrophic lateral sclerosis (ALS), multiple sclerosis, neuronal ceroid lipofuscinoses, ataxia-telangiectasia syndrome, aluminum, iron, and other heavy metal(s) overload, primary brain carcinoma/malignancy and brain metastases;

Cardiovascular: arteriosclerosis, atherosclerosis, peripheral vascular disease, myocardial infarction, chronic stable angina, unstable angina, idiopathic surgical injury (during CABG, PTCA), inflammatory heart disease [as measured and influenced by C-reactive protein (CRP) and myeloperoxidase (MPO)], vascular restenosis, low-density lipoprotein oxidation (ox-LDL), cardiomyopathies, cardiac arrhythmia (ischemic and post-myocardial infarction induced), congestive heart failure (CHF), drug toxicity (including adriamycin and doxorubicin), Keshan disease (selenium deficiency), trypanosomiasis, alcohol cardiomyopathy, venous stasis and injury (including deep venous thrombosis or DVT), thrombophlebitis;

Pulmonary: asthma, reactive airways disease, chronic obstructive pulmonary disease (COPD or emphysema), hyperoxia, hyperbaric oxygen effects, cigarette smoke inhalation effects, environmental oxidant pollutant effects, acute respiratory distress syndrome (ARDS), bronchopulmonary dysplasia, mineral dust pneumoconiosis, adriamycin toxicity, bleomycin toxicity, paraquat and other pesticide toxicities, chemical pneumonitis, idiopathic pulmonary interstitial fibrosis, infectious pneumonia (including fungal), sarcoidosis, asbestosis, lung cancer (small- and large-cell), anthrax infection, anthrax toxin exposure;

Renal: hypertensive renal disease, end-stage renal disease, diabetic renal disease, infectious glomerulonephritis, nephrotic syndrome, allergic glomerulonephritis, type I-IV hypersensitivity reactions, renal allograft rejection, nephritic antiglomerular basement membrane disease, heavy metal nephrotoxicity, drug-induced (including aminoglycoside, furosemide, and non-steroidal anti-inflammatory) nephrotoxicity, rhabdomyolisis, renal carcinoma;

Hepatic: carbon tetrachloride liver injury, endotoxin and lipopolysaccharide liver injury, chronic viral infection (including Hepatitis infection), infectious hepatitis (non-viral etiology), hemachromatosis, Wilson's disease, acetaminophen overdose, congestive heart failure with hepatic congestion, cirrhosis (including alcoholic, viral, and idiopathic etiologies), hepatocellular carcinoma, hepatic metastases;

Gastrointestinal: inflammatory bowel disease (including Crohn's disease, ulcerative colitis, and irritable bowel syndrome), colon carcinoma, polyposis, infectious diverticulitis, toxic megacolon, gastritis (including *Helicobacter pylon* infection), gastric carcinoma, esophagitis (including Barrett's esophagus), gastroesophageal reflux disease (GERD), Whipple's disease, gallstone disease, pancreatitis, abetalipoproteinemia, infectious gastroenteritis, dysentery, nonsteroidal anti-inflammatory drug-induced toxicity;

Hematopoietic/Hematologic: Pb (lead) poisoning, drug-induced bone marrow suppression, protoporphyrin photo-oxidation, lymphoma, leukemia, porphyria(s), parasitic infection (including malaria), sickle cell anemia, thallasemia, favism, pernicious anemia, Fanconi's anemia, post-infectious anemia, idiopathic thrombocytopenic purpura (ITP), autoimmune deficiency syndrome (AIDS);

Genitourinary: infectious prostatitis, prostate carcinoma, benign prostatic hypertrophy (BPH), urethritis, orchitis, testicular torsion, cervicitis, cervical carcinoma, ovarian carcinoma, uterine carcinoma, vaginitis, vaginismus;

Musculoskeletal: osteoarthritis, rheumatoid arthritis, tendonitis, muscular dystrophy, degenerative disc disease, degenerative joint disease, exercise-induced skeletal muscle injury, carpal tunnel syndrome, Guillan-Barre syndrome, Paget's disease of bone, ankylosing spondilitis, heterotopic bone formation; and Integumentary: solar radiation injury (including sunburn), thermal injury, chemical and contact dermatitis (including Rhus dermatitis), psoriasis, Bloom syndrome, leukoplakia (particularly oral), infectious dermatitis, Kaposi's sarcoma.

In the second category are multiple-organ conditions whose pathology has been linked convincingly in some way to radical and non-radical injury: aging, including age-related immune deficiency and premature aging disorders, cancer, cardiovascular disease, cerebrovascular disease, radiation injury, alcohol-mediated damage (including Wernicke-Korsakoff's syndrome), ischemia-reperfusion damage, inflammatory and auto-immune disease, drug toxicity, amyloid disease, overload syndromes (iron, copper, etc.), multi-system organ failure, and endotoxemia/sepsis.

Maladies, which may be treated with structural carotenoid analogs or derivatives, may include, but are not limited to, cardiovascular inflammation, hepatitis C infection, cancer (hepatocellular carcinoma and prostate), macular degeneration, rheumatoid arthritis, stroke, Alzheimer's disease, and/or osteoarthritis. In an embodiment, the administration of water soluble analogs or derivatives of carotenoids to a subject may inhibit and/or ameliorate the occurrence of ischemia-reperfusion injury in subjects. In some embodiments, water soluble and other structural carotenoid analogs or derivatives may be administered to a subject alone or in combination with other structural carotenoid analogs or derivatives. The occurrence of ischemia-reperfusion injury in a human subject that is experiencing, or has experienced, or is predisposed to experience myocardial infarction, stroke, peripheral vascular disease, venous or arterial occlusion and/or restenosis, organ transplantation, coronary artery bypass graft surgery, percutaneous transluminal coronary angioplasty, and cardiovascular arrest and/or death may be inhibited or ameliorated by the administration of therapeutic amounts of water soluble and/or other structural carotenoid analogs or derivatives to the subject.

"Water soluble" structural carotenoid analogs or derivatives are those analogs or derivatives which may be formulated in aqueous solution, either alone or with excipients. Water soluble carotenoid analogs or derivatives may include those compounds and synthetic derivatives which form molecular self-assemblies, and may be more properly termed "water dispersible" carotenoid analogs or derivatives. Water soluble and/or "water-dispersible" carotenoid analogs or derivatives may be preferred in some embodiments of the current invention.

Water soluble carotenoid analogs or derivatives may have a water solubility of greater than about 1 mg/mL in some embodiments. In certain embodiments, water soluble carotenoid analogs or derivatives may have a water solubility of greater than about 10 mg/mL. In some embodiments, water soluble carotenoid analogs or derivatives may have a water solubility of greater than about 50 mg/mL.

In an embodiment, the administration of water soluble analogs or derivatives of carotenoids to a subject may inhibit and/or ameliorate some types of cardiovascular disease associated with cardiac arrhythmia. In some embodiments, water soluble analogs or derivatives of carotenoids may be administered to a subject alone or in combination with other carotenoid analogs or derivatives. Carotenoid analogs or derivatives may assist in the maintenance of electrical stability in cardiac tissue. Assistance in the maintenance of electrical stability in cardiac tissue may inhibit and/or ameliorate some types of cardiovascular disease, including in particular sudden cardiac death attributable to lethal cardiac arrhythmia.

In an embodiment, the administration of water soluble analogs or derivatives of carotenoids to a subject may inhibit and/or ameliorate the occurrence of liver disease in the subject. In some embodiments, water soluble analogs or derivatives of carotenoids may be administered to a subject alone or in combination with other carotenoid analogs is or derivatives. The liver disease may be a chronic liver disease such as, for example, Hepatitis C infection.

In an embodiment, the administration of water soluble analogs or derivatives of carotenoids to a subject may inhibit and/or ameliorate the proliferation and propagation of initiated, transformed and/or cancerous or pre-cancerous cell(s). In some embodiments, water soluble analogs or derivatives of carotenoids may be administered to a subject alone or in combination with other carotenoid analogs or derivatives. Carotenoid analogs or derivatives may inhibit the proliferation rate of carcinogen-initiated cells. Carotenoid analogs or derivatives may increase connexin 43 expression. Increase of connexin 43 expression may increase, maintain, or restore gap junctional intercellular communication and thus inhibit the growth of carcinogen-initiated cells.

Embodiments may be further directed to pharmaceutical compositions comprising combinations of structural carotenoid analogs or derivatives to said subjects. The composition of an injectable structural carotenoid analog or derivative of astaxanthin may be particularly useful in the therapeutic methods described herein. In yet a further embodiment, an injectable astaxanthin structural analog or derivative is administered with another astaxanthin structural analog or derivative and/or other carotenoid structural analogs or derivatives, or in formulation with other antioxidants and/or excipients that further the intended purpose. In some embodiments, one or more of the astaxanthin structural analogs or derivatives are water soluble.

As used herein, terms such as carotenoid analog and carotenoid derivative may generally refer to in some embodiments chemical compounds or compositions derived from a naturally occurring carotenoid. In some embodiments, terms such as carotenoid analog and carotenoid derivative may generally refer to chemical compounds or compositions which are synthetically derived from non-carotenoid based parent compounds; however, which ultimately substantially resemble a carotenoid derived analog. In certain embodiments, terms such as carotenoid analog and carotenoid derivative may generally refer to a synthetic derivative of a naturally occurring carotenoid.

In an embodiment, a chemical compound including a carotenoid derivative may have the general structure (I):

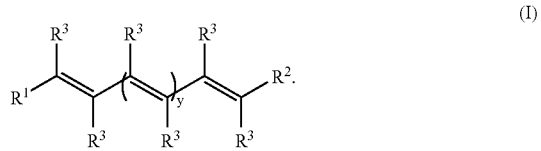

(I)

Each $R^3$ may be independently hydrogen or methyl. $R^1$ and $R^2$ may be independently H, an acyclic alkene with one or more substituents, or a cyclic ring including one or more substituents. y may be 5 to 12. In some embodiments, y may be about 3 to about 15. In certain embodiments, the maximum value of y may only be limited by the ultimate size of the chemical compound, particularly as it relates to the size of the chemical compound and the potential interference with the chemical compound's biological availability as discussed herein. In some embodiments, substituents may be at least partially hydrophilic. In some embodiment, substituents may be each independently coupled to a carotenoid analog or derivative via an ether and/or an ester functionality. These carotenoid derivatives may be used in a pharmaceutical composition.

In an embodiment, a chemical compound including a carotenoid derivative may have the general structure (Ia):

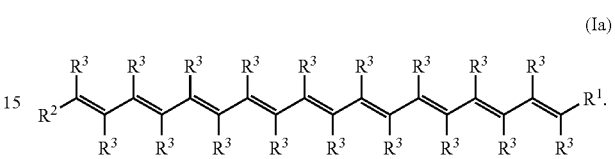

(Ia)

Each $R^3$ may be independently hydrogen or methyl. $R^1$ and $R^2$ may be independently H, an acyclic alkene with one or more substituents, or a cyclic ring including one or more substituents. In some embodiments, substituents may be at least partially hydrophilic. These carotenoid derivatives may be used in a pharmaceutical composition. In one embodiment, a pharmaceutical composition that includes carotenoid structural analogs or derivatives having general structure (Ia) may be used for treating ischemia-reperfusion injury.

As used herein, the terms "disodium salt disuccinate astaxanthin derivative", "dAST", "Cardax", "Cardax™", "rac", and "astaxanthin disuccinate derivative (ADD)" represent varying nomenclature for the use of the disodium salt disuccinate astaxanthin derivative in various stereoisomer and aqueous formulations, and represent illustrative embodiments for the intended use of this structural carotenoid analog. The diacid disuccinate astaxanthin derivative (asta-COOH) is the protonated form of the derivative utilized for flash photolysis studies for direct comparison with non-esterified, "racemic" (i.e., mixture of stereoisomers) astaxanthin. "Cardax-C" is the disodium salt disuccinate di-vitamin C derivative (derivative XXIII) utilized in superoxide anion scavenging experiments assayed by electron paramagnetic resonance (EPR) spectroscopy.

BRIEF DESCRIPTION OF THE DRAWINGS

The above brief description as well as further objects, features and advantages of the methods and apparatus of the present invention will be more fully appreciated by reference to the following detailed description of presently preferred but nonetheless illustrative embodiments in accordance with the present invention when taken in conjunction with the accompanying drawings.

FIG. 16A: the statistical mixture of stereoisomers of the disodium salt disuccinate astaxanthin derivative at $10^5$ M in 1:2 EtOH/$H_2O$; FIG. 16C: 1:2 EtOH/$H_2O$ as solvent control; FIG. 16E: TTNPB at $10^8$ M in tetrahydrofuran (THF) solvent as positive control. FIGS. 16B, D, and F: digital analysis of FIGS. 16A, C, and E, respectively, demonstrating pixels above a fixed set threshold positive for fluorescent intensity. Light gray arrows: immunoreactive junctional plaques; dark gray arrows: position of cell nuclei. Note the greater number and intensity of junctional immunoreactive plaques in the cultures treated with the statistical mixture of stereoisomers of the disodium salt disuccinate astaxanthin derivative in comparison with solvent-only treated controls. The junctional plaques shown in FIGS. 16C and D represent infrequent plaques seen in controls; most cells in these cultures were negative for Cx43 staining.

Figure 1:
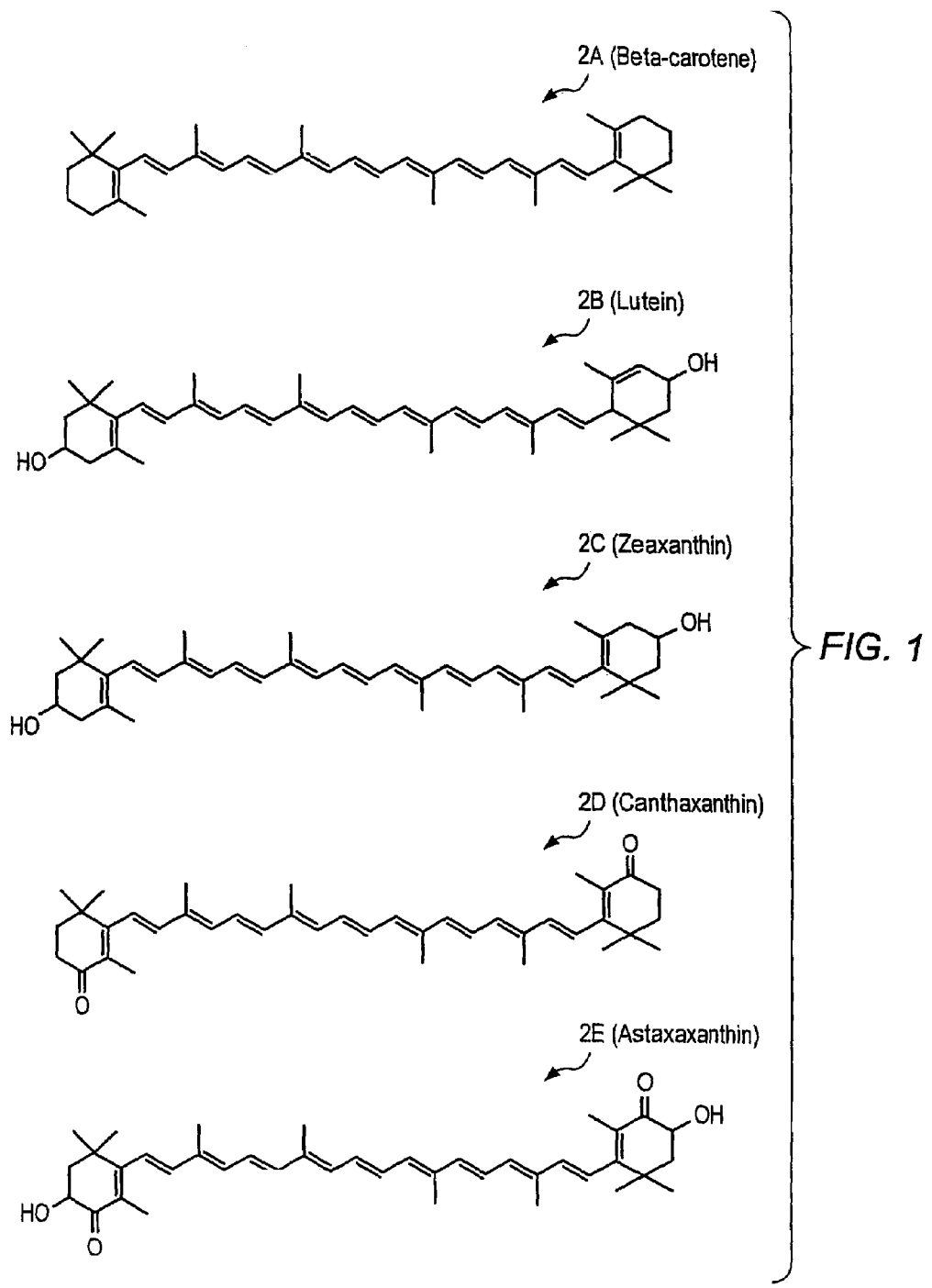
FIG. 1 depicts a graphic representation of several examples of "parent" carotenoid structures as found in nature.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

"Parent" carotenoids may generally refer to those natural compounds utilized as starting scaffold for structural carotenoid analog or derivative synthesis. Carotenoid derivatives may be derived from a naturally occurring carotenoid. Naturally occurring carotenoids may include lycopene, lycophyll, lycoxanthin, astaxanthin, beta-carotene, lutein, zeaxanthin, and/or canthaxanthin to name a few.

Carotenoids are a group of natural pigments produced principally by plants, yeast, and microalgae. The family of related compounds now numbers greater than 700 described members, exclusive of Z and E isomers. Fifty (50) have been found in human sera or tissues. Humans and other animals cannot synthesize carotenoids de novo and must obtain them from their diet. All carotenoids share common chemical features, such as a polyisoprenoid structure, a long polyene chain forming the chromophore, and near symmetry around the central double bond. Tail-to-tail linkage of two $C_{20}$ geranylgeranyl diphosphate molecules produces the parent $C_{40}$ carbon skeleton. Carotenoids without oxygenated functional groups are called "carotenes", reflecting their hydrocarbon nature; oxygenated carotenes are known as "xanthophylls." Cyclization at one or both ends of the molecule yields 7 identified end groups (illustrative structures shown in FIG. 1).

Documented carotenoid functions in nature include light-harvesting, photoprotection, and protective and sex-related coloration in microscopic organisms, mammals, and birds, respectively. A relatively recent observation has been the protective role of carotenoids against age-related diseases in humans as part of a complex antioxidant network within cells. This role is dictated by the close relationship between the physicochemical properties of individual carotenoids and their in vivo functions in organisms. The long system of alternating double and single bonds in the central part of the molecule (delocalizing the π-orbital electrons over the entire length of the polyene chain) confers the distinctive molecular shape, chemical reactivity, and light-absorbing properties of carotenoids. Additionally, isomerism around C=C double bonds yields distinctly different molecular structures that may be isolated as separate compounds [known as Z ("cis") and E ("trans"), or geometric, isomers]. Of the more than 700 described carotenoids, an even greater number of the theoretically possible mono-Z and poly-Z isomers are sometimes encountered in nature. The presence of a Z double bond creates greater steric hindrance between nearby hydrogen atoms and/or methyl groups, so that Z isomers are generally less stable thermodynamically, and more chemically reactive, than the corresponding all-E form. The all-E configuration is an extended, linear, and rigid molecule. Z-isomers are, by contrast, not simple, linear molecules (the so-called "bent-chain" isomers). The presence of any Z in the polyene chain creates a bent-chain molecule. The tendency of Z-isomers to crystallize or aggregate is much less than all-E, and Z isomers may sometimes be more readily solubilized, absorbed, and transported in vivo than their all-E counterparts. This has important implications for enteral (e.g., oral) and parenteral (e.g., intravenous, intra-arterial, intramuscular, intraperitoneal, intracoronary, and subcutaneous) dosing in mammals.

Carotenoids with chiral centers may exist either as the R (rectus) or S (sinister) configurations. As an example, astaxanthin (with 2 chiral centers at the 3 and 3' carbons) may exist as 3 possible stereoisomers: 3S, 3'S; 3R, 3'S and 3S, 3'R (identical meso forms); or 3R, 3'R. The relative proportions of each of the stereoisomers may vary by natural source. For example, *Haematococcus pluvialis* microalgal meal is 99% 3S, 3'S astaxanthin, and is likely the predominant human evolutionary source of astaxanthin. Krill (3R, 3'R) and yeast sources yield different stereoisomer compositions than the microalgal source. Synthetic astaxanthin, produced by large manufacturers such as Hoffmann-LaRoche AG, Buckton Scott (USA), or BASF AG, are provided as defined geometric isomer mixtures of a 1:2:1 stereoisomer mixture [3S, 3'S; 3R, 3'S, (meso); 3R, 3'R] of non-esterified, free astaxanthin. Natural source astaxanthin from salmonid fish is predominantly a single stereoisomer (3S,3'S), but does contain a mixture of geometric isomers. Astaxanthin from the natural source *Haematococcus pluvialis* may contain nearly 50% Z isomers. As stated above, the Z conformational change may lead to a higher steric interference between the two parts of the carotenoid molecule, rendering it less stable, more reactive, and more susceptible to reactivity at low oxygen tensions. In such a situation, in relation to the all-E form, the Z forms: (1) may be degraded first; (2) may better suppress the attack of cells by reactive oxygen species such as superoxide anion; and (3) may preferentially slow the formation of radicals. Overall, the Z forms may initially be thermodynamically favored to protect the lipophilic portions of the cell and the cell membrane from destruction. It is important to note, however, that the all-E form of astaxanthin, unlike β-carotene, retains significant oral bioavailability as well as antioxidant capacity in the form of its dihydroxy- and diketo-substitutions on the β-ionone rings, and has been demonstrated to have increased efficacy over β-carotene in most studies. The all-E form of astaxanthin has also been postulated to have the most membrane-stabilizing effect on cells in vivo. Therefore, it is likely that the all-E form of astaxanthin in natural and synthetic mixtures of stereoisomers is also extremely important in antioxidant mechanisms, and may be the form most suitable for particular pharmaceutical preparations.

The antioxidant mechanism(s) of carotenoids, and in particular astaxanthin, includes singlet oxygen quenching, direct radical scavenging, and lipid peroxidation chain-breaking. The polyene chain of the carotenoid absorbs the excited energy of singlet oxygen, effectively stabilizing the energy transfer by delocalization along the chain, and dissipates the energy to the local environment as heat. Transfer of energy from triplet-state chlorophyll (in plants) or other porphyrins and proto-porphyrins (in mammals) to carotenoids occurs much more readily than the alternative energy transfer to oxygen to form the highly reactive and destructive singlet oxygen ($^1O_2$). Carotenoids may also accept the excitation energy from singlet oxygen if any should be formed in situ, and again dissipate the energy as heat to the local environment. This singlet oxygen quenching ability has significant implications in cardiac ischemia, macular degeneration, porphyria, and other disease states in which production of singlet oxygen has damaging effects. In the physical quenching mechanism, the carotenoid molecule may be regenerated (most frequently), or be lost. Carotenoids are also excellent chain-breaking antioxidants, a mechanism important in inhibiting the peroxidation of lipids. Astaxanthin can donate a hydrogen (H.) to the unstable polyunsaturated fatty acid (PUFA) radical, stopping the chain reaction. Peroxyl radicals may also, by addition to the polyene chain of carotenoids, be the proximate cause for lipid peroxide chain termination. The appropriate dose of astaxanthin has been shown to completely suppress the peroxyl radical chain reaction in liposome systems. Astaxanthin shares with vitamin E this dual antioxidant defense system of singlet oxygen quenching and direct radical scavenging, and in most instances (and particularly at low oxygen tension in vivo) is superior to vitamin E as a radical scavenger and physical quencher of singlet oxygen.

Carotenoids, and in particular astaxanthin, are potent direct radical scavengers and singlet oxygen quenchers and possess all the desirable qualities of such therapeutic agents for inhibition or amelioration of ischemia-reperfusion injury. Synthesis of novel carotenoid derivatives with "soft-drug" properties (i.e. active as antioxidants in the derivatized form), with physiologically relevant, cleavable linkages to pro-moieties, can generate significant levels of free carotenoids in both plasma and solid organs. In the case of non-esterified, free astaxanthin, this is a particularly useful embodiment (characteristics specific to non-esterified, free astaxanthin below):

Lipid soluble in natural form; may be modified to become more water soluble;

Molecular weight of 597 Daltons [size <600 daltons (Da) readily crosses the blood brain barrier, or BBB];

Long polyene chain characteristic of carotenoids effective in singlet oxygen quenching and lipid peroxidation chain breaking; and No pro-vitamin A activity in mammals (eliminating concerns of hypervitaminosis A and retinoid toxicity in humans).

The administration of antioxidants which are potent singlet oxygen quenchers and direct radical scavengers, particularly of superoxide anion, should limit hepatic fibrosis and the progression to cirrhosis by affecting the activation of hepatic stellate cells early in the fibrogenetic pathway. Reduction in the level of ROS by the administration of a potent antioxidant can therefore be crucial in the prevention of the activation of both HSC and Kupffer cells. This protective antioxidant effect appears to be spread across the range of potential therapeutic antioxidants, including water-soluble (e.g., vitamin C, glutathione, resveratrol) and lipophilic (e.g., vitamin E, β-carotene, astaxanthin) agents. Therefore, a co-antioxidant derivative strategy in which water-soluble and lipophilic agents are combined synthetically is a particularly useful embodiment.

Vitamin E is generally considered the reference antioxidant. When compared with vitamin E, carotenoids are more efficient in quenching singlet oxygen in homogenenous organic solvents and in liposome systems. They are better chain-breaking antioxidants as well in liposomal systems. They have demonstrated increased efficacy and potency in vivo. They are particularly effective at low oxygen tension, and in low concentration, making them extremely effective agents in disease conditions in which ischemia is an important part of the tissue injury and pathology. These carotenoids also have a natural tropism for the heart and liver after oral administration. Therefore, therapeutic administration of carotenoids should provide a greater benefit in limiting fibrosis than vitamin E.

Problems related to the use of some carotenoids and structural carotenoid analogs or derivatives include: (1) the complex isomeric mixtures, including non-carotenoid contaminants, provided in natural and synthetic sources leading to costly increases in safety and efficacy tests required by such agencies as the FDA; (2) limited bioavailability upon administration to a subject; and (3) the differential induction of cytochrome P450 enzymes (this family of enzymes exhibits species-specific differences which must be taken into account when extrapolating animal work to human studies). Selection of the appropriate analog or derivative and isomer composition for a particular application increases the utility of carotenoid analogs or derivatives for the uses defined herein.

In an embodiment, the parent carotenoid may have a structure of any naturally occurring carotenoid. Some examples of naturally occurring carotenoids that may be used as parent compounds are shown in FIG. 1.

Other non-limiting examples of naturally occurring carotenoids that may be used as parent compounds may include:

Aaptopurpurin; Actinioerythrin; Actinioerythrol; Adonirubin; Adonixanthin; A.g.470; A.g.471; Agelaxanthin C; Aleuriaxanthin; Alloxanthin; Amarouciaxanthin A; Amarouciaxanthin B; Anchovyxanthin; 3',4'-Anhydrodiatoxanthin; Anhydrodeoxyflexixanthin; Anhydroeschscholtzxanthin; Anhydrolutein; Anhydroperidinin; Anhydrorhodovibrin; Anhydrosaproxanthin; Anhydrowarmingol; Anhydrowarmingone; Antheraxanthin; Aphanicin; Aphanicol; Aphanin; Aphanol; Aphanizophyll; 8'-Apo-β-caroten-8'-al; 10'-Apo-β-caroten-10'-al; 12'-Apo-β-caroten-12'-al; 14'-Apo-β-caroten-14'-al; 6'-Apo-ψ-caroten-6'-al; 8'-Apo-ψ-caroten-8'-al; β-Apo-2-carotenal; β-Apo-3-carotenal; β-Apo-4-carotenal; β-Apo-2'-carotenal; β-Apo-8'-carotenal; β-Apo-10'-carotenal; β-Apo-12'-carotenal; β-Apo-14'-carotenal; Apo-8,8'-carotenedial; 8'-Apo-β-carotene-3,8'-diol; 4'-Apo-β-caroten-4'-oic acid; 8'-Apo-β-caroten-8'-oic acid; 10'-Apo-β-caroten-10'-oic acid; 12'-Apo-β-caroten-12'-oic acid; β-Apo-2'-carotenoic acid; β-Apo-2'-carotenoic acid methylester; β-Apo-8'-carotenoic acid; β-Apo-10'-carotenoic acid; β-Apo-12'-carotenoic acid; 8'-Apo-β-caroten-3-ol; β-Apo-2'-carotenol; Apo-7-fucoxanthinol; Apo-2-lycopenal; Apo-3-lycopenal; Apo-6'-lycopenal; Apo-8'-lycopenal; Apo-10'-violaxanthal; Apo-12'-violaxanthal; Apoviolaxanthinal; Apo-2-zeaxanthinal; Apo-3-zeaxanthinal; Apo-4-zeaxanthinal; Astacein; Astacene; Astacene dipalmitate; Astaxanthin; Asterinic acid; Asteroidenone; Asym. ζ-carotene; Aurochrome; Auroxanthin; Azafrin; Azafrinaldehyde;

Bacterial phytoene; Bacterioerythrin α; Bacterioerythrin α; Bacteriopurpurin α; Bacterioruberin; α-Bacterioruberin; Bacterioruberin diglycoside; Bacterioruberin monoglycoside; α-Bacterioruberin monomethyl ether; Bisanhydrobacterioruberin; 3,4,3',4'-Bisdehydro-β-carotene; Bisdehydrolycopene; 2,2'-Bis(4-hydroxy-3-methyl-2-butenyl)-β,β-carotene; 2,2'-Bis[3-(glucosyloxy)-3-methylbutyl]-3,4,3',4'-tetradehydro-1,2,1',2'-tetrahydro-ψ,ψ-carotene-1,1'-diol; 2,2'-Bis[4-(β,D-glucopyranosyloxy)-3-methyl-2-butenyl]-γ,γ-carotene; 2,2'-Bis(4-hydroxy-3-methyl-2-butenyl)-γ,γ-carotene; 2,2'-Bis(4-hydroxy-3-methyl-2-butenyl)-ε,ε-carotene; 2,2'-Bis(3-hydroxy-3-methylbutyl-3,4,3',4'-tetradehydro-1,2,1',2'tetrahydro-ψ,ψ-carotene-1,1'-diol; 2,2'-Bis(3-methyl-2-butenyl)-ε,ε-carotene; 2,2'-Bis(3-methyl-2-butenyl)-3,4,3'-tetradehydro-1,2-dihydro-ψ,ψ-caroten-1-ol; 2,2'-Bis(3-methyl-2-butenyl)-3,4,3',4'-tetradehydro-1,2,1',2'-tetrahydro-ψ,ψ-carotene-1,1'-diol; 2,2'-Bis(3-methyl-2-butenyl)-1,2,1',2'-tetrahydro-ψ,ψ-carotene-1,1'-diol; 2,2'-Bis(O-methyl-5-C-methylpentosyloxy)-3,4,3',4'-tetradehydro-1,2,1',2'-tetrahydroψ, ψ-carotene-1,1'-diol; 3,3'-Bis(rhamnosyloxy)-β,β-carotene; 2,2'-Bis(rhamnosyloxy)-3,4,3',4'-tetradehydro-1,2,1',2'-tetrahydro-ψ,ψ-carotene-1,1'-diol; Bixin;

Caloxanthin; Calthaxanthin; Canthaxanthin; Capsanthin; Capsanthin epoxide; Capsanthinone; Capsanthone; Capsochrome; Capsorubin; Capsorubindione; Capsorubone; Carangoxanthin; 16'-Carboxyl-3',4'-dehydro-γ-carotene; Carcinoxanthin; Caricaxanthin; β-Carotenal; ψ,ψ-Caroten-20-al; Carotene; Carotene X; α-Carotene; β-Carotene; β,β-Carotene; β,γ-Carotene; β,ε-Carotene; β,φ-Carotene; β,ψ-Carotene; γ-Carotene; γ,γ-Carotene; γ,ψ-Carotene; δ-Carotene; ε-Carotene; ε₁-Carotene; ε,ε-Carotene; ε,ψ-Carotene; ζ-Carotene; ζ-Carotene, asym.; η-Carotene; θ-Carotene; ξ-Carotene; φ-Carotene; φ,φ-Carotene; φ,X-Carotene; φ,ψ-Carotene; X,X-Carotene; ψ-Carotene; ψ,α-Carotene; ψ,ψ-Carotene; θ-Carotene; β-Carotene-5,6,5',6'-diepoxide; β-Carotene 5,8,5',8'-di-epoxide; β,β-Carotene-2,2'-diol; β,β-Carotene-2,3-diol; β,β-Carotene-3,4-diol; β,β-Carotene-3,3'-diol; β,β-Carotene-4,4'-diol; β,ε-Carotene-3,2'-diol; β,ε-Carotene-3,3'-diol; β,ψ-Carotene-2,3-diol; β,ψ-Carotene-3,3'-diol; ε,ε-Carotene-3,3'-diol; φ,φ-Carotene-3,3'-diol; ψ,ψ-Carotene-16,16'-diol; β,β-Carotene-3,3'-diol dipalmitate; β,ε-Carotene-3,3'-diol dipalmitate; β,β-Carotene-2,2'-dione; β,β-Carotene-3,4-dione; β,β-Carotene-4,4'dione; β,ψ-Carotene-3,4-dione; ε,ε-Carotene-3,3'-dione; β,χ-Carotene-3',6'-dione; β,X-Carotene-3,4-dione; β,ψ-Carotene-4,4'-dione; β,φ-Carotene-3,4-dione; ψ,ψ-Carotene-4,4'-dione; α-Carotene 5,6-epoxide; β-Carotene 5,6-epoxide; ζ-Carotene epoxide; Carotene oxide; β,β-Carotene-3,4,3',4'-tetrol; β,β-Carotene-2,3,2',3'-tetrol; β,β-Carotene-3,4,3',4'-tetrone;χ,χ-Carotene-3,6,3',6'-tetrone; β,β-Carotene-2,3,2'-triol; β,β-Carotene-2,3,3'-triol; β,β-Carotene-3,4,3'-triol; β,β-Carotene-3,4,4'-triol; β,ε-Carotene-3,4,3'-triol; β,ε-Carotene-3,19,3'-triol; β,ε-Carotene-3,20,3'-triol; β,β-Carotene-3,4,4'-trione; β,β-Caroten-2-ol; β,β-Caroten-3-ol; β,β-Caroten-4-ol; β,ε-Caroten-2-ol; β,ε-Caroten-3-ol; β,ε-Caroten-3'-ol; β,ε-Caroten-4-ol; β,φ-Caroten-3-ol; β,X-Caroten-3-ol; β,ψ-Caroten-3-ol; β,ψ-Caroten-4'-ol; ε,ψ-Caroten-3-ol; φ,φ-Caroten-3-ol; ψ,ψ-Caroten-16-ol; ψ,ψ-Caroten-20-ol; Carotenonaldehyd; β-Carotenone; β,β-Caroten-2-one; β,β-Caroten-4-one; β,ε-Caroten-2-one; β,ε-Caroten-4-one; β,ψ-Caroten-4-one; γ-Caroten-4-one; α-Carotone; Celaxanthin; Chiriquixanthin A; Chiriquixanthin B; Chlorellaxanthin; Chlorobactene; Chloroxanthin; Chrysanthemaxanthin; Citranaxanthin; α-Citraurin; β-Citraurin; β-Citraurinene; β-Citraurinol; Citroxanthin; Compound X; C.p.: *Corynebacterium poinsettiae*; Corynexanthin; Corynexanthin glucoside; C.p.; C.p.; C.p.; Crocetin; γ-Crocetin; Crocetindial(dehyde); Crocetin diglucosyl ester; Crocetin dimethyl ester; Crocetin gentiobiosyl glucosyl diester; Crocetin glucosyl methyl diester; Crocetin monogentiobiosyl ester; Crocetinsemialdehyde; Crocin; Crocoxanthin; Crustaxanthin; Cryptocapsin; Cryptocapsone; Cryptochrome; α-Cryptoeutreptiellanone; β-Cryptoeutreptiellanone; Cryptoflavin; Cryptomonaxanthin; Cryptoxanthene; Cryptoxanthin; α-Cryptoxanthin; β-Cryptoxanthin; Cryptoxanthin 5,6,5',6'diepoxide; Cryptoxanthin 5,6,5',8'diepoxide; Cryptoxanthin 5,8,5',8'diepoxide; Cryptoxanthin 5,6-epoxide; Cryptoxanthin 5,8-epoxide; Cryptoxanthol; Cucurbitaxanthin; Cyclic ζ;carotene; Cynthiaxanthin;

Decahydro-β-carotene; 1,2,7,8,11,12,7',8',11',12'-Decahydro-ψ,ψ-carotene; 7,8,11,12,15,7',8',11',12',15'Decahydro-ψ,ψ-carotene; 1,2,7,8,11,12,7',8',11',12'-

Decahydro-ψ,ψ-caroten-1-ol; Decahydrolycopene; Decaprenoxanthin; Decaprenoxanthin diglucoside; Decaprenoxanthin monoglucoside; Deepoxyneoxanthin; Dehydro- see also Bisdehydro-, Didehydro-, MonodehydroDehydroadonirubin; Dehydroadonixanthin; Dehydrocarotene II; Dehydrocarotene III; Dehydro-β-carotene; 3,4-Dehydro-β-carotene; 3',4'-Dehydro-γ-carotene; 3',4'-Dehydrocryptoxanthin; Dehydrogenans-P; Dehydrogenans-P; Dehydrogenans-P; Dehydrogenans-P; Dehydrogenans-P 439 mono-OH; dehydrogenans-Phytoene; dehydrogenans-Phytofluene; Dehydrohydroxyechinenone; 3'-Dehydrolutein; 3,4-Dehydrolycopen-16-al; Dehydrolycopene; 3,4-Dehydrolycopene; 15,15'-Dehydrolycopersene; 7',8',11',12'-Dehydrononaprenoxanthin; 11',12'-Dehydrononaprenoxanthin; 3',4'-Dehydro-17'(or 18')-oxo-γ-carotene; Dehydropapilioerythrin; 11,12-Dehydrophytoene; 11',12'-Dehydrophytoene; 2'-Dehydroplectaniaxanthin; Dehydroretrocarotene; 3,4-Dehydrorhodopin; Dehydrorhodovibrin; 3',4'-Dehydrorubixanthin; Dehydrosqualene; 7,8,7',8'-Dehydrozeaxanthin; 7,8-Dehydrozeinoxanthin; Demethyl(ated) spheroidene; Deoxyflexixanthin; Deoxylutein I; Deshydroxydecaprenoxanthin; Diadinochrome; Diadinoxanthin; Dianhydroeschscholtzxanthin; 4,4'-Diapo-ζ-carotene; 4,4'-Diapocaroten-4-al; 4,4'-Diapocarotene-4,4'-dial; 8,8'-Diapocarotene-8,8'-dial; 6,6'-Diapocarotene-6,6'-dioic acid; 8,8'-Diapocarotene-8,8'-dioic acid; 4,4'-Diapocaroten-4-oic acid; 4,4'-Diaponeurosporene; 4,4'-Diaponeurosporen-4-oic acid; 4,4'-Diapophytoene; 4,4'-Diapophytofluene; 4,4'-Diapo-7,8,11,12-tetrahydro lycopene; Diatoxanthin; Didehydro-, see also Dehydro-, Monodehydro 3',4'-Didehydro-2'-apo-β-caroten-2'-al; 3',4'-Didehydro-2'-apo-β-caroten-2'-ol; 7,8-Didehydroastaxanthin; 3',4'-Didehydro-β,ψ-caroten-16'-al; 3,4-Didehydro-ψ,ψ-caroten-16-al; 3,4-Didehydro-β,β-carotene; 4,4'-Didehydro-β-carotene; 3,4-Didehydroβ,ε-carotene; 3,4-Didehydro-β,φ-carotene; 3,4-Didehydro-β,X-carotene; 3',4'-Didehydro-β,ψ-carotene; 3',4'-Didehydro-γ,ψ-carotene; 7,8-Didehydro-φ,φ-carotene; 7,8-Didehydro-φ,X-carotene; 3,4-Didehydro-ψ,ψ-carotene; 7,8-Didehydro-β,β-carotene-3,3'-diol; 7,8-Didehydro-β,ε-carotene-3,3'-diol; 3,4-Didehydro-β,β-carotene-2,2'-dione; 3',4'-Didehydro-β,ψ-caroten-16'-oic acid; 3',4'-Didehydro-β,β-caroten-3-ol; 3',4'-Didehydro-β,β-caroten-4-ol; 7,8-Didehydro-β,ε-caroten-3-ol; 7,8-Didehydro-β,φ-caroten-3-ol; 7,8-Didehydro-β,X-caroten-3-ol; 3',4'-Didehydro-β,ψ-caroten-3-ol; 3',4'-Didehydro-β,ψ-caroten-16'-ol; 3',4'-Didehydro-β,ψ-caroten-18'-ol; 3',4'-Didehydro-β,β-caroten-4-one; 3',4'-Didehydro-β,ψ-caroten-4-one; 7',8'-Didehydro-β,β-carotene 3,4,3'-triol; 3,4-Didehydro-1,2-dihydro-ψ,ψ-carotene; 3,4-Didehydro-1,2-dihydro-ψ,ψ-caroten-20-al; 6,7-Didehydro-5,6-dihydro-β,β-carotene-3,3'-diol; 3',4'-Didehydro-1',2'-dihydro-β,ψ-carotene-3,1'-diol; 3',4'-Didehydro-1',2'-dihydro-β,ψ-carotene-1',2'-diol; 3',4'-Didehydro-1',2'-dihydro-β,ψ-carotene-4,2'-dione; 3,4-Didehydro-1,2-dihydro-ψ,ψ-carotene-1,2-diol; 7',8'-Didehydro-5,6-dihydro-β,β-carotene-3,5,6,3'-tetrol; 6,7-Didehydro-5,6-dihydro-β,β-carotene-3,5,3'-triol; 7',8'-Didehydro-5,6-dihydro-β,β-carotene-3,5,3'-triol; 3',4'-Didehydro-1',2'-dihydro-β,ψ-carotene-2,1',2'-triol; 1',16'-Didehydro-1',2'-dihydro-β,ψ-caroten-2'-ol; 3',4'-Didehydro-1',2'-dihydro-β,ψ-caroten-1'-ol; 3',4'-Didehydro-1',2'-dihydro-β,ψ-caroten-2'-ol; 3,4-Didehydro-1,2-dihydro-ψ,ψ-caroten-1-ol; 3',4'-Didehydro-18'-hydroxy-γ-carotene; 7,8-Didehydroisorenieratene; 3',4'-Didehydro-4-keto-γ-carotene; 7,8-Didehydrorenieratene; 4',5'-Didehydro-4,5'-retro-β,β-carotene; 4',5'-Didehydro-4,5'-retro-β,ψ-carotene; Didehydroretro-γ-carotene; 4',5'-Didehydro-4,5'-retro-β,β-carotene-3,3'-diol; 4',5'-Didehydro-4,5'-retro-β,β-carotene-3,3'-dione; 10',11'-Didehydro-5,8,11',12' tetrahydro-10'-apo-β-carotene-3,5,8-triol; 6',7'-Didehydro-5,6,5',6' tetrahydro-β,β-carotene-3,5,6,3',5'-pentol; 6,7-Didehydro-5,6,5',6'-tetrahydro-β,β-carotene-3,5,3',5' tetrol; 3,4-Didehydro-1,2,7',8'-tetra hydro-ψ,ψ-caroten-1-ol; Didehydrotrikentriorhodin; 7,8-Didehydrozeaxanthin; Didemethylated spirilloxanthin; 1,2,1',2'-Diepoxy-2,2'-bis(3-hydroxy-3-methylbutyl)3,4-didehydro-1,2,1',2'-tetrahydro-ψ,ψ-carotene; Diepoxy-β-carotene; 5,8,5',8'-Diepoxycryptoxanthin; 5,6,5',6'-Diepoxy-5,6,5',6'-tetrahydro-β,β-carotene; 5,6,5',8'-Diepoxy-5,6,5',8'tetrahydro-β,β-carotene; 5,8,5',8'-Diepoxy-5,8,5',8'tetrahydro-β,β-carotene; 5,6,5',6'-Diepoxy-5,6,5',6'-tetrahydro-β,β-carotene-3,3'-diol; 5,6,5',8'-Diepoxy-5,6,5',8'tetrahydro-β,β-carotene-3,3'-diol; 5,8,5',8'-Diepoxy-5,8,5',8'tetrahydro-β,β-carotene-3,3'-diol; 5,6,5',6'-Diepoxy-5,6,5',6'tetrahydro-β,β-caroten-3-ol; 5,6,5',8'-Diepoxy-5,6,5',8'tetrahydro-β,β-caroten-3-ol; 5,8,5',8'-Diepoxy-5,8,5',8'tetrahydro-β,β-caroten-3-ol; 5,6,5',8'-Diepoxyzeaxanthin; 5,8,5',8'-Diepoxyzeaxanthin; Digentiobiosyl 8,8'-diapocarotene-8,8'-dioate; Di-(β,D-glucopyranosyl)-4,4'-diapocarotene-4,4'-dioate; Diglucosyl 8,8'-diapocarotene-8,8'-dioate; Dihydroanhydrorhodovibrin; 9',10'-Dihydro-9'-apo-β-carotene-3,9'-dione; 9',10'-Dihydro-9'-apo-ε-carotene-3,9'-dione; 7',8'-Dihydro-7'-apo-β-caroten-8'-one; 5',6'-Dihydroxanthin; 5'-apo-18'-nor-β-caroten-6'-one; 7,8-Dihydroastaxanthin; β-Dihydrocarotene; 1,1'-Dihydro-β-carotene; 3,4-Dihydro-β-carotene; 7,7'-Dihydro-β-carotene; 7',8'-Dihydro-β,ψ-carotene; 7',8'-Dihydro-γ-carotene; 7',8'-Dihydro-γ,ψ-carotene; 7',8'-Dihydro-δ-carotene; 7',8'-Dihydro-ε,ψ-carotene; 1,2-Dihydro-ζ-carotene; 1,2-Dihydro-ψ,ψ-carotene; 7,8-Dihydro-ψ,ψ-carotene; 7,8-Dihydro-β,β-carotene 3,3'-diol; 7',8'-Dihydro-β,ψ-carotene 3,17'-diol; 9',10'-Dihydro-β,ψ-carotene-3,17'-diol; 7',8'-Dihydro-ε,ψ-carotene-3,17'-diol; 1,2-Dihydro-ψ,ψ-carotene-1,20-diol; 5,6-Dihydro-β,β-carotene 3,5,6,3'-tetrol; 5,6-Dihydro-β,β-carotene 3,5,3'-triol; 1',2'-Dihydro-β,ψ-caroten 1'-ol; 7',8'-Dihydro-β,ψ-caroten 3-ol; 1',2'-Dihydro-φ,ψ-caroten-1'-ol; 1,2-Dihydro-ψ,ψ-caroten-1-ol; 5,6-Dihydro-β,β-carotene-3,5,6,3'-tetrol; 5,6-Dihydro-β,ε-carotene-3,5,6,3'-tetrol; 7,8(or 7',8')-Dihydrodecaprenoxanthin monoglucoside; 1',2'-Dihydro-3',4'-dehydro-3,1'-dihydroxy-γ-carotene; 1,2-Dihydro-3,4-dehydrolycopene; 1,2-Dihydro-3,4-dehydro-1-OH-lycopene; 7,8-Dihydro-4,4'-diapocarotene; 7',8'-Dihydro-4,4'-diapocaroten-4-al; 7',8'-Dihydro-4,4'-diapocaroten-4-oic acid; 1',2'-Dihydro-3',4'-didehydro-3,1'-dihydroxy-γ-caroten-2'-yl rhamnoside; 1',2'-Dihydro-1',2'-dihydroxy-4-ketotorulene; 1',2'-Dihydro-3,1'-dihydroxytorulene glucoside; 1',2'-Dihydro-3,1'-dihydroxytorulene rhamnoside; 1',2'-Dihydro-4,2'-diketotorulene; 3'-Dihydro-α-doradecin; 1',2'-Dihydro-1'-glucosyl-3,4-dehydrotorulene; 1',2'-Dihydro-1'-glucosyl-4-ketotorulene; 1',2'-Dihydro-1'-hydroxy-γ-carotene; 1',2'-Dihydro-1'-hydroxychlorobactene; 1',2'-Dihydro-2'-hydroxy-3',4'-dehydro-4-keto-γ-carotene; 1',2'-Dihydro-1'-hydroxy-3,4-dehydrotorulene glucoside; 1',2'-Dihydro-1'-hydroxy-4-keto-γ-carotene; 1',2'-Dihydro-1'-hydroxy-4-ketotorulene; 1',2'-Dihydro-1'-hydroxy-4-ketotorulene glucoside; 1',2'-Dihydro-1'-hydroxyspheroideneone; 1',2'-Dihydro-1'-hydroxytorulene glucoside; 1',2'-Dihydro-1'-hydroxytorulene rhamnoside; 1,2-Dihydrolycopene; 1',2'-Dihydrolycopene; 7,8-Dihydrolycopene; 1,2-Dihydro-1-methoxy-lycopen-20-al; Dihydromethoxylycopene; 5,6-Dihydro-4-methoxy-lycopen-6-one; 1,2-Dihydroneurosporene; 1',2'-Dihydroneurosporene; 1,2-Dihydro-1-OH-lycopene; 1',2'-Dihydro-1'-OH-torulene; 2'-Dihydrophillipsiaxanthin; Dihydrophytoene; 1,2-Dihydrophytoene; 1',2'-Dihydrophytoene; 1,2-Dihydrophytofluene; 1',2'-Dihydrophytofluene; 7,8-Dihydro-8,7'-retro-β,β- carotene; 7',8'-Dihydrorhodovibrin; 7,8(or 7',8')-Dihydrosarcinaxanthin; 3,4-Dihydrospheroidene; 11',12'-Dihydrospheroidene; 3,4-Dihydrospirilloxanthin; 3,3'-Dihydroxycanthaxanthin; 3,3'-Dihydroxy-α-carotene; 3,4-Dihydroxy-β-carotene; 2,3-Dihydroxy-β,β-carotene-4,4'-dione; 3,3'-Dihydroxy-ε-carotene; 2,3'-Dihydroxy-β,β-carotene-4,4'-dione; 3,3'-Dihydroxy-β,β-carotene-4,4'-dione; 3,3'-Dihydroxy-β,ε-carotene-4,2'-dione; 3,3'-Dihydroxy-β,χ-carotene-4,6'-dione; 3,3'-Dihydroxy-χ,χ-carotene-6,6'-dione; 2,3-Dihydroxy-β,β-caroten-4-one; 3,3'-Dihydroxy-β,β-caroten-4-one; 3,2'-Dihydroxy-β,ε-caroten-4-one; 3,3'-Dihydroxy-β,ε-caroten-4-one; 3,3-Dihydroxy-β,χ-caroten-6'-one; 3,8-Dihydroxy-χ,X-caroten-6-one; 3,3'-Dihydroxydehydro-β-carotene; 3,3'-Dihydroxy-7,8-dehydro-β-carotene; 3,3'-Dihydroxy-7,8,7',8'-dehydro-β-carotene; 3,3'-Dihydroxy-7,8-dehydro-β-carotene-5',6'-epoxide; 3,3'-Dihydroxy-2,3-didehydro-β,β-carotene-4,4'-dione; 3,3'-Dihydroxy-7,8-didehydro-β,β-carotene-4,4'-dione; 3',8'-Dihydroxy-7,8-didehydro-β,χ-carotene-3',6'-dione; 3,3'-Dihydroxy-2,3-didehydro-β,β-caroten-4-one; 3,3'-Dihydroxy-7',8'-didehydro-β,β-caroten-4-one; 3,4'-Dihydroxy-2,3-didehydro-β,β-caroten-4-one; 3,3'-Dihydroxy-2,3-didehydro-β,ε-caroten-4-one; 3,8-Dihydroxy-7',8'-didehydro-χ,X-caroten-6-one; 3,6'-Dihydroxy-7,8-didehydro-6',7'dihydro-β,ε-carotene-3',8'-dione; 3,3'-Dihydroxy-7,8-didehydro-7',8'dihydro-β,χ-carotene-6',8'-dione; 3,1'-Dihydroxy-3',4'-didehydro-1',2'-dihydro-β,ψ-caroten-4-one; 1',2'-Dihydroxy-3',4'-didehydro-1',2'-dihydro-β,ψ-caroten-4-one; 3,5-Dihydroxy-6,7-didehydro-5,6,7',8'-tetrahydro-7'-apo-β-caroten-8'-one; 6,3'-Dihydroxy-7',8'-didehydro-5,6,7,8-tetrahydro-β,β-carotene-3,8-dione; 3,3'-Dihydroxy-5,8,5',8'-diepoxy-β-carotene; 5,6-Dihydroxy-5,6-dihydro-10'-apo-β-caroten-10'-al; 5,6-Dihydroxy-5,6-dihydro-10'-apo-β-caroten-10'-oic acid; 5,6-Dihydroxy-5,6-dihydro 12'-apo-β-caroten-12'-oic acid; 3,3'-Dihydroxy-7,8-dihydro-β,β-carotene-4,4'-dione; 3,1'-Dihydroxy-1',2'-dihydrotorulene; 1',2'-Dihydroxy-1',2'-dihydrotorulene; 3,3'-Dihydroxy-4,4'-diketo-β-carotene; 3,3'-Dihydroxy-2,2'-dinor-β,β-carotene-4,4'-dione-3,3'-diacylate; 3,19-Dihydroxy-3',6'-dioxo-7,8-didehyro-β,χ-caroten-17-al; 1,1'-Dihydroxy-2,2'-dirhamnosyl-1,2,1',2'-tetrahydro-3,4,3',4'-tetrahydrolycopene; 3,3'-Dihydroxyechinenone; 3,3'-Dihydroxy-5,6-epoxy-αcarotene; 3,3'-Dihydroxy-5,8-epoxy-α-carotene; 3,3'-Dihydroxy-5,6-epoxy-β-carotene; 3,3'-Dihydroxy-5,8-epoxy-β-carotene; 2-(Dihydroxyisopentenyl)-2'-isopentenyl-β-carotene; 3,3'-Dihydroxyisopenieratene; 3,3'-Dihydroxy-4-keto-carotene; 3,3'-Dihydroxyluteochrome; Dihydroxylycopene; 3,1'-Dihydroxy-2'-(5-C-methylpentosyloxy)-3',4'-didehydro-1',2'-dihydro-β,ψ-caroten-4-one; Dihydroxyneurosporene; 2',3'-Dihydroxy-2-nor-β,β-carotene-3,4-dione; 3,3'-Dihydroxy-2-nor-13-β,β-carotene-4,4'-dione-3-acylate; 3,3'-Dihydroxy-2-nor-13-β,β-carotene-4,4'-dione-3,3'-di-acylate; 1,2-Dihydroxyphytofluene; Dihydroxypirardixanthin; 3,3'-Dihydroxyretro-β-carotene; 3,3'-Dihydroxy-2,3,2',3'-tetradehydro-β,β-carotene-4,4'-dione; 3,3'-Dihydroxy-7,8,7',8'-tetradehydro-β,β-carotene-4,4'-dione; 3,3'-Dihydroxy-2,3,2',3'-tetradehydro-β,β-carotene-4,4'-dione dipalmitate; 3,3'-Dihydroxy-7,8,7',8'-tetradehydro-β,β-caroten-4-one; 1,1'-Dihydroxy-3,4,3'4'-tetradehydro-1,2,1',2'-tetrahydrod-ψ,ψ-carotene-2,2'-dione; 3,8'-Dihydroxy-5',6',7',8'-tetrahydro-5'-apo-18'-nor-β-caroten-6'-one; 1,1'-Dihydroxy-1,2,1',2'-tetrahydro-ζ-carotene; 5,5'-Dihydroxy-5,6,5',6'-tetrahydro-β,β-carotene-3,3'-dione; 3,3'-Dihydroxy-7,8,7',8'-tetrahydro-χ,χ-carotene-6,6'-dione; 9',10'-Dihydroxy-β-zeacarotene 3,17'-diol; Diketo-, see also Dioxo- or -dione 2,2'-Diketobacterioruberin; 3,4-Diketo-β-carotene; 4,4'-Diketo-β-carotene; 4,4'-Diketo-γ-carotene; 4,4'-Diketocynthiaxanthin; 3,3'-Diketodehydro-β-carotene; 4,4'-Diketolycopene; Diketopirardixanthin; 3,3'-Diketoretro-β-carotene; 3,3'-Diketoretrodehydro-β-carotene; 2,2'-Diketospirilloxanthin; 4,4'-Diketo-7,8,7',8'-tetrade hydrozeaxanthin; 3,3'-Dimethoxy-β,β-carotene; 3,3'-Dimethoxy-β,ε-carotene; 3,3'-Dimethoxy-γ-carotene; 3,3'-Dimethoxy-3',4'-dehydro-γ-carotene; 1,1'-Dimethoxy-3,4-didehydro-1,2,1',2',7',8'-hexahydro-ψ,ψ-carotene; 1,1'-Dimethoxy-3,4-didehydro-1,2,1',2',7',8'-hexahydro-ψ,ψ-caroten-2-one; 1,1'-Dimethoxy-3,4-didehydro-1,2,1',2'-tetrahydro-ψ,ψ-carotene; 1,1'-Dimethoxy-3',4'-didehydro-1,2,1',2'-tetrahydro-ψ,ψ-caroten-4-one; 1,1'-Dimethoxy-1,2,7,8,1',2'-hexahydro-ψ,ψ-carotene; 1,1'-Dimethoxy-1,2,7,8,11,12,1',2'-octahydro-ψ,ψ-carotene; 1,1'-Dimethoxy-3,4,3',4'-tetradehydro-1,2,1',2'-tetrahydro-ψ,ψ-carotene; 1,1'-Dimethoxy-3,4,3',4'-tetradehydro-1,2,1',2'-tetrahydro-ψ,ψ-carotene-2,2'-dione; 1,1'-Dimethoxy-1,2,1',2'-tetrahydro-ψ,ψ-caroten-20-al; 1,1'-Dimethoxy-1,2,1',2'-tetrahydro-ψ,ψ-carotene; 1,1'-Dimethoxy-1,2,1',2'-tetrahydro-ψ,ψ-carotene-4,4'-dione; 1,1'-Dimethoxy-1,2,1',2'-tetrahydrolycopene; 1,1'-Dimethoxy-1,1',2,2'-tetrahydroneurosporene; Dimethylcrocetin; Dimethyl-6,6'-diapocarotene-6,6'-dioate; Dimethyl-8,8'-diapocarotene-8,8'-dioate; Dineapolitanosyl-8,8'-diapocarotene-8,8'-dioate; 2,2'-Dinor-β,β-carotene-3,4,3',4'tetrone; Dinoxanthin; 3,3'-Dioxi-4-oxo-β-carotene; Dioxo-, see also Diketo- or -dione 5,6-Dioxo-10'-apo-5,6-seco-β-caroten-10'-al; 5,6,5',6'-Diseco-β,β-carotene 5,6,5',6'-tetrone; 7,8,11,12,13,14,15,7',8',11',12',15'-Dodecahydro-13,15':14,15' biscyclo-15,15'-seco-ψ,ψ-caroten-15-ol; Dodecahydrolycopene; α-Doradecin; β-Doradecin; α-Doradexanthin; β-Doradexanthin;

Echinenone; Echininone; Eloxanthin; 6-Epikarpoxanthin; 3'-Epilutein; 5,6-Epoxy-α-carotene; 5,8-Epoxy-α-carotene; 5,8-Epoxy-β-carotene; 1,2-Epoxy-1,2,7,8,11,12,7',8',11',12'-decahydro-ψ,ψ-carotene; 5,6-Epoxy-7',8'-didehydro-5,6-dihydro-β,β-carotene-3,3'-diol; 5,8-Epoxy-7',8'-didehydro-5,8-dihydro-β,β-carotene-3,3'-diol; 1',2'-Epoxy-3',4'-didehydro-1',2'-dihydro-β,ψ-caroten-2-ol; 5',6'-Epoxy-6,7-didehydro-5,6,5',6'-tetrahydro-β,β-carotene-3,5,19(or 19'), 3'-tetrol; 5',6'-Epoxy-6,7-didehydro-5,6,5',6'-tetrahydro-β,β-carotene-3,5,3'-triol; 5',6'-Epoxy-6,7-didehydro-5,6,5',6'-tetrahydro-β,β-carotene-3,5,3'-triol 3-acetate; 5',8'-Epoxy-6,7-didehydro-5,6,5',8'-tetrahydro-β,β-carotene-3,5,3'-triol; 5,6-Epoxy-5,6-dihydro-12'-apo-β-carotene-3,12'-diol; 5,8-Epoxy-5,8-dihydro-10'-apo-β-carotene-3,10'-diol; 5,8-Epoxy-5,8-dihydro-12'-apo-β-carotene-3,12'-diol; 5,6-Epoxy-5,6-dihydro-β,β-carotene; 5,8-Epoxy-5,8-dihydro-β,β-carotene; 5,6-Epoxy-5,6-dihydro-β,ε-Ecarotene; 5,8-Epoxy-5,8-dihydro-β,ε-carotene; 1',2'-Epoxy-1',2'-dihydro-β,ψ-carotene; 1',2'-Epoxy-1',2'-dihydro-ε,ψ-carotene; 1,2-Epoxy-1,2-dihydro-ψ,ψ-carotene; 5,6-Epoxy-5,6-dihydro-ψ,ψ-carotene; 5,6-Epoxy-5,6-dihydro-β,β-carotene-3,3'-diol; 5,8-Epoxy-5,8-dihydro-β,β-carotene-3,3'-diol; 5,6-Epoxy-5,6-dihydro-β,ε-carotene-3,3'-diol; 5,6-Epoxy-5,6-dihydro-β,ε-carotene-3,3'-diol dipalmitate; 5,8-Epoxy-5,8-dihydro-β,ε-carotene-3,3'-diol; 5,6-Epoxy-5,6-dihydro-β,ε-carotene-3,3',6'-triol; 5,8-Epoxy-5,8-dihydro-β,ε-carotene-3,3',6'-triol; 5,6-Epoxy-5,6-dihydro-β,β-caroten-2-ol; 5,6-Epoxy-5,6-dihydro-β,β-caroten-3-ol; 5',8'-Epoxy-5',8'dihydro-β,β-caroten-3-ol; 5,6-Epoxy-5,6-dihydro-β,ε-caroten-2-ol; 5,6-Epoxy-5,6-dihydro-β,ψ-caroten-3-ol; 5,8-Epoxy-5,8-dihydro-β,ψ-caroten-3-ol; 5,8-Epoxy-3,3'-dihydroxy-α-carotene; 5,6-Epoxy-3,3'-dihydroxy-7',8'didehydro-5,6,7,8-tetrahydrod-β,β-caroten-8-one; 5',6'-Epoxy-3,3'-dihydroxy-7,8-didehydro-5',6'-dihydro-10,11, 20-trinor-β,β-caroten-19',11'-olide; 5',6'-Epoxy-3,3'- dihydroxy-4,7-didehydro-5',6'-dihydro-10,11,20-trinor-β,β-caroten-19',11'-olide 3-acetate; 5',6'-Epoxy-3,3'-dihydroxy-7,8-didehydro-5',6'-dihydro-10,11,20-trinor-β,β-caroten-19',11'-olide 3-acetate; 5,6-Epoxy-3,3'-dihydroxy-5,6-dihydro-β,χ-caroten-6'-one; 5,8-Epoxy-3,3'-dihydroxy-5,8-dihydro-β,χ-caroten-6'-one; 5,6-Epoxy-3,3'-dihydroxy-5,6,7',8'-tetrahydro-β,ε-caroten-11',19'-olide; 1',2'-Epoxy-2'-(2,3-epoxy-3-methylbutyl)-2-(3-hydroxy-3-methylbutyl)-3',4'-didehydro-1,2,1',2'-tetrahydro-ψ,ψ-caroten-1-ol; 1,2-Epoxy-1,2,7,8,7',8'-hexahydro-ψ,ψ-carotene; 5,6-Epoxy-3-hydroxy-8'-apo-β-caroten-8'-al; 5,6-Epoxy-5,6-dihydro-10'-apo-β-carotene-3,10'-diol; 5,8-Epoxy-3-hydroxy-γ-carotene; 5,8-Epoxy-3-hydroxy-5,8-dihydro-8'-apo-β-caroten-8'-al; 5,6-Epoxy-3-hydroxy-5,6-dihydro-10'-apo-β-caroten-10'-al 502;5,6-Epoxy-3-hydroxy-5,6-dihydro-12'-apo-β-caroten-12'-al; 5,6-Epoxy-3-hydroxy-5,6,7',8'-tetrahydro-7'-apo-β-caroten-8'-one; 5,8-Epoxylutein; 1,2-Epoxy-1,2,7,8,11,12,7',8'octahydro-ψ,ψ-carotene; 1,2-Epoxy-1,2,7,8,7',8',11',12'octahydro-ψ,ψ-carotene; 1',2'-Epoxy-7,8,11,12,1',2',7',8'-octahydro-β,ψ-caroten-2-ol; 1,2-Epoxyphytoene; 5,8-Epoxyrubixanthin; 5',8'-Epoxy-5,6,5',8'-tetrahydro-β,β-carotene-3,5,6,3'tetrol; 5',6'-Epoxy-5,6,5',6'-tetrahydro-β,β-carotene-3,5,6,3'-tetrol; 5,6-Epoxy-3',4',7',8'-tetrahydro-5,6-dihydro-β,β-caroten-4-one; 5,6-Epoxy-3,3',5',19'-tetrahydroxy-6',7'-didehydro-5,6,7,8,5',6'-hexahydro-β,β-caroten-8-one 3'-acetate 19'-hexanoate; 5,6-Epoxy-3,3',5'-trihydroxy-6',7'-didehydro-5,6,7,8,5',6'-hexahydro-β,β-caroten-8-one; 5,6-Epoxy-3,3',5'-trihydroxy-6',7'-didehydro-5,6,7,8,5',6'-hexahydro-β,β-caroten-8-one 3'-acetate; 5',6'-Epoxy-3,5,3'-trihydroxy-6,7-didehydro-5,6,5',6'-tetrahydro-10,11,20-trinor-β,β-caroten-19',11'-olide; 5',6'-Epoxy-3,5,3'-trihydroxy-6,7-didehydro-5,6,5',6'-tetrahydro-10,11,20-trinor-β,β-caroten-19',11'-olide 3-acetate; 4',5'-Epoxy-3,6,3'-trihydroxy-7,8,4',5',7',8'-hexahydro-γ,ε-caroten-8-one; 5,6-Epoxyzeaxanthin; 5,8-Epoxyzeaxanthin; Eschscholtzxanthin; Eschscholtzxanthone; 4'-Ethoxy-β,β-caroten-4-one; 4'-Ethoxy-4-keto-β-carotene; Euglenanone; Euglenarhodon; Eutreptiellanone;

Flavacin; Flavochrome; Flavorhodin; Flavoxanthin; Flexixanthin; Foliachrome; Foliaxanthin; Fritschiellaxanthin; Fucochrome; Fucoxanthin; Fucoxanthinol; Fucoxanthol;

Gazaniaxanthin; β,D-Gentiobiosyl β,D-glucosyl 8,8'-diapocarotene-8,8'-dioate; Gentiobiosyl hydrogen-8,8'-dioate; Gentiobiosyl neapolitanosyl 8,8'-diapocarotene-8,8'-dioate; β,D-Glucosyl hydrogen-4,4'-diapocarotene-4,4'-dioate; 4'-β,D-Glucosyl 4-hydrogen-7',8'-dihydro-4,4'-diapocarotene-4,4'-dioate; β,D-Glucosyl hydrogen-8,8'-diapocarotene-8,8'-dioate; β,D-Glucosyl methyl-8,8'-diapocarotene-8,8'-dioate; Glucopyranosyloxy (see Glucosyloxy); 4-Glucosyloxy-4,4'-diaponeurosporene; 1'-Glucosyloxy-3',4'-didehydro-1',2'-dihydro-β,ψ-carotene; 1-Glucosyloxy-3,4-didehydro-1,2-dihydro-ψ,ψ-carotene;

2'-Glucosyloxy-3',4'-didehydro-1',2'-dihydro-β,ψ-carotene-3,1'-diol; 1'-Glucosyloxy-3',4'-didehydro-1',2'-dihydro-β,ψ-caroten-3-ol; 1'-Glucosyloxy-3',4'-didehydro-1',2'-dihydro-β,ψ-caroten-2'-ol; 1'-Glucosyloxy-3',4'-didehydro-1',2'-dihydro-β,ψ-caroten-4-one; 1-Glucosyloxy-3,4-didehydro-1,2,7',8'-tetrahydro-ψ,ψ-carotene; 1-Glucosyloxy-1,2-dihydro-ψ,ψ-caroten-20-al; 1-Glucosyloxy-1',2'-dihydro-β,ψ-carotene; 1-Glucosyloxy-1',2'-dihydro-φ,ψ-carotene; 1-Glucosyloxy-1,2-dihydro-ψ,ψ-carotene; 4-Glucosyloxy-7',8'-dihydro-4,4'-diapocarotene; 1'-Glucosyloxy-2'-hydroxy-3',4'-didehydro-1',2'-dihydro-β,ψ-caroten-4-one; 2-(4-Glucosyloxy-3-methyl-2-butenyl)-2'-(4-hydroxy-3-methyl-2-butenyl)-γ,γ-carotene; 2-(4-Glucosyloxy-3-methyl-2-butenyl)-2'-(4-hydroxy-3-methyl-2-butenyl)-ε,ε-carotene; 2-(4-Glucosyloxy-3-methyl-2-butenyl)-2'-(4-hydroxy-3-methyl-2-butenyl)-7,8-dihydro-ε,ε-carotene; 2'-(4-Glucosyloxy-3-methyl-2-butenyl)-2-(3-methyl-2-butenyl)-ε,ε-caroten-18-ol; 2-[3-(Glucosyloxy)-3-methylbutyl]-2'-(3-hydroxy-3-methylbutyl)-3,4,3',4'-tetradehydro-1,2,1',2'-tetrahydro-ψ,ψ-carotene-1,1'-diol; 1'-Glucosyloxy-3,4,3',4'-tetradehydro-1',2'-dihydro-β,ψ-carotene; Glycymerin; Guaraxanthin;

Halocynthiaxanthin; Helenien; Heteroxanthin; Hexadecahydrolycopene; 2,3,2',3',4',5'-Hexadehydro-4,5'-retro-β,β-carotene; 1,2,7,8,11,12-Hexahydro-ψ,ψ-carotene; 1,2,7,8,1',2'-Hexahydro-ψ,ψ-carotene; 1,2,7,8,7',8'-Hexahydro-ψ,ψ-carotene; 7,8,11,12,7',8'-Hexahydro-ψ,ψ-carotene; 7,8,11,12,7',8'-Hexahydro-β,ψ-caroten-2-ol; 15,7',8',11',12',15'-Hexahydro-β,ψ-caroten-2-ol; 1,2,7',8',11',12'-Hexahydro-ψ,ψ-caroten-1-ol; 7,8,11,12,7',8'-Hexahydro-ψ,ψ-caroten-16-ol; 7,8,11,12,7',8'-Hexahydro-4,4'-diapocarotene; 1,2,7,8,11,12-Hexahydrolycopene; 1',2',7',8'11',12'-Hexahydrolycopene; 7,8,11,12,7',8'-Hexahydrolycopene; 7,8,1',2',7',8'-Hexahydrolycopene; 3,4,3',4',7',8'-Hexahydrospirilloxanthin; 19'-Hexanoyloxyfucoxanthin; 19-Hexanoyloxyparacentrone; 1-Hexosyl-1,2-dihydro-3,4-didehydroapo-8'-lycopenol; O-Hexosyl-1'-hydroxy-1',2'-dihydro-γ-carotene; O-Hexosy-1-4-keto-1'-hydroxy-1',2'-dihydro-3',4'-didehydro-γ-carotene; Hopkinsiaxanthin; Hydroxy-, see also Monohydroxy-, OH or -ol 3-Hydroxy-β-apo-2-carotenal; 3-Hydroxy-8'-apo-β-caroten-8'-al; 3-Hydroxy-10'-apo-β-caroten-10'-al; 3-Hydroxy-12'-apo-β-caroten-12'-al; 3-Hydroxy-8'-apo-ε-caroten-8'-al; 3-Hydroxy-8'-apo-β-caroten-8'-oic acid; 9'-Hydroxy-9'-apo-β-caroten-3-one; 9'-Hydroxy-9'-apo-ε-caroten-3-one; Hydroxyasteroidenone; 3-Hydroxycanthaxanthin; 3-Hydroxy-β,ψ-caroten-18'-al; 3-Hydroxy-α-carotene; 3'-Hydroxy-α-carotene; 4-Hydroxy-α-carotene; 2-Hydroxy-β-carotene; 3-Hydroxy-β-carotene; 4-Hydroxy-β-carotene; 3-Hydroxy-γ-carotene; 4'-Hydroxy-γ-carotene; 3-Hydroxy-δ-carotene; 2-Hydroxy-β,β-carotene-4,4'-dione; 3-Hydroxy-β,β-carotene-4,4'-dione; 3'-Hydroxy-β,β-carotene-3,4-dione; 4'-Hydroxy-β,β-carotene-3,4-dione; 3-Hydroxy-β,ε-carotene-4,3'-dione; 3'-Hydroxy-β,ε-carotene-3,4-dione; 3-Hydroxy-β,χ-carotene-3',6'-dione; 3'-Hydroxy-β,β-carotene-3,4,4'-trione; 2'-Hydroxy-β,β-caroten-2-one; 2-Hydroxy-β,β-caroten-4-one; 3-Hydroxy-β,β-caroten-4-one; 3'-Hydroxy-β,β-caroten-4-one; 4'-Hydroxy-β,β-caroten-4-one; 3-Hydroxy-β,ε-caroten-4-one; 3-Hydroxy-β,ε-caroten-3'-one; 3'-Hydroxy-β,χ-caroten-6'-one; 3Hydroxy-β,ψ-caroten-4'-one; 3-Hydroxy-β,ψ-caroten-4-one; 3-Hydroxy-ε,ε-caroten-3'-one; 3'-Hydroxy-ψ,ψ-caroten-4-one; 3-Hydroxycitranaxanthin; 3-Hydroxy-7,8-dehydro-α-carotene; 3'-Hydroxy-3,4-dehydro-β-carotene; 3-Hydroxy-3',4'-dehydro-γ-carotene; 4-Hydroxy-4,4'-diaponeurosporene; 3-Hydroxy-2,3-didehydro-β,β-carotene-4,4'-dione; 2'-Hydroxy-3,4-didehydro-β,β-caroten-2-one; 3-Hydroxy-2,3-didehydro-β,β-caroten-4-one; 3-Hydroxy-2,3-didehydro-β,ε-caroten-4-one; 3-Hydroxy-2,3-didehydro-β,X-caroten-4-one; 3-Hydroxy-2,3-didehydro-β,φ-caroten-4-one; 3-Hydroxy-3',4'-didehydro-β,ψ-caroten-4-one; 3-Hydroxy-7,8-didehydro-7',8'-dihydro-7'-apo-β-carotene-4,8'-dione; 3-Hydroxy-7,8-didehydro-7',8'-dihydro-7'-apo-β-caroten-8'-one; 3-Hydroxy-7',8'-didehydro-7,8-dihydro-χ,X-carotene-6,8-dione; 1'-Hydroxy-3',4'-didehydro-1',2'-dihydro-β,ψ-caroten-4-one; 1'-Hydroxy-3',4'-didehydro-1',2'-dihydro-β,ψ-caroten-2'-one; 2'-Hydroxy-3',4'-didehydro-1',2'-dihydro-β,ψ-caroten-4-one; 5-Hydroxy-4',5'-didehydro-4,5-dihydro-β,β-caroten-4,4',5'-retro-β,β-carotene-3,3'-dione; 3'-Hydroxy-2',3'-didehydro-2-nor-β,β-carotene-3,4,4'-trione; 3'-Hydroxy-4,5-didehydro-4,5'-retro-β,β-caroten-3-one; 3-Hydroxy-5,8,5',8'-diepoxy-β-carotene; 3-Hydroxy- 7',8'-dihydro-7'-apo-β-caroten-8'-one; 3-Hydroxy-5',6'-dihydro-5'-apo-18'-nor-β-caroten-6'-one; 1-Hydroxy-1,2-dihydro-ψ,ψ-caroten-20-al; 1'-Hydroxy-1',2'-dihydro-γ-carotene; 3-Hydroxy-7,8-dihydro-χ,X-carotene-6,8-dione; 4'-Hydroxy-5',6'-dihydro-β,β-caroten-4-one; 1'-Hydroxy-1',2'-dihydro-β,ψ-caroten-4-one; 8'-Hydroxy-7',8'-dihydrocitranaxanthin; 4-Hydroxy-7',8'-dihydro-4,4'-diapocarotene; 4'-Hydroxy-5',6'-dihydroechinenone; 1'-Hydroxy-1',2'-dihydro-2-isopentenyl-2'-(hydroxyisopentenyl)torulene; 1-Hydroxy-1,2-dihydrolycopene; 1-Hydroxy-1,2-dihydroneurosporene; 1'-Hydroxy-1',2'-dihydroneurosporene; 1-Hydroxy-1,2-dihydrophytoene; 1(or 1')-Hydroxy-1,2 (or 1',2')-dihydrophytofluene; 8'-Hydroxy-7',8'-dihydroreticulataxanthin; 1'-Hydroxy-1',2'-dihydrospheroidene; 2'-Hydroxy-1',2'-dihydrotorulene; 2-Hydroxy-1',2'-dihydrotorulene-1',2'-oxide; 5-Hydroxy-5,6-dihydrozeaxanthin; 3-Hydroxy-3',4'-diketo-α-carotene; 3-Hydroxy-4,4'-diketo-β-carotene; 3'-Hydroxy-3,4-diketo-β-carotene; 2'-Hydroxy-3,1'-dimethoxy-3',4'-didehydro-1',2'-dihydro-β,ψ-caroten-4-one; 4-Hydroxy-3',4'-dioxo-β-carotene; 2-Hydroxyechinenone; 3-Hydroxyechinenone; 3'-Hydroxyechinenone; 4'-Hydroxyechinenone; 3-Hydroxy-5,8-epoxy-β-carotene; 3'-Hydroxy-3,6-epoxy-5,6-dihydro-β,ε-caroten-4-one; 3'-Hydroxy-3,6-epoxy-7',8'-dihydro-5,6-dihydro-β,β-caroten-4-one; 3'-Hydroxyeuglenanone; 2'-Hydroxyflexixanthin; 1-Hydroxy-1,2,7',8',11',12'-hexahydrolycopene; 1'-Hydroxy-3,4,1',2',11',12'hexahydrospheroidene; 2-(4-Hydroxy-3-hydroxymethyl-2-butenyl)-2'-(3-methyl-2-butenyl)-β,β-carotene; 3-Hydroxyisorenieratene; 3-Hydroxy-4-keto-α-carotene; 3-Hydroxy-3'-keto-α-carotene; 3-Hydroxy-4-keto-β-carotene; 3-Hydroxy-4'-keto-β-carotene; 4-Hydroxy-4'-keto-β-carotene; 1'-Hydroxy-2'-keto-1',2'-dihydrotorulene; 3-Hydroxy-3'-keto-retrodehydrocarotene; 19-Hydroxylutein; 16-Hydroxylycopene; 3-Hydroxy-3'-methoxy-β-carotene; 1'-Hydroxy-1-methoxy-3,4-didehydro-1,2,1',2',7',8'-hexahydro-ψ,ψ-caroten-2-one; 1'-Hydroxy-1-methoxy-1,2,1',2',7',8'-hexahydro-ψ,ψ-caroten-4-one; 1'-Hydroxy-1-methoxy-3,4,3',4'-tetradehydro-1,2,1',2'-tetrahydro-ψ,ψ-caroten-2-one; 1'-Hydroxy-1-methoxy-1,2,1',2'-tetrahydro-ψ,ψ-caroten-4-one; 2-(4-Hydroxy-3-methyl-2-butenyl)-β,β-carotene; 2-(4-Hydroxy-3-methyl-2-butenyl)-ε,ψ-carotene; 2-(3-Hydroxymethyl-but-2-enyl)-7',8'-dihydro-δ-carotene; 2-(4-Hydroxy-3-methyl-2-butenyl)-7',8'-dihydro-ε,ψ-carotene; 2-(4-Hydroxy-3-methyl-2-butenyl)-2'-(3-methyl-2-butenyl)-ε,ε-carotene; 2-(4-Hydroxy-3-methyl-2-butenyl)-2'-(3-methyl-2-butenyl)-ε,ε-caroten-18-ol; 2'-(4-Hydroxy-3-methyl-2-butenyl)-2-(3-methyl-2-butenyl)-3',4'-didehydro-1',2'-dihydro-β,ψ-caroten-1'-ol; 2(or 2')-(4-Hydroxy-3-methyl-2-butenyl)-2'(or 2)-(3-methyl-2-butenyl)-3',4'-didehydro-1',2'-dihydro-ε,ψ-caroten-1'-ol; 2'-(4-Hydroxy-3-methyl-2-butenyl)-2-(3-methyl-2-butenyl)-7,8(or 7',8')-dihydro-ε,ε-caroten-18-ol; 2-(4-Hydroxy-3-methyl-2-butenyl)-7,8,7',8'-tetrahydro-ε,ψ-carotene; 2-(4-Hydroxy-3-methyl-2-butenyl)-7',8',11',12'-tetrahydro-ε,ψ-carotene; 16-(3-Hydroxy-3-methylbutyl)-16'-(3-methyl-2-butenyl)-7,8,11,12,15,7',8',11',12',15'-decahydro-ψ,ψ-carotene; 2-(3-Hydroxy-3-methylbutyl)-2'-(3-methyl-2-butenyl)-3,4,3',4'-tetradehydro-1,2,1',2'-tetrahydro-ψ,ψ-carotene-1,1'-diol; 2-Hydroxy-monocyclic-phytofluene; 4-Hydroxymyxoxanthophyll; Hydroxyneurosporene; 15-Hydroxy-7',8',9',10',11',12',13',14'-octahydro-6'-apo-β-caroten-7'-one; 1'-Hydroxy-3,4,7,8,1',2',11',12'-octahydrospheroidene; 3'-Hydroxy-4-oxo-β-carotene; 3-Hydroxy-4-oxo-2,3-dehydro-β-carotene; 4'-Hydroxy-3-oxoechinenone; Hydroxyphytoene; Hydroxyphytofluene; 4'-Hydroxy-4-oxo-pirardixanthin; 2-Hydroxyplectaniaxanthin; 3-Hydroxy-4,5'-retro-5'-apo-β-caroten-5'-one; 3-Hydroxy-4',12'-retro-β,β-carotene-3',12'-dione; 3'-Hydroxyrubixanthin; 3'-Hydroxy-5,6-seco-β,β-carotene-5,6-dione; 3-Hydroxy-semi-β-carotenone; 3-Hydroxysintaxanthin; Hydroxyspheroidene; Hydroxyspheroidenone; Hydroxyspirilloxanthin; 8'-Hydroxy-5',6',7',8'-tetrahydro-5'-apo-18'-nor-β-caroten-6'-one; 4'-Hydroxy-5,6,5',6'-tetrahydro-β,β-caroten-4-one; 1-Hydroxy-3,4,3',4'-tetradehydro-1,2-dihydro-ψ,ψ-caroten-2-one; 1-Hydroxy-1,2,7',8'-tetrahydrolycopene; 1'-Hydroxy-3,4,1',2'-tetrahydrospheroidene; 3-Hydroxytorulene; 16-Hydroxytorulene; 18'-Hydroxytorulene; 3-Hydroxy-3,4,4'-triketo-β-carotene; 3-Hydroxy-β-zeacarotene; 5-Hydroxyzeaxanthin;

Idoxanthin; Isoagelaxanthin A; Isobixin; Isocarotene; Iso-ζ-carotene; Iso-ξ-carotene; Isocrocetin; Isocryptoxanthin; Isofucoxanthin; Isofucoxanthinol; Isolutein; Isomethylbixin; Isomytiloxanthin; 2-Isopentenyl-3,4-dehydrorhodopin; Isorenieratene; '-Isorenieratene; 3,3'-Isorenieratenediol; 3-Isorenieratenol; Isotedaniaxanthin; Isotedanin; Isozeaxanthin;

Karpoxanthin; Keto—, see also oxo or—one Ketocapsanthin; 4-Ketocapsanthin; 4-Keto-α-carotene; 4-Keto-β-carotene; 4-Keto-γ-carotene; 4-Ketocynthiaxanthin; 4-Keto-3',4'-dehydro-β-carotene; 4-Keto-1',2'-dihydro-1'-hydroxytorulene; 2-Keto-7',8'-dihydrorhodovibrin; 4-Keto-3,3'-dihydroxy-α-carotene; 4'-Keto-3-hydroxy-γ-carotene; 4-Keto-3'-hydroxylycopene; 4-Ketolutein 332 4-Ketomyxol 2'-(methylpentoside); 4-Ketomyxoxanthophyll; 2-Keto-OH-spirilloxanthin; 4-Ketophleixanthophyll; 2-Ketorhodovibrin; 4'-Ketorubixanthin; 2-Ketospirilloxanthin; 4-Ketotorulene; 4-Ketozeaxanthin;

Lactucaxanthin; Latochrome; Latoxanthin; Leprotene; Lilixanthin; Loniceraxanthin; Loroxanthin; Lusomycin; Lutein; Lutein dimethyl ether; Lutein dipalmitate; Lutein epoxide; Luteochrome; Luteol; Luteoxanthin; Lycopenal; Lycopen-20-al; Lycopene; Lycopene-16,16'-diol; Lycopene 1,2-epoxide; Lycopene 5,6-epoxide; Lycopen-16-ol; Lycopen-20-ol; Lycopersene; Lycophyll; Lycoxanthin;

Mactraxanthin; Manixanthin; 1-Mannosyloxy-3,4-didehydro-1,2-dihydro-8'-apo-ψ-caroten-8'-ol; 3'-Methoxy-β,β-caroten-3-ol; 3-Methoxy-β,X-carotene; 1-Methoxy-1,2,7,8,11,12,7',8',11',12'-decahydro-ψ,ψ-carotene; 1'-Methoxy-1,2,7,8,11,12,1',2',7',8'-decahydro-ψ,ψ-caroten-1-ol; 1-Methoxy-3,4-didehydro-1,2-dihydro-ψ,ψ-caroten-20-al; 1'-Methoxy-3',4'-didehydro-1',2'-dihydro-β,ψ-carotene; 1-Methoxy-3,4-didehydro-1,2-dihydro-ψ,ψ-carotene; 1-Methoxy-3,4-didehydro-1,2,7',8',11',12'-hexahydro-ψ,ψ-carotene; 1'-Methoxy-3',4'-didehydro-1,2,7,8,1',2'-hexahydro-ψ,ψ-caroten-1-ol; 1-Methoxy-3,4-didehydro-1,2,7',8'-tetrahydro-ψ,ψ-carotene; 1'-Methoxy-3',4'-didehydro-1,2,1',2'-tetrahydro-ψ,ψ-caroten-1-ol; 1-Methoxy-3,4-didehydro-1,2,7',8'-tetrahydro-ψ,ψ-caroten-2-one; 1-Methoxy-1,2-dihydro-ψ,ψ-caroten-20-al; 1-Methoxy-1,2-dihydro-ψ,ψ-carotene; 1'-Methoxy-1,2-dihydro-β,ψ-caroten-4'-one; 1'-Methoxy-1',2'-dihydro-X, ψ-caroten-4'-one; 1-Methoxy-1,2-dihydro-ψ,ψ-caroten-4-one; 1'-Methoxy-1',2'-dihydro-3',4'-dehydro-γ-carotene; 1-Methoxy-1,2-dihydro-3,4-dehydrolycopene; 1-Methoxy-1,2-dihydro-3,4-didehydrolycopen-20-al; 1-Methoxy-1,2-dihydrolycopene; 4-Methoxy-5,6-dihydrolycopene; 1-Methoxy-1,2-dihydroneurosporene; 1-Methoxy-1,2-dihydrophytoene; 1-Methoxy-1,2-dihydrophytofluene; 1'-Methoxy-1',2'-dihydrospheroidene; 3-Methoxy-19,3'-dihydroxy-7,8-didehydro-β,χ-carotene-6,8-dione; 1-Methoxy-1,2,7',8',11',12'-hexahydro-ψ,ψ-carotene; 1'-Methoxy-1,2,7,8,1',2'-hexahydro-ψ,ψ-caroten-1-ol; 1-Methoxy-1,2,7',8',11',12'-hexahydro-ψ,ψ-caroten-4-one; 1-Methoxy-1'-hydroxy-1,2,1',2'- tetrahydrophytofluene; 1-Methoxy-2-keto-7',8'-dihydro-3,4-dehydrolycopene; Methoxylycopenal; 1-Methoxy-1,2,7,8,7',8',11',12'-octahydro-ψ,ψ-carotene; 1'-Methoxy-1,2,7,8,11,12,1',2'-octahydro-ψ,ψ-caroten-1-ol; 1-Methoxy-4-oxo-1,2-dihydro-8'-apo-ψ-caroten-8'-al; 1-Methoxy-4-oxo-1,2-dihydro-12'-apo-ψ-caroten-12'-al; Methoxyphytoene; Methoxyphytofluene; Methoxyspheroidene; 1'-Methoxy-3,4,3',4'-tetradehydro-1,2,1',2'-tetrahydro-ψ,ψ-caroten-1-ol; 1-Methoxy-1,2,7',8'-tetrahydro-ψ,ψ-carotene; 1-Methoxy-1,2,7',8'-tetrahydro-ψ,ψ-caroten-4-one; 1-Methoxy-1,2,7',8'-tetrahydro-3,4-dehydrolycopene; 3-Methoxy-19,3',8'-trihydroxy-7,8-didehydro-β,χ-caroten-6'-one; Methyl 4'-apo-β-caroten-4'-oate; Methyl 8'-apo-β-caroten-8'-oate; Methyl 6'-apo-ψ-caroten-6'-oate; Methyl apo-6'-lycopenoate; Methylbixin; 2-(3-Methyl-2-butenyl)-β,β-caroten-18(or 18')-ol; 2-(3-Methyl-2-butenyl)-3,4-didehydro-1,2-dihydro-ψ,ψ-caroten-1-ol; 2-(3-Methyl-2-butenyl)-7,8,7',8'-tetrahydro-ε,ψ-caroten-18-ol; Methyl 3',4'-didehydro-β,ψ-caroten-16'-oate; Methyl 1-hexosyl-1,2-dihydro-3,4-didehydro-apo-8'-lycopenoate; Methyl hydrogen 6,6'-diapocarotene-dioate; Methyl 1-mannosyloxy-3,4-didehydro-1,2-dihydro-8'-apo-ψ-caroten-8'-oate; Methyl 1'-methoxy-4'-oxo-1',2'-dihydro-X,ψ-caroten-16 (or 17 or 18)-oate; 2'-(O-Methyl-5-C-methylpentosyloxy)-3',4'-didehydro-1',2'-dihydro-β,ψ-carotene-3,1'-diol; Metridene; Mimulaxanthin; Monadoxanthin; Monoanhydrobacterioruberin; Monodehydro-β-carotene; Monodehydrolycopene; Monodemethyl(ated) spirilloxanthin; Monoepoxy-, see Epoxy-Monohydroxy cyclophytoene; Monohydroxy cyclophytofluene; Mutatochrome; Mutatoxanthin; Mytiloxanthin; Mytiloxanthinone; Myxobactin; Myxobactone; Myxol 2'-glucoside; Myxol 2'-O-methyl-methylpentoside; Myxol 2'-rhamnoside; Myxoxanthin; Myxoxanthol; Myxoxanthophyll;

Neocarotene; Neochrome; Neo-β-carotene B; Neo-β-cryptoxanthin A; Neoxanthin; Neoxanthin 3-acetate; Neurosporaxanthin; Neurosporaxanthin methyl ester; Neurosporene; Nonaprenoxanthin; 2'-Nor-astaxanthin diester; Norbixin; Nostoxanthin;

Octahydro-β-carotene; 1,2,7,8,11,12,7',8'-Octahydro-ψ,ψ-carotene; 7,8,11,12,7',8',11',12'-Octahydro-ψψ-carotene; 1,2,7,8,11,12,7',8'-Octahydro-ψ,ψ-carotene-1,2-diol; 1,2,7,8,1',2',7',8'-Octahydro-ψ,ψ-carotene-1,1'-diol; 1,2,7,8,11,12,7',8'-Octahydro-ψ,ψ-caroten-1-ol; 7,8,11,12,7',8',11',12'-Octahydro-β,ψ-caroten-2-ol; 1,2,7,8,7',8',11',12'-Octahydro-ψ,ψ-caroten-1-ol; 7,8,11,12,7',8',11',12'-Octahydro-4,4'-diapocarotene; Octahydrolycopene; 5,6,7,8,5',6',7',8'-Octahydrolycopene; 7,8,11,12,7',8',11',12'-Octahydrolycopene; 3,4,3',4',7',8',11',12'-Octahydrospirilloxanthin; OH, see also Hydroxy- or -ol OH-Chlorobactene; OH-Chlorobactene glucoside; OH-Lycopene; 2-OH-Monocyclophytoene; 2-OH-Monocyclophytofluene; OH-Neurosporene; OH-Okenone; OH-P 481; OH-P 482; OH-P 511; OH-R; OH-Rhodopin; OH-Sintaxanthin 5,6-epoxide; OH-Spheroidene; OH-Spheroidenone; OH-7,8,11,12-Tetrahydrolycopene; OH-Y; Okenone; Ophioxanthin; Oscillaxanthin; Oscillol 2,2'-di(O-methylmethylpentoside); Oscillol 2,2'-dirhamnoside; Ovoester; Oxo-, see also Keto or -one 3-Oxocanthaxanthin; 4'-Oxo-4,4'-diapocaroten-4-oic acid; 8'-Oxo-8,8'-diapocarotenoic acid; 3-Oxoechinenone; 4-Oxosaproxanthin; 16'-Oxotorulene; 6'-Oxychrysanthemaxanthin;

P 412; P 444; P 450; P 452; P 481; P 500; P 518; 1'-[(χ-O-Palmitoyl-β,D-glucosyl)oxy]-3',4'-didehydro-1',2'-dihydro-β,ψ-caroten-2'-ol; Papilioerythrin; Papilioerythrinone; Paracentrone; Parasiloxanthin; Pectenol; Pectenolone; Pectenoxanthin; Pentaxanthin; Peridinin; Peridininol; Persicachrome; Persicaxanthin; Phillipsiaxanthin; Philosamiaxanthin; Phleixanthophyll; Phleixanthophyll palmitate; Phoeniconone; Phoenicopterone; Phoenicoxanthin; Physalien; Physoxanthin; Phytoene; $C_{30}$-Phytoene; Phytoene 1,2-(ep)oxide; Phytoenol; Phytofluene; Phytofluene epoxide; Phytofluenol; Pigment R; Pigment X; Pigment Y; Plectaniaxanthin; Poly-cis-γ-carotene; Poly-cis-ψ-carotene; Poly-cis-lycopene; Prasinoxanthin; Prelycopersene pyrophosphate; Prephytoene pyrophosphate; Pro-γ-carotene; Prolycopene; Proneurosporene; Protetrahydrolycopene; Pseudo-α-carotene; Pyrenoxanthin; Pyrrhoxanthin; Pyrrhoxanthinol;

7-cis: Renieracistene; Renierapurpurin; Renieratene; Reticulaxanthin; Retinylideneteiglic acid; Retrobisdehydro(-β-)carotene; Retrodehydro(-β-)carotene; Retrodehydro-γ-carotene; Retrodehydrozeaxanthin; Rhamnopyranosyloxy-, see Rhamnosyloxy-2'-O-Rhamnosyl-4-ketomyxol; 2'-O-Rhamnosylmyxol; 3'-Rhamnosyloxy-β,β-caroten-3-ol; 1-Rhamnosyloxy-3',4'-didehydro-1',2'-dihydro-β,ψ-carotene; 2'-Rhamnosyloxy-3',4'-didehydro-1',2'-dihydro-β,ψ-carotene-3,1'-diol; 2'-Rhamnosyloxy-3',4'-didehydro-1',2'-dihydro-β,ψ-carotene-3,4,1'-triol; 1'-Rhamnosyloxy-3',4'-didehydro-1',2'-dihydro-β,ψ-caroten-3-ol; Rhodoauranxanthin; Rhodopin; Rhodopin(-20-)al; Rhodopinal glucoside; Rhodopin glucoside; Rhodopinol; Rhodopurpurin; Rhodotorulene; Rhodovibrin; Rhodoviolascin; Rhodoxanthin; Roserythrin; Rubichrome; Rubixanthin; Rubixanthin 5,6-epoxide; Rubixanthone;

Salmon acid; Salmoxanthin; Saproxanthin; Sarcinaxanthin; Sarcinaxanthin diglucoside; Sarcinaxanthin monoglucoside; Sarcinene; 5,6-Seco-β,β-carotene-5,6-dione; 5,6-Seco-β,ε-carotene-5,6-dione; Semi-α-carotenone; Semi-β-carotenone; Sidnyaxanthin; Sintaxanthin; Siphonaxanthin; Siphonein; Sodium-3,19-dihydroxy-7,8-di-dehydro-β,χ-carotene-3',6'-dione 3-sulfate; Sodium-3,19-dihydroxy-3',6'-dioxo-7,8-didehydro-β,χ-caroten-17'-al 3-sulfate; Sodium-3,19,3'-trihydroxy-7,8-didehydro-6'-oxo-β,χ-caroten-17'-oate 3-sulfate; Sodium-3,19,17'-trihydroxy-7,8-didehydro-β,χ-carotene-3',6'-dione 3-sulfate; Sphaerobolin; Spheroidene; Spheroidenone; Spirilloxanthin; Sulcatoxanthin;

Tangeraxanthin; Taraxanthin; Taraxanthin dipalmitate; Taraxien; Tareoxanthin; Tedaniaxanthin; Tedanin; Ternstroemiaxanthin; Tethyatene; 7,8,7',8'-Tetradehydroastaxanthin; 3,4,3',4'-Tetradehydro-β,β-carotene; 3,4,3',4'-Tetradehydro-ψ,ψ-carotene; 7,8,7',8'-Tetradehydro-β,β-carotene-3,3'-diol; 3,4,3',4'-Tetradehydro-β,β-carotene-2,2'-dione; 3',4',7',8'-Tetradehydro-β,β-caroten-3-ol; 3,4,3',4'-Tetradehydrolycopene; 6,7,6',7'-Tetradehydro-5,6,5',6'-tetrahydro-β,β-carotene-3,3'-diol; 6,7,6',7'-Tetradehydro-5,6,5',6'-tetrahydro-β,β-carotene-3,5,3',5'-tetrol; 7,8,7',8'-Tetradehydrozeaxanthin; 3,4,3',4'-Tetradehydrobisanhydrobacterioruberin; 5,6,5',6'-Tetrahydrocanthaxanthin; 7,8,7',8'-Tetrahydrocapsorubin; Tetrahydro-β-carotene; 7,8,7',8'-Tetrahydro-β,β-carotene; 7',8',11',12'-Tetrahydro-β,ψ-carotene; 7',8',11',12'-Tetrahydro-γ-carotene; 7',8',11',12'-Tetrahydro-γψ-carotene; 1,2,7,8-Tetrahydro-ψ,ψ-carotene; 1,2,1',2'-Tetrahydro-ψ,ψ-carotene; 7,8,11,12-Tetrahydro-ψ,ψ-carotene; 7,8,7',8'-Tetrahydro-ψ,ψ-carotene; 5,6,5',6'-Tetrahydro-β,β-carotene-4,4'-diol; 7,8,7',8'-Tetrahydro-β,β-carotene-3,3'-diol; 7',8',9',10'-Tetrahydro-β,ψ-carotene-3,17'-diol; 1,2,1',2'-Tetrahydro-ψ,ψ-carotene-1,1'-diol; 5,6,5',6'-Tetrahydro-β,β-carotene-4,4'-dione; 5,6,5',6'-Tetrahydro-β,β-carotene-3,5,6,3',5',6'-hexol; 1,2,7,8-Tetrahydro-ψ,ψ-caroten-1-ol; 1,2,7',8'-Tetrahydro-ψ,ψ-caroten-1-ol; 7,8,11,12-Tetrahydro-4,4'-diapocarotene; 7,8,7',8'-Tetrahydro-4,4'-diapocarotene; Tetrahydrolycopene; 1,2,1',2'-Tetrahydrolycopene; 5,6,5',6'-Tetrahydrolycopene; 7,8,11,12-Tetrahydrolycopene;

7,8,7',8'-Tetrahydrolycopene; 7',8',11',12'-Tetrahydrolycopene; 1,2,1',2'-Tetrahydrolycopene-1,1'-diol; 1,2,1',2'-Tetrahydroneurosporene; 3,4,11',12'-Tetrahydrospheroidene; 3,4,7,8-Tetrahydrospirilloxanthin; 3,4,3',4'-Tetrahydrospirilloxanthin; 3,4,3',4'-Tetrahydrospirilloxanthin-20-al; 5,6,5',6'-Tetrahydro-3,4,3',4'-tetrol 4,4'-disulfate; 2,3,2',3'-Tetrahydroxy-β,β-carotene-4,4'-dione; 2,3,2',3'-Tetrahydroxy-β,β-caroten-4-one; 3,19,3',17'-Tetrahydroxy-β,χ-caroten-6'-one 3-sulfate; 3,5,3',5'-Tetrahydroxy-6',7'-didehydro-5,8,5',6'-tetrahydro-β,β-caroten-8-one; 3,3',5,5'-Tetrahydroxy-6'-hydro-7-dehydro-β-carotene; 3,4,3',4'-Tetrahydroxypirardixanthin; 3,4,3',4'-Tetrahydroxy-5,6,5',6'-tetrahydro-β,β-carotene; (3,4,3',4')-Tetraketo-β-carotene; 4,5,4',5'-Tetraketo-β-carotene; Thiothece-425; Thiothece-460; Thiothece-474; Thiothece-478; Thiothece-484; Thiothece-OH-484; Tilefishxanthin I; Tilefishxanthin II; Tilefishxanthin III; Tilefishxanthin IV; Torularhodin; Torularhodinaldehyde; Torularhodin methyl ester; Torulenal; Torulene; Torulenecarboxylic acid; 2,3,2'-Trihydroxy-β,β-caroten-4-one; 3,3',4'-Trihydroxy-β,β-caroten-4-one; 3,4,3'-Trihydroxy-β,χ-caroten-6'-one; 3,3',5'-Trihydroxy-6',7'-dehydro-α-carotene; 3,3',8'-Trihydroxy-7,8-didehydro-β,χ-carotene-4,6'-dione; 3,3',8'-Trihydroxy-7,8-didehydro-β,χ-caroten-6'-one; 3,19,3'-Trihydroxy-7,8-didehydro-β,χ-caroten-6'-one 3-sulfate; 3,1',2'-Trihydroxy-3',4'-didehydro-1',2'-dihydro-β,ψ-caroten-4-one; 3,5,19-Trihydroxy-6,7-didehydro-5,6,7',8'-tetrahydro-7'-apo-β-caroten-8'-one 3-acetate 19-hexanoate; 3,5,6'-Trihydroxy-6,7-didehydro-5,6,7',8'-tetrahydro-β,ε-carotene-3',8'-dione; 3,5,3'-Trihydroxy-5,6-dihydro-β-carotene; 3,3',5'-Trihydroxy-5',6'-dihydro-β-carotene 5',6'-epoxide; 3,19,3'-Trihydroxy-7,8-dihydro-β,ε-caroten-8-one; 3,19,3'-Trihydroxy-7,8-dihydro-β,ε-caroten-8-one 19-laurate; 3,6,3'-Trihydroxy-7,8-dihydro-γ,ε-caroten-8-one; 3,3',19-Trihydroxy-7,8-dihydro-8-oxo-α-carotene; 3,3',6'-Trihydroxy-5,8-epoxy-α-carotene; 3,4,4'-Trihydroxypirardixanthin; 1,1',2'-Trihydroxy-3,4,3',4'-tetradehydro-1,2,1',2'-tetrahydro-ψ,ψ-caroten-2-one; 3,4,4'-Trihydroxy-5,6,5',6'-tetrahydro-β,β-carotene; Trikentriorhodin; 3,4,4'-Triketo-β-carotene; 3,1',2'-Trimethoxy-3',4'-didehydro-1',2'-dihydro-β,ψ-caroten-4-one; Triophaxanthin; Triphasiaxanthin; Trisanhydrobacterioruberin; Trollein; Trollichrome; Trolliflavin; Trolliflor; Trollixanthin; Tunaxanthin;

Unidentified II; Unknown 370; Unknown 437; Uriolide;

Vaucheriaxanthin; Violaxanthin; Violeoxanthin; Violerythrin;

Warmingol; Warmingone; Webbiaxanthin;

Xanthophyll; Xanthophyll K₁; Xanthophyll K₁S; Xanthophyll dipalmitate; Xanthophyll epoxide;

α-Zeacarotene; β-Zeacarotene; β₁-Zeacarotene; α-Zeacarotene-3,17'-diol; β-Zeacarotene-3,17'-diol; β-Zeacaroten-3-ol; Zeaxanthene; Zeaxanthin; Zeaxanthin diepoxide; Zeaxanthin dimethyl ether; Zeaxanthin dirhamnoside; Zeaxanthin dipalmitate; Zeaxanthin 5,6-epoxide; Zeaxanthin 5,8-epoxide; Zeaxanthin furanoxide; Zeaxanthin monomethyl ether; Zeaxanthin monorhamnoside; Zeaxanthol; and Zeinoxanthin. The above list of naturally occurring carotenoids is meant to a be a non-limiting example of naturally occurring carotenoids. The list is not comprehensive as there are still more naturally occurring molecules which have been discovered and to be discovered which will fall within the category of carotenoids.

In some embodiments, the total synthesis of naturally occurring as well as synthetic carotenoids as starting scaffolds for carotenoid analogs or derivatives may be a method of generation of said carotenoid analogs or derivatives.

In some embodiments, the carotenoid derivatives may include compounds having a structure including a polyene chain (i.e., backbone of the molecule). The polyene chain may include between about 5 and about 15 unsaturated bonds. In certain embodiments, the polyene chain may include between about 7 and about 12 unsaturated bonds. In some embodiments a carotenoid derivative may include 7 or more conjugated double bonds to achieve acceptable antioxidant properties.

In some embodiments, decreased antioxidant properties associated with shorter polyene chains may be overcome by increasing the dosage administered to a subject or patient.

In some embodiments, a chemical compound including a carotenoid derivative may have the general structure (I):

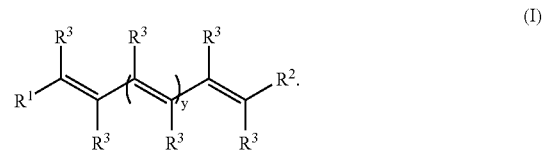

Each $R^3$ may be independently hydrogen or methyl. $R^1$ and $R^2$ may be independently H, an acyclic alkene with one or more substituents, or a cyclic ring including one or more substituents. y may be 5 to 12. In some embodiments, y may be about 3 to about 15. In certain embodiments, the maximum value of y may only be limited by the ultimate size of the chemical compound, particularly as it relates to the size of the chemical compound and the potential interference with the chemical compound's biological availability as discussed herein. In some embodiments, substituents may be at least partially hydrophilic. These carotenoid derivatives may be used in a pharmaceutical composition.

In some embodiments, the carotenoid derivatives may include compounds having the structure (Ia):

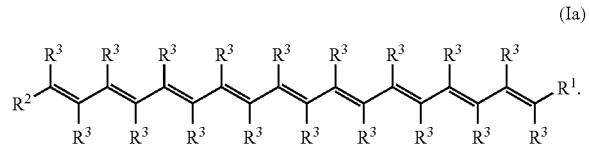

Each $R^3$ may be independently hydrogen, methyl, alkyl, alkenyl, or aromatic substituents. $R^1$ and $R^2$ may be independently H, an acyclic alkene with at least one substituent, or a cyclic ring with at least one substituent having general structure (II):

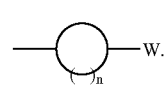

where n may be between 4 to 10 carbon atoms. W is the substituent.

In some embodiments, each cyclic ring may be independently two or more rings fused together to form a fused ring system (e.g., a bicyclic system). Each ring of the fused ring system may independently contain one or more degrees of unsaturation. Each ring of the fused ring system may be independently aromatic. Two or more of the rings forming the fused ring system may form an aromatic system.

In some embodiments, a chemical compound including a carotenoid derivative may have the general structure (Ib):

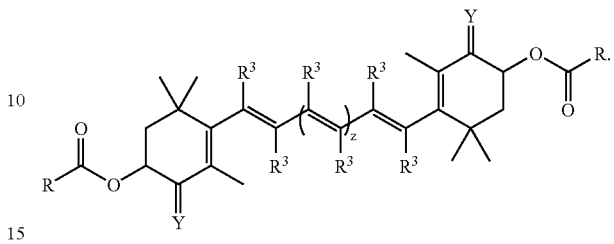

(Ib)

Each $R^3$ may be independently hydrogen or methyl. Each Y may be independently O or $H_2$. Each R may be independently $OR^1$ or $R^1$. Each $R^1$ may be independently -alkyl-$NR^2{}_3{}^+$, -aromatic-$NR^2{}_3{}^+$, -alkyl-$CO_2{}^-$, -aromatic-$CO_2{}^-$, -amino acid-$NH_3{}^+$, -phosphorylated amino acid-$NH_3{}^+$, polyethylene glycol, dextran, H, alkyl, or aryl. Each $R^2$ may be independently H, alkyl, or aryl. z may be 5 to 12. In some embodiments, z may be about 3 to about 15. In certain embodiments, the maximum value of z may only be limited by the ultimate size of the chemical compound, particularly as it relates to the size of the chemical compound and the potential interference with the chemical compound's biological availability as discussed herein. In some embodiments, substituents may be at least partially hydrophilic. These carotenoid derivatives may be used in a pharmaceutical composition.

In some embodiments, a chemical compound including a carotenoid derivative may have the general structure (Ic):

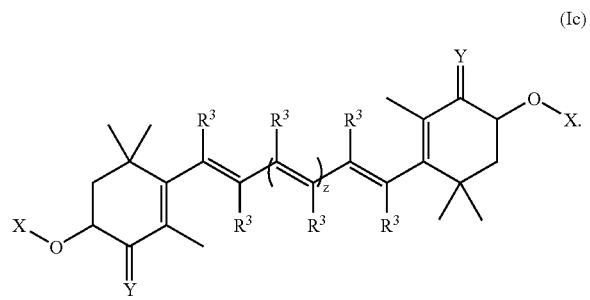

(Ic)

Each $R^3$ may be independently hydrogen or methyl. Each Y may be independently O or $H_2$. Each X is independently

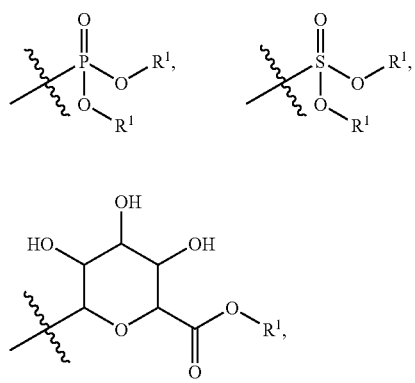

-alkyl-$NR^1{}_3{}^+$, -aromatic-$NR^1{}_3{}^+$, -alkyl-$CO_2{}^-$, -aromatic-$CO_2{}^-$, -amino acid-$NH_3{}^+$, -phosphorylated amino acid-$NH_3{}^+$, polyethylene glycol, dextran, alkyl, or aryl. Each $R^1$ is independently -alkyl-$NR^2{}_3{}^+$, -aromatic-$NR^2{}_3{}^+$, -alkyl-$CO_2{}^-$, -aromatic-$CO_2{}^-$, -amino acid-$NH_3{}^+$, -phosphorylated amino acid-$NH_3{}^+$, polyethylene glycol, dextran, H, alkyl, aryl, or alkali salt. Each $R^2$ may be independently H, alkyl, or aryl. z may be 5 to 12. In some embodiments, z may be about 3 to about 15. In certain embodiments, the maximum value of z may only be limited by the ultimate size of the chemical compound, particularly as it relates to the size of the chemical compound and the potential interference with the chemical compound's biological availability as discussed herein. In some embodiments, substituents may be at least partially hydrophilic. These carotenoid derivatives may be used in a pharmaceutical composition.

In some non-limiting examples, five- and/or six-membered ring carotenoid derivatives may be more easily synthesized. Synthesis may come more easily due to, for example, the natural stability of five- and six-membered rings. Synthesis of carotenoid derivatives including five- and/or six-membered rings may be more easily synthesized due to, for example, the availability of naturally occurring carotenoids including five- and/or six-membered rings. In some embodiments, five-membered rings may decrease steric hindrance associated with rotation of the cyclic around the molecular bond connecting the cyclic ring to the polyene chain. Reducing steric hindrance may allow greater overlap of any π oribitals within a cyclic with the polyene chain, thereby increasing the degree of conjugation and effective chromophore length of the molecule. This may have the salutatory effect of increasing antioxidant capacity of the carotenoid derivatives.

In some embodiments, a substituent (W) may be at least partially hydrophilic. A hydrophilic substituent may assist in increasing the water solubility of a carotenoid derivative. In some embodiments, a carotenoid derivative may be at least partially water soluble. The cyclic ring may include at least one chiral center. The acyclic alkene may include at least one chiral center. The cyclic ring may include at least one degree of unsaturation. In some cyclic ring embodiments, the cyclic ring may be aromatic. One or more degrees of unsaturation within the ring may assist in extending the conjugation of the carotenoid derivative. Extending conjugation within the carotenoid derivative may have the salutatory effect of increasing the antioxidant properties of the carotenoid derivatives. The cyclic ring may include a substituent. The substituent may be hydrophilic. In some embodiments, the cyclic ring may include, for example (a), (b), or (c):

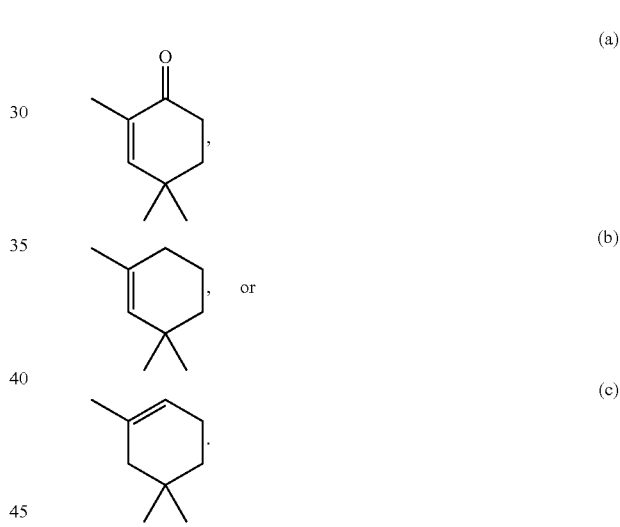

In some embodiments, the substituent may include, for example, a carboxylic acid, an amino acid, an ester, an alkanol, an amine, a phosphate, a succinate, a glycinate, an ether, a glucoside, a sugar, or a carboxylate salt.

In some embodiments, each substituent —W may independently include —XR. Each X may independently include O, N, or S. In some embodiments, each substituent —W may independently comprises amino acids, esters, carbamates, amides, carbonates, alcohol, phosphates, or sulfonates. In some substituent embodiments, the substituent may include, for example (d) through (rr):

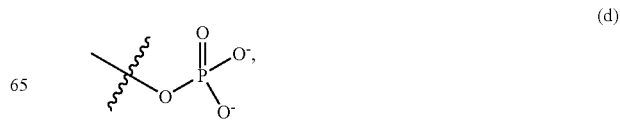

(d)

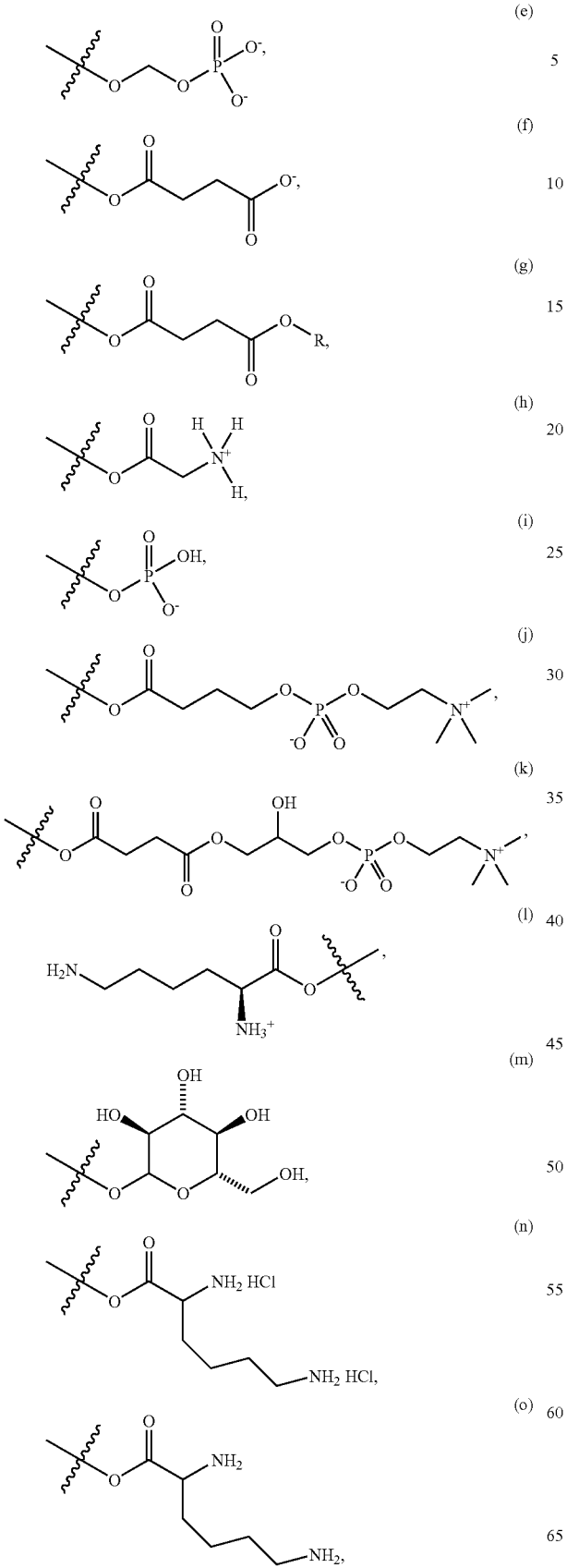
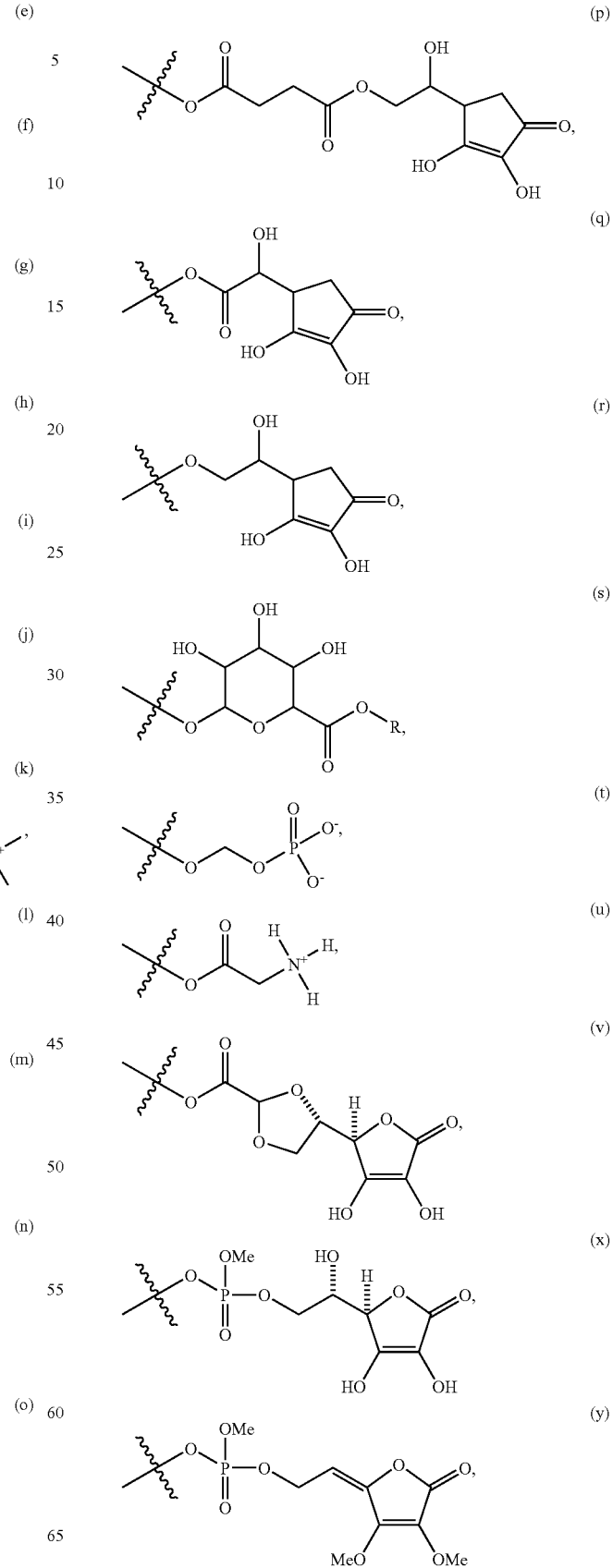

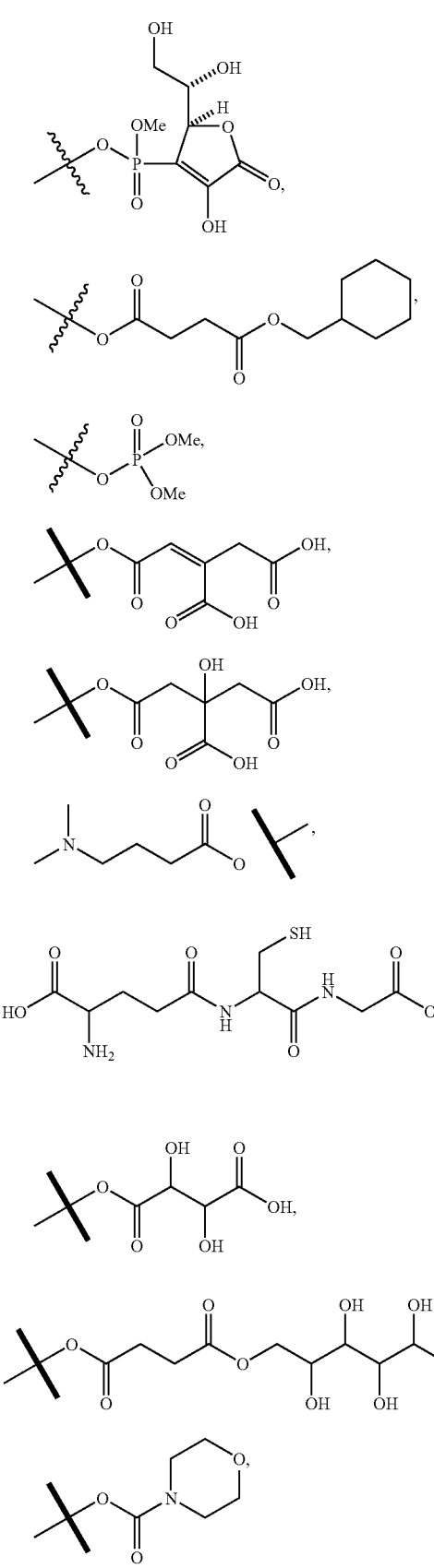

-continued

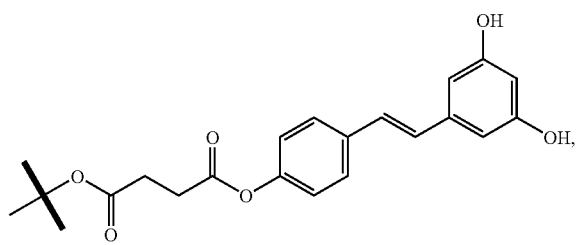
(pp)

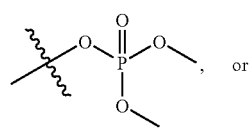
(qq), or

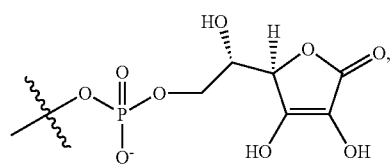
(rr)

where each R is, for example, independently -alkyl-$NR^1_3{}^+$, -aromatic-$NR^1_3{}^+$, -alkyl-$CO_2{}^-$, -aromatic-$CO_2{}^-$, -amino acid-$NH_3{}^+$, -phosphorylated amino acid-$NH_3{}^+$, polyethylene glycol, dextran, H, alkyl, or aryl. In some embodiments, substituents may include any combination of (d) through (rr). In some embodiments, negatively charged substituents may include alkali metals, one metal or a combination of different alkali metals in an embodiment with more than one negatively charged substituent, as counter ions. Alkali metals may include, but are not limited to, sodium, potassium, and/or lithium.

Water soluble carotenoid analogs or derivatives may have a water solubility of greater than about 1 mg/mL in some embodiments. In certain embodiments, water soluble carotenoid analogs or derivatives may have a water solubility of greater than about 10 mg/mL. In some embodiments, water soluble carotenoid analogs or derivatives may have a water solubility of greater than about 50 mg/mL.

The absolute size of a carotenoid derivative (in 3 dimensions) is important when considering its use in biological and/or medicinal applications. Some of the largest naturally occurring carotenoids are no greater than about $C_{50}$. This is probably due to size limits imposed on molecules requiring incorporation into and/or interaction with cellular membranes. Cellular membranes may be particularly co-evolved with molecules of a length of approximately 30 nm. In some embodiments, carotenoid derivatives may be greater than or less than about 30 nm in size. In certain embodiments, carotenoid derivatives may be able to change conformation and/or otherwise assume an appropriate shape which effectively enables the carotenoid derivative to efficiently interact with a cellular membrane.

Although the above structure, and subsequent structures, depict alkenes in the E configuration this should not be seen as limiting. Compounds discussed herein may include embodiments where alkenes are in the Z configuration or include alkenes in a combination of Z and E configurations within the same molecule. The compounds depicted herein may naturally convert between the Z and E configuration and/or exist in equilibrium between the two configurations.

In an embodiment, a chemical compound may include a carotenoid derivative having the structure (III)

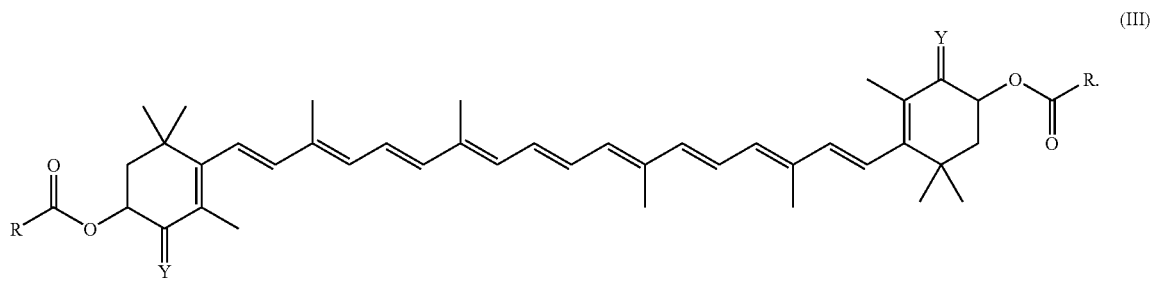
(III)

Each Y may be independently O or $H_2$. Each R may be independently $OR^1$ or $R^1$. Each $R^1$ may be independently -alkyl-$NR^2_3{}^+$, -aromatic-$NR^2_3{}^+$, -alkyl-$CO_2{}^-$, -aromatic-$CO_2{}^-$, -amino acid-$NH_3{}^+$, -phosphorylated amino acid-$NH_3{}^+$, polyethylene glycol, dextran, H, alkyl, peptides, poly-lysine or aryl. In addition, each $R^2$ may be independently H, alkyl, or aryl. The carotenoid derivative may include at least one chiral center.

In a specific embodiment where Y is $H_2$, the carotenoid derivative has the structure (IV)

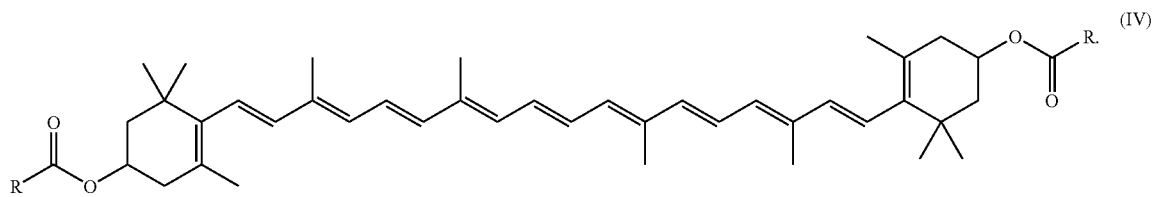

(IV)

In a specific embodiment where Y is O, the carotenoid derivative has the structure (V)

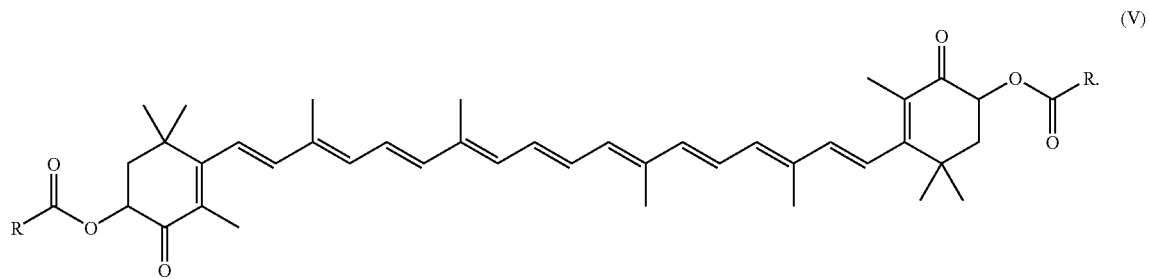

(V)

In an embodiment, a chemical compound may include a carotenoid derivative having the structure (VI)

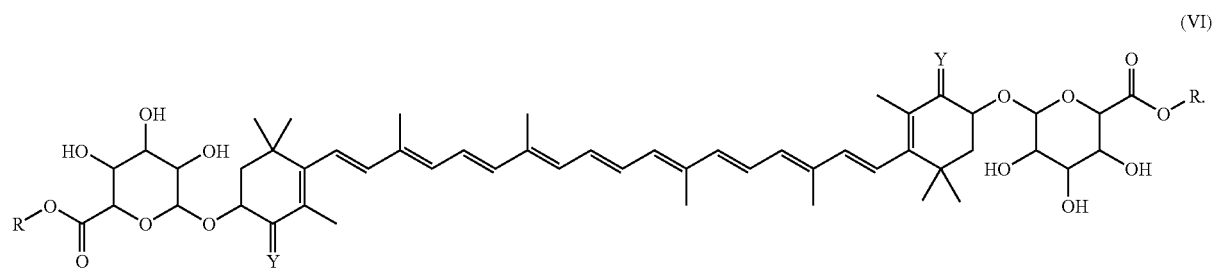

(VI)

Each Y may be independently O or $H_2$. Each R may be independently H, alkyl, or aryl. The carotenoid derivative may include at least one chiral center. In a specific embodiment Y may be $H_2$, the carotenoid derivative having the structure (VII)

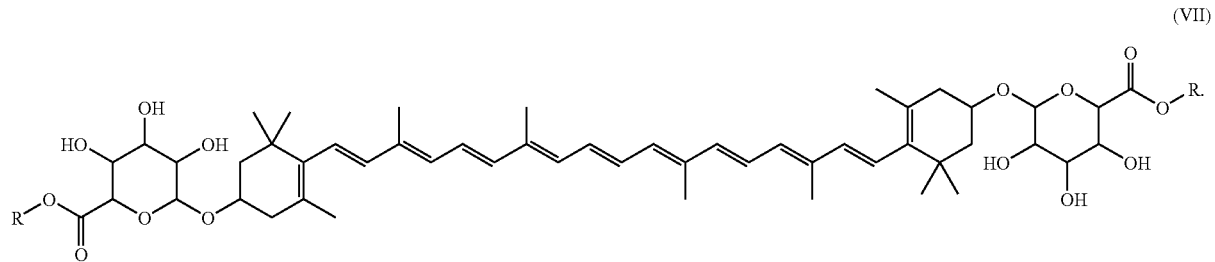

(VII)

In a specific embodiment where Y is O, the carotenoid derivative has the structure (VIII)

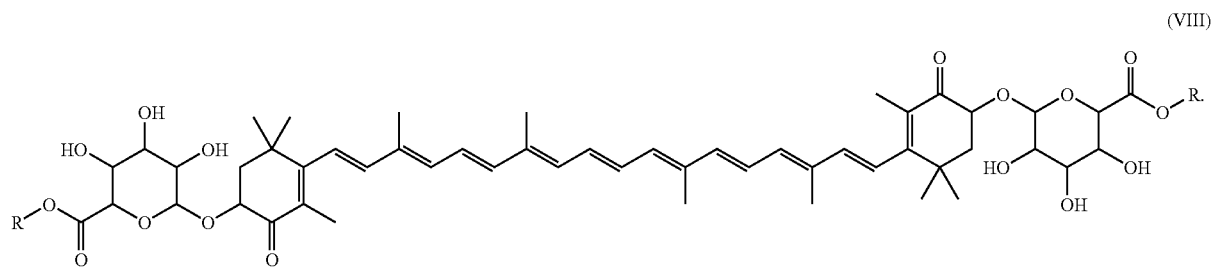

(VIII)

In an embodiment, a chemical compound may include a carotenoid derivative having the structure (IX)

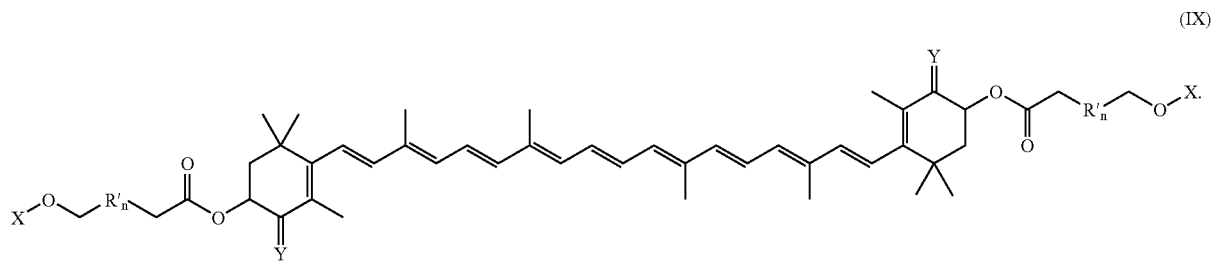

(IX)

Each Y may be independently O or $H_2$. Each R' may be $CH_2$. n may be 1 to 9. Each X may be independently

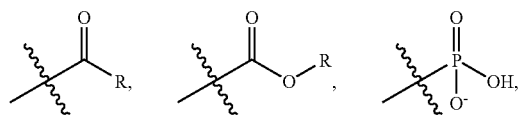

-continued

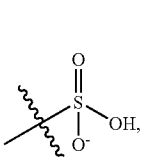

or

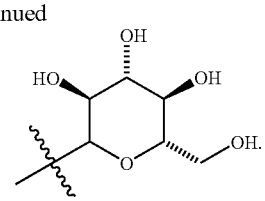

Each R may be independently -alkyl-$NR^1_3{}^+$, -aromatic-$NR^1_3{}^+$, -alkyl-$CO_2{}^-$, -aromatic-$CO_2{}^-$, -amino acid-$NH_3{}^-$, -phosphorylated amino acid-$NH_3{}^+$, polyethylene glycol, dextran, H, alkyl, or aryl. Each $R^1$ may be independently H, alkyl, or aryl. The carotenoid derivative may include at least one chiral center.

In a specific embodiment where Y is $H_2$, the carotenoid derivative has the structure (X)

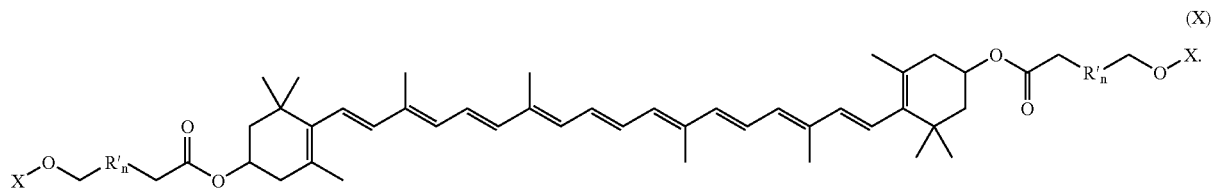

(X)

In a specific embodiment where Y is O, the carotenoid derivative has the structure (XI)

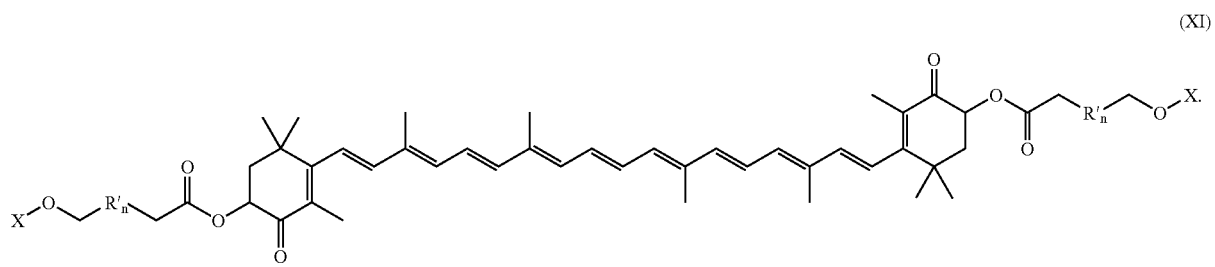

(XI)

In an embodiment, a chemical compound may include a carotenoid derivative having the structure (XII)

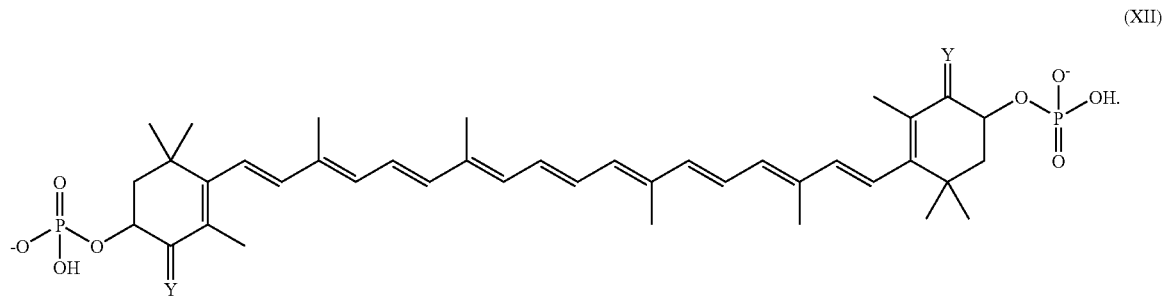

(XII)

Each Y may be independently O or $H_2$. The carotenoid derivative may include at least one chiral center. In a specific embodiment Y may be $H_2$, the carotenoid derivative having the structure (XIII)

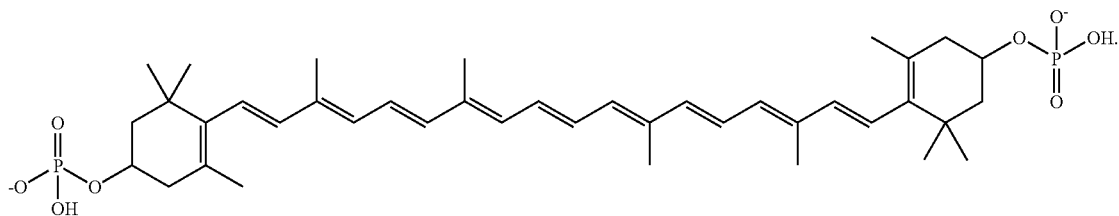
(XIII)
In a specific embodiment where Y is O, the carotenoid derivative has the structure (XIV)
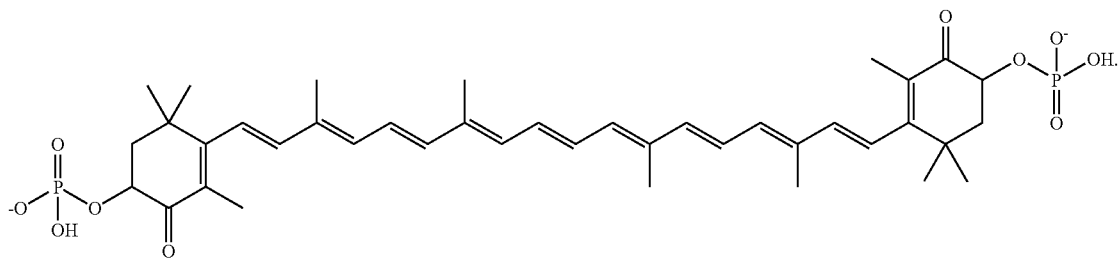
(XIV)
In some embodiments, a chemical compound may include a disuccinic acid ester carotenoid derivative having the structure (XV)
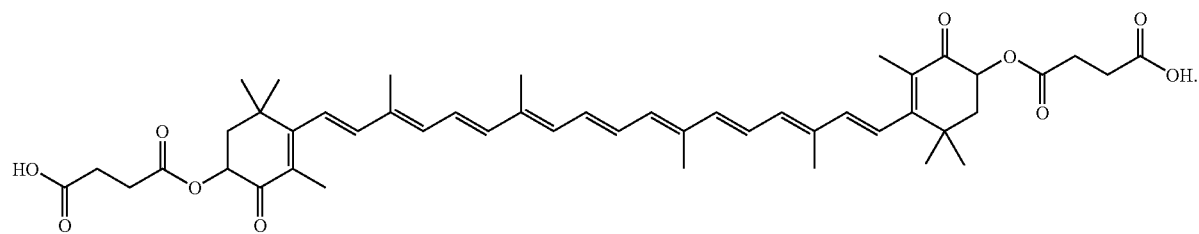
(XV)

In some embodiments, a chemical compound may include a disodium salt disuccinic acid ester carotenoid derivative having the structure (XVI)

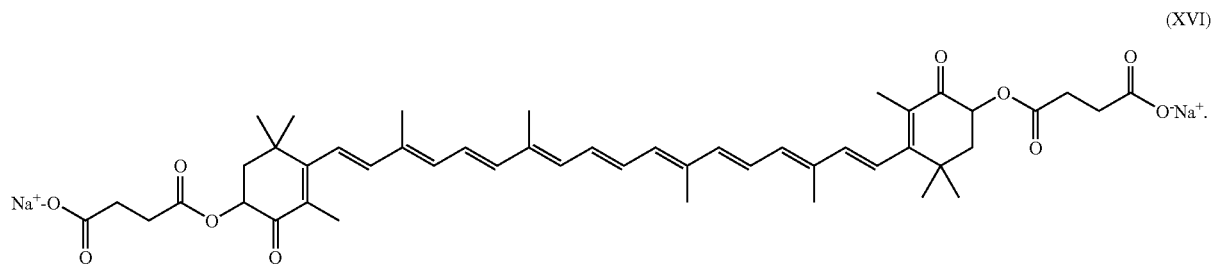

(XVI)

In some embodiments, a chemical compound may include a carotenoid derivative with a co-antioxidant, in particular one or more analogs or derivatives of vitamin C (i.e., L ascorbic acid) coupled to a carotenoid. Some embodiments may include carboxylic acid and/or carboxylate derivatives of vitamin C coupled to a carotenoid (e.g., structure (XVII))

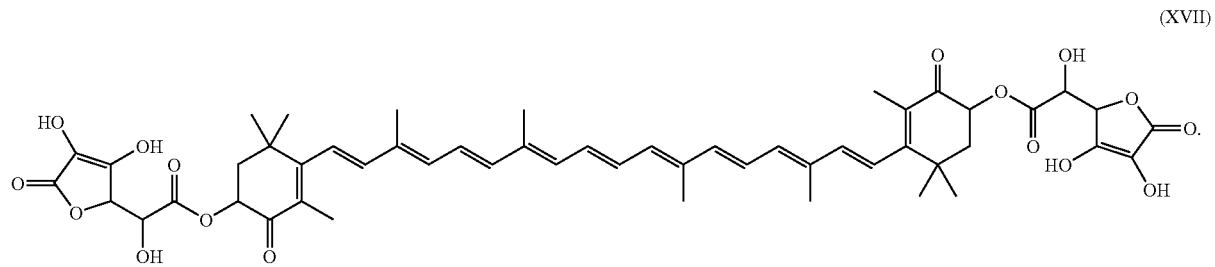

(XVII)

*Carbohydr. Res.* 1978, 60, 251-258, herein incorporated by reference, discloses oxidation at C-6 of ascorbic acid as depicted in EQN. 5.

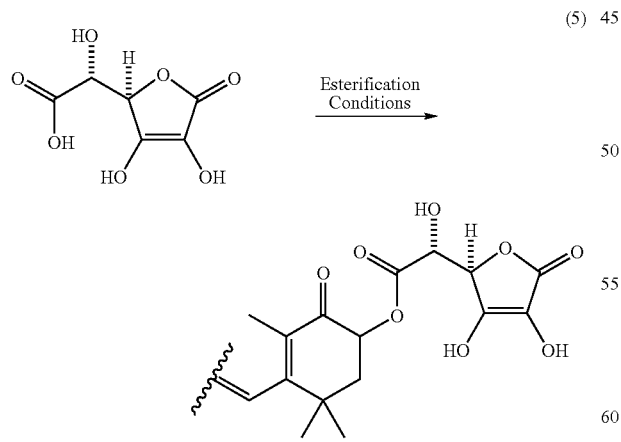

(5)

Some embodiments may include vitamin C and/or Vitamin C analogs or derivatives coupled to a carotenoid. Vitamin C may be coupled to the carotenoid via an ether linkage (e.g., structure (XVIII))

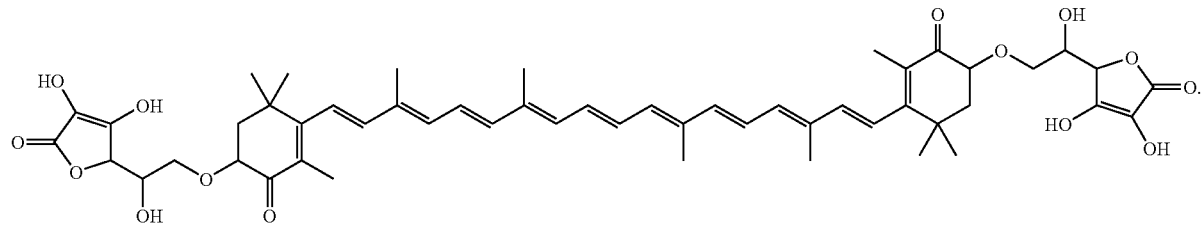

(XVIII)

Some embodiments may include vitamin C disuccinate analogs or derivatives coupled to a carotenoid) e.g., structure (XIX))

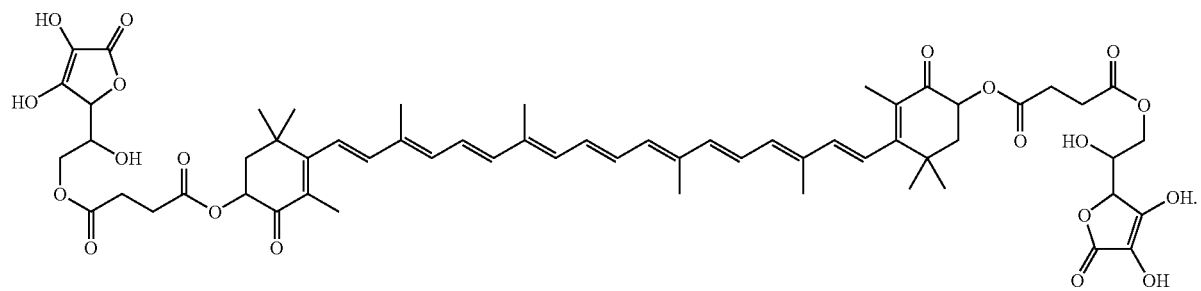

(XIX)

Some embodiments may include solutions or pharmaceutical preparations of carotenoids and/or carotenoid derivatives combined with co-antioxidants, in particular vitamin C and/or vitamin C analogs or derivatives. Pharmaceutical preparations may include about a 2:1 ratio of vitamin C to carotenoid respectively.

In some embodiments, co-antioxidants (e.g., vitamin C) may increase solubility of the chemical compound. In certain embodiments, co-antioxidants (e.g., vitamin C) may decrease toxicity associated with at least some carotenoid analogs or derivatives. In certain embodiments, co-antioxidants (e.g., vitamin C) may increase the potency of the chemical compound synergistically. Co-antioxidants may be coupled to a carotenoid derivative. Co-antioxidants may coupled (e.g., a covalent bond) to the carotenoid derivative. Co-antioxidants may be included as a part of a pharmaceutically acceptable formulation.

In some embodiments, a carotenoid (e.g., astaxanthin) may be coupled to vitamin C forming an ether linkage. The ether linkage may be formed using the Mitsunobu reaction as in EQN. 1.

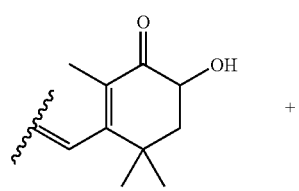

(1)

-continued

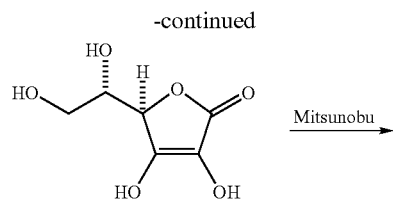

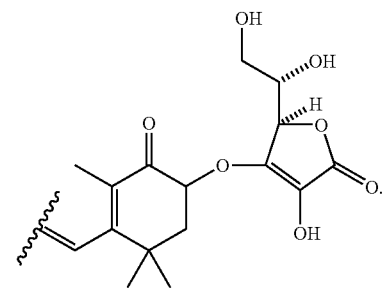

In some embodiments, vitamin C may be selectively esterified. Vitamin C may be selectively esterified at the C-3 position (e.g., EQN. 2). *J. Org. Chem.* 2000, 65, 911-913, herein incorporated by reference, discloses selective esterification at C-3 of unprotected ascorbic acid with primary alcohols.

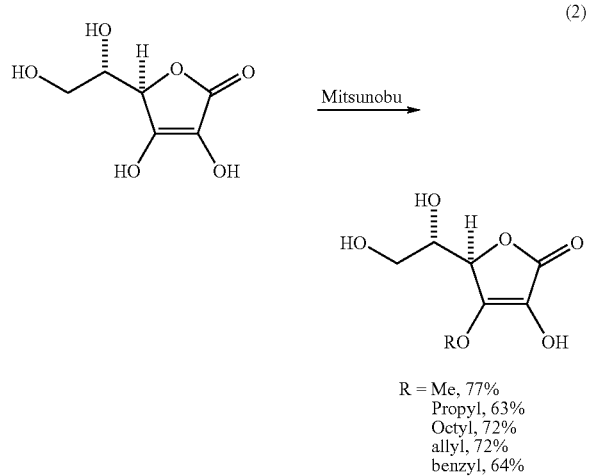

(2)

R = Me, 77%
Propyl, 63%
Octyl, 72%
allyl, 72%
benzyl, 64%

In some embodiments, a carotenoid may be coupled to vitamin C. Vitamin C may be coupled to the carotenoid at the C-6, C-5 diol position as depicted in EQNS. 3 and 4 forming an acetal.

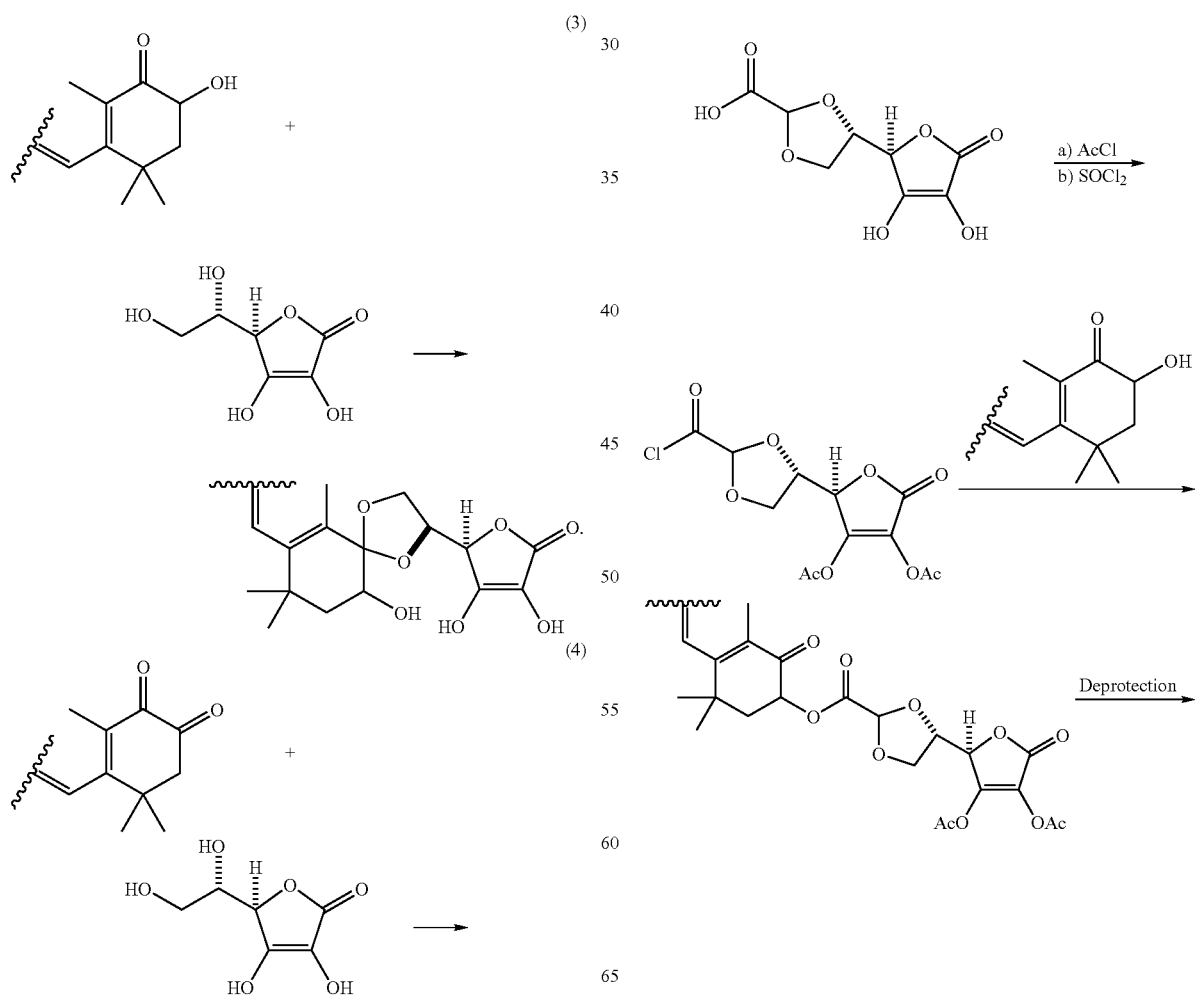

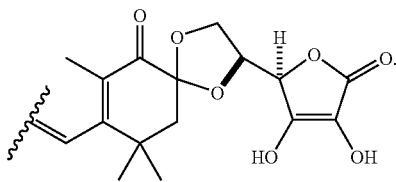

In some embodiments, a carotenoid may be coupled to a water soluble moiety (e.g., vitamin C) with a glyoxylate linker as depicted in EQN. 6. *Tetrahedron* 1989, 22, 6987-6998, herein incorporated by reference, discloses similar acetal formations.

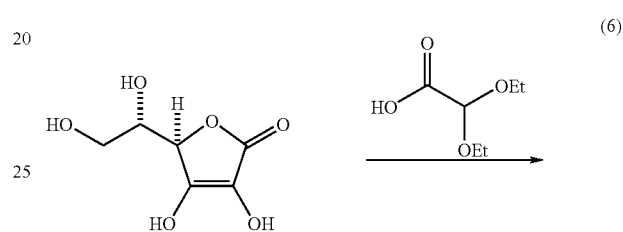

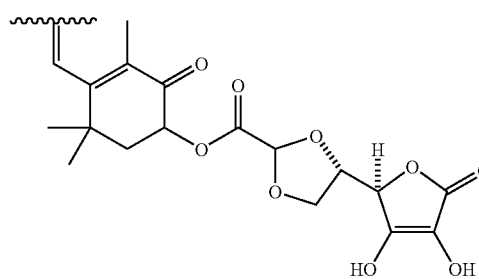

In some embodiments, a carotenoid may be coupled to a water soluble moiety (e.g., vitamin C) with a glyoxylate linker as depicted in EQN. 7. *J. Med. Chem.* 1988, 31, 1363-1368, herein incorporated by reference, discloses the glyoxylic acid chloride.

(7)

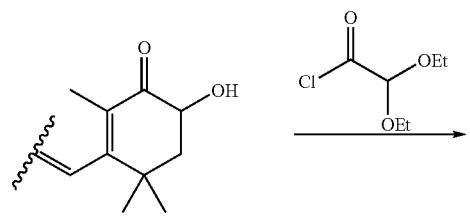

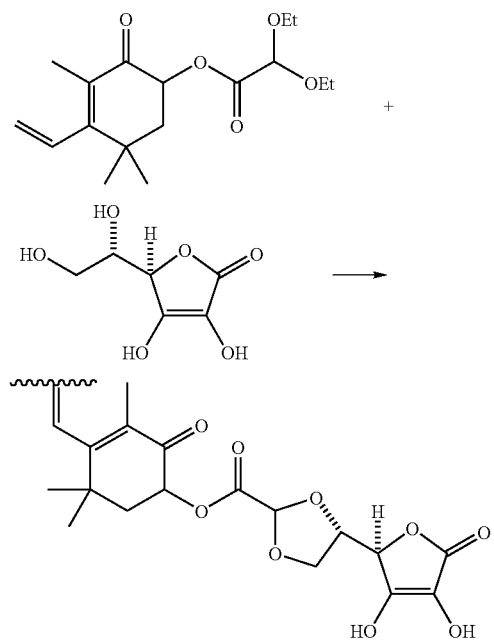

In some embodiments, a carotenoid may be coupled to a water soluble moiety (e.g., vitamin C) with a phosphate linker as depicted in EQN. 8. *Carbohydr. Res.* 1988, 176, 73-78, herein incorporated by reference, discloses the L-ascorbate 6-phosphate.

(8)

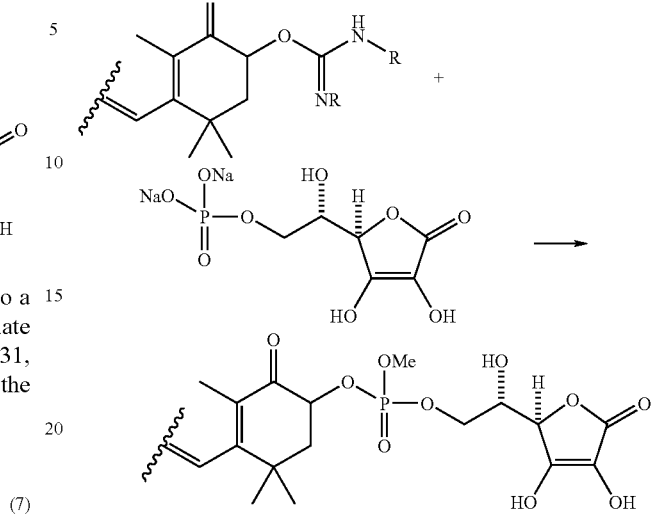

In some embodiments, a carotenoid may be coupled to a water soluble moiety (e.g., vitamin C) with a phosphate linker as depicted in EQN. 9. *Carbohydr. Res.* 1979, 68, 313-319, herein incorporated by reference, discloses the 6-bromo derivative of vitamin C. *Carbohydr. Res.* 1988, 176, 73-78, herein incorporated by reference, discloses the 6-bromo derivative of vitamin C's reaction with phosphates.

(9)

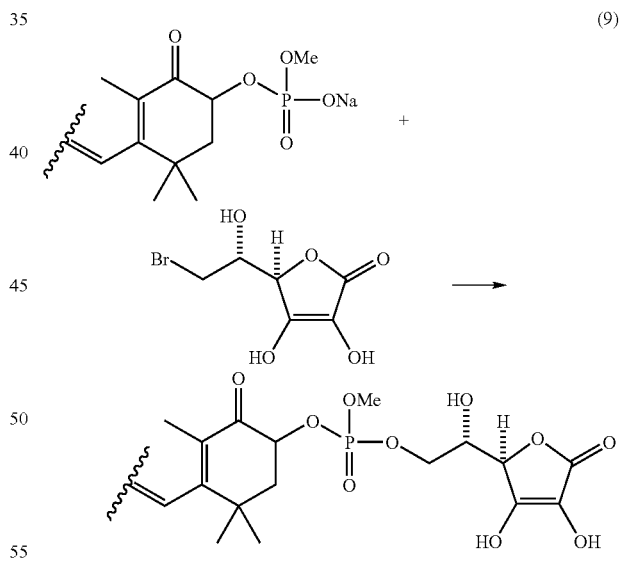

In some embodiments, a carotenoid may be coupled to a water soluble moiety (e.g., vitamin C) with a phosphate linker as depicted in EQN. 10. *J. Med. Chem.* 2001, 44, 1749-1757 and *J. Med. Chem.* 2001, 44, 3710-3720, herein incorporated by reference, disclose the allyl chloride derivative and its reaction with nucleophiles, including phosphates, under mild basic conditions.

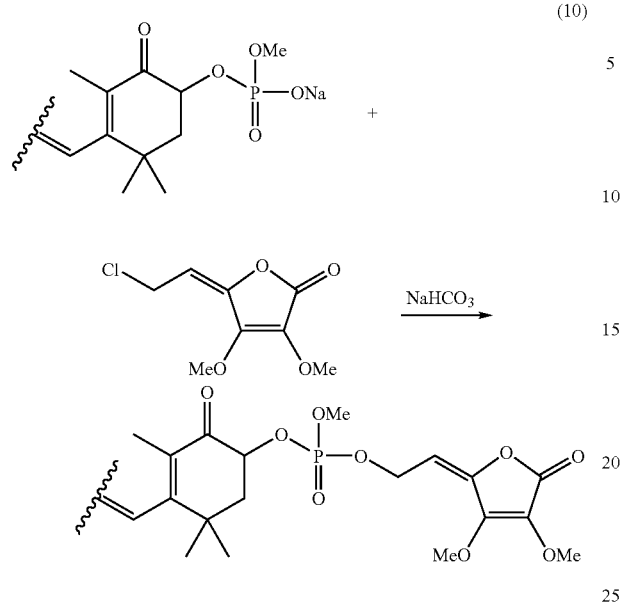

(10)

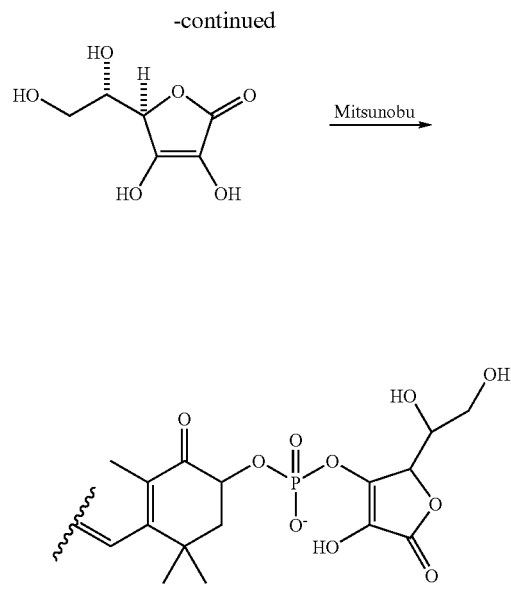

In some embodiments, a carotenoid may be coupled to a water soluble moiety (e.g., vitamin C) with a phosphate linker as depicted in EQN. 11. Vitamin C may be coupled to the carotenoid using selective esterification at C-3 of unprotected ascorbic acid with primary alcohols.

In some embodiments, a carotenoid may be coupled to a water soluble moiety (e.g., vitamin C) with a phosphate linker as in LXVII. Structure LXVII may include one or more counterions (e.g., alkali metals).

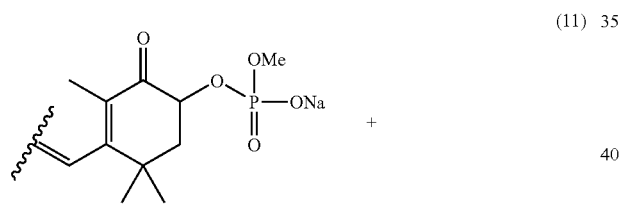

(11)

LXVII

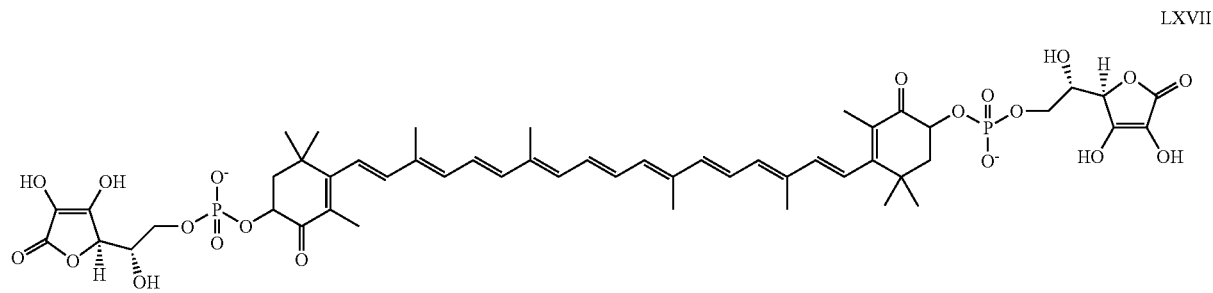

EQN. 12 depicts an example of a synthesis of a protected form of LXVII.

(12)
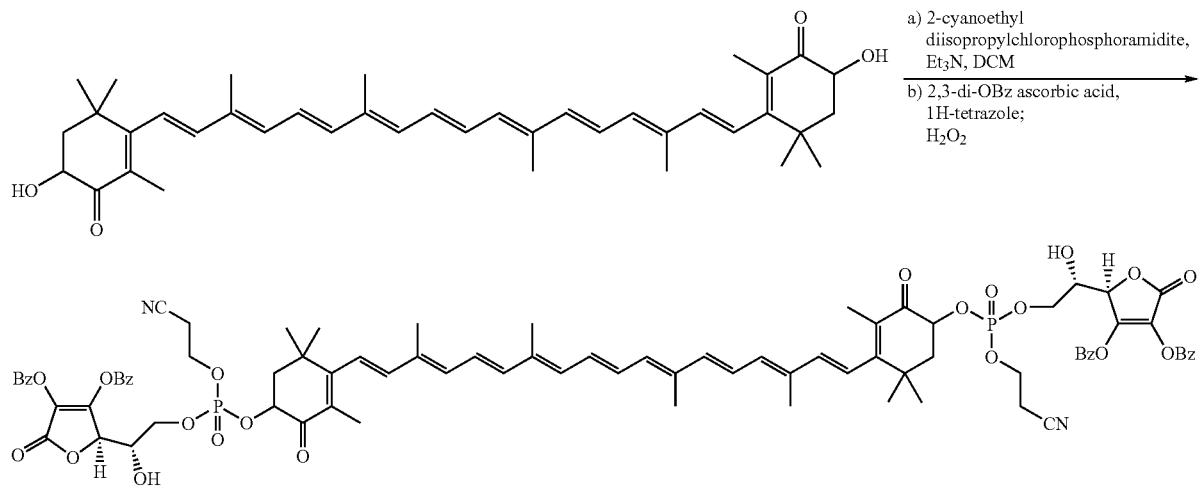
In some embodiments, a chemical compound may include a carotenoid derivative including one or more amino acids (e.g., lysine) and/or amino acid analogs or derivatives (e.g., lysine hydrochloric acid salt) coupled to a carotenoid [e.g., structure (XX)].
(XX)
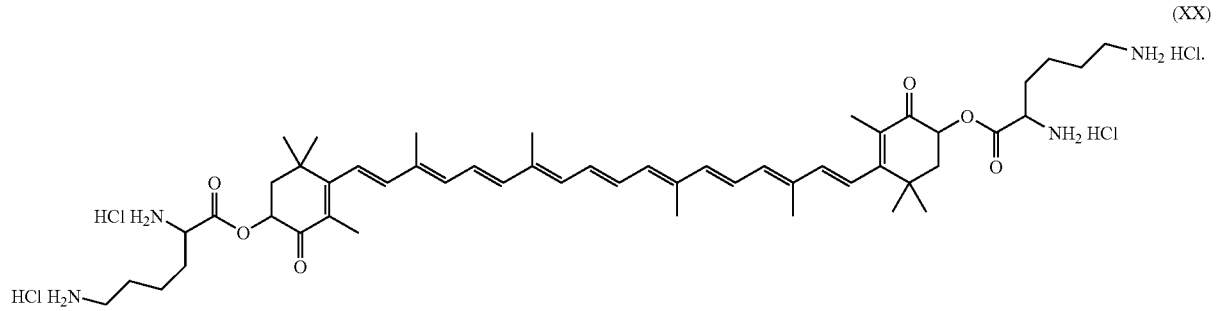
In some embodiments, a carotenoid analog or derivative may include:
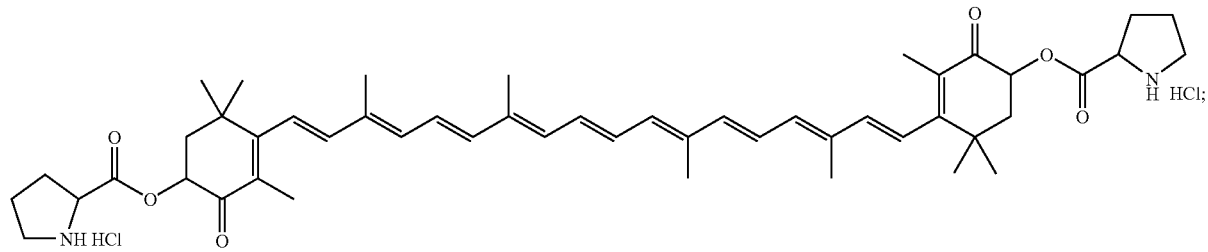

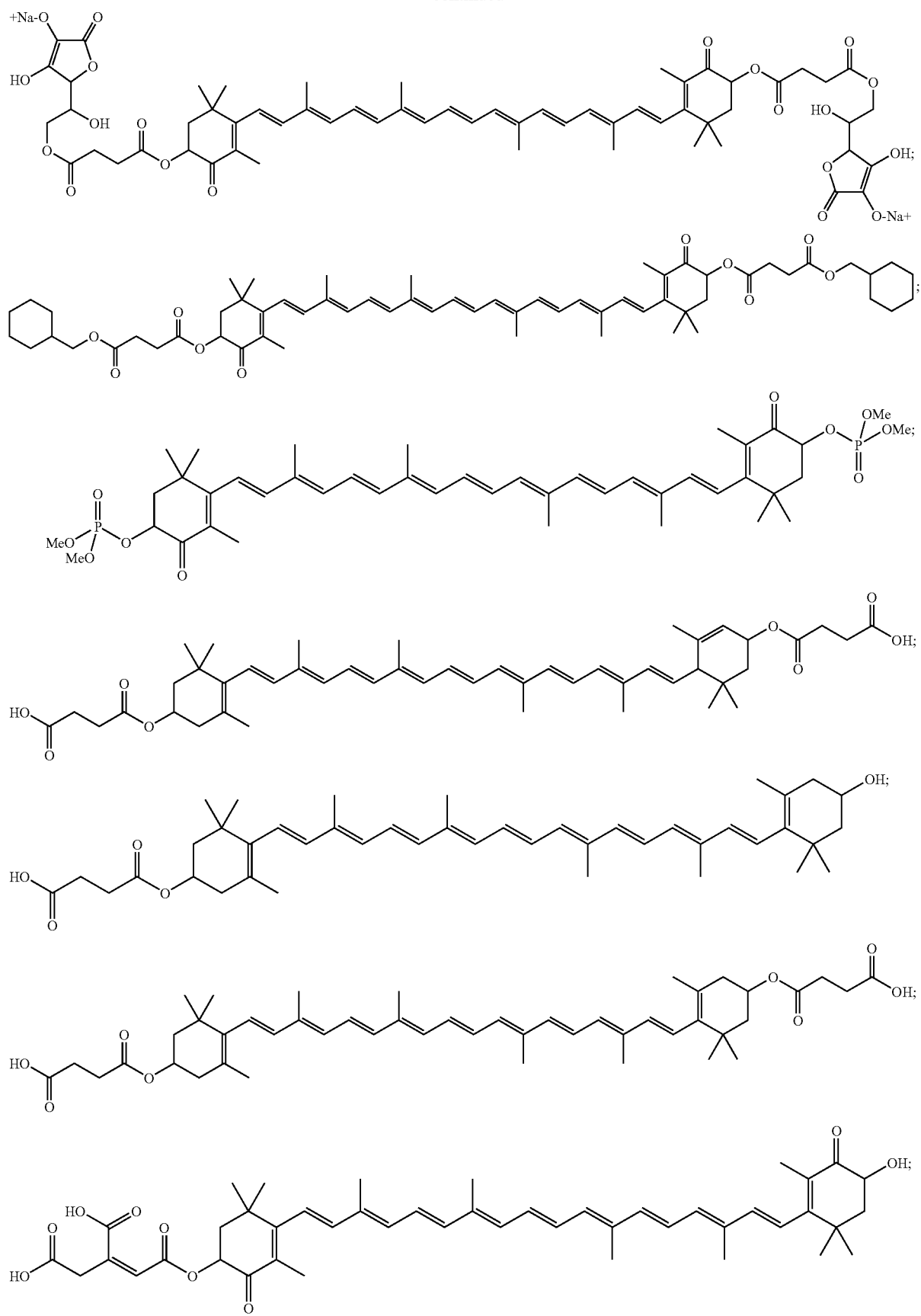

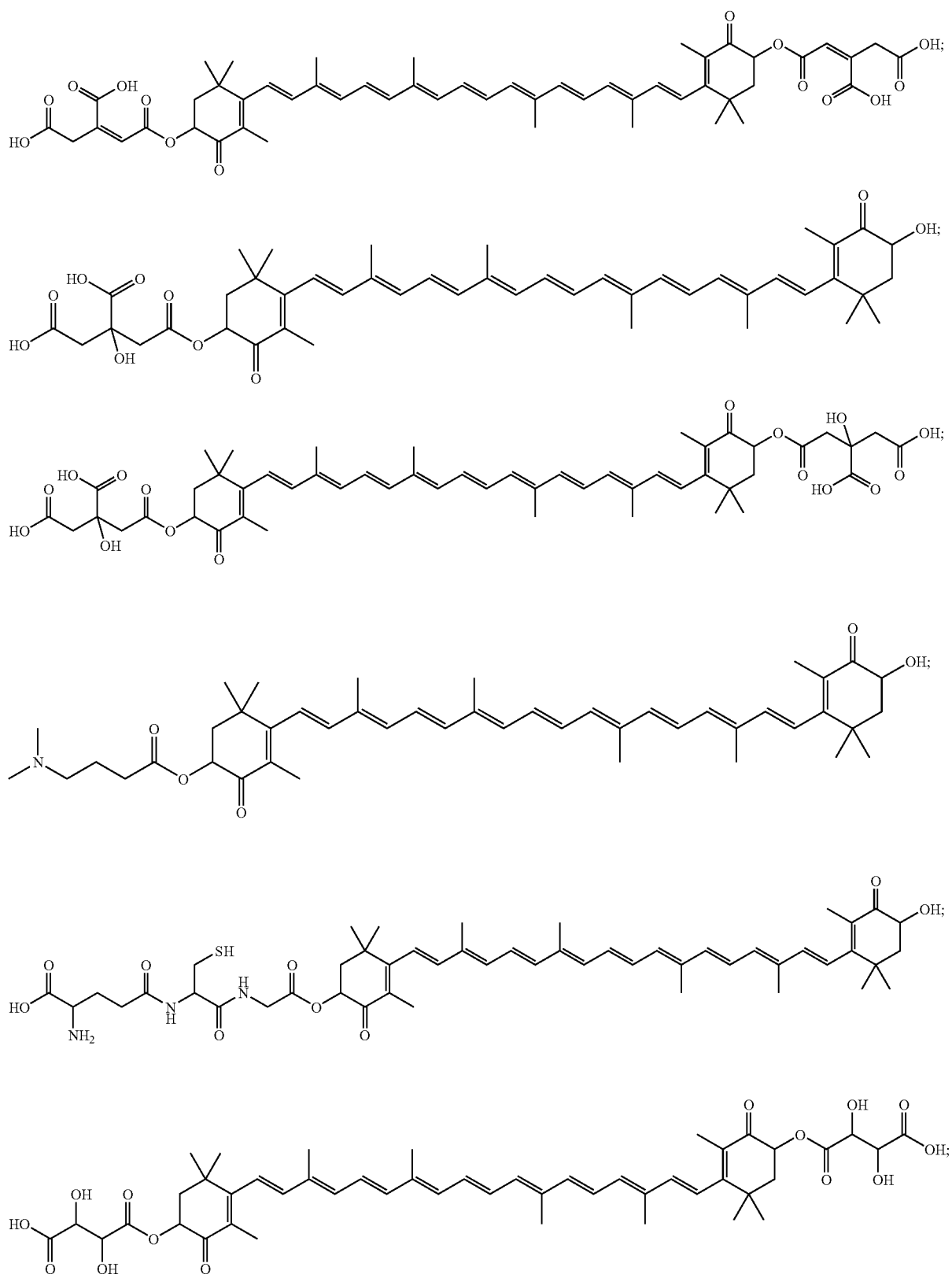

-continued
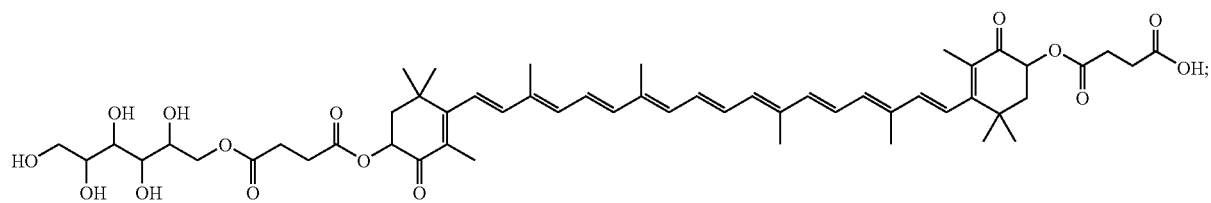
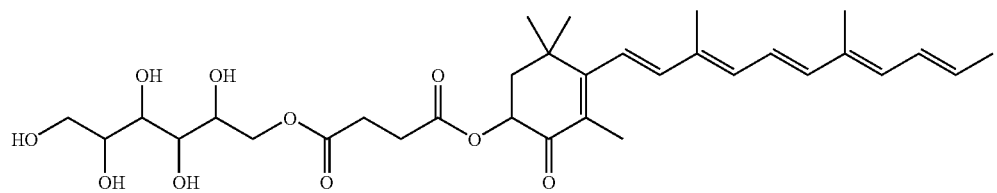
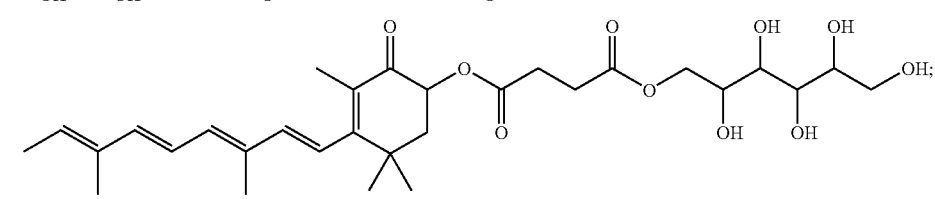
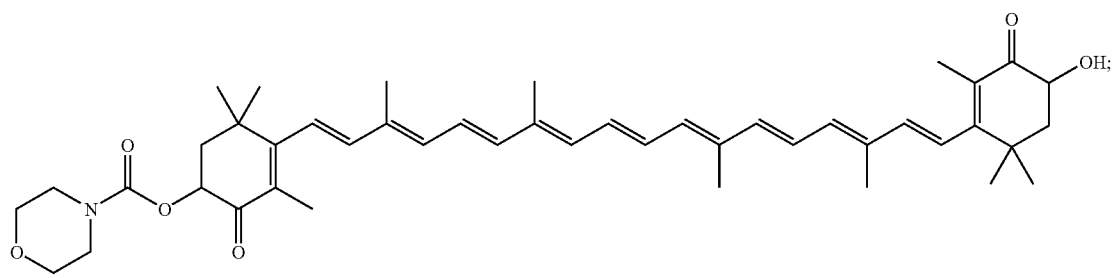
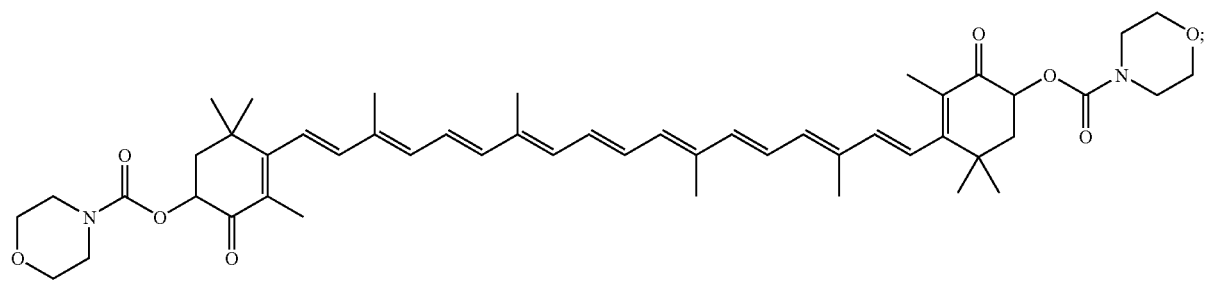
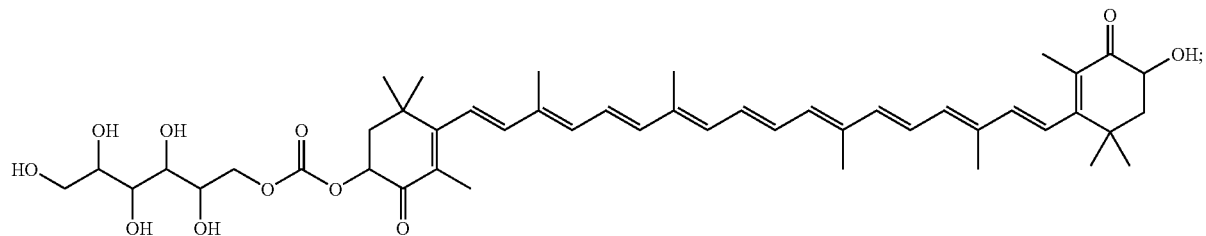

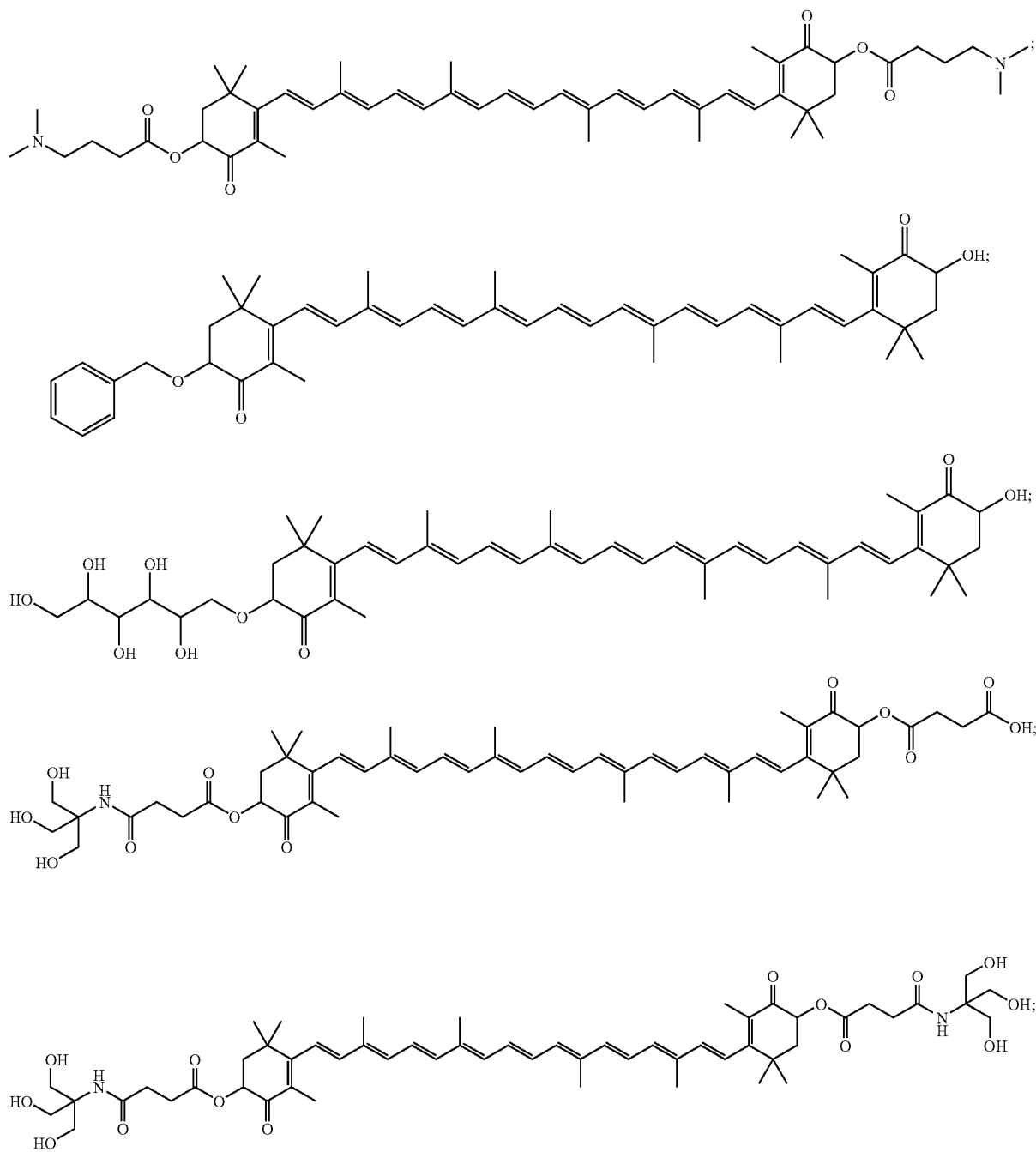

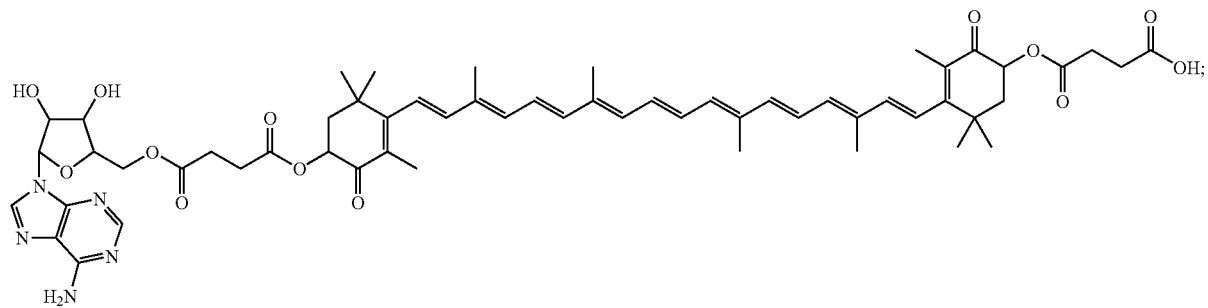
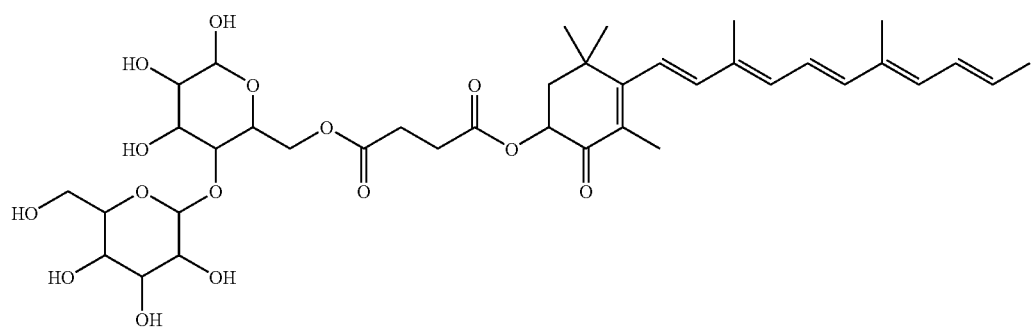
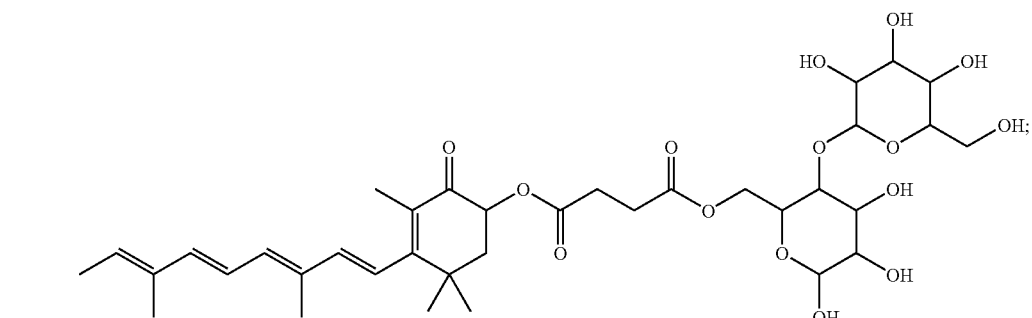
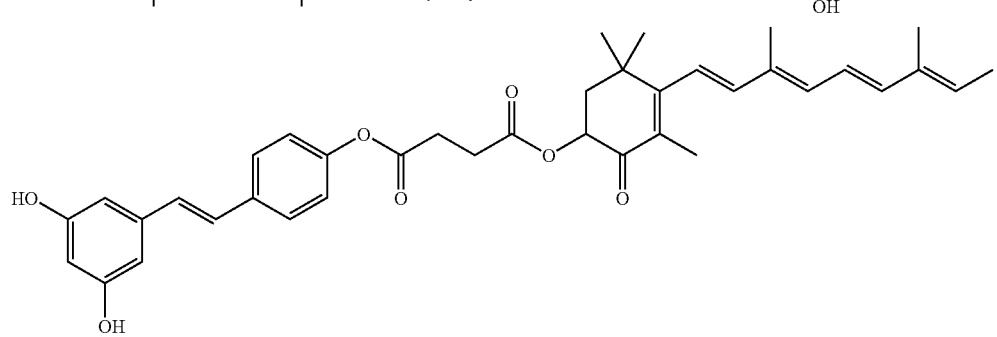
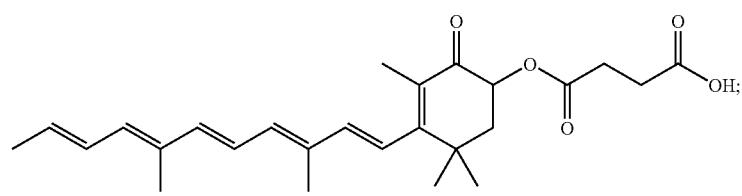

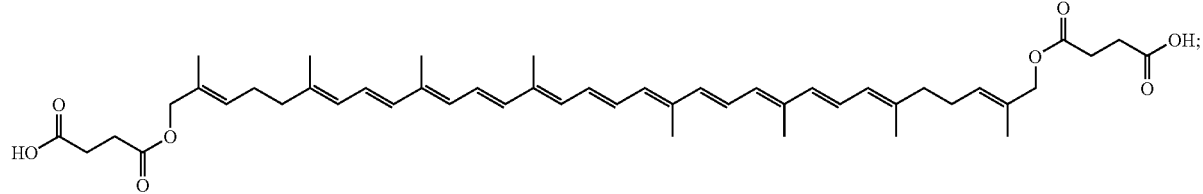
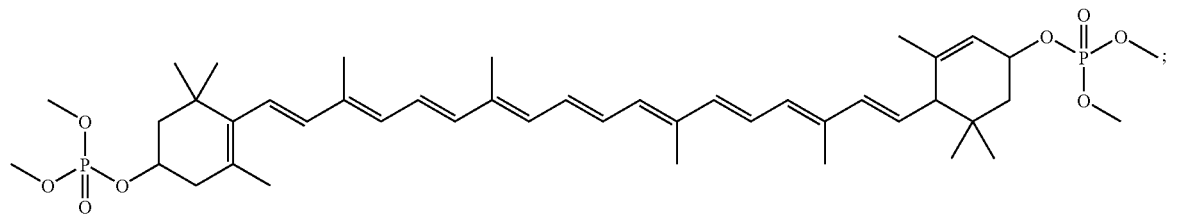
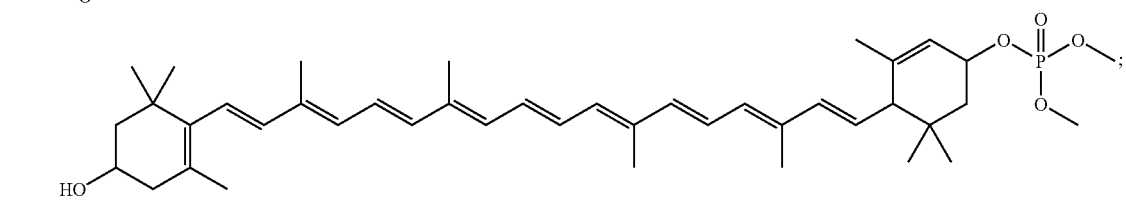
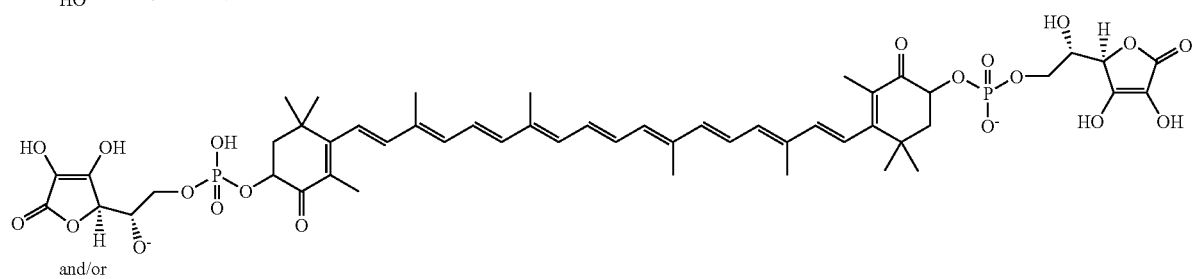
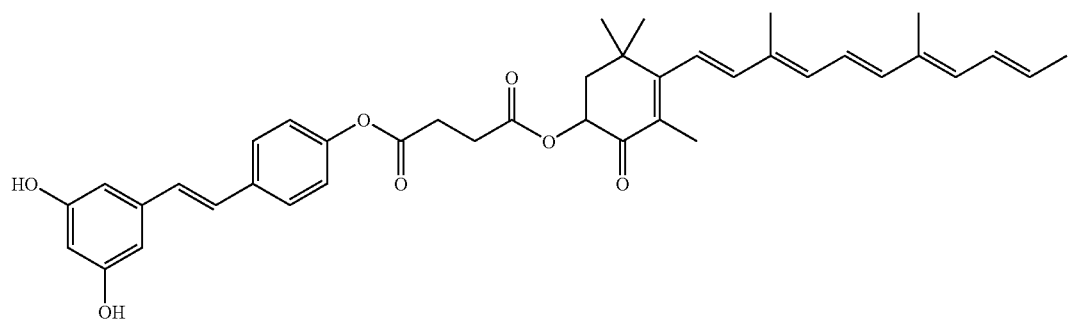
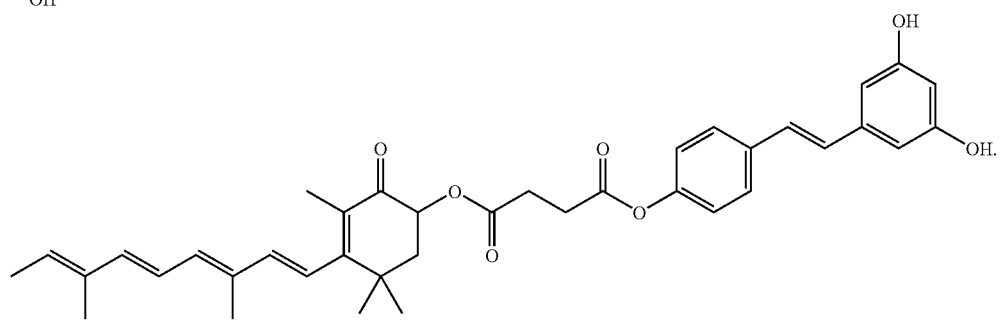
In an embodiment, the carotenoid derivatives may be synthesized from naturally occurring carotenoids. The carotenoids may include structures 2A-2E depicted in FIG. 1. In some embodiments, the carotenoid derivatives may be synthesized from a naturally occurring carotenoid including one or more alcohol substituents. In other embodiments, the carotenoid derivatives may be synthesized from a derivative of a naturally occurring carotenoid including one or more alcohol substituents. The synthesis may result in a single stereoisomer. The synthesis may result in a single geometric isomer of the carotenoid derivative. The synthesis/synthetic sequence may include any prior purification or isolation steps carried out on the parent carotenoid. The synthesis may be a total synthesis. An example may include, but is not limited to, a 3S,3'S all-E carotenoid derivative, where the parent carotenoid is astaxanthin. The synthetic sequence may include protecting and subsequently deprotecting various functionalities of the carotenoid and/or substituent precursor. The alcohols may be deprotonated with a base. The deprotonated alcohol may be reacted with a substituent precursor with a good leaving group. The base may include any non-nucleophilic base known to one skilled in the art such as, for example, dimethylaminopyridine (DMAP). The deprotonated alcohol may act as a nucleophile reacting with the substituent precursor, displacing the leaving group.

Leaving groups may include, but are not limited to, Cl, Br, tosyl, brosyl, mesyl, or trifyl. These are only a few examples of leaving groups that may be used, many more are known and would be apparent to one skilled in the art. In some embodiments, it may not even be necessary to deprotonate the alcohol, depending on the leaving group employed. In other examples the leaving group may be internal and may subsequently be included in the final structure of the carotenoid derivative, a non-limiting example may include anhydrides or strained cyclic ethers. For example, the deprotonated alcohol may be reacted with succinic anhydride. In an embodiment, the disuccinic acid ester of astaxanthin may be further converted to the disodium salt. Examples of synthetic sequences for the preparation of some of the specific embodiments depicted are described in the Examples section. The example depicted below is a generic non-limiting example of a synthetic sequence for the preparation of carotenoid derivatives.

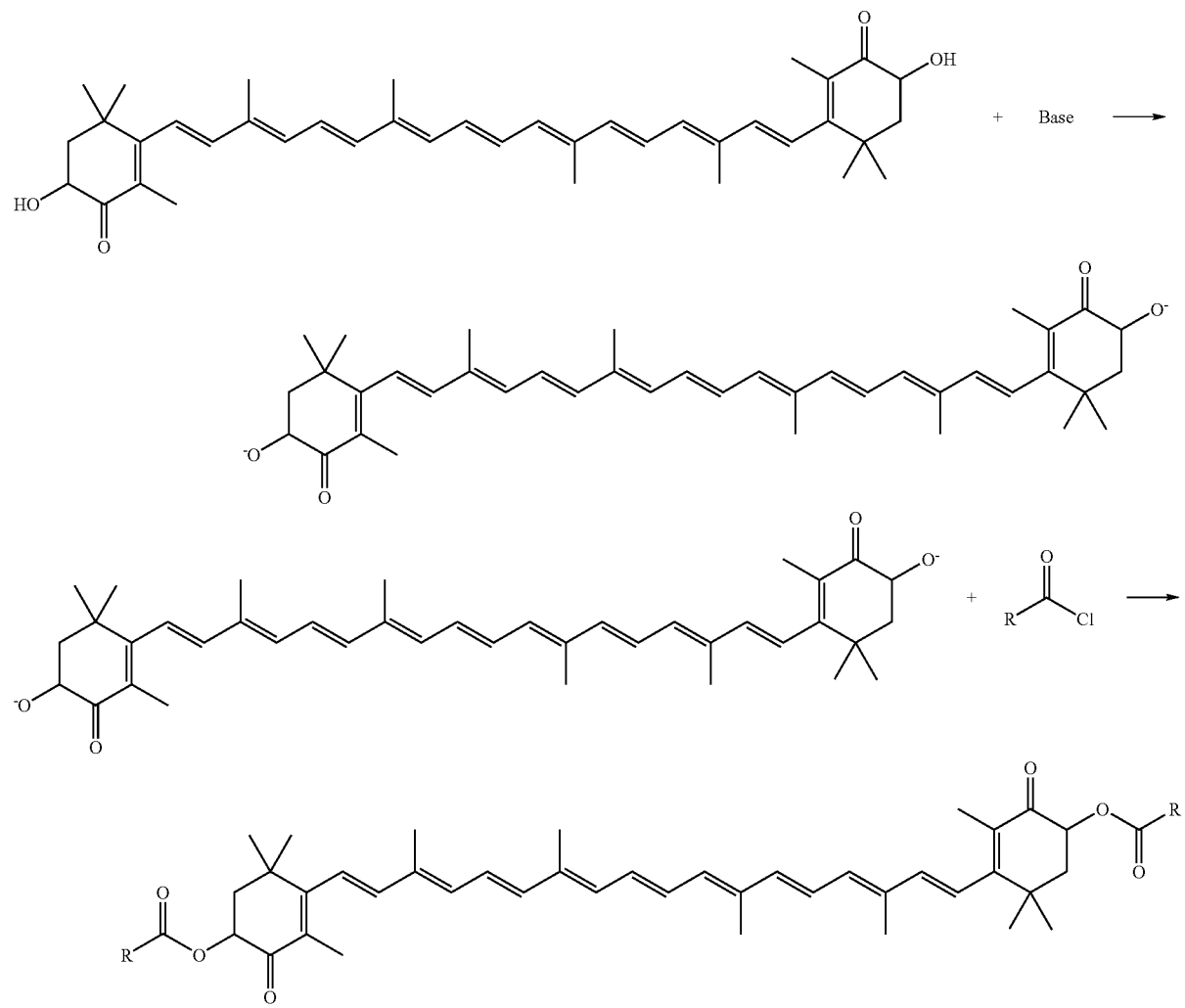

Ischemia-Reperfusion (I/R) Injury: Pathophysiologic Features

Reperfusion of ischemic myocardium results in significant cellular and local alterations in at-risk tissue which exacerbate damage created by the ischemic insult. Specifically, vascular and microvascular injury, endothelial dysfunction, accelerated cellular necrosis, and granulocyte activation occur subsequent to ischemia-reperfusion. Vascular and microvascular injury results from complement activation, the interaction of circulating and localized C-reactive protein with C1q and phosphocholine on exposed cells forming the membrane attack complex (MAC) with ensuing cell death and increased endothelial permeability, superoxide anion ($O_2$—) generation by affected endothelium and activated leukocytes, microemboli, cytokine release (in particular IL-6), and activation of platelets with IIb-IIIa receptor activation, and subsequent release of ADP and serotonin. Endothelial dysfunction follows, with subsequent generation of superoxide anion by the dysfunctional endothelium, further damaging the affected endothelium in a positive feedback cycle. It has been shown that ischemia-reperfusion results in early and severe injury to the vasculature, which further compromises myocyte survival. Granulocyte activation also occurs during ischemia-reperfusion. The activation and degranulation of this cell lineage results in the release of myeloperoxidase (MPO), elastases, proteases, and oxygen-derived radical and non-radical species (most importantly superoxide anion, hypochlorite, singlet oxygen, and hydrogen peroxide after the "respiratory burst"). Oxygen-derived radical and non-radical (e.g. singlet oxygen) species are implicated in much of the damage associated with ischemia and reperfusion, and lipid peroxidation has clearly been shown to be a sequel of reperfusion as measured by thiobarbituric acid reactive substances (TBARS), malondialdehyde (MDA), or conjugated diene formaton.

The ischemic insult to both the endothelium of coronary vessels and the myocardium itself creates conditions favoring the production of radicals and other non-radical oxygen-derived species capable of damaging tissue herein collectively referred to as reactive oxygen species ("ROS"). The endothelium-based xanthine dehydrogenase-xanthine oxidase system in humans is a source of the superoxide anion ($O_2$—). The human myocardium lacks this enzyme system. In healthy tissue, 90% of the enzyme exists as the dehydrogenase (D) form; it is converted to the oxidase (O) form in ischemic tissue. The (O)-form, using molecular oxygen as the electron acceptor, produces the superoxide anion $O_2$— in the coronary endothelium. Superoxide anion is then available to create additional tissue damage in the local environment. The superoxide anion is not the most reactive or destructive radical species in biological systems on its own. However, it is the source of some shorter- and longer-lived, more damaging radicals and/or ROS such as the hydroxyl radical, hydrogen peroxide, singlet oxygen, and peroxyl radicals (e.g. peroxynitrite). As such, it can be considered the "lynchpin" radical in I/R injury. The biological reactions of the superoxide radical to form these important oxidants are shown below:

(1) superoxide anion may accept a single electron ("monovalent reduction"), producing peroxide ($O_2^{-2}$). Coupled with 2 protons, peroxide then forms hydrogen peroxide ($H_2O_2$). $H_2O_2$ diffuses easily through cell membranes and cannot readily be excluded from the cytoplasm, where it may react with cellular components or activate central inflammatory cascades such as nuclear factor kappa-B (NF-kappa-B), which are also implicated in the additional inflammatory damage in I/R injury.

(2) superoxide anion typically reacts with itself to produce hydrogen peroxide and oxygen ("dismutation"). Superoxide dismutation may be spontaneous, or catalyzed by the enzyme superoxide dismutase (SOD), a reaction which results in the formation of oxidized SOD:

$$2O_2^- + 2H^+ \rightarrow H_2O_2 + {}^3O_2$$

(3) superoxide anion may serve as a reducing agent and donate a single electron ("monovalent reduction") to a metal cation. For example, in the two step process below, ferric iron ($Fe^{3+}$) is reduced and subsequently acts as a catalyst to convert hydrogen peroxide ($H_2O_2$) into the hydroxyl radical (HO.).

$$O_2^- + Fe^{3+} \rightarrow {}^3O_2 + Fe^{2+} \quad \text{(step 1)}$$

Ferrous iron ($Fe^{2+}$), the reduced metal cation, subsequently catalyzes the breaking of the oxygen-oxygen bond of hydrogen peroxide. This produces one hydroxyl radical (HO.) and one hydroxide ion ($HO^-$). The reaction is known as the Fenton reaction, particularly important in ischemia-reperfusion injury where iron and/or copper compartmentalization has been lost (typically through hemolysis of red blood cells, RBCs):

$$Fe^{2+} + H_2O_2 \rightarrow Fe^{3+} + HO. + HO^- \quad \text{(step 2)}$$

Hydroxyl radicals readily cross cellular membranes. Hydroxyl radical damage is "diffusion rate-limited", that is, the 3-dimensional distance in which damage may beinflicted is related to the radical's rate of diffusion. The hydroxyl radical is a particularly toxic ROS. Hydroxyl radicals may add to organic substrates (represented by R in the reaction below) and form a hydroxylated adduct which is itself a radical. In the case of ischemia-reperfusion injury, polyunsaturated fatty acids (PUFAs) in endothelial and myocyte membranes are particularly susceptible to hydroxyl radical damage:

$$HO. + R \rightarrow HOR. \text{(hydroxylated adduct)}$$

The adduct formed above may further oxidize in the presence of metal cations or molecular oxygen. This results in oxidized, stable product(s). In the first case, the extra electron is transferred to the metal ion, and in the second case, to oxygen (forming superoxide). Two adduct radicals may also react with each other forming oxidized, stable, and crosslinked products plus water. This is an important process in the oxidation of membrane proteins:

$$HOR. + HOR. \rightarrow R\text{—}R + 2H_2O$$

In addition, hydroxyl radicals may oxidize organic substrates by abstracting electrons from such molecules:

$$HO. + R \rightarrow R. + OH^-$$

The oxidized substrate (R.) is a radical. Such radicals may react with other molecules in a chain reaction. Carotenoids are particularly efficient lipid-peroxidation chain breakers. In one instance, the reaction with ground-state oxygen produces peroxyl radicals (ROO.):

$$R. + {}^3O_2 \rightarrow ROO.$$

Peroxyl radicals are very reactive. They may react with other organic substrates in a chain reaction:

$$ROO. + RH \rightarrow ROOH + R.$$

Chain reactions are common in the oxidative damage of PUFAs and other susceptible membrane lipids. Measurement of the rate of oxygen consumption is one indication of the initiation and progress of the chain reaction. It is important to note that, in liposomal model systems, non-esterified, free astaxanthin at the appropriate dose is capable of complete suppression of the chain reaction and accompanying oxygen consumption.

(4) superoxide anion may react with the hydroxyl radical (HO.) to form singlet oxygen ($^1O_2^*$). Singlet oxygen is not a radical, but is highly reactive and damaging in cardiac biological systems. Singlet oxygen has been implicated in the destruction of membrane-bound proteins such as 5'-nucleotidase, important in the maintenance or restoration of local concentrations of vasodilatory compounds such as adenosine (shown to be effective in humans for reduction of infarct size):

$$O_2^- + HO. \rightarrow {}^1O_2^* + HO^-$$

(5) superoxide anion may also react with the radical nitric oxide (NO.), producing peroxynitrite (OONO$^-$). Peroxynitrite is a highly reactive and damaging molecule in biological systems.

$$O_2^- + NO. \rightarrow OONO^-$$

Polymorphonuclear leukocytes (PMNs), in particular neutrophils, and activated macrophages are a rich source of oxygen-derived radical and non-radical species. The NADPH-oxidase system located in phagocyte cell membranes is an important source of radicals following stimulation. The PMNs and activated macrophages rapidly consume oxygen in the "respiratory burst" and convert it to superoxide anion and subsequently hydrogen peroxide ($H_2O_2$), as well as significant amounts of singlet oxygen. PMNs are additionally a source of hypochlorite, another damaging reactive oxygen species. While important in phagocytic cell activity in infection, in the local environment during ischemia and reperfusion, further cellular injury occurs as these ROS attack normal and damaged host cells in the local area.

Neutrophils are a primary source of oxygen radicals during ischemia-reperfusion after prolonged myocardial ischemia, particularly in animal models of experimental infarction. Many prior studies have documented oxygen radical formation during ischemia-reperfusion, but few addressed the source(s) of such radicals in vivo, or had examined radical generation in the context of prolonged myocardial ischemia. Neutrophils are recruited in large amounts within the previously ischemic tissue and are thought to induce injury by local release of various mediators, chiefly oxygen radicals. Previously, the contribution of activated neutrophils to ischemia-reperfusion injury and potential myocardial salvage remained unclear. A methodology was developed to detect radicals, in particular superoxide anion, without interfering with the blood-borne mechanisms of radical generation.

Open- and closed-chest dogs underwent aorta and coronary sinus catheterization (Duilio et al. 2001). No chemicals were infused. Instead, blood was drawn into syringes pre-filled with a spin trap and analyzed by electron paramagnetic resonance (EPR) spectroscopy. After 90 minutes of coronary artery occlusion, the transcardiac concentration of oxygen radicals rose several-fold 10 minutes after reflow, and remained significantly elevated for at least 1 hour. Radicals were mostly derived from neutrophils, in particular superoxide anion. These radicals exhibited marked reduction after the administration of (1) neutrophil NADPH-oxidase inhibitors and (2) a monoclonal antibody (R15.7) against neutrophil CD18-adhesion molecule. The first intervention was designed to reduce the neutrophil respiratory burst, and the second to reduce recruitment of neutrophils to the site(s) of ischemia-reperfusion injury. The reduction of radical generation by the monoclonal antibody R15.7 was also associated with a significantly smaller infarct size and with a concomitant decrease in no-reflow areas. It was demonstrated for the first time that activated neutrophils were a major source of oxidants in hearts reperfused in vivo after prolonged ischemia, that this phenomenon was long-lived, and that anti-neutrophil interventions could effectively prevent the increase in transcardiac concentration of oxygen radicals during reperfusion. In these animal models of experimental infarction, the lack of pre-existing pathology prior to coronary artery occlusion may over-emphasize the contribution of neutrophilic recruitment and activation to I/R injury; indeed, in the human atherosclerotic situation, activated macrophages and activated T-lymphocytes already residing in the "area-at-risk" may also contribute substantially to I/R injury. These resident inflammatory cells themselves are also sources of superoxide anion and other ROS.

Ischemia causes depletion of ATP in cells in the affected area. At the level of the mitochondrial electron transport chain, which normally "leaks" approximately 5% of the processed electrons in healthy tissue, further leakage of partially-reduced oxygen species (in particular $O_2$—) is favored when the respiratory chain becomes largely reduced. This happens primarily during ischemia. The net effect in the local cellular environment is a tip in the balance of the redox status from anti-oxidant to pro-oxidant, which is at the same time less capable of absorbing additional radical insult(s) without further cellular damage.

Prevention of Ischemia-Reperfusion Injury: Pharmacologic Agents Used in Previous Animal and/or Human Trials The following compounds have been evaluated, either in animal models or in limited human trials, as therapeutic agents for the reduction of ischemia-reperfusion injury and/or myocardial salvage during acute myocardial infarction (AMI). Most are biological antioxidants.

Superoxide dismutase (and derivatives or mimetics)
Catalase
Glutathione and glutathione peroxidase
Xanthine oxidase inhibitors
Vitamins B, C, E (and derivatives)
Calcium antagonists
ACE inhibitors
Sulphydryl thiol compounds (in particular N-acetylcysteine)
Iron chelators (desferioxamine)
Anti-inflammatories (e.g., ibuprofen)
Phosphocreatine
N-2-mercaptopropionyl glycine (MPG)
Probucol (and derivatives)
Melatonin
Coenzyme Q-10

Seminal work by Singh and co-workers in India previously demonstrated that human patients presenting with acute myocardial infarction are depleted in endogenous antioxidants, and that supplementation with antioxidant cocktails and/or monotherapy with coenzyme Q10 (a potent lipophilic antioxidant) were useful to achieve both myocardial salvage and improvement in traditional hard clinical endpoints (such as total cardiac deaths and nonfatal reinfarction) at 30 days post-AMI. The AMISTAD trials demonstrated the usefulness of adenosine as a myocardial salvage agent in 3 separate groups of patients. RheothRx™ (a rheological agent) was also efficacious as a salvage agent in human trials, but was abandoned secondary to renal toxicity. Most recently, Medicure, Inc. demonstrated the utility of a vitamin B derivative for myocardial salvage in a small Phase II pilot study in collaboration with the Duke Clinical Research Institute. Hence, the "translational" problem (from efficacy in animal models of experimental infarction to human clinical efficacy) identified in previous reviews of I/R injury is now better understood. However, the commercial window-of-opportunity still exists, as no agent has been specifically approved for human use as a salvage agent.

Timing of Treatment For Myocardial Ischemia-Reperfusion Injury

As discussed above, early reperfusion of acute myocardial infarctions (primarily with pharmacological or surgical reperfusion) halts cell death due to ischemia, but paradoxically causes further injury—most likely by oxidant mechanisms. Horwitz et al. (1999) identified the window of opportunity during which antioxidants must be present in therapeutic concentrations to prevent reperfusion injury during 90 minutes of ischemia, and 48 hours of subsequent reperfusion, in 57 dogs. Statistical analyses in the trial focused on identifying components of group membership responsible for differences in infarct size, and revealed that duration of treatment was a major determinant. If begun at any time within the first hour of reperfusion, infusions of greater than or equal to 3 hours markedly diminished infarct size. Duilio et al. (2001) further clarified this issue by demonstrating that oxygen consumption reflective of the peroxyl radical chain reaction begins 10 minutes after reperfusion, and that radical activity remains elevated for at least the first hour of reperfusion in a canine model. Singh et al. (1996) previously demonstrated in human patients that myocardial salvage, and improvement of hard clinical endpoints (nonfatal reinfarction, death) was possible starting antioxidant therapy on average 13 hours post-MI, and continuing for 28 days. Therefore, plasma antioxidants with long half-lives may be particularly appropriate for this setting, as they may be administered as a loading dose and allowed to decay in the plasma throughout the critical early post-AMI period (0 to 24 hours). The plasma half-lives of carotenoids administered orally range from approximately 21 hours for the xanthophylls ("oxygenated" carotenoids including astaxanthin, capsanthin, lutein, and zeaxanthin) to 222 hours for carotenes ("hydrocarbon" carotenoids such as lycopene). The significant difference in plasma antioxidant half-life (7 minutes) in the trial by Horwitz et al. (1999), for superoxide dismutase and its mimetics in human studies, versus a nearly 21 hour half-life for xanthophylls and nearly 9 days for carotenes, highlights the pharmacokinetic advantages and potential cardioprotection against I/R injury by carotenoids in AMI in humans.

Critical Appraisal of Antioxidants in Ischemia-Reperfusion Injury: Human Studies Mean levels of vitamins A, C, E, and β-carotene were significantly reduced in patients presenting with AMI, compared with control patients in a study conducted by Singh et al. (1994). Lipid peroxides were significantly elevated in the AMI patients. The inverse relationship between AMI and low plasma levels of vitamins remained significant after adjustment for smoking and diabetes in these patients. Similarly, 38 patients with AMI were studied by Levy et al. (1998), and exhibited significantly decreased levels of vitamins A, E, and β-carotene compared with age-matched, healthy control subjects. After thrombolysis, lipid peroxidation products increased significantly in the serum of treated patients. Thrombolytic therapy also caused a significant decrease in plasma vitamin E levels. These descriptive studies indicate that upon presentation with AMI, it is likely that serum levels of antioxidant vitamins will be decreased in patients undergoing an acute coronary event. Pharmacologic intervention with antioxidant compounds in the acute setting would likely remedy deficiencies in antioxidant vitamins and total body antioxidant status.

Prospective human intervention trials with antioxidants in the setting of primary and/or secondary prevention of CVD are similarly limited, but have been largely successful. Four out of five recent human studies strongly support the effectiveness of vitamin E in reducing heart disease risk and complication rates. The Secondary Prevention with Antioxidants of Cardiovascular Disease in End-Stage Renal Disease study, in patients with significant kidney disease, revealed a 70% reduction in nonfatal MI in patients given 800 IU per day of natural source vitamin E. Similarly, as mentioned herein, a number of agents have now been successfully applied to myocardial salvage applications in humans.

Delivery of a low molecular weight compound intravenously in the acute setting to inhibit or ameliorate I/R injury will require an evaluation of its immunogenicity. The incidence of transfusion-type and other adverse reactions to the rapid infusion of the compound must be minimized. Compounds with a molecular weight <1000 Da, e.g. aspirin, progesterone, and astaxanthin, are likely not immunogenic unless complexed with a carrier. As molecular weight increases to between 1000 and 6000 Da, e.g. insulin and ACTH, the compound may or may not be immunogenic. As molecular weight increases to >6000 Da, the compound is likely to be immunogenic. In addition, lipids are rarely immunogenic, again unless complexed to a carrier. Astaxanthin, as a xanthophyll carotenoid, is highly lipid soluble in natural form. It is also small in size (597 Da). Therefore, an injectable astaxanthin structural analog or derivative has a low likelihood of immunogenicity in the right formulation, and is a particularly desirable compound for the current therapeutic indication.

Prevention of Arrhythmia: Pharmacologic Agents Used in Previous Animal Trials

Studies conducted by Gutstein et al. (2001) evaluated genetically modified mice incapable of expressing connexin 43 in the myocardium [Cx43 conditional knockout (CKO) mice]. Gutstein et al. discovered that despite normal heart structure and contractile performance, Cx43 CKO mice uniformly developed sudden cardiac death, apparently from spontaneous ventricular lethal tachycardia(s). This data supports the critical role of the gap junction channel, and connexin 43 in particular, in maintaining cardiac electrical stability. Connexin 43, which is capable of being induced by carotenoids, is the most widely expressed connexin in human tissues. Carotenoids, and carotenoid structural analogs or derivatives, therefore, may be used for the treatment of arrhythmia.

Prevention of Cancer: Pharmacologic Agents Used in Previous Animal Trials

Carotenoids have been evaluated, mostly in animal models, for their possible therapeutic value in the prevention and treatment of cancer. Previously the antioxidant properties of carotenoids were the focus of studies directed towards carotenoids and their use in cancer prevention. Studies conducted by Bertram et al. (1991) pointed towards the fact that although carotenoids were antioxidants, this particular property did not appear to be the major factor responsible for their activity as cancer chemopreventive agents. It was, however, discovered that the activity of carotenoids was strongly correlated with their ability to upregulate gap junctional communication. It has been postulated that gap junctions serve as conduits for antiproliferative signals generated by growth-inhibited normal cells. Connexin 43, which is capable of being induced by carotenoids, is the most widely expressed connexin in human tissues. Upregulation of connexin 43, therefore, may be the mechanism by which carotenoids are useful in the chemoprevention of cancer in humans and other animals. And recently, a human study by Nishino et al. (2003) demonstrated that a cocktail of carotenoids (10 mg lycopene, 5 mg each of α- and β-carotene) given by chronic oral administration was efficacious in the chemoprevention of hepatocellular carcinoma in high-risk cirrhotic patients in Japan. It is likely, then, that more potent cancer-chemopreventive carotenoids (such as astaxanthin), which accumulate more dramatically in liver, will be particularly useful embodiments.

Use of Carotenoids for the Treatment of Ischemia-Reperfusion Injury, Liver Disease, Arrhythmia, and Cancer As used herein the terms "inhibiting" and "ameliorating" are generally defined as the prevention and/or reduction of the negative consequences of a disease state. Thus, the methods and compositions described herein may have value as both an acute and a chronic (prophylactic) modality.

As used herein the term "ischemia-reperfusion injury" is generally defined as the pathology attributed to reoxygenation of previously ischemic tissue (either chronically or acutely ischemic), which includes atherosclerotic and thromboembolic vascular disease and its related illnesses. In particular, major diseases or processes including myocardial infarction, stroke, peripheral vascular disease, venous or arterial occlusion and/or restenosis, organ transplantation, coronary artery bypass graft surgery, percutaneous transluminal coronary angioplasty, and cardiovascular arrest and/or death are included, but are not seen as limiting for other pathological processes which involve reperfusion of ischemic tissue in their individual pathologies.

As used herein the term "arrhythmia" is generally defined as any variation from the normal rhythm of the heart beat, including sinus arrhythmia, premature beat, heart block, atrial fibrillation, atrial flutter, ventricular tachycardia, ventricular fibrillation, torsades de pointes, pulsus alternans and paroxysmal tachycardia. As used herein the term "cardiac arrhythmia" is generally defined as a disturbance of the electrical activity of the heart that manifests as an abnormality in heart rate or heart rhythm. Arrhythmia is most commonly related to cardiovascular disease, and in particular, ischemic heart disease.

As used herein the term "cancer" is generally considered to be characterized by the uncontrolled, abnormal growth of cells. In particular, cancer may refer to tissue in a diseased state including pre-cancerous, carcinogen-initiated and carcinogen-transformed cells.

As used herein the terms "structural carotenoid analogs or derivatives" may be generally defined as carotenoids and the biologically active structural analogs or derivatives thereof. "Derivative" in the context of this application is generally defined as a chemical substance derived from another substance either directly or by modification or partial substitution. "Analog" in the context of this application is generally defined as a compound that resembles another in structure but is not necessarily an isomer. Typical analogs or derivatives include molecules which demonstrate equivalent or improved biologically useful and relevant function, but which differ structurally from the parent compounds. Parent carotenoids are selected from the more than 700 naturally-occurring carotenoids described in the literature, and their stereo- and geometric isomers. Such analogs or derivatives may include, but are not limited to, esters, ethers, carbonates, amides, carbamates, phosphate esters and ethers, sulfates, glycoside ethers, with or without spacers (linkers).

As used herein the terms "the synergistic combination of more than one structural analog or derivative of carotenoids" may be generally defined as any composition including one structural carotenoid analog or derivative combined with one or more other structural carotenoid analogs or derivatives or co-antioxidants, either as derivatives or in solutions and/or formulations.

As used herein the terms "subject" may be generally defined as all mammals, in particular humans.

As used herein the terms "administration" may be generally defined as the administration of the pharmaceutical or over-the-counter (OTC) or nutraceutical compositions by any means that achieves their intended purpose. For example, administration may include parenteral, subcutaneous, intravenous, intracoronary, rectal, intramuscular, intraperitoneal, transdermal, or buccal routes. Alternatively, or concurrently, administration may be by the oral route. The dosage administered will be dependent upon the age, health, weight, and/or disease state of the recipient, kind of concurrent treatment, if any, frequency of treatment, and/or the nature of the effect desired.

In some embodiments, techniques described herein may be applied to the inhibition and/or amelioration of any disease or disease state related to reactive oxygen species. Any techniques described herein directed towards the inhibition of ischemia-reperfusion injury may also be applied to the inhibition or amelioration of a liver disease, a non-limiting example being Hepatitis C infection. Techniques described herein directed towards the inhibition and/or amelioration of ischemia-reperfusion injury may also be applied to the inhibition and/or amelioration of arrhythmia. Techniques described herein directed towards the inhibition and/or amelioration of ischemia-reperfusion injury may also be applied to the inhibition and/or amelioration of cancer. In some embodiments, techniques described herein may be used for controlling connexin 43 expression. Techniques described herein may be used to control gap junctional communication. In some embodiments, techniques described herein may be used for controlling C-reactive protein levels.

An embodiment may include the administration of structural carotenoid analogs or derivatives alone or in combination to a subject such that the occurrence of ischemia-reperfusion injury is thereby inhibited and/or ameliorated. The structural carotenoid analogs or derivatives may be water soluble and/or water dispersible derivatives. The carotenoid derivatives may include any substituent that substantially increases the water solubility of the naturally occurring carotenoid. The carotenoid derivatives may retain and/or improve the antioxidant properties of the parent carotenoid. The carotenoid derivatives may retain the non-toxic properties of the parent carotenoid. The carotenoid derivatives may have increased bioavailability, relative to the parent carotenoid, upon administration to a subject. The parent carotenoid may be naturally occurring.

Another embodiment may include the administration of a composition comprised of the synergistic combination of more than one structural analog or derivative of carotenoids to a subject such that the occurrence of ischemia-reperfusion injury is thereby reduced. The composition may be a "racemic" (i.e. mixture of the potential stereoisomeric forms) mixture of carotenoid derivatives. Included as well are pharmaceutical compositions comprised of structural analogs or derivatives of carotenoids in combination with a pharmaceutically acceptable carrier. In one embodiment, a pharmaceutically acceptable carrier may be serum albumin. In one embodiment, structural analogs or derivatives of carotenoids may be complexed with human serum albumin (i.e., HSA) in a solvent. HSA may act as a pharmaceutically acceptable carrier.

In some embodiments, compositions may include all compositions of 1.0 gram or less of a particular structural carotenoid analog, in combination with 1.0 gram or less of one or more other structural carotenoid analogs or derivatives and/or co-antioxidants, in an amount which is effective to achieve its intended purpose. While individual subject needs vary, determination of optimal ranges of effective amounts of each component is with the skill of the art. Typically, a structural carotenoid analog or derivative may be administered to mammals, in particular humans, orally at a dose of 5 to 100 mg per day referenced to the body weight of the mammal or human being treated for ischemia-reperfusion injury. Typically, a structural carotenoid analog or derivative may be administered to mammals, in particular humans, parenterally at a dose of between 5 to 1000 mg per day referenced to the body weight of the mammal or human being treated for ischemia-reperfusion injury. In other embodiments, about 100 mg of a structural carotenoid analog or derivative is either orally or parenterally administered to treat or prevent ischemia-reperfusion injury.

The unit oral dose may comprise from about 0.25 mg to about 1.0 gram, or about 5 to 25 mg, of a structural carotenoid analog. The unit parenteral dose may include from about 25 mg to 1.0 gram, or between 25 mg and 500 mg, of a structural carotenoid analog. The unit intracoronary dose may include from about 25 mg to 1.0 gram, or between 25 mg and 100 mg, of a structural carotenoid analog. The unit doses may be administered one or more times daily, on alternate days, in loading dose or bolus form, or titrated in a parenteral solution to commonly accepted or novel biochemical surrogate marker(s) or clinical endpoints as is with the skill of the art.

In addition to administering a structural carotenoid analog or derivative as a raw chemical, the compounds may be administered as part of a pharmaceutical preparation containing suitable pharmaceutically acceptable carriers, preservatives, excipients and auxiliaries which facilitate processing of the structural carotenoid analog or derivative which may be used pharmaceutically. The preparations, particularly those preparations which may be administered orally and which may be used for the preferred type of administration, such as tablets, softgels, lozenges, dragees, and capsules, and also preparations which may be administered rectally, such as suppositories, as well as suitable solutions for administration by injection or orally or by inhalation of aerolsolized preparations, may be prepared in dose ranges that provide similar bioavailability as described above, together with the excipient. While individual needs may vary, determination of the optimal ranges of effective amounts of each component is within the skill of the art.

The pharmaceutical preparations may be manufactured in a manner which is itself known to one skilled in the art, for example, by means of conventional mixing, granulating, dragee-making, softgel encapsulation, dissolving, extracting, or lyophilizing processes. Thus, pharmaceutical preparations for oral use may be obtained by combining the active compounds with solid and semi-solid excipients and suitable preservatives, and/or co-antioxidants. Optionally, the resulting mixture may be ground and processed. The resulting mixture of granules may be used, after adding suitable auxiliaries, if desired or necessary, to obtain tablets, softgels, lozenges, capsules, or dragee cores.

Suitable excipients may be fillers such as saccharides (e.g., lactose, sucrose, or mannose), sugar alcohols (e.g., mannitol or sorbitol), cellulose preparations and/or calcium phosphates (e.g., tricalcium phosphate or calcium hydrogen phosphate). In addition binders may be used such as starch paste (e.g., maize or corn starch, wheat starch, rice starch, potato starch, gelatin, tragacanth, methyl cellulose, hydroxypropylmethylcellulose, sodium carboxymethylcellulose, and/or polyvinyl pyrrolidone). Disintegrating agents may be added (e.g., the above-mentioned starches) as well as carboxymethyl-starch, cross-linked polyvinyl pyrrolidone, agar, or alginic acid or a salt thereof (e.g., sodium alginate). Auxiliaries are, above all, flow-regulating agents and lubricants (e.g., silica, talc, stearic acid or salts thereof, such as magnesium stearate or calcium stearate, and/or polyethylene glycol, or PEG). Dragee cores are provided with suitable coatings which, if desired, are resistant to gastric juices. Softgelatin capsules ("softgels") are provided with suitable coatings, which, typically, contain gelatin and/or suitable edible dye(s). Animal component-free and kosher gelatin capsules may be particularly suitable for the embodiments described herein for wide availability of usage and consumption. For this purpose, concentrated saccharide solutions may be used, which may optionally contain gum arabic, talc, polyvinyl pyrrolidone, polyethylene glycol (PEG) and/or titanium dioxide, lacquer solutions and suitable organic solvents or solvent mixtures, including dimethylsulfoxide (DMSO), tetrahydrofuran (THF), acetone, ethanol, or other suitable solvents and co-solvents. In order to produce coatings resistant to gastric juices, solutions of suitable cellulose preparations such as acetylcellulose phthalate or hydroxypropylmethyl-cellulose phthalate, may be used. Dye stuffs or pigments may be added to the tablets or dragee coatings or softgelatin capsules, for example, for identification or in order to characterize combinations of active compound doses, or to disguise the capsule contents for usage in clinical or other studies.

Other pharmaceutical preparations which may be used orally include push-fit capsules made of gelatin, as well as soft, thermally-sealed capsules made of gelatin and a plasticizer such as glycerol or sorbitol. The push-fit capsules may contain the active compounds in the form of granules which may be mixed with fillers such as, for example, lactose, binders such as starches, and/or lubricants such as talc or magnesium stearate and, optionally, stabilizers and/or preservatives. In soft capsules, the active compounds may be dissolved or suspended in suitable liquids, such as fatty oils such as rice bran oil or peanut oil or palm oil, or liquid paraffin. In some embodiments, stabilizers and preservatives may be added.

In some embodiments, pulmonary administration of a pharmaceutical preparation may be desirable. Pulmonary administration may include, for example, inhalation of aerosolized or nebulized liquid or solid particles of the pharmaceutically active component dispersed in and surrounded by a gas.

Possible pharmaceutical preparations which may be used rectally include, for example, suppositories, which consist of a combination of the active compounds with a suppository base. Suitable suppository bases are, for example, natural or synthetic triglycerides, or parrafin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include, but are not limited to, aqueous solutions of the active compounds in water-soluble and/or water dispersible form, for example, water-soluble salts, esters, carbonates, phosphate esters or ethers, sulfates, glycoside ethers, together with spacers and/or linkers. Suspensions of the active compounds as appropriate oily injection suspensions may be administered, particularly suitable for intramuscular injection. Suitable lipophilic solvents, co-solvents (such as DMSO or ethanol), and/or vehicles including fatty oils, for example, rice bran oil or peanut oil and/or palm oil, or synthetic fatty acid esters, for example, ethyl oleate or triglycerides, may be used. Aqueous injection suspensions may contain substances which increase the viscosity of the suspension including, for example, sodium carboxymethyl cellulose, sorbitol, dextran, and/or cyclodextrins. Cyclodextrins (e.g., β-cyclodextrin) may be used specifically to increase the water solubility for parenteral injection of the structural carotenoid analog. Liposomal formulations, in which mixtures of the structural carotenoid analog or derivative with, for example, egg yolk phosphotidylcholine (E-PC), may be made for injection. Optionally, the suspension may contain stabilizers, for example, antioxidants such as BHT, and/or preservatives, such as benzyl alcohol.

EXAMPLES

Having now described the invention, the same will be more readily understood through reference to the following example(s), which are provided by way of illustration, and are not intended to be limiting of the present invention.

Regarding the synthesis and characterization of compounds described herein, reagents were purchased from commercial sources and used as received unless otherwise indicated. Solvents for reactions and isolations were reagent grade and used without purification unless otherwise indicated. All of the following reactions were performed under nitrogen ($N_2$) atmosphere and were protected from direct light. "Racemic" astaxanthin (as the mixture of stereoisomers 3S,3'S, meso, and 3R,3'R in a 1:2:1 ratio) was purchased from Divi's Laboratories, Ltd (Buckton Scott, India). "Racemic" lutein and zeaxanthin were purchased from Indofine Chemical Co., Inc. Thin-layer chromatography (TLC) was performed on Uniplate Silica gel GF 250 micron plates. HPLC analysis for in-process control (IPC) was performed on a Varian Prostar Series 210 liquid chromatograph with an Alltech Rocket, Platinum-C18, 100 Å, 3 μm, 7×53 mm, PN 50523; Temperature: 25° C.; Mobile phase: (A=water; B=10% dichloromethane/methanol), 40% A/60% B (start); linear gradient to 100% B over 8 min; hold 100% B over 4 min, linear gradient to 40% A/60% B over 1 min; Flow rate: 2.5 mL/min; Starting pressure: 2050 PSI; PDA Detector wavelength: 474 nm. NMR was recorded on a Bruker Advance 300 and mass spectroscopy was taken on a ThermoFinnigan AQA spectrometer. LC/MS was recorded on an Agilent 1100 LC/MSD VL ESI system; column: Zorbax Eclipse XDB-C18 Rapid Resolution (4.6×75 mm, 3.5 μm, USUT002736); temperature: 25° C.; starting pressure: 107 bar; flow rate: 1.0 mL/min.; mobile phase (% A=0.025% TFA in $H_2O$, % B=0.025% TFA in acetonitrile) Method 1 (compounds 8-21, 23-27, 30,31): 70% A/30% B (start), step gradient to 50% B over 5 min., step gradient to 98% B over 8.30 min., hold at 98% B over 15.20 min., step gradient to 30% B over 15.40 min.; Method 2 (compounds 28,29): 70% A/30% B (start), step gradient to 50% B over 4 min., step gradient to 90% B over 7.30 min., step gradient to 98% B over 10.30 min., hold at 98% B over 15.20 min., step gradient to 30% B over 15.40 min.; Method 3 (compound 22): 70% A/30% B (start), step gradient to 50% B over 5 min., step gradient to 98% B over 8.30 min., hold at 98% B over 25.20 min., step gradient to 30% B over 25.40 min.; PDA Detector: 470 nm; LRMS: +mode, ESI.

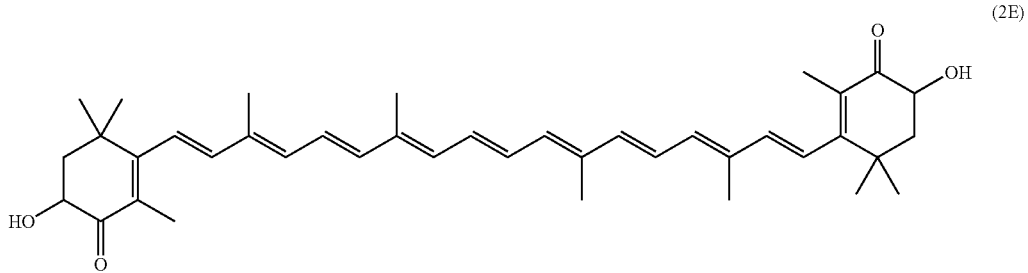

(2E)

Astaxanthin (2E). HPLC retention time: 11.629 min., 91.02% (AUC); LRMS (ESI) m/z (relative intensity): 598 ($M^+$+2H) (60), 597 ($M^+$+H) (100); HPLC retention time: 12.601 min., 3.67% (AUC); LRMS (ESI) m/z (relative intensity): 597 ($M^+$+H) (100); HPLC retention time: 12.822 min., 5.31% (AUC); LRMS (ESI) m/z (relative intensity): 597 ($M^+$+H) (100).

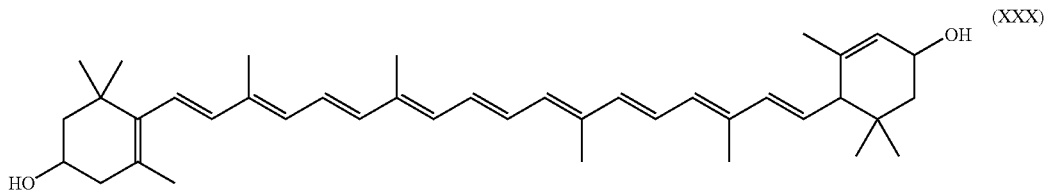

(XXX)

Lutein (XXX). HPLC retention time: 12.606 min., 100% (AUC); LRMS (ESI) m/z (relative intensity): 568 ($M^+$) (100).

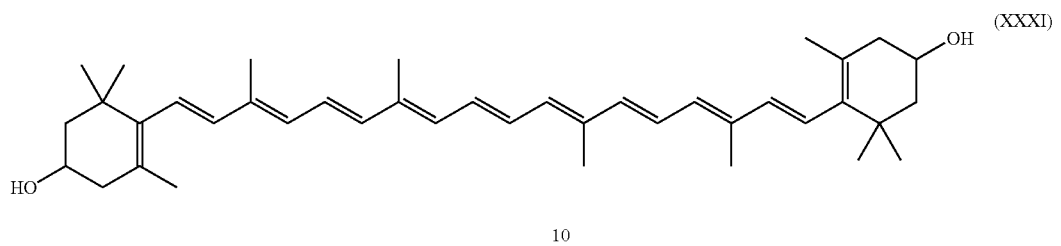

(XXXI)

Zeaxanthin (XXXI). HPLC retention time: 12.741 min., 100% (AUC); LRMS (ESI) m/z (relative intensity): 568 (M$^+$) (100).

Example 1

Synthesis of XV (the Disuccinic Acid Ester of Astaxanthin (Succinic Acid mono-(4-{18-[4-(3-carboxy-propionyloxy)-2,6,6-trimethyl-3-oxo-cyclohex-1-enyl]-3,7,12,16-tetramethyl-octadeca-1,3,5,7,9,11,13,15,17-nonaenyl}-3,5,5-trimethyl-2-oxo-cyclohex-3-enyl) ester))

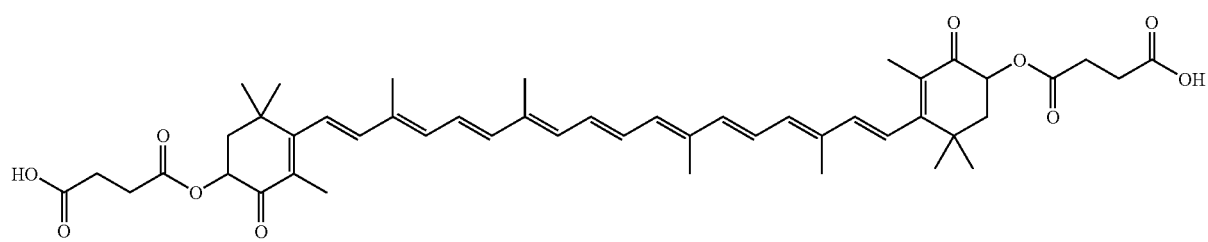

(XV)

To a solution of astaxanthin 2E (6.0 g, 10.05 mmol) in DCM ("dichloromethane") (50 mL) at room temperature was added DIPEA ("NN-diisopropylethylamine") (35.012 mL, 201 mmol), succinic anhydride (10.057 g, 100.5 mmol), and DMAP ("4-(dimethylamino)pyridine") (0.6145 g, 5.03 mmol). The reaction mixture was stirred at room temperature for 48 hours, at which time the reaction was diluted with DCM, quenched with brine/1M HCl (60 mL/10 mL), and then extracted with DCM. The combined organic layers were dried over Na$_2$SO$_4$ and concentrated to yield astaxanthin disuccinate (XV) (100%) HPLC retention time: 10.031 min., 82.57% (AUC); LRMS (ESI) m/z (relative intensity): 798 (M$^+$+2H) (52), 797 (M$^+$+H) (100); HPLC retention time: 10.595 min., 4.14% (AUC); LRMS (ESI) m/z (relative intensity): 797 (M$^+$+H) (40), 697 (100); HPLC retention time: 10.966 min., 5.68% (AUC); LRMS (ESI) m/z (relative intensity): 797 (M$^+$+H) (100), 679 (31); HPLC retention time: 11.163 min., 7.61% (AUC); LRMS (ESI) m/z (relative intensity): 797 (M$^+$+H) (38), 679 (100), and no detectable astaxanthin 2E.

Example 2

Synthesis of Error! Reference source not found. (the Disodium Salt of the Disuccinic Acid Ester of Astaxanthin (Succinic acid mono-(4-{18-[4-(3-carboxy-propionyloxy)-2,6,6-trimethyl-3-oxo-cyclohex-1-enyl]-3,7,12,16-tetramethyl-octadeca-1,3,5,7,9,11,13,15,17-nonaenyl}-3,5,5-trimethyl-2-oxo-cyclohex-3-3-enyl) ester))

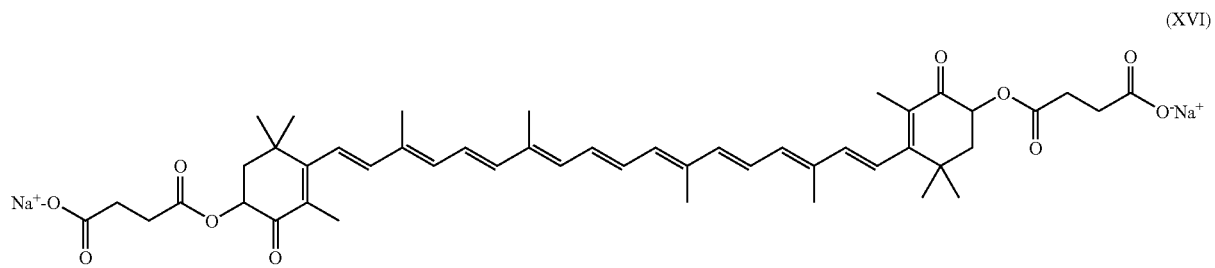

(XVI)

Disuccinic acid ester of astaxanthin XV (2 g, 2.509 mmol) and 200 mL ethanol were stirred at room temperature under nitrogen in a 500 mL round-bottom flask. Sodium ethoxide (340 mg, 5.019 mmol, Acros #A012556101) was added as a solid in a single portion and the solution was allowed to stir overnight. The following day, the precipitate was filtered off and washed with ethanol followed by methylene chloride to afford a purple solid, the disodium salt of the disuccinic acid ester of astaxanthin, XVI [1.41 g, 67%] and was placed on a high vacuum line to dry. $^1$H-NMR (Methanol-$d_4$) 6.77-6.28 (14 H, m), 5.53 (2 H, dd, J=12.6, 6.8), 2.68-2.47 (8 H, m), 2.08-1.88 (22 H, m), 1.37 (6 H, s), 1.24 (6H, s); $^{13}$C NMR (CDCl$_3$) δ 196.66, 180.80, 175.01, 163.69, 144.12, 141.38, 138.27, 136.85, 136.12, 135.43, 132.35, 129.45, 126.22, 124.71, 72.68, 44.09, 38.63, 34.02, 32.34, 31.19, 26.86, 14.06, 13.19, 12.91; Mass spectroscopy +ESI, 819.43 monosodium salt, 797.62 disuccinic acid ester of astaxanthin XV; HPLC 7.41 min (99.84%).

Example 3

Synthesis of the BocLys(Boc)OH Ester of Astaxanthin (XXI).

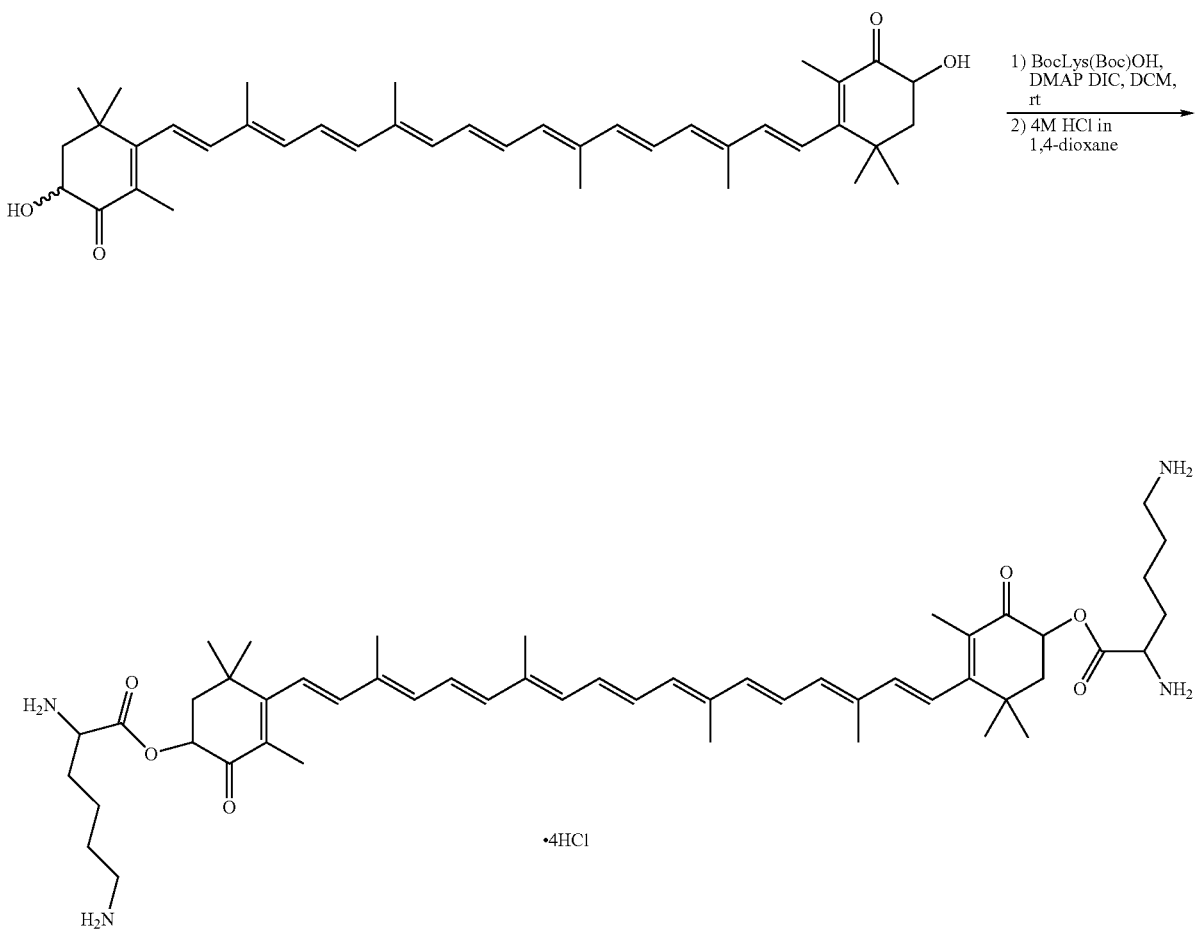

HPLC: Column: Waters Symmetry C18 3.5 micron 4.6 mm×150 mm; Temperature: 25° C.; Mobile phase: (A=0.025% TFA in $H_2O$; B=0.025% TFA in MeCN), 95% A/5% B (start); linear gradient to 100% B over 12 min, hold for 4 min; linear gradient to 95% B/5% A over 2 min; linear gradient to 95% A/5% B over 4 min; Flow rate: 2.5 mL/min; Detector wavelength: 474 nm.

To a mixture of astaxanthin 2E (11.5 g, 19.3 mmol) and BocLys(Boc)OH (20.0 g, 57.7 mmol) in methylene chloride (500 mL) were added 4-dimethylaminopyridine (DMAP) (10.6 g, 86.6 mmol) and 1,3-diisopropylcarbodiimide ("DIC") (13.4 g, 86.7 mmol). The round-bottomed flask was covered with aluminum foil and the mixture was stirred at ambient temperature under nitrogen overnight. After 16 hours, the reaction was incomplete by HPLC and TLC. An additional 1.5 equivalents of DMAP and DIC were added to the reaction and after 2 hours, the reaction was complete by HPLC. The mixture was then concentrated to 100 mL and a white solid (1,3-diisopropylurea) was filtered off. The filtrate was flash chromatographed through silica gel (10% to 50% Heptane/EtOAc) to give the desired product as a dark red solid (XXI) (28.2 g, >100% yield). $^1$H NMR (DMSO-$d_6$) δ 7.24 (2 H, t, J=6.3 Hz), 6.78 (2 H, d, 5.0 Hz), 6.57-6.27 (14 H, m), 5.50-5.41 (2 H, m), 3.99-3.97 (2 H, d, 6.0 Hz), 2.90 (4 H, m), 2.03 (4 H, m), 2.00 (6 H, s), 1.97 (6 H, s), 1.82 (6 H, s), 1.70-1.55 (4 H, m), 1.39-1.33 (36 H, m), 1.24-1.13 (8 H, m), 1.01-0.99 (6 H, m), 0.86-0.83 (6 H, m). HPLC: 21.3 min (24.6% AUC)); 22.0 min (48.1% (AUC)); 22.8 min (20.6% (AUC)). TLC (1:1 Heptane/EtOAc: $R_f$ 0.41; $R_f$ 0.5; $R_f$ 0.56). LC/MS analysis was performed on a Agilent 1100 LC/MSD VL ESI system by flow injection in positive mode; Mobile Phase: A=0.025% TFA in $H_2O$; B=0.025% TFA in MeCN, 10% A/90% B(start); Starting pressure: 10 bar; PDA Detector 470 nm. +ESI, m/z=1276.1(M+Na$^+$).

Example 4

Synthesis of the Tetrahydrochloride Salt of the Dilysinate Ester of Astaxanthin (XX).

A mixture of DiBocLys(Boc) ester of astaxanthin (XXI) (20.0 g, 16.0 mmol) and HCl in 1,4-dioxane (4.00 M, 400 mL, 1.60 mol, 100 eq) was stirred at ambient temperature under a nitrogen atmosphere. The round-bottomed flask was covered with aluminum foil and the reaction was stirred for 1 hour, at which time the reaction was complete by HPLC. The title compound XX precipitated and was collected by filtration, washed with ether (3×100 mL) and dried (14.7 g, 92%, 91.6% purity by HPLC). A portion (13.5 g) of the crude solid was dissolved in 500 mL of a 1:2 methanol/methylene chloride mixture and stirred under nitrogen. Diethyl ether (168 mL) was then added dropwise and the precipitated solid was collected by filtration to afford the desired product XX as a dark red solid (8.60 g, 63.7% yield). $^1$H NMR (DMSO-$d_6$) δ 8.65 (6 H, s), 8.02 (6 H, s), 6.78-6.30 (14 H, m), 5.59-5.51 (2 H, m), 4.08 (2 H, m), 2.77 (4 H, m), 2.09-2.07 (4 H, m), 2.01 (6 H, s), 1.97 (6 H, s), 1.90-1.86 (4 H, m), 1.84 (6 H, s), 1.61-1.58 (8 H, m), 1.37 (6 H, s), 1.22 (6 H, s). HPLC: 7.8 min (97.0% (AUC)). LC/MS analysis was performed on an Agilent 1100 LC/MSD VL ESI system with Zorbax Eclipse XDB-C18 Rapid Resolution 4.6×75 mm, 3.5 microns, USUT002736; Temperature: 25° C.; Mobile Phase: (% A=0.025% TFA in $H_2O$; % B=0.025% TFA in MeCN), 70% A/30% B (start); linear gradient to 50% B over 5 min, linear gradient to 100% B over 7 min; Flow rate: 1.0 mL/min; Starting pressure: 108 bar; PDA Detector 470 nm. Mass spectrometry +ESI, m/z=853.9(M+H$^+$), m/z=875.8(M+Na$^+$); LC 4.5 min.

Example 5

Synthesis of the Bis-(2-OTBS Ascorbic Acid) 6-Ester of Astaxanthin Disuccinate (XXII).

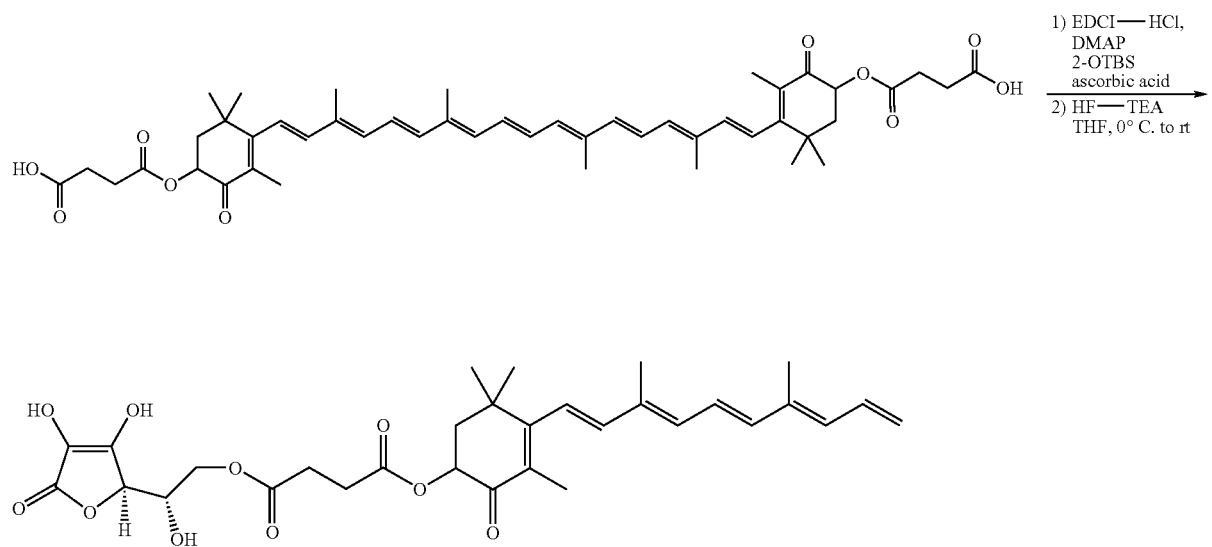

-continued

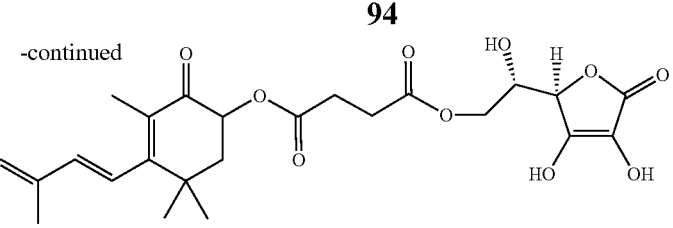

HPLC: Column: Waters Symmetry C18 3.5 micron 4.6 mm×150 mm; Temperature: 25° C.; Mobile phase: (A=0.025% TFA in water; B=0.025% TFA in acetonitrile), 95% A/5% B (start); linear gradient to 100% B over 5 min, hold for 10 min; linear gradient to 95% B over 2 min; linear gradient to 95% A/5% B over 3 min; Flow rate: 1.0 mL/min; Detector wavelength: 474 nm.

To a stirring solution of astaxanthin disuccinate (XV) (20.00 g, 25.1 mmol) in 600 mL of dichloromethane was added 4-dimethylaminopyridine (DMAP) (6.13 g, 50.2 mmol), 2-O-tert-butyldimethylsilyl (OTBS) ascorbic acid (XXVI) (21.86 g, 75.3 mmol), and 1-(3-dimethylaminopropyl)-3-ethylcarbodiimide hydrochloride (EDCI-HCl) (12.02 g, 62.75 mmol). After 14 h, the reaction mixture was flash chromatographed through silica gel (1.0 kg silica gel, eluent 0.5% HOAc/5% MeOH/EtOAc). Fraction 10 was concentrated to afford dark red solid (6.47 g, 19.2% yield, 58% AUC purity by HPLC). The crude product XXII was flashed chromatographed through silica gel (600 g silica gel, eluent 0.25% HOAc/5% MeOH/EtOAc). Fractions 6-10 were concentrated under vacuum to afford dark red solid (1.50 g, 4.4% yield, 94.8% AUC purity by HPLC $^1$H-NMR (CDCl$_3$) δ 11.13 (2H, s), 6.78-6.28 (14 H, m), 5.43 (2 H, dd, J=12.2, 7.1 Hz), 5.34 (2H, s), 4.78 (2H, d, J=5.4 Hz), 4.11-4.07 (6H, m), 2.69-2.65 (8 H, m), 2.05-1.97 (22 H, m), 1.81 (6 H, s), 1.33 (6 H, s), 0.92 (18 H, s), 0.15 (6 H, s), 0.14 (6H, s); HPLC 13.4 min [94.8% (AUC)]; Mass spectroscopy -ESI, m/z=1340.6 (M$^-$).

Example 6

Synthesis of the Bis-Ascorbic Acid 6-Ester of Astaxanthin Disuccinate (XIX)

To a stirring solution of the bis-(2-OTBS ascorbic acid) 6-ester of astaxanthin disuccinate (XXII) (100 mg, 0.075 mmol) in THF (5 mL) at 0° C. was added HF.Et$_3$N (121 μL, 0.745 mmol). The reaction was stirred for 1 h at 0° C. then warmed to rt. The reaction was stirred 2.5 h before being quenched by pouring into a separatory funnel containing 5 mL IPAC and 5 mL of water. The aqueous layer was removed and the organic layer was washing with water (2×5 mL). The organic solvents were removed by rotary evaporation to give a dark red solid XIX, which was used without purification. $^1$H-NMR (CDCl$_3$) δ 11.12 (2 H, s), 8.40 (2 H, s), 6.87-6.28 (14 H, m), 5.43-5.32 (4 H, m), 4.69 (s, 2H), 4.09 (s, 4H), 3.99 (s, 2H), 2.68-2.50 (m, 8H), 2.00-1.76 (22 H, m), 1.36-1.19 (12 H, m); HPLC 8.9 min [80.7% (AUC)]; Mass spectroscopy +ESI, m/z=1113.2 (M+H$^+$).

Example 7

Synthesis of the Sodium Salt of the Bis-Ascorbic Acid 6-Ester of Astaxanthin Disuccinate (XXIII)

To a stirring solution of the crude bis-ascorbic acid 6-ester of astaxanthin disuccinate (X1X) (0.075 mmol) in acetone (5 mL) at rt was added triethylorthoformate (62 μL, 0.373 mmol). The solution was stirred 15 min then a solution of sodium 2-ethylhexanoate in acetone (93 μL, 0.019 mmol, 0.20 M) was added dropwise. The resulting precipitate was removed by filtration. The filtrate was cooled to 0° C. and treated with additional sodium 2-ethylhexanoate in acetone (373 μL, 0.075 mmol, 0.20 M). The reaction was stirred for 5 min then the solid material was collected by filtration, washed with acetone (5 mL), and dried under high vacuum to give a dark red solid XXIII (27.8 mg, 32.2% yield): HPLC 8.9 min [88.2% (AUC)], Mass spectroscopy+APCI, m/z=1113.3 (M+3H−2Na$^+$).

Example 8

Synthesis of the Dicyclohexylmethyl Ester of Astaxanthin Disuccinate (XMV)

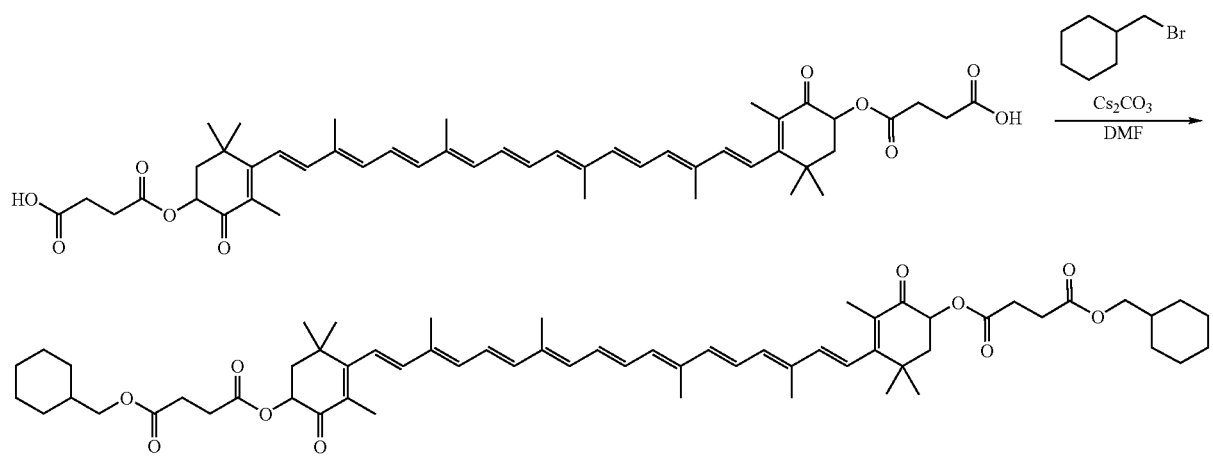

HPLC: Column: Alltech Rocket, Platinum-C18, 100 Å, 3 μm, 7×53 mm; Temperature: 25° C.; Mobile phase: (A=0.025% TFA in water; B=0.025% TFA in acetonitrile), 70% A/30% B (start); hold for 40 sec; linear gradient to 50% B over 4 min 20 sec; linear gradient to 100% B over 1 min 30 sec, hold for 4 min 40 sec; linear gradient to 70% A/30% B in 20 sec; Flow rate: 2.5 mL/min; Detector wavelength: 474 nm.

To a stirred solution of the astaxanthin disuccinate (XV) (100 mg, 0.125 mmol) and N,N-dimethylformamide (6.0 mL) in a 25 mL round-bottom flask was added cesium carbonate (90.0 mg, 0.275 mmol) at room temperature under $N_2$ and covered with aluminum foil. The reaction was stirred for 15 minutes then bromomethyl cyclohexane (52.0 μL, 0.375 mmol) was added. After 2 days, the reaction was quenched by adding 4 mL of a saturated solution of sodium bicarbonate and diluted with 50 mL of dichloromethane. The diluted solution was washed twice with 25 mL of water before drying over anhydrous sodium sulfate. The organic solution was filtered and the solvent was removed by rotary evaporation. The crude residue was purified by flash chromatography (10-50% EtOAc/heptane) to afford a dark red solid XXIV (40.2 mg, 32.5% yield): $^1$H-NMR (CDCl$_3$) δ 7.03-6.17 (14 H, m), 5.54 (2 H, dd, J=12.9, 6.7 Hz), 3.92 (4 H, d, J=6.4 Hz), 2.82-2.63 (8 H, m), 2.08-1.92 (14 H, m), 1.90 (6 H, s), 1.75-1.62 (14 H, m), 1.34-1.20 (22 H, m); HPLC 8.9 min [83.9% (AUC)]; TLC (3:7 EtOAc/heptane: $R_f$ 0.38); Mass spectroscopy +ESI, m/z=989.6 (M+H$^+$).

Example 9

Synthesis of 2-OTBS-5,6-Isopropyledine Ascorbic Acid (XXV)

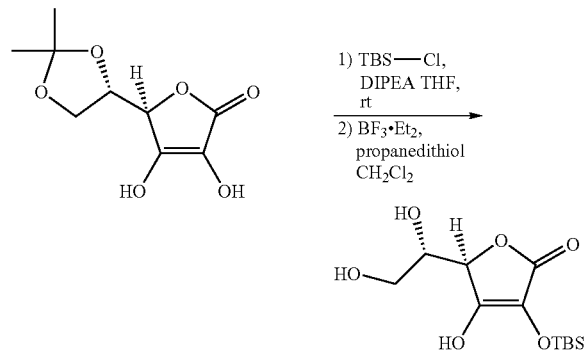

HPLC: Alltech Rocket, Platinum-C18, 100A, 3 μm, 7×53 mm, PN 50523; Temperature: 25° C.; Mobile phase: (A=0.025% TFA in water; B=0.025% TFA in acetonitrile), 90% A/10% B (start); linear gradient to 30% B over 3 min; linear gradient to 90% B over 3 min, hold for 2 min; linear gradient to 90% A/10% B over 1 min, then hold for 1 min; Flow rate: 2.5 mL/min; Detector wavelength: 256 nm.

To a stirring solution of 5,6-isopropyledine ascorbic acid (100.0 g, 463 mmol) in 1.00 L THF was added tert-butyldimethylsilyl chloride (TBSCI) (76.7 g, 509 mmol) at rt followed by addition of N,N-diisopropylethylamine (DIPEA) (161 mL, 925 mmol) over 30 min. The reaction was stirred 14 h at rt, then concentrated under vacuum. The mixture was dissolved in methyl tert-butyl ether (MTBE) (1.00 L) and extracted with 1 M potassium carbonate (1.00 L) in a separatory funnel. The aqueous layer was extracted one more time with MTBE (1.00 L), and the pH of the aqueous layer was adjusted to pH 6 using 2 N HCl. The aqueous layer was extracted twice with isopropyl acetate (IPAC) (1.00 L) and concentrated to afford an off white solid Example 10

Synthesis of 2-OTBS Ascorbic Acid (XXVI)

To a stirring solution of 2-OTBS-5,6-isopropyledine ascorbic acid (XXV) (150.4 g, 455 mmol) in 1.50 L of dichloromethane at rt was added propanedithiol (54.0 mL, 546 mmol) under nitrogen. The solution was cooled to −45° C., and then BF$_3$—OEt$_2$ (58.0 mL, 455 mmol) was added dropwise at a rate that kept the temperature below −40° C. After 1 h, the reaction was complete by HPLC. The reaction was quenched by pouring the cold reaction mixture into a separatory funnel containing 1.00 L of IPAC and 500 mL of a saturated solution of ammonium chloride and 500 mL of water. The organic layer was concentrated to a white solid. In order to purge the propane dithiol, the solid was reslurried in dichloromethane (250 mL) for 2 h and heptane (1.00 L) was added and stirred for 1 h. The mixture was concentrated under vacuum to a volume of 500 mL. The mixture was filtered and dried under vacuum to afford an of white solid XXVI (112.0 g, 85% yield): $^1$H-NMR (DMSO d$_6$) δ 11.0 (1 H, s), 4.89 (2 H, s), 4.78 (1 H, d, J=1.2 Hz), 3.82-3.80 (1 H, m), 3.45-3.42 (2 H, m), 0.923 (9 H, s), 0.14 (6H, s); HPLC 4.9 min [92.0% (AUC)]; Mass spectroscopy −ESI, m/z=289.0 (M−H$^-$).

Example 11

Synthesis of the bis-dimethylphosphate Ester of Astaxanthin (XXVII)

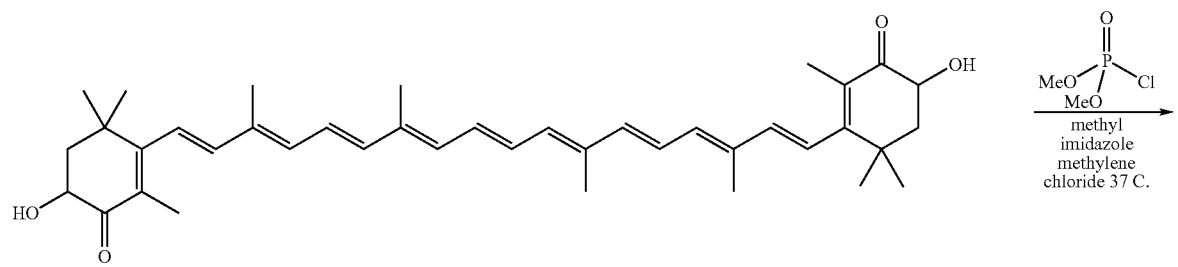

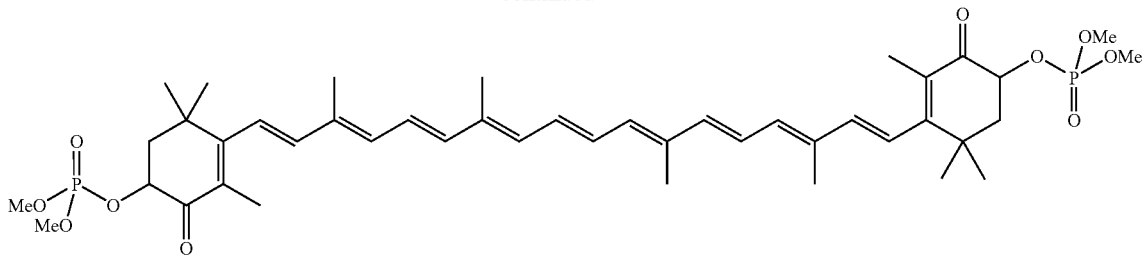

HPLC: Waters Symmetry C18, 3 μm, 4.6×150 mm, WAT200632, Temperature: 25° C.; Mobile phase: (A=water; B=10% DCM/MeOH), 10% A/90% B (start); linear gradient to 100% B over 9 min; hold 100% B over 11 min, linear gradient to 10% A/90% B over 1 min; Flow rate: 1.0 mL/min; Detector wavelength: 474 nm.

To a mixture of astaxanthin 2E (500 mg, 0.84 mmol) and methyl imidazole (0.50 mL, 6.27 mmol) in methylene chloride at 37° C. was added dimethylbromophosphate (2 M, 5.04 mL) (Ding, 2000). After 24 h, the reaction was not complete by HPLC and dimethylbromophosphate (2 M, 5.04 mL) was added. After 48 h, the reaction was not complete by HPLC and dimethylbromophosphate (2 M, 5.04 mL) was added. After 72 h, the reaction was complete by HPLC. The reaction was diluted with methylene chloride (20 mL) and quenched with water (20 mL). The layers were separated and the aqueous layer was extracted again with 20 mL of methylene chloride. The organic layers were combined and concentrated under vacuum to afford 2.69 g (>100% yield) of XXVII. $^1$H NMR (CDCl$_3$) δ 6.58-6.14 (14 H, m), 5.05-4.95 (2 H, m), 3.91-3.60 (12 H, m), 2.11-2.04 (4 H, m), 2.04-1.92 (12 H, m), 1.85 (6 H, s), 1.26 (6 H, s), 1.15 (6 H, s). HPLC: 4.29 min (86.7% AUC)). Mobile Phase: A=0.025% TFA in H$_2$O; B=0.025% TFA in acetonitrile, 10% A/90% B(start); PDA Detector 474 nm. +ESI, m/z = 813.62 (M+1).

Example 12

Synthesis of the BocProOH Ester of Astaxanthin (XXVIII)

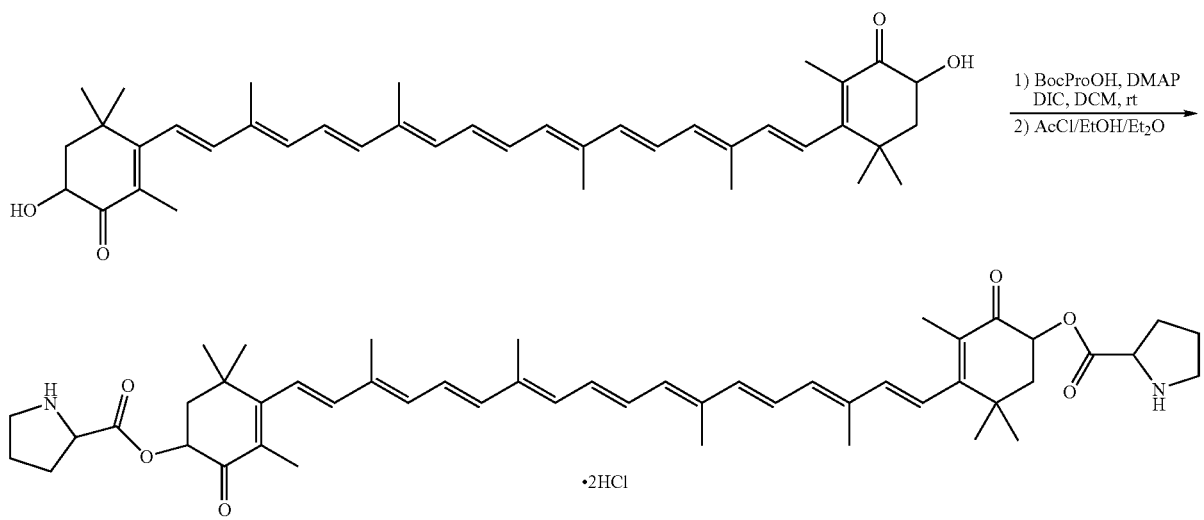

LC/MS Analysis: LC/MS analysis was performed on an Agilent 1100 LC/MSD VL ESI system with Zorbax Eclipse XDB-C18 Rapid Resolution 4.6×75 mm, 3.5 μm, USUT002736; Temperature: 25° C.; Mobile Phase:(% A=0.025% TFA in H$_2$O; % B=0.025% TFA in MeCN), 70% A/30% B(start); linear gradient to 50% B over 5 min, linear gradient to 98% B over 3 min, hold at 98% B for 17 min; Flow rate: 1.0mL/min; Starting pressure: 108 bar; PDA Detector 470 nm, 373 nm, 214 nm. LRMS: +mode, ESI.

To a mixture of astaxanthin 2E (5.00 g, 8.38 mmol) and BocProOH (10.8 g, 50.3 mmol) in methylene chloride (500 mL) were added 4-dimethylaminopyridine (DMAP) (6.14 g, 50.3 mmol) and 1,3-diisopropylcarbodiimide (DIC) (7.79 mL, 50.3 mmol). The mixture was stirred at ambient temperature under nitrogen overnight. After 16 hours, the reaction was complete by TLC. The mixture was then concentrated to dryness and the crude residue was 'slurried with 100 mL of diethyl ether and filtered through a pad of Celite. The filtrate was flash chromatographed through silica gel (Et$_2$O) to give the desired product XXVIII as a dark red solid (8.56 g, >100% yield). LC: 17.5 min [23.1% AUC)]; 18.2 min [45.1% (AUC)]; 19.4 min [22.0% (AUC)]. TLC (3:2 EtOAc/Hexane: R$_f$ 0.51; R$_f$ 0.55; R$_f$ 0.59). MS +ESI, m/z=1013.8 (M+Na$^+$).

Example 13

Synthesis of the Dihydrochloride Salt of the Diprolinate Ester of Astaxanthin (XXIX)

A mixture of diethyl ether (130 mL) and EtOH (48.9 mL, 838 mmol) was cooled to −78° C. under a nitrogen atmosphere. Acetyl chloride (82.0 mL, 838 mmol) was added dropwise to the cooled mixture over 30 minutes. The reaction was removed from the cooling bath and allowed to slowly warm to room temperature. The contents of the flask were poured into a separate round-bottomed flask containing DiBocPro ester of astaxanthin (XXVIII) (8.31 g, 8.38 mmol) and a stirrer bar. The flask was covered with aluminum foil and the reaction was stirred at ambient temperature under nitrogen overnight. After 16 hours the reaction was complete by LC. The title compound XXIX precipitated and was collected by filtration, washed with ether (3×100 mL) and dried (6.37 g, 88.0% crude yield, 75.2% purity by LC). LC: 8.00 min [75.2% (AUC)]. MS +ESI, m/z=791.7 (M+H$^+$).

Example 14

Synthesis of Lutein Disuccinate (XXXII)

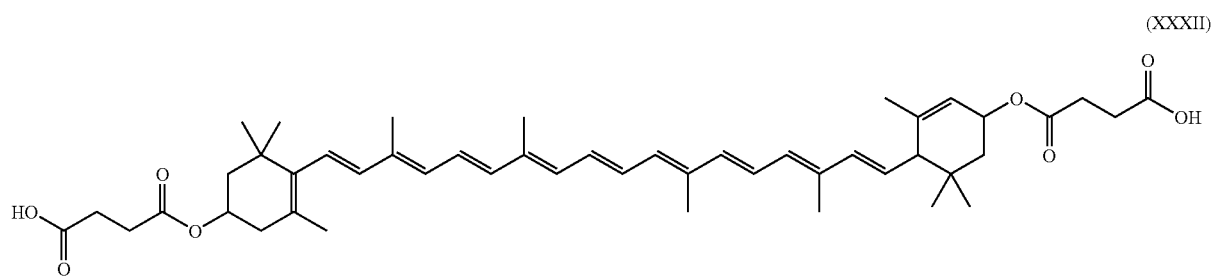

(XXXII)

To a solution of lutein (XXX) (0.010 g, 0.018 mmol) in DCM (2 mL) at room temperature was added DIPEA (0.063 mL, 0.360 mmol), succinic anhydride (0.036 g, 0.360 mmol), and DMAP (0.021 g, 0.176 mmol). The reaction mixture was stirred at room temperature for 48 hours, at which time the reaction was diluted with DCM, quenched with brine/1M HCl (6 mL/1 mL), and then extracted with DCM. The combined organic layers were dried over Na$_2$SO$_4$ and concentrated to yield lutein disuccinate (XXII) (93.09%) HPLC retention time: 11.765 min., 93.09% (AUC); LRMS (ESI) m/z (relative intensity): 769 (M$^+$) (24), 651 (100), and no detectable lutein XXX.

Example 15

Synthesis of Succinic Acid Esters of Zeaxanthin (XXXIII, XXXIV)

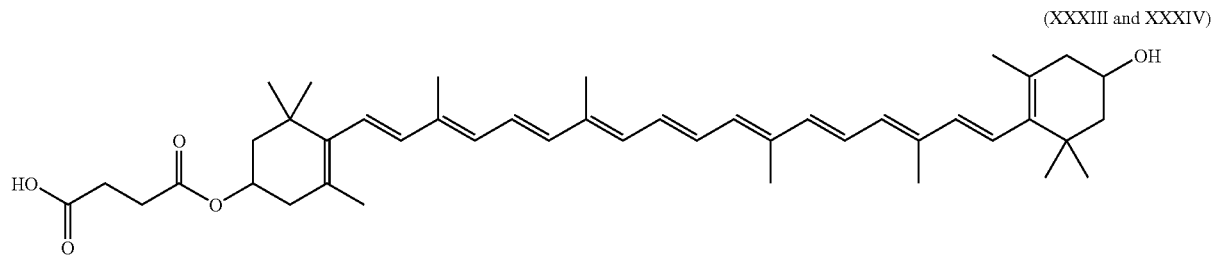

(XXXIII and XXXIV)

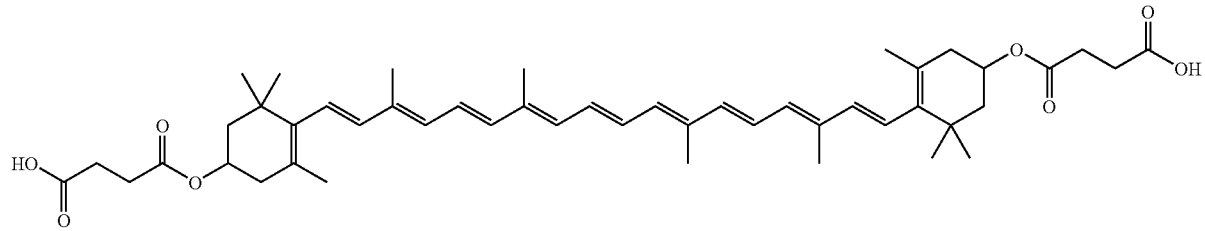

To a solution of zeaxanthin (XXXI) (0.010 g, 0.018 mmol) in DCM (2 mL) at room temperature was added DIPEA (0.063 mL, 0.360 mmol), succinic anhydride (0.036 g, 0.360 mmol), and DMAP (0.021 g, 0.176 mmol). The reaction mixture was stirred at room temperature for 48 hours, at which time the reaction was diluted with DCM, quenched with brine/1M HCl (6 mL/1 mL), and then extracted with DCM. The combined organic layers were dried over $Na_2SO_4$ and concentrated to yield zeaxanthin monosuccinate (XXXIII) (2.86%) HPLC retention: 12.207 min., 2.86% (AUC); LRMS (ESI) m/z (relative intensity): 669 ($M^+$+H) (53), 668 ($M^+$) (100), zeaxanthin disuccinate (XXXIV) (97.14%) HPLC retention time: 11.788 min., 67.42% (AUC); LRMS (ESI) m/z (relative intensity): 792 ($M^+$+Na) (42), 769 ($M^+$) (73), 651 (100); HPLC retention time: 13.587 min., 11.19% (AUC); LRMS (ESI) m/z (relative intensity): 792 ($M^+$+Na) (36), 769 ($M^+$) (38), 663 (100); HPLC retention time: 13.894 min., 18.53% (AUC); LRMS (ESI) m/z (relative intensity): 769 ($M^+$) (62), 663 (77), 651 (100), and no detectable zeaxanthin XXXI.

Example 16

Synthesis of Aconitic Acid Esters of Astaxanthin (XXXV, XXXVI)

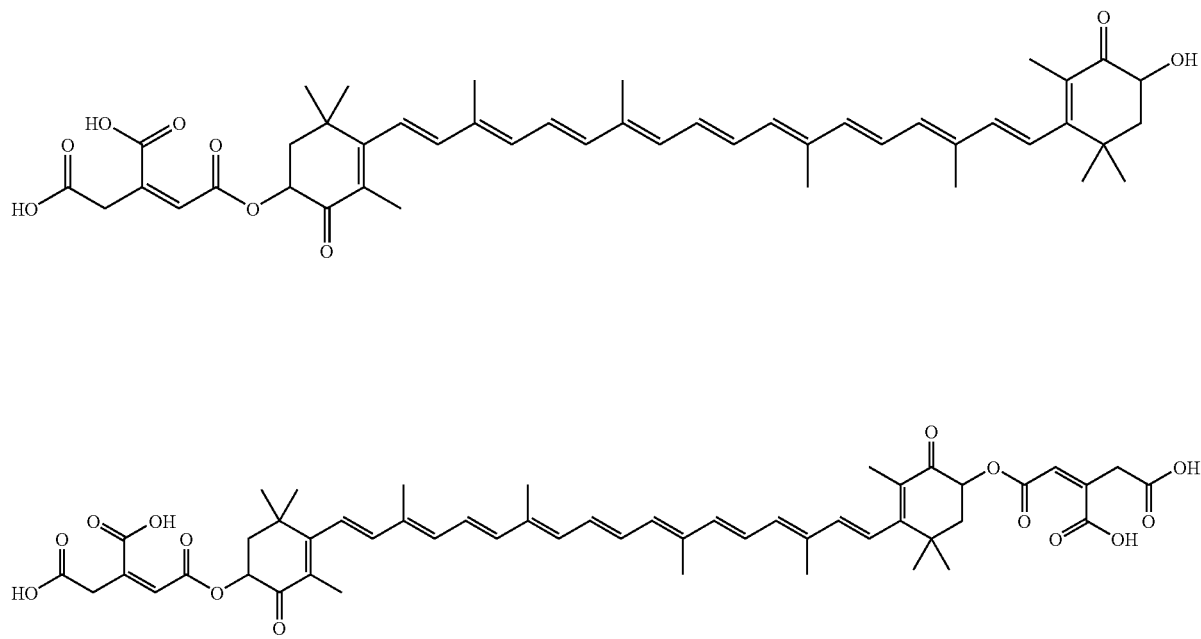

To a solution of astaxanthin 2E (0.100 g, 0.168 mmol) in DCM/DMF ("N,N-dimethylformamide") (4 mL/2 mL) at room temperature was added DIPEA (0.878 mL, 5.04 mmol), cis-aconitic anhydride (0.2622 g, 1.68 mmol), and DMAP (0.4105 g, 3.36 mmol). The reaction mixture was stirred at room temperature for 36 hours, at which time the reaction was diluted with DCM, quenched with brine/1M HCl (20 mL/3 mL), and then extracted with DCM. The combined organic layers were concentrated to yield aconitic monoester (XXXV) (13.25%) HPLC retention time: 10.485 min., 4.95% (AUC); LRMS (ESI) m/z (relative intensity): 777 (M$^+$+Na+2H) (57), 623 (100); HPLC retention time: 10.722 min., 8.30% (AUC); LRMS (ESI) m/z (relative intensity): 777 (M$^+$+Na+2H) (6), 709 (100), aconitic diester (XXXVI) (27.67%) HPLC retention time: 9.478 min., 15.44% (AUC); LRMS (ESI) m/z (relative intensity): 933 (M$^+$+Na+2H) (10), 831 (100); HPLC retention time: 9.730 min., 12.23% (AUC); LRMS (ESI) m/z (relative intensity): 913 (M$^+$+4H) (4), 843 (100), and astaxanthin 2E (44.40%).

Example 17

Synthesis of Citric Acid Esters of Astaxanthin (XXXVII, XXXVIII)

To a suspension of citric acid (0.5149 g, 2.86 mmol) in DCM (8 mL) at room temperature was added DIPEA (1.167 mL, 0.6.70 mmol), DIC (0.525 mL, 3.35 mmol), DMAP (0.4094 g, 3.35 mmol), and astaxanthin 2E (0.200 g, 0.335 mmol). The reaction mixture was stirred at room temperature for 36 hours, at which time the reaction was diluted with DCM, quenched with brine/1M HCl (20 mL/3 mL), and then extracted with DCM. The combined organic layers were concentrated to yield citric acid monoester (XXXVII) (26.56%) HPLC retention time: 9.786 min., 17.35% (AUC); LRMS (ESI) m/z (relative intensity): 773 (M$^+$+3H) (14), 771 (M$^+$+H) (100); HPLC retention time: 9.989 min., 9.21% (AUC); LRMS (ESI) m/z (relative intensity): 773 (M$^+$+3H) (50), 771 (M$^+$+H) (100), citric acid diester (XXXVIII) (7.81%) HPLC retention time: 8.492 min., 3.11% (AUC); LRMS (ESI) m/z (relative intensity): 968 (M$^+$+Na) (75), 967 (100), 946 (M$^+$+H) (37); HPLC retention time: 8.708 min., 2.43% (AUC); LRMS (ESI) m/z (relative intensity): 968 (M$^+$+Na) (95), 946 (M$^+$+H) (100); HPLC retention time: 8.952 min., 2.27% (AUC); LRMS (ESI) m/z (relative intensity): 946 (M$^+$+H) (19), 500 (100), and astaxanthin 2E (21.26%).

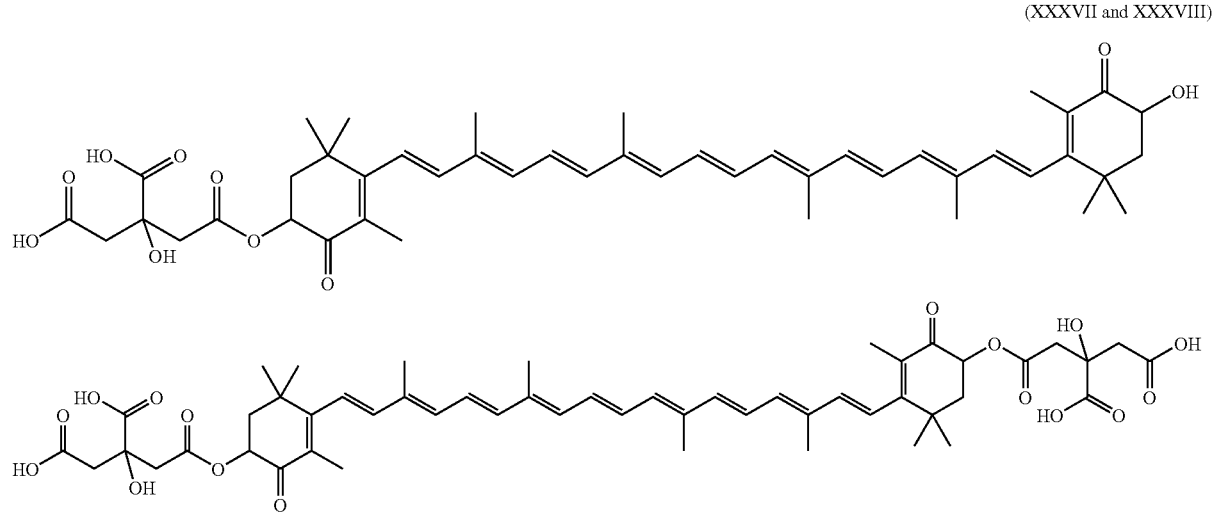

(XXXVII and XXXVIII)

Example 18

Synthesis of Dimethylaminobutyric Acid Monoester of Astaxanthin (XXXIX)

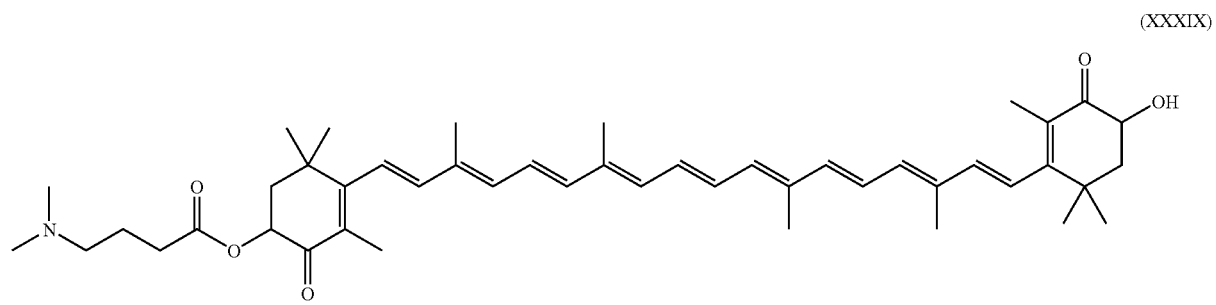

(XXXIX)

To a suspension of 4-(dimethylamino)-butyric acid hydrochloride (0.2816 g, 1.68 mmol) in DCM/DMF (3 mL/3 mL) at room temperature was added DIPEA (0.878 mL, 5.04 mmol), HOBT ("1-hydroxybenzotriazole")-$H_2O$ (0.3094 g, 2.02 mmol), DMAP (0.4105 g, 3.36 mmol), and astaxanthin 2E (0.100 g, 0.168 mmol). The reaction mixture was stirred at room temperature for 36 hours, at which time the reaction was diluted with DCM, quenched with brine/1M HCl (20 mL/3 mL), and then extracted with DCM. The combined organic layers were concentrated to yield 4-(dimethylamino) butyric acid monoester (XXXIX) (24.50%) HPLC retention time: 9.476 min., 20.32% (AUC); LRMS (ESI) m/z (relative intensity): 732 ($M^+$+Na) (13), 729 (100); HPLC retention time: 9.725 min., 4.18% (AUC); LRMS (ESI) m/z (relative intensity): 732 ($M^+$+Na) (50), 729 (100), and astaxanthin (61.21%).

Example 19

Synthesis of Glutathione Monoester of Astaxanthin
(L)

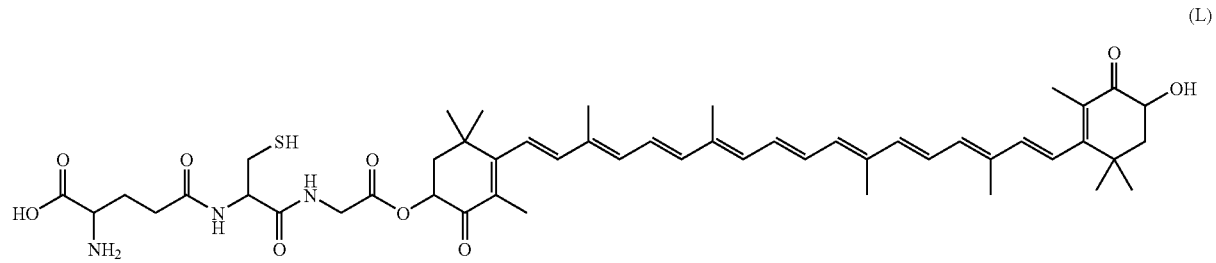

To a suspension of reduced glutathione (0.5163 g, 1.68 mmol) in DCM/DMF (3 mL/3 mL) at room temperature was added DIPEA (0.878 mL, 5.04 mmol), HOBT-$H_2O$ (0.3094 g, 2.02 mmol), DMAP (0.4105 g, 3.36 mmol), DIC (0.316 mL, 2.02 mmol), and astaxanthin 2E (0.100 g, 0.168 mmol). The reaction mixture was stirred at room temperature for 36 hours, at which time the reaction was diluted with DCM, quenched with brine/1M HCl (20 mL/3 mL), and then extracted with DCM. The combined organic layers were concentrated to yield glutathione monoester (L) (23.61%) HPLC retention time: 9.488 min., 16.64% (AUC); LRMS (ESI) m/z (relative intensity): 886 ($M^+$) (13), 810 (54), 766 (100); HPLC retention time: 9.740 min., 3.57% (AUC); LRMS (ESI) m/z (relative intensity): 886 ($M^+$) (24), 590 (78), 546 (100); HPLC retention time: 9.997 min., 3.40% (AUC); LRMS (ESI) m/z (relative intensity): 886 ($M^+$) (25), 869 (85), 507 (100), and astaxanthin (68.17%).

Example 20

Synthesis of Tartaric Acid Diester of Astaxanthin
(LI)

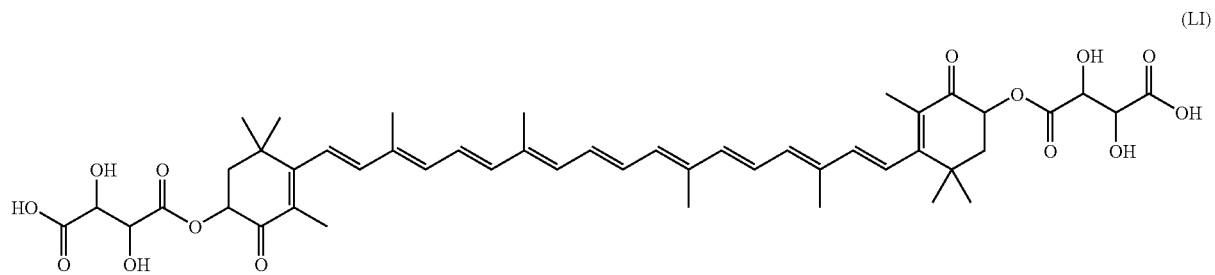

To a suspension of (L)-tartaric acid (0.4022 g, 2.68 mmol) in DCM/DMF (5 mL/5 mL) at room temperature was added DIPEA (1.167 mL, 0.6.70 mmol), HOBT-H$_2$O (0.5131 g, 3.35 mmol), DMAP (0.4094 g, 3.35 mmol), and astaxanthin 2E (0.200 g, 0.335 mmol). The reaction mixture was stirred at room temperature for 36 hours, at which time the reaction was diluted with DCM, quenched with brine/1M HCl (20 mL/3 mL), and then extracted with DCM. The combined organic layers were concentrated to yield tartaric acid diester (LI) (18.44%) HPLC retention time: 9.484 min., 14.33% (AUC); LRMS (ESI) m/z (relative intensity): 884 ($M^+$+Na+H) (100), 815 (72), 614 (72); HPLC retention time: 9.732 min., 4.11% (AUC); LRMS (ESI) m/z (relative intensity): 883 ($M^+$+Na) (100), 539 (72), and astaxanthin 2E (67.11%).

Example 21

Synthesis of Sorbitol Monoester of Astaxanthin Disuccinate (LII)

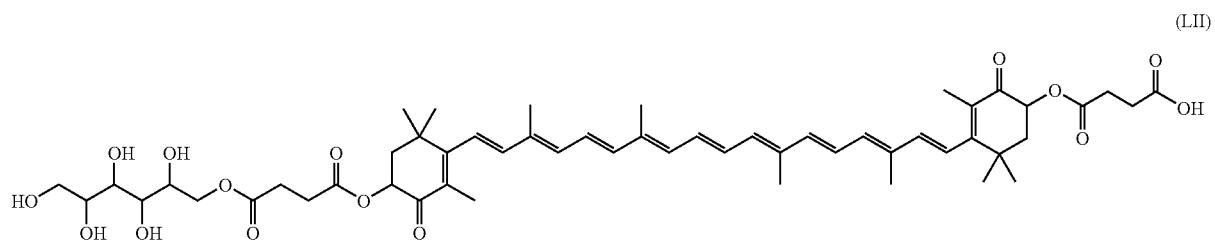

To a solution of astaxanthin disuccinate (XV) (0.200 g, 0.251 mmol) in DMF (10 mL) at room temperature was added DIPEA (1.312 mL, 7.53 mmol), HOBT-H$_2$O (0.4610 g, 3.01 mmol), DMAP (0.6133 g, 5.02 mmol), and (D)-sorbitol (0.4572 g, 2.51 mmol). The reaction mixture was stirred at room temperature for 36 hours, at which time the reaction was diluted with DCM, quenched with brine/1M HCl (20 mL/3 mL), and then extracted with DCM. The combined organic layers were concentrated to yield sorbitol monoester (LII) (3.52%) HPLC retention time: 9.172 min., 3.52% (AUC); LRMS (ESI) m/z (relative intensity): 984 ($M^+$+Na) (28), 503 (100), and astaxanthin disuccinate XV (91.15%).

Example 22

Synthesis of Sorbitol Diester of Astaxanthin Disuccinate (LIII)

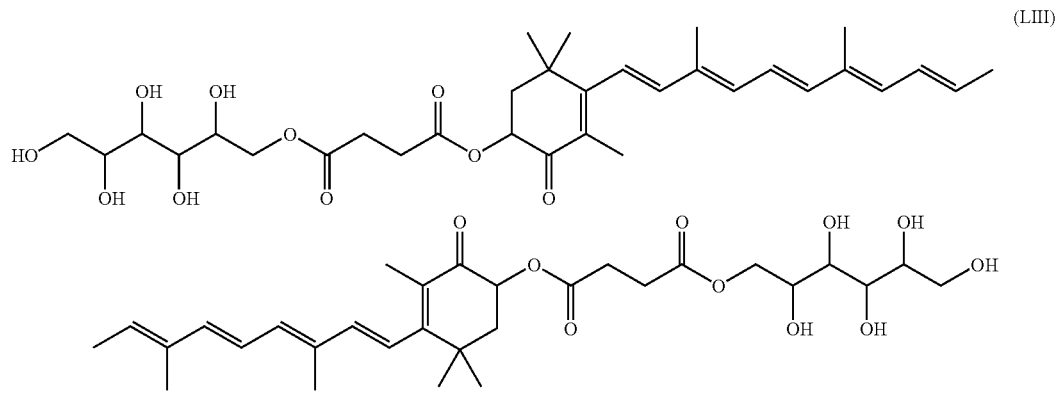

(LIII)

To a solution of astaxanthin disuccinate (XV) (0.100 g, 0.125 mmol) in DCM/DMF (3 mL/3 mL) at room temperature was added DIPEA (0.656 mL, 3.76 mmol), HOBT-H$_2$O (0.2313 g, 1.51 mmol), DMAP (0.3067 g, 2.51 mmol), DIC (0.236 mL, 1.51 mmol), and (D)-sorbitol (0.2286 g, 1.25 mmol). The reaction mixture was stirred at room temperature for 36 hours, at which time the reaction was diluted with DCM, quenched with brine/1M HCl (20 mL/3 mL), and then extracted with DCM. The combined organic layers were concentrated to yield sorbitol diester (LIII) (44.59%) HPLC retention time: 8.178 min., 11.58% (AUC); LRMS (ESI) m/z (relative intensity): 1148 (M$^+$+Na) (40), 545 (100); HPLC retention time: 8.298 min., 33.01% (AUC); LRMS (ESI) m/z (relative intensity): 1148 (M$^+$+Na) (20), 545 (100), and no detectable astaxanthin disuccinate XV.

Example 23

Synthesis of Morpholine Carbamates of Astaxanthin (LIV, LV)

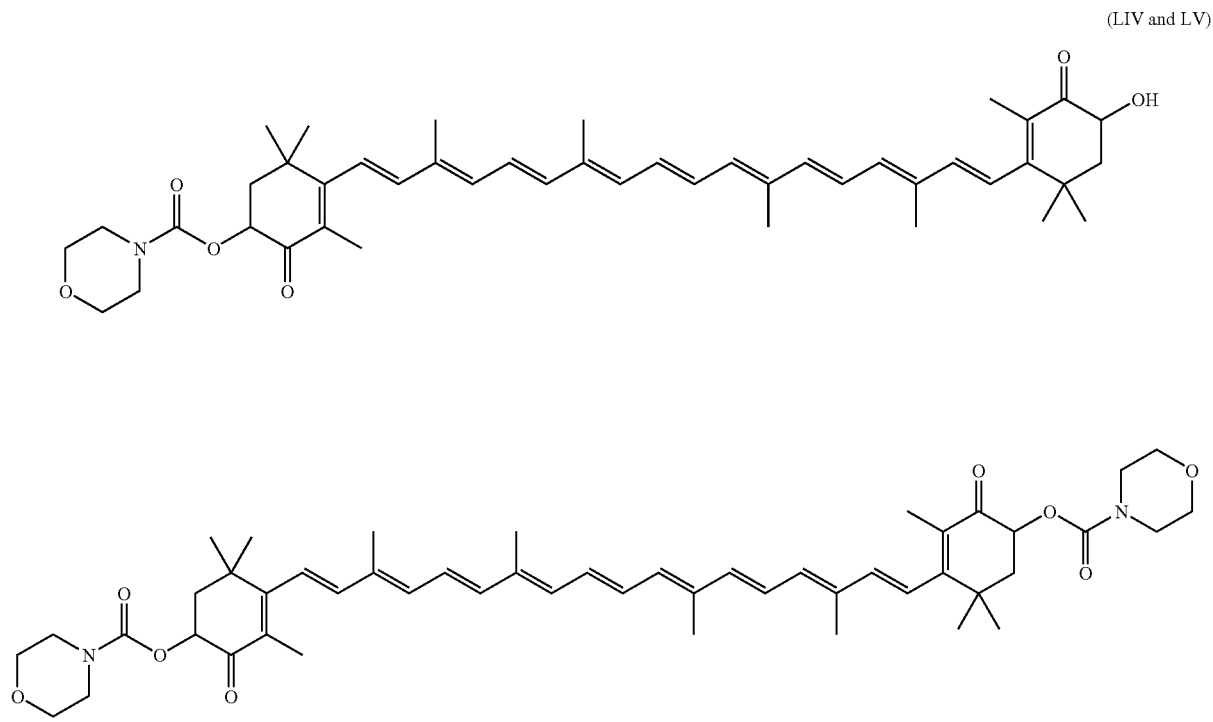

(LIV and LV)

To a solution of astaxanthin 2E (0.100 g, 0.168 mmol) in DCM/DMF (3 mL/3 mL) at room temperature was added DIPEA (0.878 mL, 5.04 mmol), DMAP (0.4105 g, 3.36 mmol), and 4-morpholine carbonyl chloride (0.196 mL, 1.68 mmol). The reaction mixture was stirred at room temperature for 36 hours, at which time the reaction was diluted with DCM, quenched with brine/1M HCl (20 mL/3 mL), and then extracted with DCM. The combined organic layers were concentrated to yield 4-morpholine monocarbamate (LIV) (33.17%) HPLC retention time: 11.853 min., 29.01% (AUC); LRMS (ESI) m/z (relative intensity): 710 (M$^+$) (100); HPLC retention time: 13.142 min., 1.37% (AUC); LRMS (ESI) m/z (relative intensity): 710 (M$^+$) (100); HPLC retention time: 13.383 min., 2.79% (AUC); LRMS (ESI) m/z (relative intensity): 710 (M$^+$) (100), 4-morpholine dicarbamate (LV) (33.42%) HPLC retention time: 12.049 min., 29.71% (AUC); LRMS (ESI) m/z (relative intensity): 824 (M$^+$+H) (54), 823 (M$^+$) (100); HPLC retention time: 13.761 min., 1.29% (AUC); LRMS (ESI) m/z (relative intensity): 823 (M$^+$) (100), 692 (75); HPLC retention time: 14.045 min., 2.42% (AUC); LRMS (ESI) m/z (relative intensity): 823 (M$^+$) (100), 692 (8), and astaxanthin 2E (22.10%).

Example 24

Synthesis of Mannitol Monocarbonate of Astaxanthin (LVII)

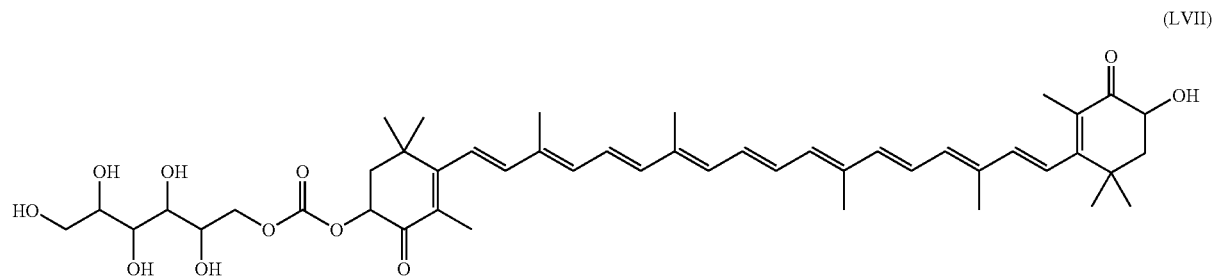

(LVII)

To a solution of astaxanthin 2E (0.100 g, 0.168 mmol) in DCM (4 mL) at 0° C. was added DIPEA (0.585 mL, 3.36 mmol), and 1,2,2,2-tetrachloroethyl chloroformate (0.103 mL, 0.672 mmol). The reaction mixture was stirred at 0° C. for 2 hours, then at room temperature for 1.5 hours, at which time (D)-mannitol (0.3060 g, 1.68 mmol), DMF (3 mL), and DMAP (0.2052 g, 1.68 mmol) were added to the reaction. The reaction mixture was stirred at room temperature for 24 hours, at which time the reaction was diluted with DCM, quenched with brine (20 mL), and then extracted with DCM. The combined organic layers were concentrated to yield mannitol monocarbonate (LVII) (10.19%) HPLC retention time: 9.474 min., 10.19% (AUC); LRMS (ESI) m/z (relative intensity): 827 (M$^+$+Na) (50), 804 (M$^+$) (25), 725 (58), 613 (100), and astaxanthin 2E (53.73%).

Example 25

Synthesis of (Dimethylamino)butyric Acid Diester of Astaxanthin (LVIII)

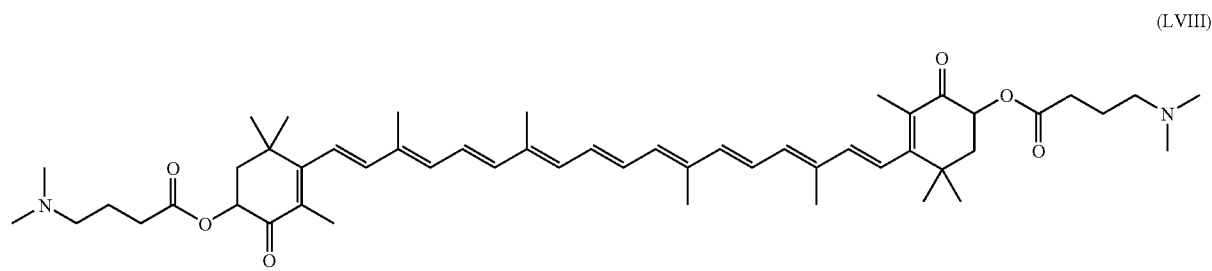

(LVIII)

To a suspension of 4-(dimethylamino)butyric acid hydrochloride (0.2816 g, 1.68 mmol) in DCM/DMF (3 mL/3 mL) at room temperature was added DIPEA (0.878 mL, 5.04 mmol), DMAP (0.4105 g, 3.36 mmol), HOBT-$H_2O$ (0.3094 g, 2.02 mmol), DIC (0.316 mL, 2.02 mmol), and astaxanthin 2E (0.100 g, 0.168 mmol). The reaction mixture was stirred at room temperature for 36 hours, at which time the reaction was diluted with DCM, quenched with brine/1M HCl (20 mL/3 mL), and then extracted with DCM. The combined organic layers were concentrated to yield (dimethylamino) butyric acid diester (LVIII) (77.70%) HPLC retention time: 7.850 min., 56.86% (AUC); LRMS (ESI) m/z (relative intensity): 824 ($M^+$+H) (64), 823 ($M^+$) (100); HPLC retention time: 8.443 min., 3.87% (AUC); LRMS (ESI) m/z (relative intensity): 823 ($M^+$) (5), 641 (20), 520 (100); HPLC retention time: 9.021 min., 16.97% (AUC); LRMS (ESI) m/z (relative intensity): 824 ($M^+$+H) (58), 823 ($M^+$) (100), and no detectable astaxanthin 2E.

Example 26

Synthesis of Benzyl Monoether of Astaxanthin (LIX)

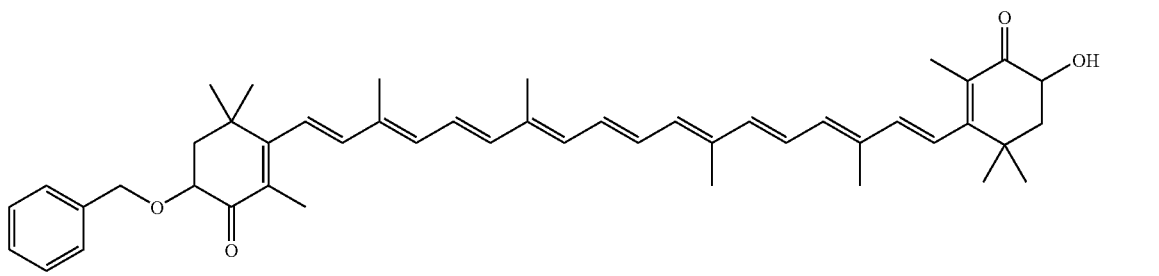

(LIX)

To a solution of astaxanthin 2E (0.100 g, 0.168 mmol) and benzyl bromide (0.400 mL, 3.36 mmol) in DCM/DMF (3mL/3 mL) at 0° C. was added KHMDS ("potassium bis(trimethylsilyl)amide") (6.72 mL; 0.5M in toluene, 3.36 mmol). The reaction mixture was stirred at 0° C. for 1 hour and then allowed to warm to room temperature. The mixture was stirred at room temperature for 24 hours, at which time the reaction was diluted with DCM, quenched with brine/ 1M HCl (20 mL/3 mL), and then extracted with DCM. The combined organic layers were concentrated to yield benzyl monoether (LIX) (15.06%) HPLC retention time: 12.705 min., 15.06% (AUC); LRMS (ESI) m/z (relative intensity): 686 ($M^+$) (93), 597 (100), and astaxanthin 2E (67.96%).

Example 27

Synthesis of Mannitol Monoether of Astaxanthin (LX)

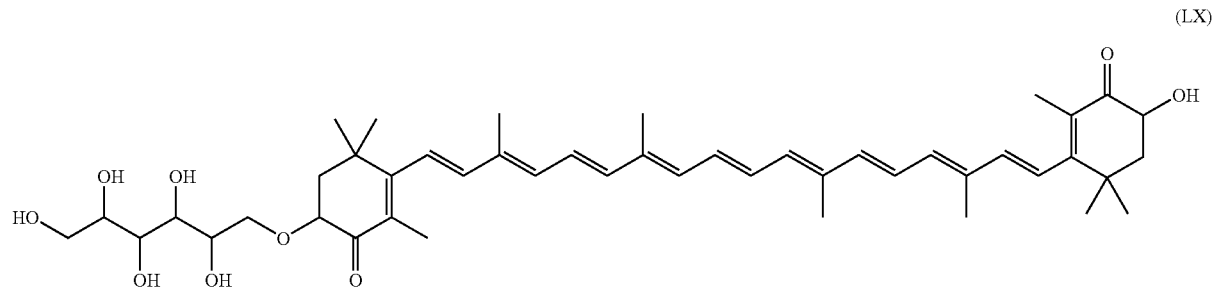

(LX)

To a solution of astaxanthin 2E (0.200 g, 0.335 mmol) in DCM (15 mL) at room temperature was added 48% HBr (10 mL) and H₂O (30 mL). The aqueous layer was extracted with DCM and the combined organic layers were dried over Na₂SO₄ and concentrated to yield the bromide derivative of astaxanthin as a dark red oil. To a solution of the crude bromide in DCM/DMF (6 mL/6 mL) at room temperature was added DIPEA (1.58 mL, 9.09 mmol), DMAP (0.3702 g, 3.03 mmol), and (D)-mannitol (0.5520 g, 3.03 mmol). The reaction mixture was stirred at room temperature for 24 hours, at which time the reaction was diluted with DCM, quenched with brine/1M HCl (20 mL/3 mL), and then extracted with DCM. The combined organic layers were concentrated to yield mannitol monoether (LX) (4.40%) HPLC retention time: 9.479 min., 4.40% (AUC); LRMS (ESI) m/z (relative intensity): 783 (M⁺+Na) (64), 710 (66), 653 (100), and astaxanthin 2E (79.80%).

Example 28

Synthesis of Tris(hydroxymethyl)aminomethane Monoamide of Astaxanthin Disuccinate (LXI)

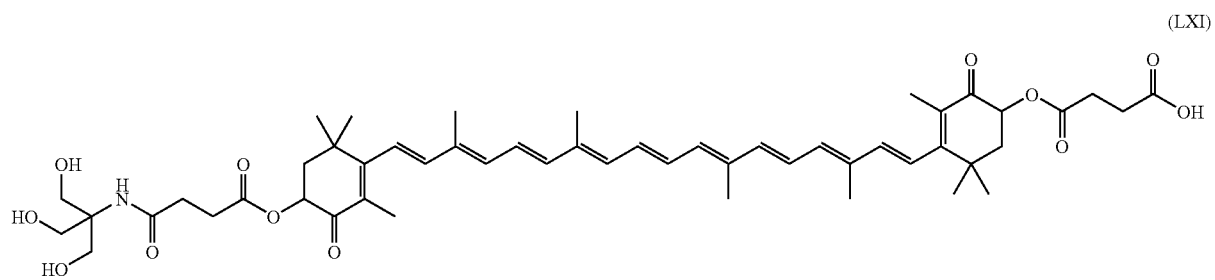

(LXI)

To a solution of astaxanthin disuccinate (XV) (0.100 g, 0.125 mmol) in DCM/DMF (3 mL/3 mL) at room temperature was added DIPEA (0.653 mL, 3.75 mmol), DMAP (0.3054 g, 2.50 mmol), HOBT-H₂O (0.2297 g, 1.50 mmol), and tris(hydroxymethyl)aminomethane (0.1514 g, 1.25 mmol). The reaction mixture was stirred at room temperature for 36 hours, at which time the reaction was diluted with DCM, quenched with brine/1M HCl (20 mL/3 mL), and then extracted with DCM. The combined organic layers were concentrated to yield tris(hydroxymethyl)aminomethane monoamide (LXI) (4.40%) HPLC retention time: 9.521 min., 3.50% (AUC); LRMS (ESI) m/z (relative intensity): 923 (M⁺+Na) (36), 900 (M⁺) (80), 560 (100); HPLC retention time: 9.693 min., 0.90% (AUC); LRMS (ESI) m/z (relative intensity): 923 (M⁺+Na) (11), 813 (33), 500 (100), and astaxanthin disuccinate XV (84.34%).

Example 29

Synthesis of Tris(hydroxymethyl)aminomethane Diamide of Astaxanthin Disuccinate (LXII)

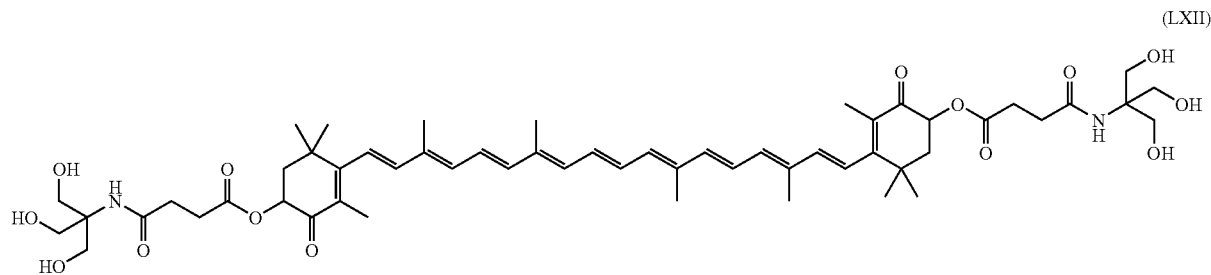

(LXII)

To a solution of astaxanthin disuccinate (XV) (0.100 g, 0.125 mmol) in DCM/DMF (3 mL/3 mL) at room temperature was added DIPEA (0.653 mL, 3.75 mmol), DMAP (0.3054 g, 2.50 mmol), HOBT-H$_2$O (0.2297 g, 1.50 mmol), DIC (0.235 mL, 1.50 mmol), and tris(hydroxymethyl)aminomethane (0.1514 g, 1.25 mmol). The reaction mixture was stirred at room temperature for 36 hours, at which time the reaction was diluted with DCM, quenched with brine/1M HCl (20 mL/3 mL), and then extracted with DCM. The combined organic layers were concentrated to yield tris(hydroxymethyl)aminomethane diamide (LXII) (66.51%) HPLC retention time: 8.086 min., 19.34% (AUC); LRMS (ESI) m/z (relative intensity): 1026 (M$^+$+Na) (22), 1004 (M$^+$+H) (84), 1003 (M$^+$) (100), 502 (83); HPLC retention time: 8.715 min., 47.17% (AUC); IRMS (ESI) m/z (relative intensity): 1004 (M$^+$+H) (71), 1003 (M$^+$) (100), 986 (62), and astaxanthin disuccinate XV (18.61%).

Example 30

Synthesis of Adenosine Monoester of Astaxanthin Disuccinate (LXIII)

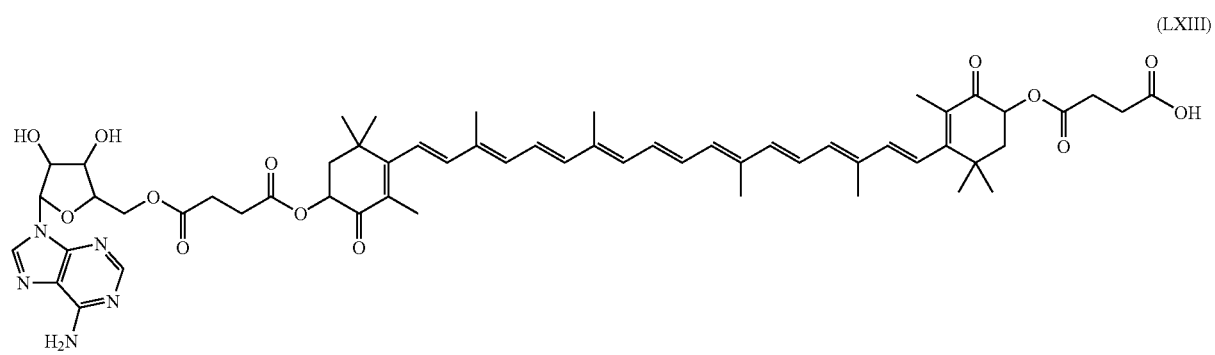

(LXIII)

To a solution of astaxanthin disuccinate (XV) (0.100 g, 0.125 mmol) in DCM/DMF (3 mL/3 mL) at room temperature was added DIPEA (0.653 mL, 3.75 mmol), DMAP (0.3054 g, 2.50 mmol), HOBT-H$_2$O (0.1914 g, 1.25 mmol), and (−)-adenosine (0.3341 g, 1.25 mmol). The reaction mixture was stirred at room temperature for 48 hours, at which time the reaction was diluted with DCM, quenched with brine/1M HCl (20 mL/3 mL), and then extracted with DCM. The combined organic layers were concentrated to yield adenosine monoester (LXIII) (21.13%) HPLC retention time: 9.005 min., 2.43% (AUC); LRMS (ESI) m/z (relative intensity): 1047 (M$^+$+H) (36), 1046 (M$^+$) (57), 524 (100); HPLC retention time: 9.178 min., 10.92% (AUC); LRMS (ESI) m/z (relative intensity): 1047 (M$^+$+H) (80), 1046 (M$^+$) (100), 829 (56), 524 (94); HPLC retention time: 9.930 min., 7.78% (AUC); LRMS (ESI) m/z (relative intensity): 1046 (M$^+$) (100), 524 (34), and astaxanthin disuccinate XV (58.54%).

Example 31

Synthesis of Maltose Diester of Astaxanthin Disuccinate (LXIV)

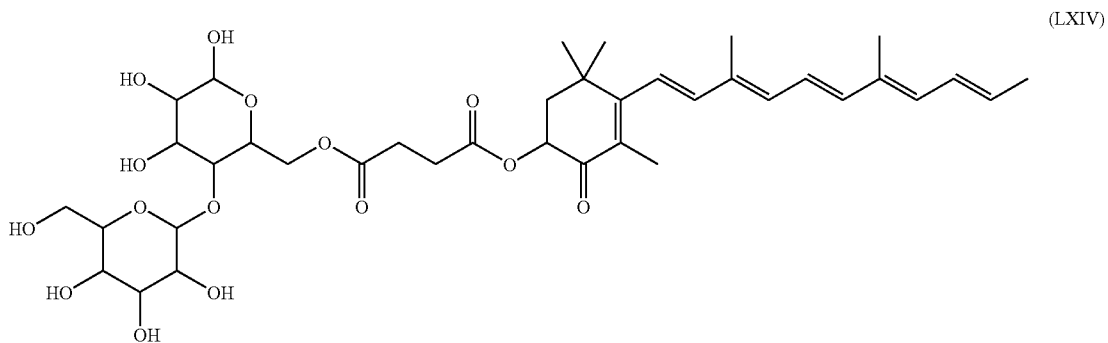

(LXIV)

-continued

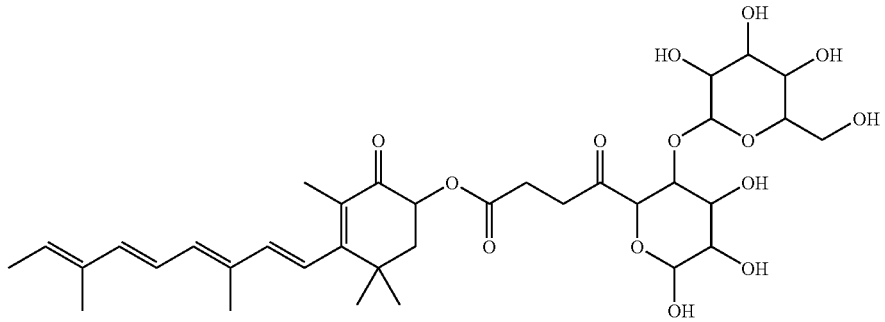

To a solution of astaxanthin disuccinate (XV) (0.100 g, 0.125 mmol) in DCM/DMF (3 mL/3 mL) at room temperature was added DIPEA (0.653 mL, 3.75 mmol), DMAP (0.3054 g, 2.50 mmol), HOBT-H$_2$O (0.2297 g, 1.50 mmol), DIC (0.235 mL, 1.50 mmol), and (D)-maltose-H$_2$O (0.4504 g, 1.25 mmol). The reaction mixture was stirred at room temperature for 36 hours, at which time the reaction was diluted with DCM, quenched with brine/1M HCl (20 mL/3 mL), and then extracted with DCM. The combined organic layers were concentrated to yield maltose diester (LXIV) (25.22%) HPLC retention time: 7.411 min., 12.53% (AUC); LRMS (ESI) m/z (relative intensity): 1468 (M$^+$+Na) (18), 1067 (16), 827 (100); HPLC retention time: 7.506 min., 12.69% (AUC); LRMS (ESI) m/z (relative intensity): 1468 (M$^+$+Na) (52), 827 (76), 745 (100), and astaxanthin disuccinate XV (22.58%).

Example 32

Synthesis of Resveratrol Esters of Astaxanthin Dissucinate (LXV, LXVI)

(LXV and LXVI)

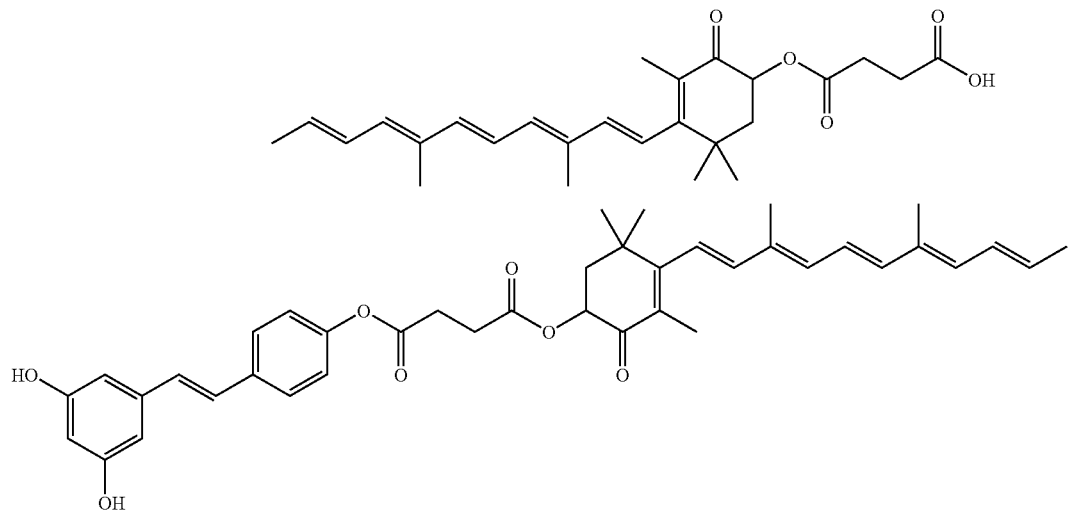

-continued

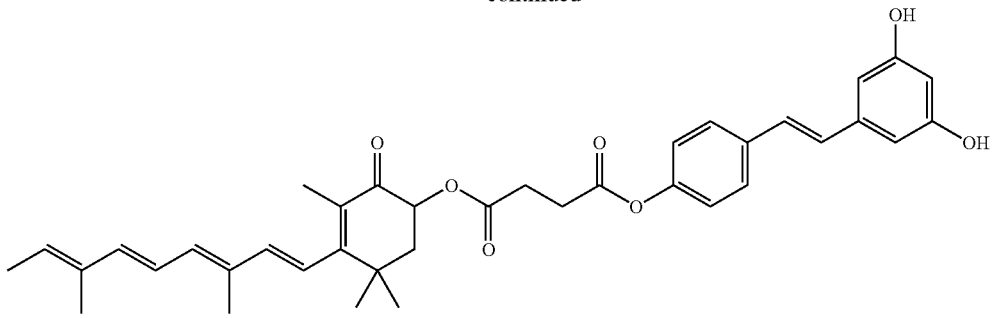

To a solution of astaxanthin disuccinate (X(V) (0.100 g, 0.125 mmol) in DCM/DMF (3 mL/3 mL) at room temperature was added DIPEA (0.653 mL, 3.75 mmol), DMAP (0.3054 g, 2.50 mmol), HOBT-H$_2$O (0.2297 g, 1.50 mmol), DIC (0.235 mL, 1.50 mmol), and resveratrol (0.2853 g, 1.25 mmol). The reaction mixture was stirred at room temperature for 24 hours, at which time the reaction was diluted with DCM, quenched with brine/1M HCl (20 mL/3 mL), and then extracted with DCM. The combined organic layers were concentrated to yield resveratrol monoester (LXV) (1.12%) HPLC retention time: 10.039 min., 1.12% (AUC); LRMS (ESI) m/z (relative intensity): 1009 (M$^+$+2H) (18), 1007 (M$^+$) (21), 637 (100), resveratrol diester (LXVI) (60.72%) HPLC retention time: 10.324 min., 15.68% (AUC); LRMS (ESI) m/z (relative intensity): 1217 (M$^+$) (28), 1007 (100), 609 (69), 504 (85); HPLC retention time: 10.487 min., 29.26% (AUC); LRMS (ESI) m/z (relative intensity): 1218 (M$^+$+H) (80), 1217 (M+) (100), 609 (60); HPLC retention time: 10.666 min., 15.78% (AUC); LRMS (ESI) m/z (relative intensity): 1218 (M$^+$+H) (84), 1217 (M$^+$) (100), 609 (71), and no detectable astaxanthin disuccinate XV.

Example 33

Synthesis of the Bis(2,3-di-OBz Ascorbic Acid) Bis(2-cyanoethyl) Phosphate Triester of Astaxanthin (LXVII)

(LXVII)

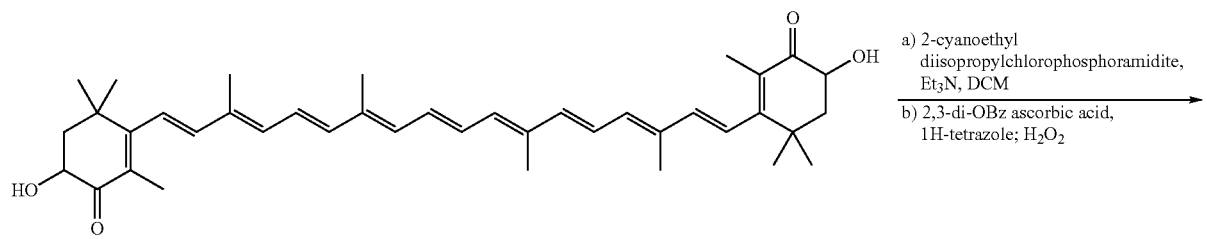

a) 2-cyanoethyl diisopropylchlorophosphoramidite, Et$_3$N, DCM b) 2,3-di-OBz ascorbic acid, 1H-tetrazole; H$_2$O$_2$

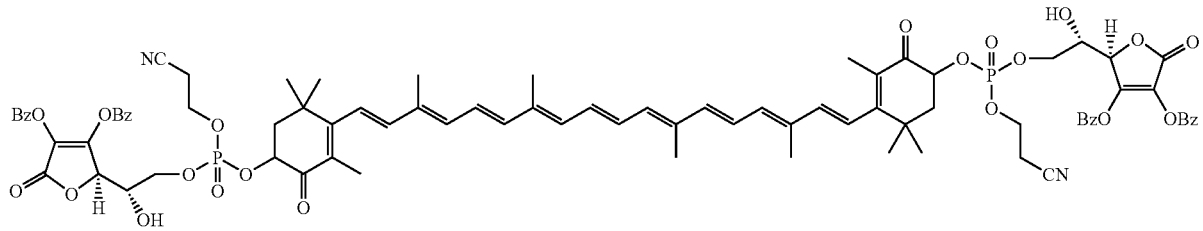

To a stirring solution of astaxanthin 2E (100 mg, 0.168 mmol) in 2 mL of dichloromethane were added triethylamine (63 μL, 0.454 mmol) and 2-cyanoethyl diisopropylchlorophosphoramidite (79 μL, 0.353 mmol). The reaction was stirred for 15 min then another portion of 2-cyanoethyl diisopropylchlorophosphoramidite (15 μL, 0.033 mmol) was added. After 1 h reaction time, the solution was treated with 2,3-di-OBz ascorbic acid (149 mg, 0.386 mmol) and 1H-tetrazole (27 mg, 0.39 mmol). The reaction was judged complete after 3 h by tlc analysis (40% EtOAc/heptane), and quenched by adding 30% hydrogen peroxide solution (48 mL, 0.42 mmol) in 1 mL tetrahydrofuran. The reaction was diluted with 20 mL of DCM and washed with 1 M sodium thiosulfate (20 mL), water (20 mL), and 0.25 M HCl (20 mL). The organic layer was dried over anhydrous sodium sulfate, filtered, and concentrated to give a crude red solid. Mass spectroscopy analysis of the crude solid detected the mass ion of the desired product (+ESI, m/z 1595 (M$^+$)).

Example 34

Synthesis of Lycophyll Disuccinate (LXVIII)

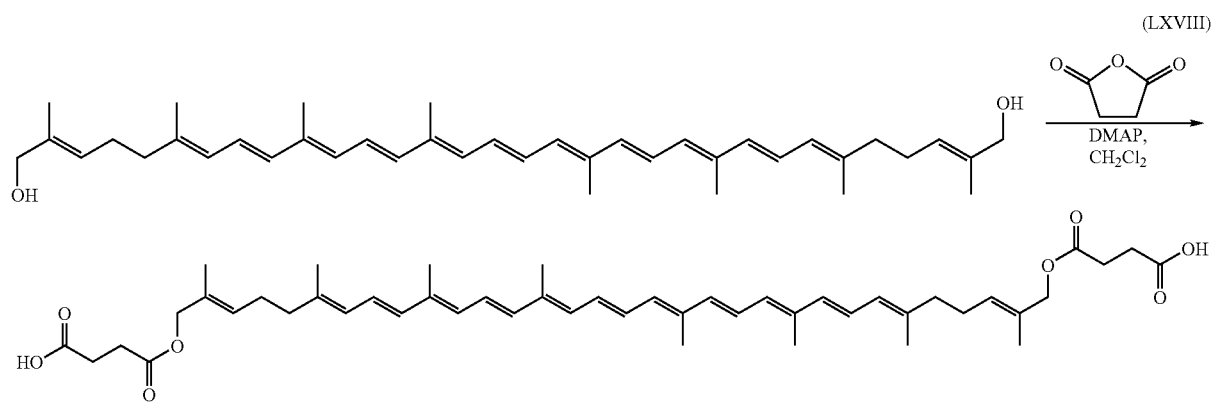

To a stirring solution of lycophyll (28.0 mg, 0.0492 mmol) in 10 mL of dichloromethane were added succinic anhydride (12.3 mg, 0.123 mmol) and dimethylaminopyridine (15.0 mg, 0.123 mmol). The reaction vessel was wrapped in aluminum foil and stirred at ambient temperature overnight. After 16 hours, the reaction was complete by TLC. The mixture was then concentrated to give a crude red solid. Mass spectroscopic analysis of the crude solid detected the mass ion of the desired product LXVIII (–APCI, m/z 767((M–H)$^-$)). LC/MS analysis was performed on an Agilent 1100 LC/MSD VL ESI system with Zorbax Eclipse XDB-C18 Rapid Resolution 4.6×75 mm, 3.5 μm, USUT002736; Temperature: 25° C.; Mobile Phase:(% A=0.025% TFA in H$_2$O; % B=0.025% TFA in MeCN), 70% A/30% B(start); hold at 30% B for 1 min, linear gradient to 98% B over 10 min, hold at 98% B for 9 min; Flow rate: 1.0 mL/min; Starting pressure: 112 bar; PDA Detector 470 nm, 373 nm, 214 nm. LRMS: –mode, APCI.

Example 35

Synthesis of Bis(methyl) Phosphates of Lutein ("xanthophyll") (LXIX and LXX)

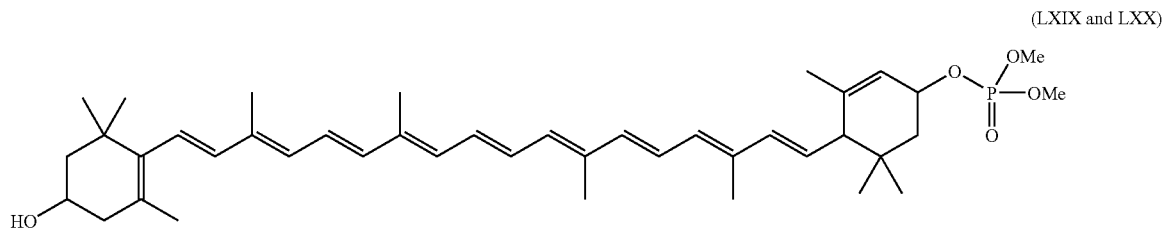

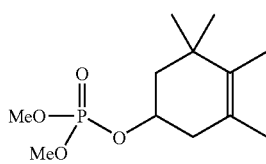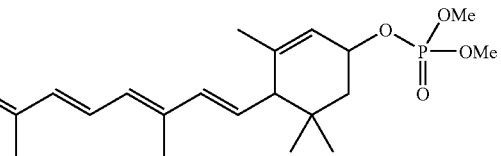

General.

Reactions were performed under nitrogen ($N_2$) atmosphere and were protected from direct light. Racemic lutein 2B ("xanthophyll") was purchased from ChemPacific. Flash chromatography was performed on Natland International Corporation 230-400 mesh silica gel using the indicated solvents. LC/MS was recorded on an Agilent 1100 LC/MSD VL ESI system; column: Zorbax Eclipse XDB-C18 Rapid Resolution (4.6×75 mm, 3.5 µm, USUT002736); temperature: 25° C.; starting pressure: 107 bar; flow rate: 1.0 mL/min.; mobile phase (% A=0.025% TFA in $H_2O$, % B=0.025% TFA in acetonitrile) Method: 70% A/30% B (start), step gradient to 50% B over 5 min., step gradient to 98% B over 8.30 min., hold at 98% B over 25.20 min., step gradient to 30% B over 25.40 min.; PDA Detector: 470 nm; LRMS: +mode, ESI.

Bis(methyl) Phosphates of Lutein ("Xanthophyll"). To a solution of trimethyl phosphite (0.533 mL, 4.52 mmol) in DCM (5 mL) at 0° C. was added $I_2$ (1.06 g, 4.20 mmol). The mixture was stirred at 0° C. for 10 minutes or until all $I_2$ went into solution to produce a clear, colorless solution. The solution was allowed to warm to room temperature, and was stirred for an additional 5 minutes. The solution was slowly added dropwise to a mixture of xanthophyll (0.60 g, 1.05 mmol) and pyridine (3.40 mL, 42.0 mmol) at −78° C. The solution was stirred for 10 minutes at −78° C., quenched with brine, and extracted with DCM. The combined organic layers were washed with brine, dried over $Na_2SO_4$, and concentrated. Purification of the residue using flash chromatography (66% hexanes/ethyl acetate, 1% TEA) yielded bis(methyl) monophosphate LXIX (0.080 g) HPLC retention time: 18.048 min.; LRMS (ESI) m/z (relative intensity): 676 ($M^+$) (10), 675 (18), 659 (30), 533 (100); and bis(methyl) diphosphate LXX (0.130 g) HPLC retention time: 13.111 min.; LRMS (ESI) m/z (relative intensity): 807 ($M^++Na$) (15), 785 ($M^++H$) (10), 676 (40), 675 (20), 659 (100), 533 (90).

Rigorous Determination of Water Solubility of the Disodium Disuccinate Astaxanthin Derivative (XVI)

A total of 30 mg of sample (disodium disuccinate astaxanthin derivative, as the all-trans mixture of stereoisomers 3S,3'S, meso, and 3R,3'R in a 1:2:1 ratio) was added to 2 mL of sterile-filtered (0.2 µM Millipore®) deionized (DI) water in a 15 mL glass centrifuge tube. The tube was wrapped in aluminum foil and the mixture was shaken for 2 hours, then centrifuged at 3500 rpm for 10 minutes. The aqueous solution was filtered through a 0.45 micron PVDF disposable filter device. A 1 mL volume of filtrate was then diluted appropriately with DI water, and the concentration of the solution was measured at 480 nm using a four point calibration curve prepared from fresh sample. After taking the dilutions into account, the concentration of the saturated solution of the disodium disuccinate astaxanthin derivative was 8.64 mg/mL.

Experimental Data for Inhibition and/or Amelioration of Disease

Figure 27:
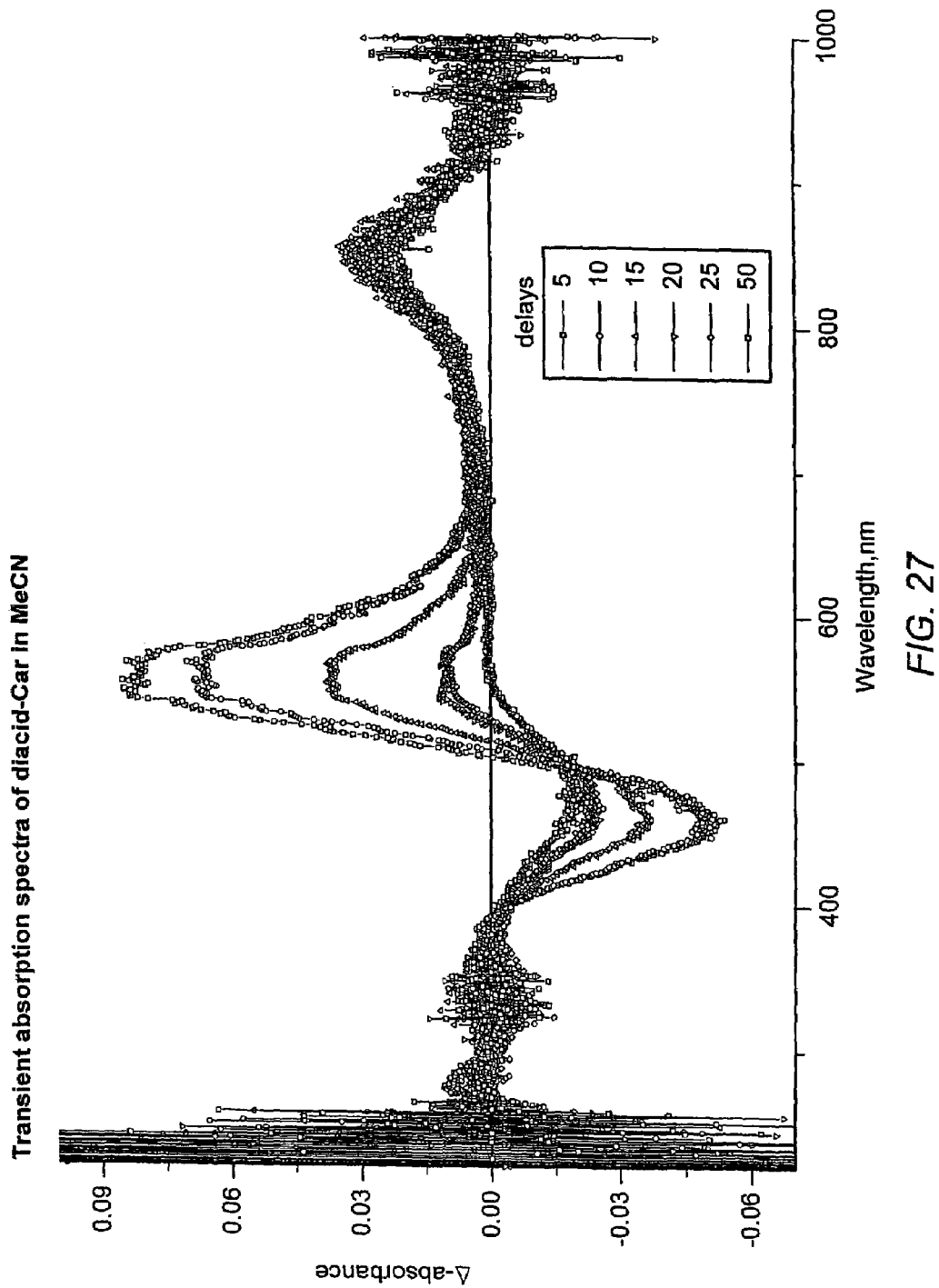
FIG. 27 depicts transient absorption versus delay for the diacid disuccinate astaxanthin derivative (astaCOOH) using flash photolysis. The experiment was performed in acetonitrile (MeCN) using nitronaftalin (NN) as photosensitizer. The spectra obtained demonstrate that the diacid disuccinate astaxanthin derivative behaves h identically to non-esterified, free racemic astaxanthin as a radical quencher (formation of the carotenoid radical cation), identifying the derivative as an active "soft-drug" which generates non-esterified, free astaxanthin in vivo after both oral and intravenous delivery.
Figure 28:
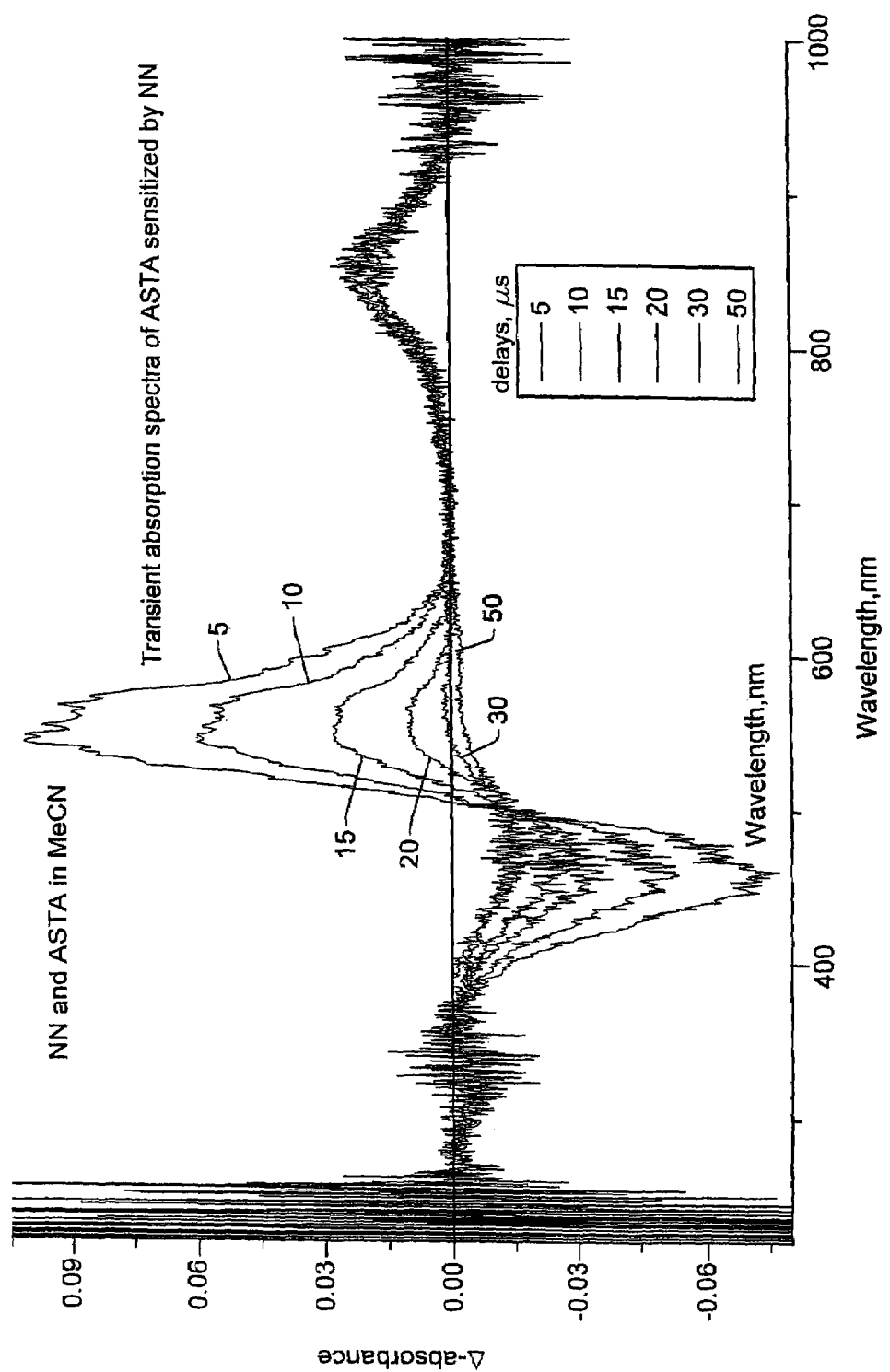
FIG. 28 depicts transient absorption versus delay for the reference compound non-esterified, free racemic astaxanthin (asta)] using flash photolysis. The experiment was performed in acetonitrile (MeCN) using nitronaftalin (NN) as photosensitizer. The spectra obtained are nearly superimposable on those obtained for the diacid disuccinate astaxanthin derivative (astaCOOH), suggesting identical radical-cation forming properties for both compounds.

Comparison of Radical-Cation Forming Ability: Non-esterified, Free Astaxanthin and Diacid Disuccinate Astaxanthin Using Flash Photolysis FIG. 27 and FIG. 28 depict the results of spectral analysis after flash photolysis of the formation of triplet and carotenoid cation radical states for non-esterified, free astaxanthin 2E and the diacid disuccinate astaxanthin derivative XV were obtained. Formation of the carotenoid cation radical is a measure of the potential biophysical behavior of the novel derivative as an antioxidant. If a derivative retains the antioxidant behavior of non-esterified, free astaxanthin, then all previously documented (i.e. literature precedent) therapeutic applications for astaxanthin can be reasonably assumed for the novel derivative, including at least singlet oxygen quenching, lipid peroxidation chain-breaking, and/or direct radical scavenging.

Irradiating carotenoids (car) directly does not result in the formation of carotenoid triplets ($^3$car); a photosensitizer is needed. In this experiment, nitronaftalin (NN) was used as the photosensitizer. After irradiation, the excited sensitizer (NN*) forms a sensitizer triplet ($^3$NN). When $^3$NN encounters a carotenoid, energy and electron transfer reactions with $^3$NN take place. The resulting relatively stable $^3$car and carotenoid cation radicals (car*+) are detected by characteristic absorption bands. Non-polar solvents (e.g. hexane) favor the formation of $^3$car, and more polar solvents (alcohols, water) favor the formation of the car.+. The anion radical of the sensitizer (NN.−) is not typically seen because of a low absorption coefficient.

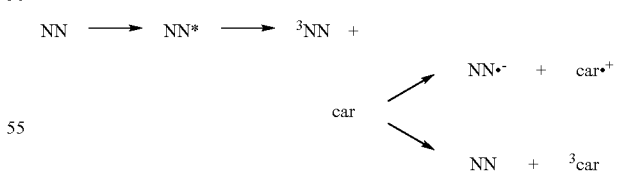

A. Spectra with Astaxanthin Disuccinic Acid (astaCOOH).

Transient Absorption Spectra of astaCOOH in Acetonitrile (MeCN), Sensitizer NN.

Negative peaks in the spectra demonstrate ground state depletion of NN and astaCOOH XV. The positive peak at 550 nm shows the formation of the astaCOOH XV triplet; the positive peak at 850 nm shows the formation of the astaCOOH XV cation radical. The $^3$car decays rather quickly. After 15 µs, half of the $^3$car has disappeared, and after 50 µs, no $^3$car is left. The car.$^+$ is stable within this time frame.

B. Spectra with Reference Compound [Non-esterified, Free Astaxanthin (asta)].

Transient Absorption Spectra of Asta in Acetonitrile (MeCN), Sensitizer NN.

The spectrum of asta 2E is nearly identical to that of astaCOOH XV. After 50 µs, the $^3$car has disappeared. During this time frame, the car.$^+$ is stable. Negative and positive peaks in the absorption spectra for astaCOOH XV and asta 2E are superimposable.

Brief Discussion of Flash Photolysis Results:

There appears to be little difference between the diacid disuccinate astaxanthin derivative (astaCOOH, XV) and non-esterified, free astaxanthin (asta, 2E) during flash photolysis experiments. AstaCOOH XV behaves like asta 2E in the flash photolysis experiments. Therefore, esterification of free astaxanthin 2E with succinic acid does not alter the photophysical properties and the cation radical lifetime. Both compounds were photostable during the flash photolysis experiments. The disuccinate astaxanthin XV derivative retains the potent antioxidant potential of astaxanthin 2E, and is active in the esterified state. It can therefore be considered a "soft" drug (active as the modified entity)—and not a prodrug for therapeutic applications—conferring the valuable propert(ies) of dual-phase radical scavenging activity to this derivative (i.e. aqueous- and lipid-phase radical scavenging).

Induction of Connexin 43 Protein Expression

The methods for cell culture, Western blotting, quantitative densitometric analysis, and total protein evaluation are described in detail in Rogers et al. (1990), with modifications suggested in Bertram (1999). In brief, mouse embryonic fibroblast CH3/10T$^{1/2}$ cells were treated with the following formulations in a 4 mL cell culture system with media containing 2% calf serum:
1. TTNPB [p-(E)-2-(5,6,7,8-tetrahydro-5,5,8,8-tetramethyl-2-napthyl) propenyl benzoic acid] $10^{-8}$ M in acetone [positive control for connexin 43 upregulation (4 µL in 4 mL]
2. Disodium salt disuccinate astaxanthin derivative XVI/ H$_2$O at $10^{-5}$ M (40 µl in 4 mL)
3. Disodium salt disuccinate astaxanthin derivative XVI/ H$_2$O at $10^{-6}$ M (4 µl in 4 mL)
4. Disodium salt disuccinate astaxanthin derivative XVI/ H$_2$O at $10^{-7}$ M (1:10 dilution and 4 µl in 4 mL)
5. Disodium salt disuccinate astaxanthin derivative XVI H$_2$O/ethanol [EtOH] formulation at 10-5 M (40 µl in 4 mL)
6. Disodium salt disuccinate astaxanthin derivative XVI H$_2$O/EtOH formulation at $10^{-6}$ M (4 µl in 4 mL)
7. Sterile H$_2$O control (40 µl in 4 mL)
8. Sterile H$_2$O/EtOH control (20 µL EtOH, 20 µL H$_2$O in 4 mL)
9. Media control (4 mL)

Cells were harvested after 96 hours incubation with test compounds and control solutions. All media solutions were identical in color, however after treatment with the disodium salt disuccinate astaxanthin derivative XVI at both $10^{-5}$ dilutions, the color subjectively changed to an orange-red color. Cells treated with TTNPB appeared striated with light microscopy, evidence of differentiation to myocytes, an expected result in this cell culture system. After harvest and pelleting of cells, tubes containing both $10^{-5}$ disodium salt disuccinate astaxanthin derivative XVI solutions were bright red; both $10^{-6}$ dilution tubes were a pink color. As documented previously for other colored carotenoids, this was subjective evidence for cellular uptake of the test compounds.

Figure 29:
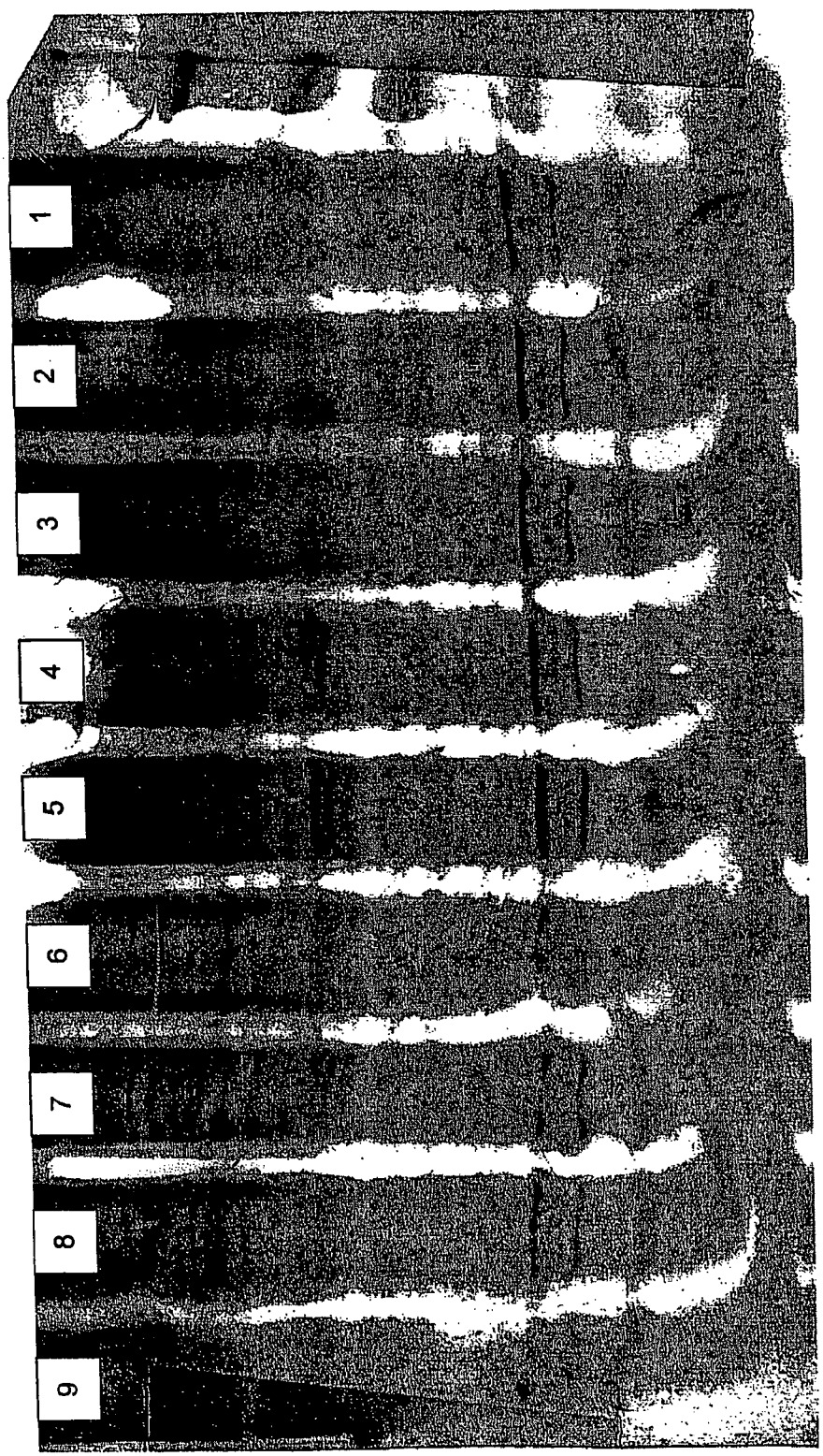
FIG. 29 depicts a pictorial representation of a Western blot of a polyacrylamide gel with anti-connexin 43 antibody.
Figure 30:
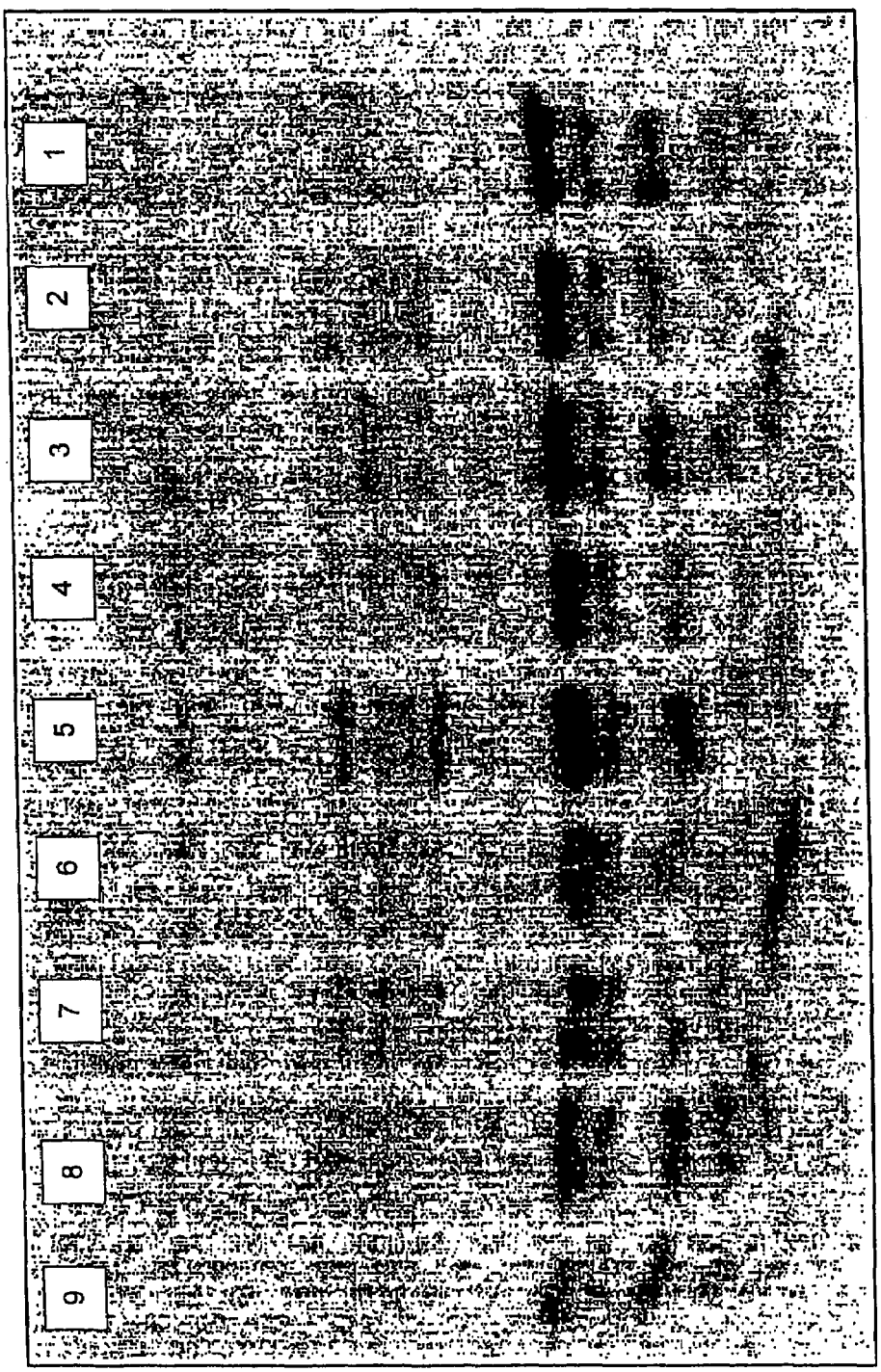
FIG. 30 depicts a pictorial representation of quantitative densitometric images of Western blots with anti-connexin 43 antibodies followed by HRP chemiluminescence on a Bio-rad imager.

Cells were then lysed, and 50 µg of each protein was electrophoresed on a 10% polyacrylamide gel. The gel was then transferred to a nitrocellulose filter. Total protein was assayed with Coomassie blue staining (FIG. 29; lanes 6, 7, and 9 were smeared secondary to gel transfer, and were not included in the quantitative comparison [FIG. 31]). Western blotting was performed with anti-connexin 43 antibodies followed by HRP chemiluminescence on a Biorad imager (FIG. 30). The original gel was stripped once, and the Western blot repeated twice prior to visualization. The results were normalized to the Lane 8 control (EtOH/H$_2$O), which demonstrates background constitutive expression of connexin 43 protein in a control condition (no test compound). The results of relative connexin 43 induction by positive controls and test compounds are shown in FIG. 31.

Brief Discussion of Cx43 Results.

Figure 31:
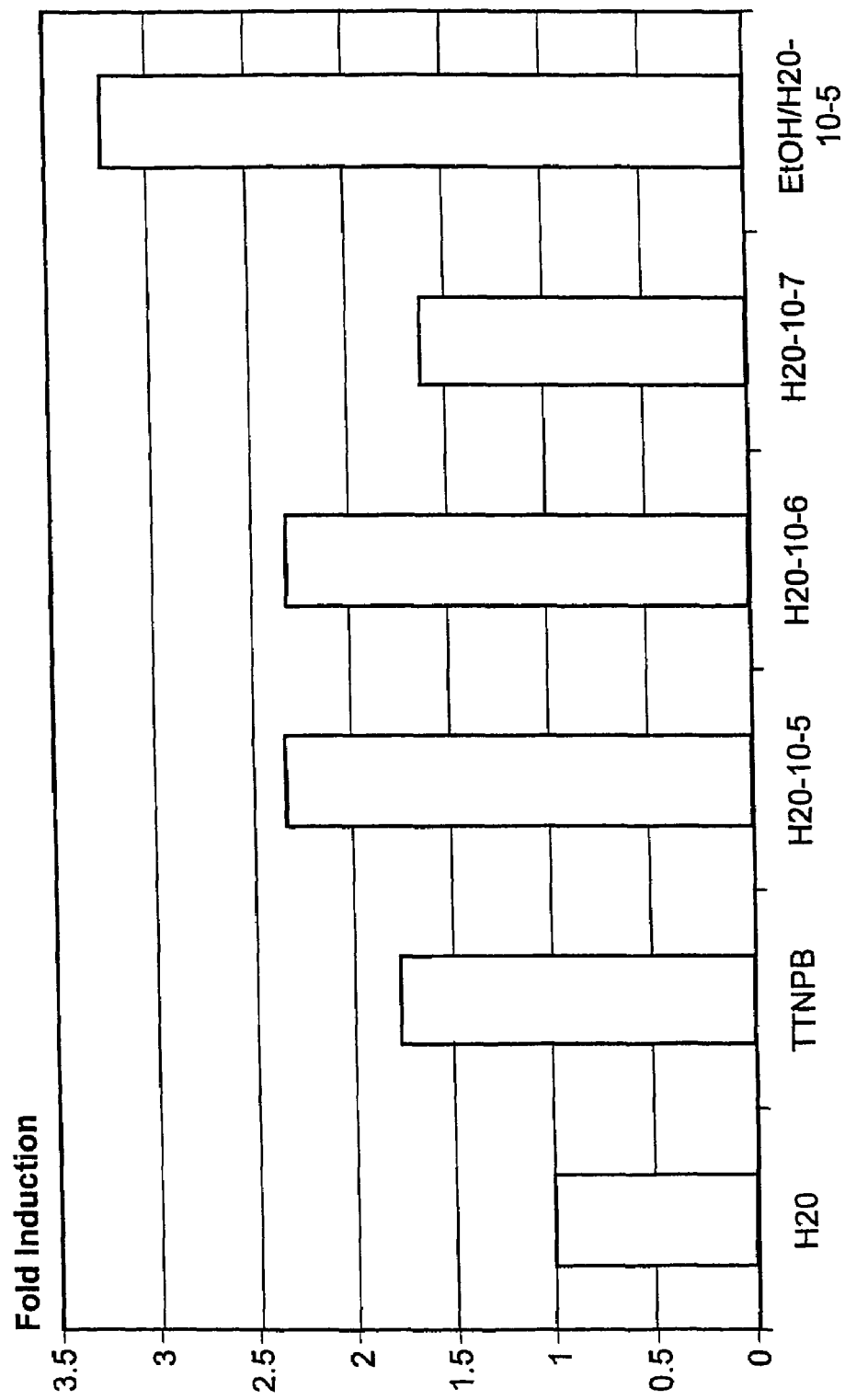
FIG. 31 depicts a graph of relative fold-induction of connexin 43 expression by positive control (TTNPB, potent synthetic retinoid) and test compounds (disodium salt disuccinate astaxanthin derivative in four water and/or ethanol (EtOH)/water formulations: $H_2O\text{-}10^{-5}$, $H_2O\text{-}10^{-6}$, $H_2O\text{-}10^{-7}$, and $EtOH/H_2O\text{-}10^{-5}$) versus sterile water control ($H_2O$) at 96 hours post-dosing.

All disodium salt disuccinate astaxanthin derivative XVI formulations tested induced connexin 43 protein expression over the levels expressed constitutively in water and ethanol/water controls (FIG. 31). The probability of detecting an induction of connexin 43 protein expression in 5 separate test conditions in the absence of a true treatment effect (null hypothesis control µ$_1$=treatment mean µ$_2$) is 1 in $2^5$, or p=0.03. Disodium salt disuccinate astaxanthin derivatives XVI formulated in water induced connexin 43 protein expression in each test condition (from $10^{-5}$ to $10^{-7}$ M). The decrease in the lowest disodium salt disuccinate astaxanthin derivative XVI/water combination tested suggests dose-dependency in the induced response. The relative induction was increased in the single test condition evaluated with a final ethanolic concentration in media of 0.5%. This finding is highly suggestive of increased bioavailability of this formulation, as ethanol is known to reduce aggregation of disodium salt disuccinate astaxanthin derivatives XVI in aqueous solutions. Solutions of disodium salt disuccinate astaxanthin derivatives XVI in water at concentrations greater than $10^{-7}$ and in ethanol/water combinations at $10^{-5}$ appear to have higher inductions levels than the positive TTNPB control. TTNPB is a highly potent retinoid that is effective at inducing connexin 43 expression at the 96-hour time point at $10^{-8}$ M.

Induction of Intercellular Gap Junctional Communication (GJC) in Murine Fibroblasts by the Disodium Salt Disuccinate Astaxanthin Derivatives A series of experiments were performed to assess the ability of the disodium salt disuccinate astaxanthin derivatives XVI to induce gap junctional communication (GJC) in an immortalized line of murine fibroblasts. Studies were conducted:
(1) at the functional level to measure cell/cell communication by increased dye transfer between confluent cells in monolayer culture;
(2) at the molecular level as measured by the ability of these compounds to induce expression of connexin43 (Cx43) protein. Cx43 is the structural unit of the intercellular channels in these fibroblasts that allows GJC;
(3) at the cellular level as shown by the ability of the disodium salt disuccinate astaxanthin derivatives XVI to increase the number and size of Cx43 immunoreactive plaques in regions of the plasma membrane in direct contact with adjacent cells.

(1) Communication Assays. Experiments were performed to assess the ability of the disodium salt disuccinate astaxanthin derivative XVI [as a statistical mixture of the all-trans (all-E) stereoisomers, 3S,3'S, meso, and 3R,3'R in 1:2:1 ratio] to enhance gap junctional intercellular communication (GJC) between mouse embryonic fibroblast C3H/10T 1/2 cells. This ability has been previously highly correlated with the ability of carotenoids to inhibit carcinogen-induced neoplastic transformation (Zhang, 1992). Moreover, Cx43-mediated junctional communication between cardiac myocytes is responsible for transfer of signals that maintain synchronous contractions and prevent cardiac arrhythmias (Peters, 1995).

Junctional permeability was assayed by microinjection of the fluorescent dye Lucifer Yellow CH (Sigma, St. Louis, Mo.) into individual confluent cells essentially as described previously (Zhang, 1994). Briefly, confluent cultures of C3H/10T1/2 cells were treated for 4 days with: (1) the disodium salt disuccinate astaxanthin derivative XVI ($1\times10^{-5}$ M) dissolved in a 1:2 ethanol/water (EtOH/H$_2$O) formulation; (2) a synthetic retinoid, TTNPB ($1\times10^{-8}$ M) dissolved in tetrahydrofuran as a positive control; or (3) 1:2 EtOH/H$_2$O treated cells as a negative control. Single cells in each dish were identified under phase contrast optics and pressure injected using a microinjection needle (Eppendorf, Hamburg, Germany) loaded with the fluorescent dye Lucifer Yellow as a 10% solution. The needle was controlled by a remote micromanipulator and cells and microscope were positioned on a pneumatic anti-vibration table. Successful injection of Lucifer Yellow was confirmed by brief illumination with UV light, which causes yellow fluorescence of Lucifer Yellow. This dye is sufficiently small to pass through gap junctions and is electrically charged, and can thus only enter cells adjacent to the injected cell if they are in junctional communication. After 2 minutes to allow for junctional transfer, digital images were taken under UV illumination. The number of fluorescent cells adjacent to the injected cell was later determined by digital image analysis using an unbiased density threshold method and the SigmaScan software program (Jandel Scientific). This number of communicating cells was used as an index of junctional communication, as described previously (Hossain, 1993).

The results of this analysis demonstrated that the disodium salt disuccinate astaxanthin derivative XVI ($1\times10^{-5}$ M) dissolved in a 1:2 EtOH/H$_2$O formulation effectively increased the extent of junctional communication over that seen in 1:2 EtOH/H$_2$O treated controls. Of 22 microinjected treated cells 15 (56%) were functionally coupled by gap junctions, in contrast to only 3 out of 11 (27%) control cells. These differences were statistically different ($p<0.04$; paired Student's t-test). Representative photomicrographs are shown in FIG. 14:

Panel A: treatment with the statistical mixture of stereoisomers of the disodium salt disuccinate astaxanthin at $1\times10^{-5}$ M in 1:2 EtOH/H$_2$O;

Panel C: 1:2 EtOH/H$_2$O solvent negative control;

Panel E: TTNPB at $1\times10^{-8}$ M in tetrahydrofuran as solvent, positive control; and Panels B, D, F: digital analysis of micrographs A, C, E respectively, demonstrating pixels above a set threshold positive for Lucifer Yellow fluorescence. Because cell nuclei have the most volume, they accumulate the most Lucifer Yellow and exhibit the most fluorescence.

(2) Molecular Studies. Both the mixture of stereoisomers of the disodium salt disuccinate astaxanthin derivative XVI and purified enantiomeric forms of the disodium salt disuccinate astaxanthin derivative XVI (3S,3'S, meso, and 3R,3'R forms at >90% purity by HPLC) increase expression of Cx43 protein in murine fibroblasts as assessed by immuno-(Western) blotting essentially as described (Zhang, 1992 and 1994). Briefly, mouse embryonic fibroblast C3H10T1/2 cells were cultured in Eagle's basal medium with Earle's salts (Atlanta Biologicals, Atlanta, Ga.), supplemented with 5% fetal calf serum (Atlanta Biologicals, Atlanta, Ga.) and 25 μg/mL gentamicin sulfate (Sigma, St. Louis, Mo.), and incubated at 37° C. in 5% CO$_2$. On the $7^{th}$ day after seeding in 100 millimeter (mm) dishes, the confluent cells were treated for four days with the disodium salt disuccinate astaxanthin derivatives XVI and then harvested and analyzed for Cx43 protein induction as described. Protein content was measured using the Protein Assay Reagent kit (Pierce Chemical Co., Rockford, Ill.) according to manufacturer's instructions. Cell lysates containing 100 μg of protein were analyzed by Western blotting using the NuPage western blotting kit and apparatus (Invitrogen, Carlsbad, Calif.) and Cx43 protein detected using a rabbit polyclonal antibody (Zymed, San Francisco, Calif.) raised against a synthetic polypeptide corresponding to the C-terminal domain of mouse, human and rat Cx43. Cx43 immunoreactive bands were visualized by chemiluminescence using an anti-rabbit HRP-conjugated secondary antibody (Pierce Chemical Co., Rockford, Ill.). Digital images were obtained with a cooled CCD camera, and quantitative densitometry was then performed (Bio-Rad, Richmond, Calif.). Equal protein loading of the lanes was confirmed by staining with Coomassie blue protein stain and digital image analysis.

Figure 15A:
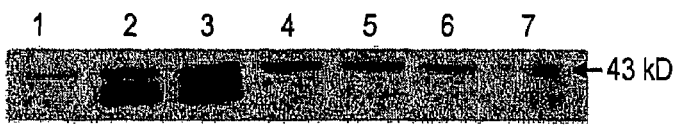
FIG. 15A depicts connexin 43 protein expression in cells treated with the mixture of stereoisomers of the disodium salt disuccinate astaxanthin derivatives as assessed by quantitative Western blot analysis. The upper bands are believed to represent the phosphorylated forms of the protein assembled into gap junctions; lower bands unassembled proteins (Saez, 1998). Lane 1: 1:2 ethanol (EtOH)/$H_2O$ (solvent only negative control); Lane 2: TTNPB, a synthetic retinoid, in acetone at $10^{-8}$ M (positive control); Lane 3: Retinyl acetate in acetone at $10^{-5}$ M (positive control); Lane 4: Statistical mixture ("rac") of stereoisomers of the disodium salt disuccinate astaxanthin derivative at $10^{-5}$ M delivered in a 1:2 formulation of EtOH/$H_2O$; Lane 5: 3R,3'R-disodium salt disuccinate astaxanthin derivative at $10^{-5}$ M delivered in a 1:2 formulation of EtOH/$H_2O$; Lane 6: 3S,3'S disodium salt disuccinate astaxanthin derivative at $10^{-5}$ M delivered in a 1:2 formulation of EtOH/$H_2O$; and Lane 7: Meso (3R,3'S) disodium salt disuccinate astaxanthin derivative at $10^{-5}$ M delivered in a 1:2 formulation of EtOH/$H_2O$.
Figure 15B:
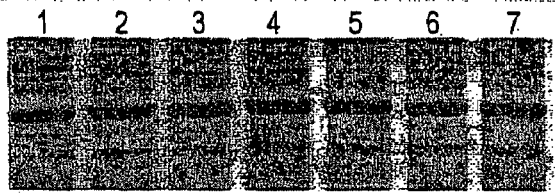
FIG. 15B depicts an immunoblot stained with Coomassie blue to demonstrate equal protein loading of all the bands. This confirms that differences in immunolabeling are not an artifact due to variability in total protein loaded and/or transferred to the membrane.
Figure 15C:
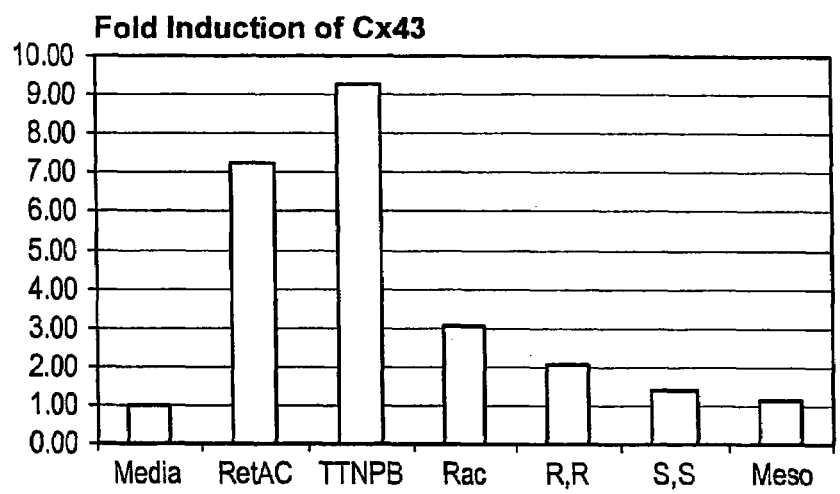
FIG. 15C depicts digital analysis of relative induction levels of connexin 43 protein expression by the disodium salt disuccinate astaxanthin derivative(s) versus positive and solvent-only treated controls. Lanes as in FIG. 15A. The fold induction is normalized to control levels of Cx43 expression in the 1:2 EtOH/$H_2O$ treated negative controls set to an arbitrary unit=1.0.
Figure 15D:
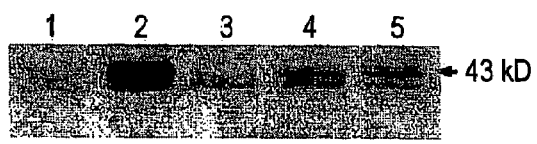
FIG. 15D depicts the dose-response curve of Cx43 protein expression in murine embryonic fibroblast cells (10T1/2) treated with the statistical mixture of stereoisomers of the disodium salt disuccinate astaxanthin derivatives as assessed by quantitative Western blot analysis. The upper bands are believed to represent the phosphorylated forms of the protein assembled into gap junctions; lower bands unassembled proteins. Lane 1: 1:2 EtOH/$H_2O$ (solvent only negative control). Lane 2: TTNPB in acetone at $10^{-8}$ M (positive control). Lane 3: disodium salt disuccinate astaxanthin derivative ("rac") at $10^{-5}$ M delivered in a 1:2 formulation of EtOH/$H_2O$. Lane 4: disodium salt disuccinate astaxanthin derivative ("rac") at $5\times10^{-6}$ M delivered in a 1:2 formulation of EtOH/$H_2O$. Lane 5: disodium salt disuccinate astaxanthin derivative ("rac") at $10^{-6}$ M delivered in a 1:2 formulation of EtOH/$H_2O$.
Figure 15E:
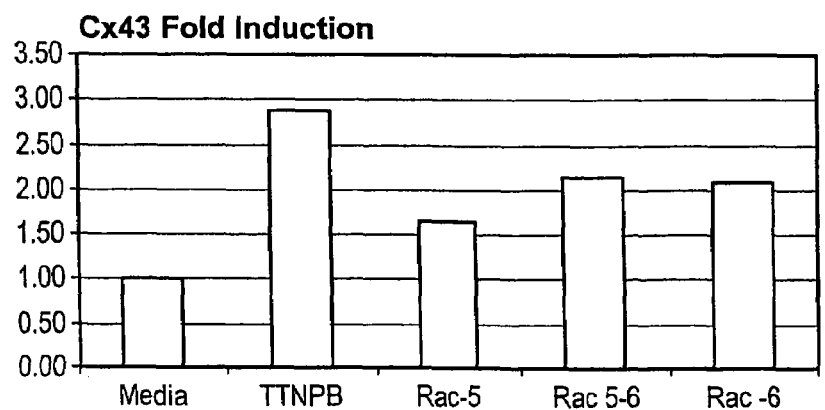
FIG. 15E depicts digital analysis of relative induction levels of connexin 43 protein expression by the statistical mixture of stereoisomers of the disodium salt disuccinate astaxanthin derivative versus positive and solvent-only treated controls. Lanes as in FIG. 15D. The fold induction is normalized to control levels of Cx43 expression in the 1:2 EtOH/$H_2O$ treated controls set to an arbitrary unit=1.0.
Figure 16A:
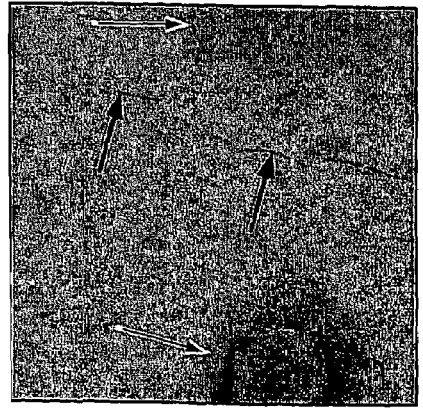
FIG. 16A-FIG. 16F depicts that the statistical mixture of stereoisomers of the disodium salt disuccinate astaxanthin derivative increases the assembly of Cx43 immunoreactive junctional plaques. Confluent cultures of 10T1/2 cells were treated for 4 days as described above with the statistical mixture of stereoisomers of the disodium salt disuccinate astaxanthin derivative: (1) at $10^{-5}$ M in 1:2 EtOH/$H_2O$; (2) with 1:2 EtOH/$H_2O$ as solvent only negative control; or (3) TTNPB at $10^{-8}$ M in tetrahydrofuran (THF) solvent as positive control. Cells were immunostained with a Cx43 antibody as described in text.
Figure 16B:
Figure 16C:
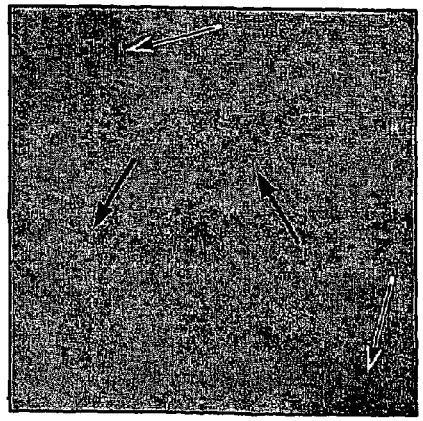
Figure 16D:
Figure 16E:
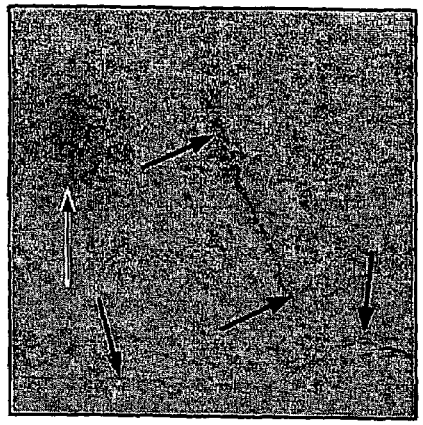
Figure 16F:
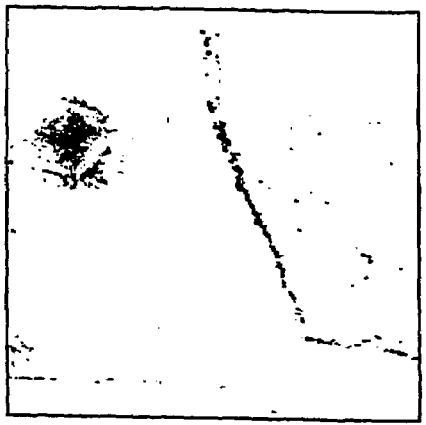

In this experiment the disodium salt disuccinate astaxanthin derivatives XVI were added to cell cultures in a formulation of 1:2 ethanol/H$_2$O at $1\times10^{-5}$ M. The statistical mixture of stereoisomers and purified enantiomeric forms demonstrated increased expression of Cx43 in comparison to cell cultures treated with 1:2 ethanol/H$_2$O alone (FIG. 15A and FIG. 15B). Treatment with the statistical mixture of stereoisomers of the disodium salt disuccinate astaxanthin derivative XVI elicited the highest induction level of Cx43 of all derivatives tested. These induction levels were several-fold less than induction levels seen with the retinoids tetrahydrotetramethylnapthyl propenylbenzoic acid (TTNPB) (Hoffman-LaRoche, Nutley, N.J.) and retinyl acetate (Sigma, St. Louis, Mo.) included as positive controls; this relative potency difference is consistent with previous studies.

(3) Cellular Studies. The statistical mixture of stereoisomers of the disodium salt disuccinate astaxanthin derivative XVI increases assembly of Cx43 in treated murine 10T1/2 cells in regions of cell/cell contact consistent with formation of functional gap junctions.

In this experiment expression and assembly of Cx43 into plaques was assessed by immunofluorescent staining. Procedures were essentially as described in Zhang (1992). Briefly, confluent cultures of C3H/10T1/2 cells were grown on Permanox plastic 4-chamber slides (Nalge Nunc International, Naperville, Ill.) and treated for 4 days with: (1) the disodium salt disuccinate astaxanthin derivative XVI (statistical mixture of stereoisomers) dissolved in a 1:2 EtOH/H$_2$O formulation; (2) the retinoid TTNPB at $1\times10^{-8}$ M in tetrahydrofuran as a positive control; or (3) 1:2 EtOH/H$_2$O as a solvent control. Cells were fixed with $-20°$ C. methanol overnight, washed in buffer, blocked in 1% bovine serum albumin (Sigma, St, Louis, Mo.) in PBS, and incubated with the rabbit polyclonal anti-Cx43 antibody (Zymed, San Francisco, Calif.) as in (2) above and detected with Alexa568 conjugated anti-rabbit secondary (Molecular Probes, Eugene, Oreg.). Slides were illuminated with 568 mn light and images were acquired at a wavelength of 600 nm using the Zeiss Axioscope light microscope and a Roper Scientific cooled CCD camera. Slides treated with the TTNPB retinoid control and the statistical mixture of stereoisomers of the disodium salt disuccinate astaxanthin derivative XVI at $1 \times 10^{-5}$ M exhibited assembly of immunoreactive Cx43 into plaques in regions of the cell membrane in direct contact with adjacent cells. Such assembly is consistent with the location and formation of plaques of gap junctions, known to be formed by the aggregation of multiple individual gap junctions in cell populations which are junctionally connected (Perkins, 1997). In cultures treated with solvent as control, such immunoreactive plaques were infrequent and were smaller than those detected in cells treated with the statistical mixture of stereoisomers of the disodium salt disuccinate astaxanthin derivative XVI or with TTNPB as positive control. The frequency of these plaques and their size is consistent with the functional differences in gap junction permeability as detected by the Lucifer Yellow dye transfer experiments described in section 1, and FIG. 14 (TTNPB>statistical mixture of stereoisomers of the disodium salt disuccinate astaxanthin XVI>solvent control), and with the degree of induction of Cx43 as detected in the immunoblot experiments described in section 2 and FIG. 15.

Representative photomicrographs are shown in FIG. 16.

Inhibition of Carcinogen-induced Neoplastic Transformation by Non-esterified, Free Astaxanthin 2E in Murine Fibroblasts Non-esterified, free astaxanthin 2E is generated in the mammalian gut after oral administration of esterified astaxanthin. Only free astaxanthin is found in mammalian plasma and solid organs. This was again demonstrated in single- and multiple dose oral pharmacokinetic studies; the results are described herein. Inherent esterase activity of serum albumin, and the action of promiscuous esterases in serum and solid organs rapidly generates non-esterified, free astaxanthin after parenteral administration of the disodium disuccinate astaxanthin derivative (XVI). Flash photolysis experiments also demonstrated that the disodium disuccinate astaxanthin derivative XVI and non-esterified, free astaxanthin have identical antioxidant behavior in terms of formation of the carotenoid cation radical. An experiment was performed to assess the ability of non-esterified, free astaxanthin (the in vivo final cleavage product of the disodium salt disuccinate astaxanthin derivative (XVI), tested as the all-trans mixture of stereoisomers 3S,3'S, meso, and 3R,3'R in a 1:2:1 ratio) to inhibit neoplastic transformation in the C3H10T1/2 cell culture model developed in the lab of the late Charles Heidelberger (Reznikoff, 1973). This cell culture system has been shown to effectively mimic the initiation and transformation events of tumor formation in whole animals (Bertram, 1985). In these cells, treatment with the carcinogenic polycyclic hydrocarbon 3-methylcholanthrene (MCA) produces an initiation event in a small proportion of treated cells that leads 5 weeks later to morphological transformation in these cells, exhibited by the presence of transformed foci. Injection of these transformed cells into syngeneic mice results in the formation of sarcomas at the site of injection demonstrating the carcinogenic nature of the transformation (Reznikoff, 1973). This assay has been adapted to the detection of cancer preventive agents (Bertram, 1989), and cancer preventive retinoids and carotenoids have been demonstrated to inhibit transformation in this system (Bertram, 1991; Pung, 1988; and Merriman, 1979).

This experiment was conducted according to protocols established previously (Bertram, 1991 and Pung, 1988). In brief, the 10T1/2 cells, derived from mouse embryonic fibroblasts, were seeded at a density of $10^3$ cells/60 mm dish in Eagle's Basal Media (BME) (Atlanta Biologicals, Atlanta, Ga.), supplemented with 4% fetal calf serum (Atlanta Biologicals, Atlanta, Ga.) and 25 µg/mL gentamicin sulfate (Sigma, St. Louis, Mo.). Cells were treated 24 hours later with 5.0 µg/ml MCA (Sigma, St. Louis, Mo.) in acetone or with 0.5% acetone (final concentration) as a control. Media was changed 24 hours after MCA treatment. Cells were treated with astaxanthin in THF or with retinol acetate in acetone 7 days later, and re-treated every 7 days for 4 weeks. Other dishes were treated with the appropriate solvent controls. After 5 weeks from the start of the experiment, cells were fixed with methanol and stained with 10% Giemsa stain (Sigma, St. Louis, Mo.) and scored for type II and type III foci as per Reznikoff (1973).

Figure 34:
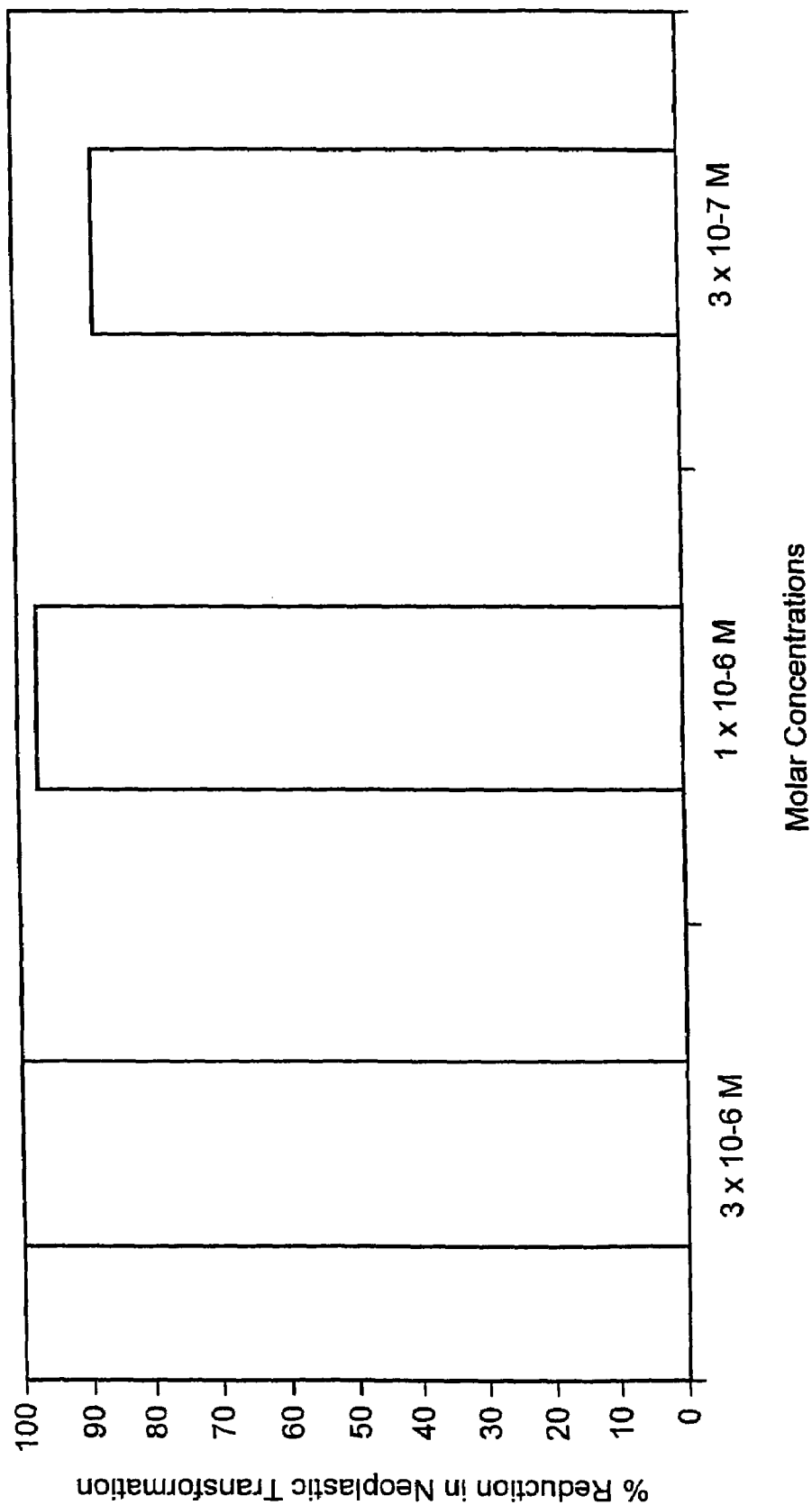
FIG. 34 depicts effects of non-esterified, free astaxanthin (as the all-trans mixture of stereoisomers) on MCA-induced neoplastic transformation in mouse embryonic fibroblast (10T1/2) cells. Non-esterified, free astaxanthin is produced rapidly in vivo after oral and intravenous administration of novel carotenoid derivatives, and is detected in high concentration in both plasma and solid organs (see FIG. 22 and FIG. 23). Non-esterified, free astaxanthin demonstrated levels of reduction of neoplastic transformation (100%) above any other carotenoid tested in this assay at similar concentrations, demonstrating the increased utility of this compound for cancer chemoprevention applications.
Figure 35C:
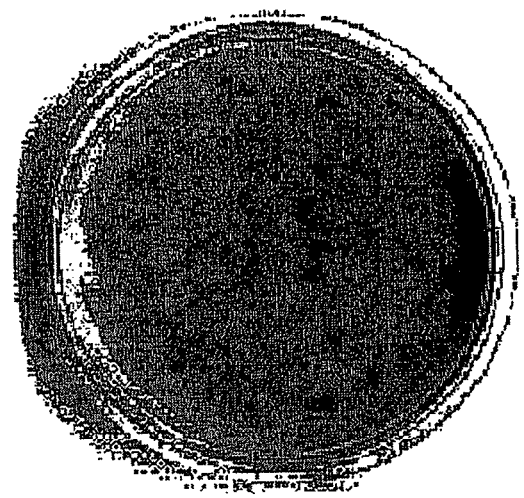
FIG. 35A-FIG. 35C depicts a comparison of an astaxanthin-treated dish to control dishes (see description for FIG. 34).
Figure 35B:
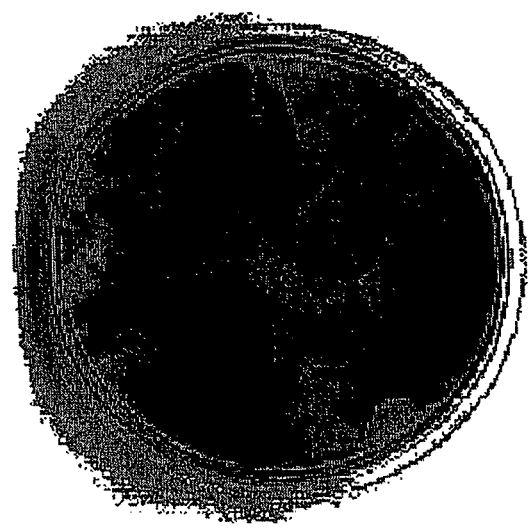
Figure 35A:
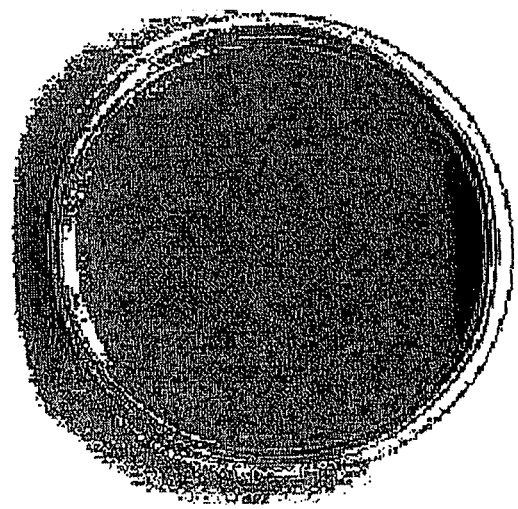
Figure 36:
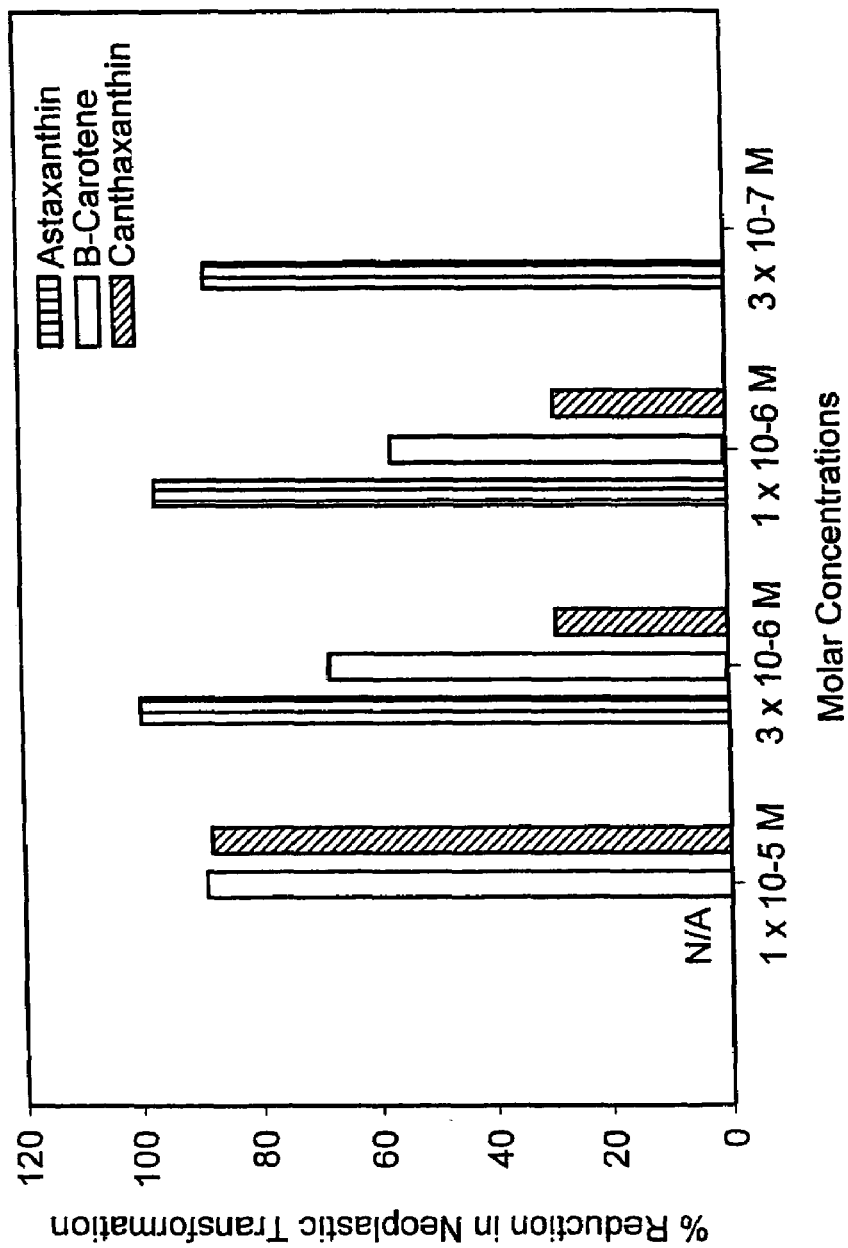
FIG. 36 depicts a comparison of astaxanthin (as the mixture of stereoisomers) to previously tested carotenoids in this laboratory using this assay (see description for FIG. 34).

The results of this analysis demonstrated that 4-week treatment with astaxanthin 2E caused a concentration-dependent decrease in the numbers of MCA-induced transformed foci in comparison to cells treated with MCA and with THF as a solvent control (depicted in FIG. 34). FIG. 34 depicts effects of non-esterified, free astaxanthin (as the all-trans mixture of stereoisomers) on MCA-induced neoplastic transformation. Graph represents a total of 68 cultures treated with astaxanthin 2E at $3 \times 10^{-6}$ M, $1 \times 10^{-6}$ M and $3 \times 10^{-7}$ M, delivered in a THF vehicle of 0.3%, 0.1% and 0.03%, respectively. Controls were as follows: a total of 16 dishes did not receive carcinogen and were treated with 0.05% ethanol solvent; controls did not exhibit any transformation events. A total of 20 dishes were treated with MCA and 1% THF solvent, yielding a transformation rate of 0.92 foci/dish. Percent reduction (% reduction) of transformation in astaxanthin-treated dishes was calculated by a comparison of the mean foci/dish of each treatment with the MCA-treated controls. Inferential statistics were performed using the paired Student's t-test; calculated P values of 0.00004, 0.00001, and 0.00006, respectively, were obtained. $P<0.05$ was considered significant. Treatment with $3 \times 10^{-6}$ M astaxanthin 2E resulted in complete suppression of the transformed phenotype (FIG. 35). FIG. 35 depicts a comparison of astaxanthin-treated dish to control dishes. Representative dishes treated with: A, no MCA with solvent control; B, MCA 5.0 µg/ml with 1% THF as solvent control; C, MCA with $3 \times 10^{-6}$ M astaxanthin (as the all-trans mixture of stereoisomers) in THF. It is notable that this level of inhibition far exceeded that reported previously for all other carotenoids tested using identical protocols (Bertram, 1991). A comparison of the current data to data previously reported for percent reduction in neoplastic transformation at the concentrations tested revealed astaxanthin 2E to be a far more potent inhibitor of transformation than either β-carotene or canthaxanthin (FIG. 36). FIG. 36 depicts a comparison of astaxanthin 2E (as the mixture of stereoisomers) to previously tested carotenoids. Data was compiled comparing the percent reduction of MCA-induced neoplastically transformed foci/dish in cultures treated with astaxanthin 2E to the percent reduction of foci/dish from data previously reported by the Bertram laboratory after treatment with β-carotene and canthaxanthin (Bertram, 1991) using identical protocols. The percent reduction at the highest concentration tested previously (1×10$^{-5}$ M) is reported here for β-carotene and canthaxanthin; this higher concentration of astaxanthin 2E was not utilized because of astaxanthin's greater measured activity at lower concentrations. These studies demonstrate the potential for the cleaved astaxanthin moiety of the synthesized derivative to be a highly effective cancer chemoprevention agent, after both oral and parenteral administration. Coupled with the liver accumulation pharmacokinetic data also reported here (after both single- and multiple-dose strategies), the use of this compound forms a particularly useful embodiment.

Inhibition of Reactive Oxygen Species

Figure 2:
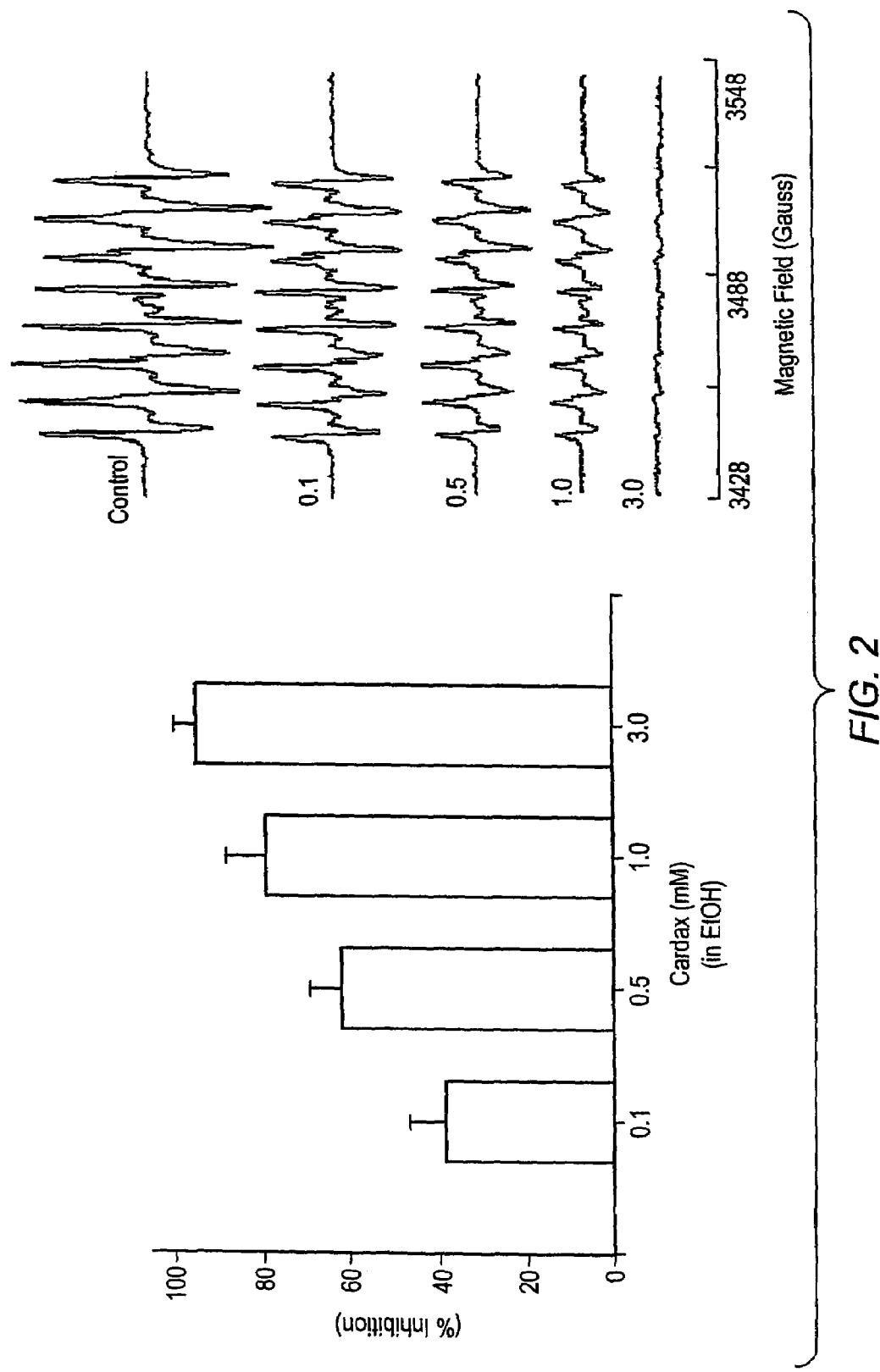
FIG. 2 depicts an effect of disodium salt disuccinate astaxanthin derivative on the reactive oxygen species superoxide anion as monitored using electron paramagnetic resonance (EPR) spectroscopy.

In an experiment, neutrophils were isolated on a Percoll gradient from whole blood from a human volunteer. The isolated neutrophils were then re-suspended in phosphate-buffered saline, and maximally stimulated with phorbol ester to induce the respiratory burst and production of superoxide anion. To the solution of activated human neutrophils, the disodium salt disuccinate astaxanthin derivative XVI was added at various concentrations, and the superoxide signal [as measured with electron paramagnetic resonance (EPR) spectroscopy] was subsequently measured. The disodium salt disuccinate astaxanthin derivative XVI (as the mixture of stereoisomers) reduced the measured superoxide anion signal in a dose-dependent manner (FIG. 2); near complete suppression of the superoxide anion signal was achieved at 3 mM concentration. FIG. 2 demonstrates the strong superoxide signal after activation in controls, then the results of titration with the disodium salt disuccinate astaxanthin derivative XVI from 100 μM to 3 mM. The disodium salt disuccinate astaxanthin derivative XVI tested at 100 μM scavenged 28% of the total signal. At 3 mM, almost no superoxide signal remained. These results demonstrate that cardioprotection in ischemia-reperfusion injury, as has been demonstrated with the other anti-neutrophil interventions described above, can also be achieved with the carotenoid derivative described here. In addition to reducing the superoxide anion signal important in ischemia-reperfusion injury, it is also likely that myocardial salvage can be achieved with the described carotenoid derivative, as superoxide anion plays a major role in tissue injury and death during prolonged myocardial ischemia.

Figure 3:
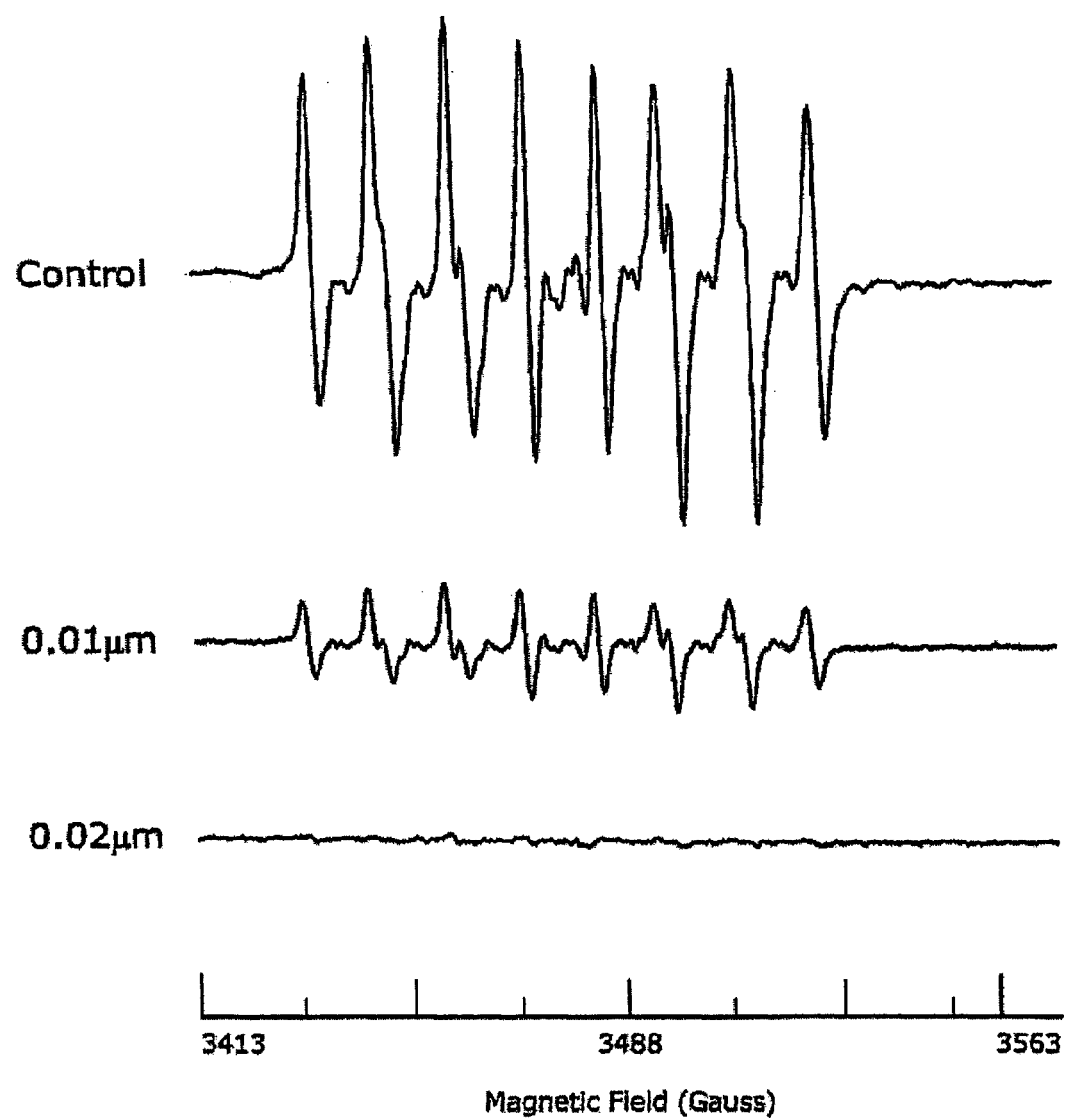
FIG. 3 depicts an effect of a disodium salt disuccinate astaxanthin derivative/free vitamin C solution on the reactive oxygen species superoxide anion as monitored using electron paramagnetic resonance (EPR) spectroscopy.

FIG. 3 depicts an effect of a disodium salt disuccinate astaxanthin derivative XVI/Vitamin C solution on reactive oxygen species (superoxide anion) as monitored using EPR spectroscopy. The solution included a mixture of about 2 to about 1 of vitamin C to disodium salt disuccinate astaxanthin derivative XVI respectively. The disodium salt disuccinate astaxanthin derivative XVI/Vitamin C solution reduced the measured superoxide anion signal in a dose-dependent manner (FIG. 3); complete suppression of the superoxide anion signal was achieved at 0.02 μM concentration. FIG. 3 demonstrates the strong superoxide signal after activation in controls, then the results of titration with the disodium salt disuccinate astaxanthin derivative XVI/Vitamin C solution from 0.01 μM to 0.02 μM.

Figure 21:
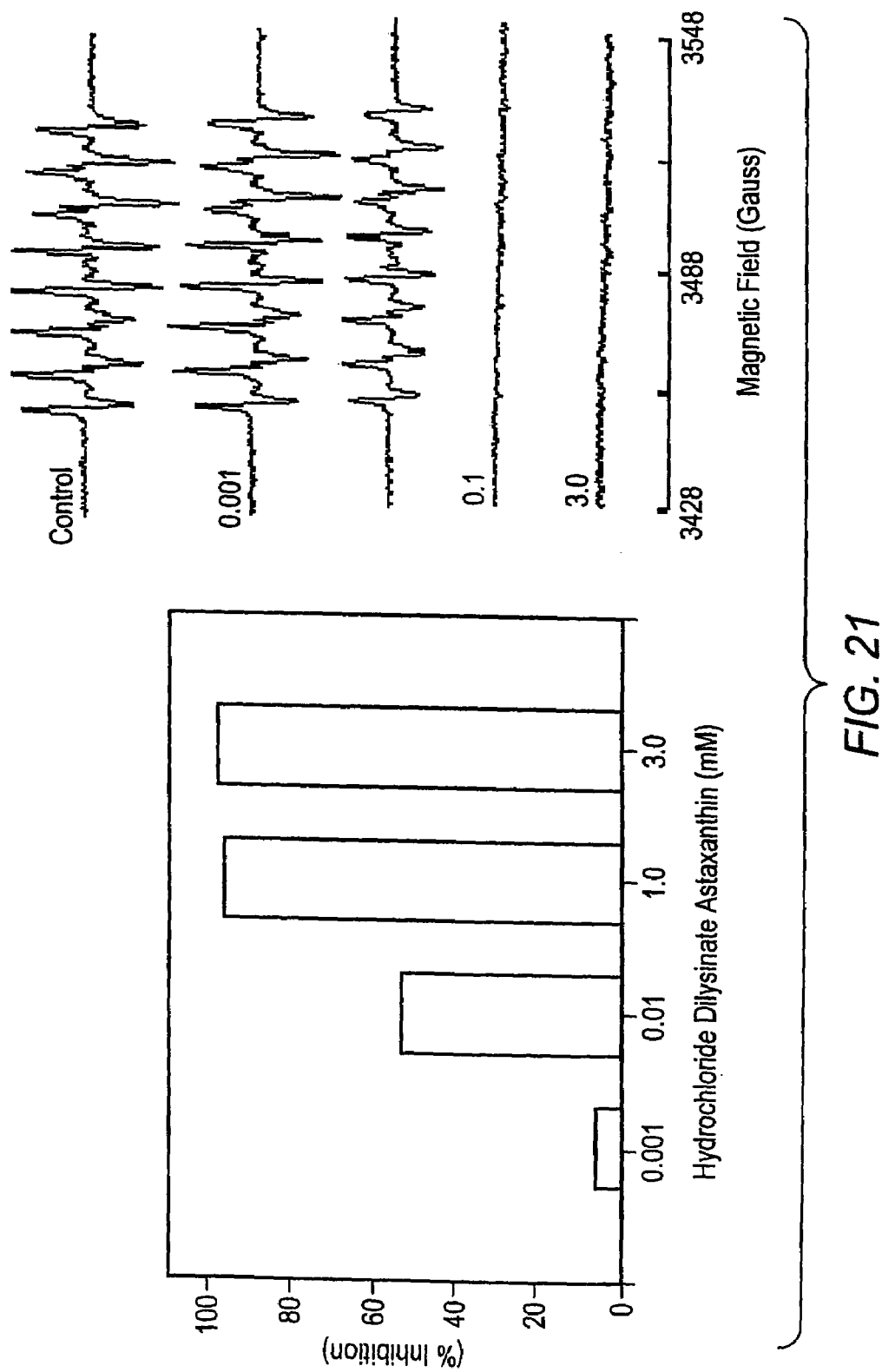
FIG. 21 depicts the mean percent inhibition of superoxide anion signal as detected by DEPMPO spin trap by the hydrochloride salt dilysine astaxanthin derivative. This derivative was highly water soluble (>50 mg/mL), and did not require a co-solvent for excellent radical-quenching ability in this assay. Compare the superoxide anion inhibition of this derivative with that depicted in FIG. 20, for a derivative that forms supramolecular assemblies in pure aqueous formulation.
Figure 22:
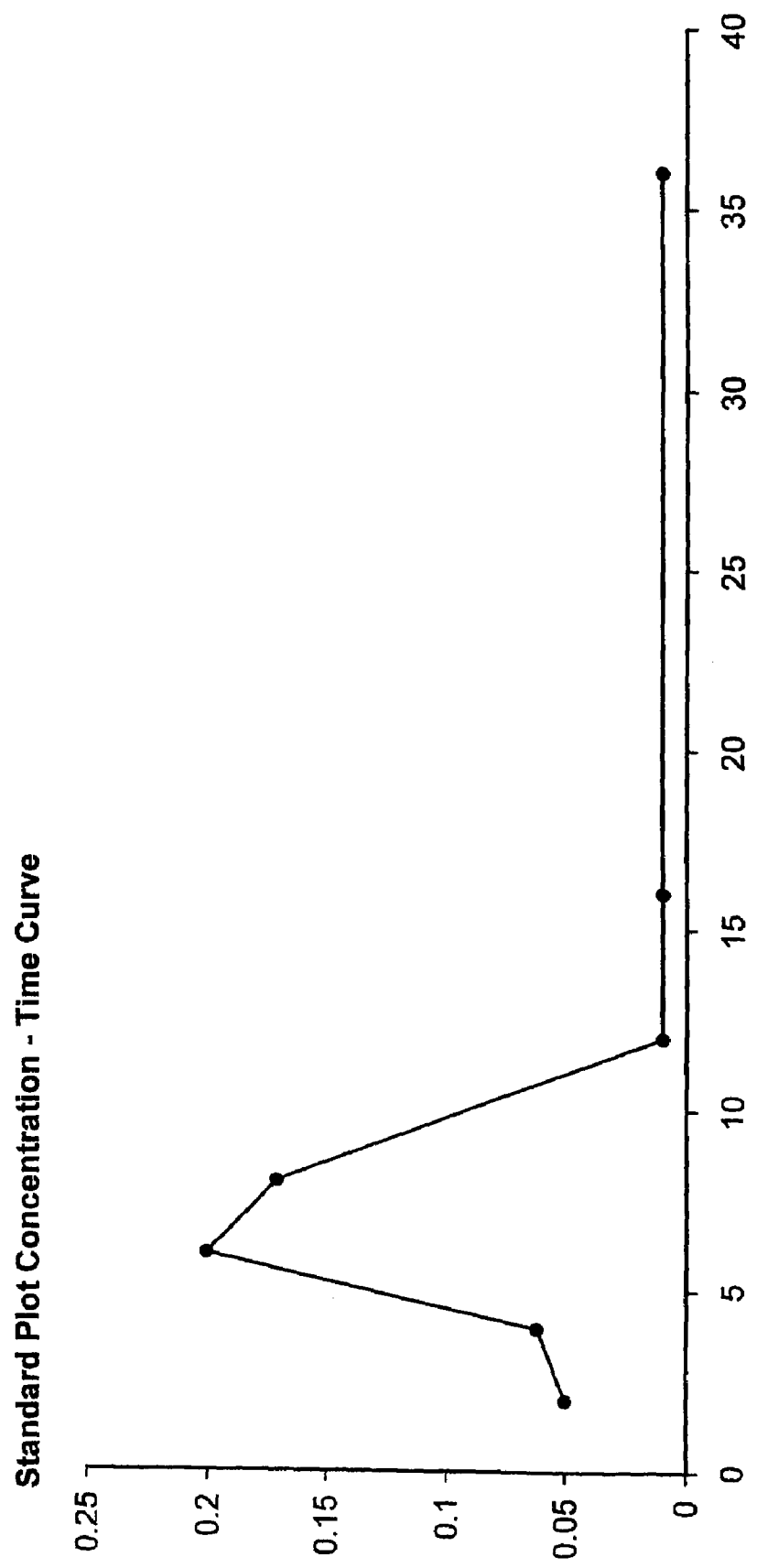
FIG. 22 depicts a standard plot of concentration of non-esterified, free astaxanthin versus time for plasma after single dose oral gavage in black mice. Only non-esterified, free astaxanthin is detected in plasma, corroborating the complete de-esterification of the carotenoid analog or derivative in the mammalian gut.
Figure 23:
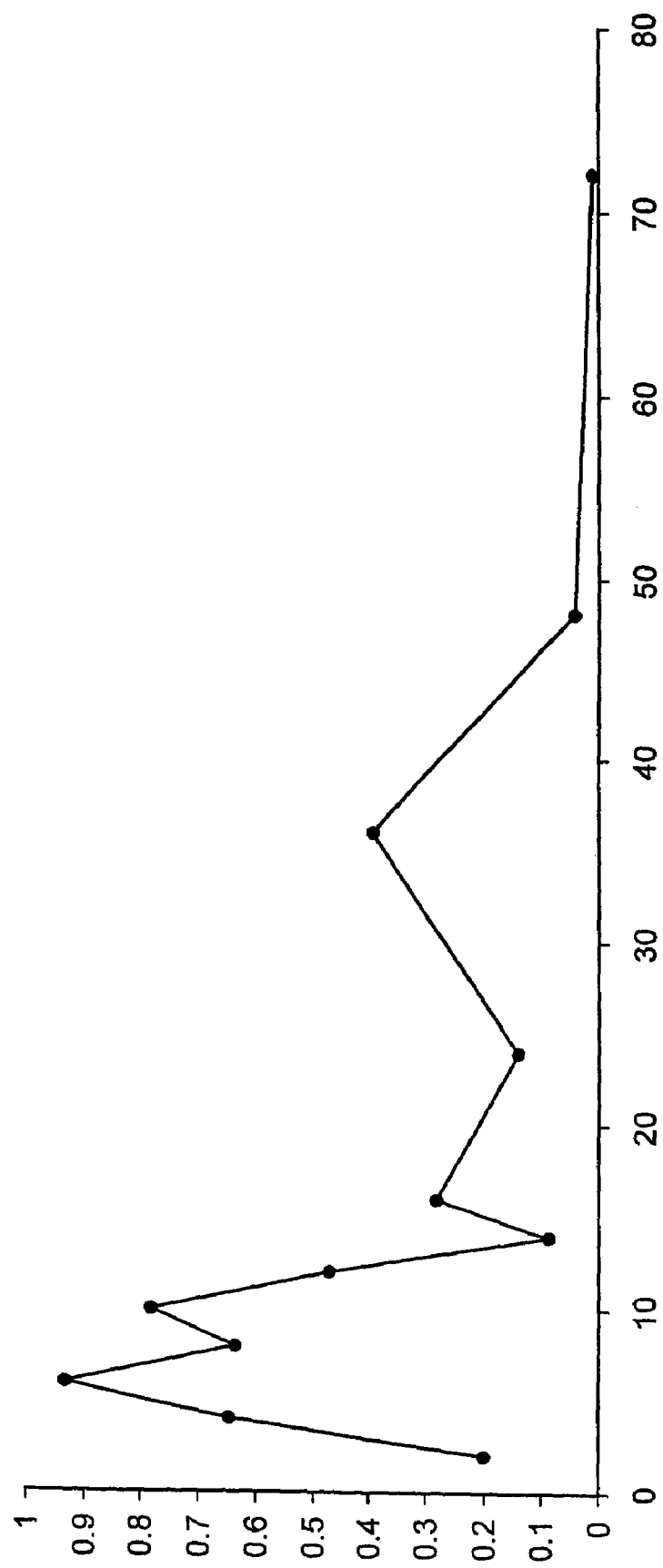
FIG. 23 depicts a standard plot of concentration of non-esterified, free astaxanthin verses time for liver after single dose oral gavage in black mice. Only non-esterified, free astaxanthin is detected in liver, also corroborating (see FIG. 22 for plasma) the complete de-esterification of the carotenoid analog or derivative in the mammalian gut, as has been described previously. At every time point, liver levels of non-esterified, free astaxanthin are greater than that observed in plasma, a finding suggesting vastly improved solid-organ delivery of free carotenoid in the novel emulsion vehicle used in this study.
Figure 24:
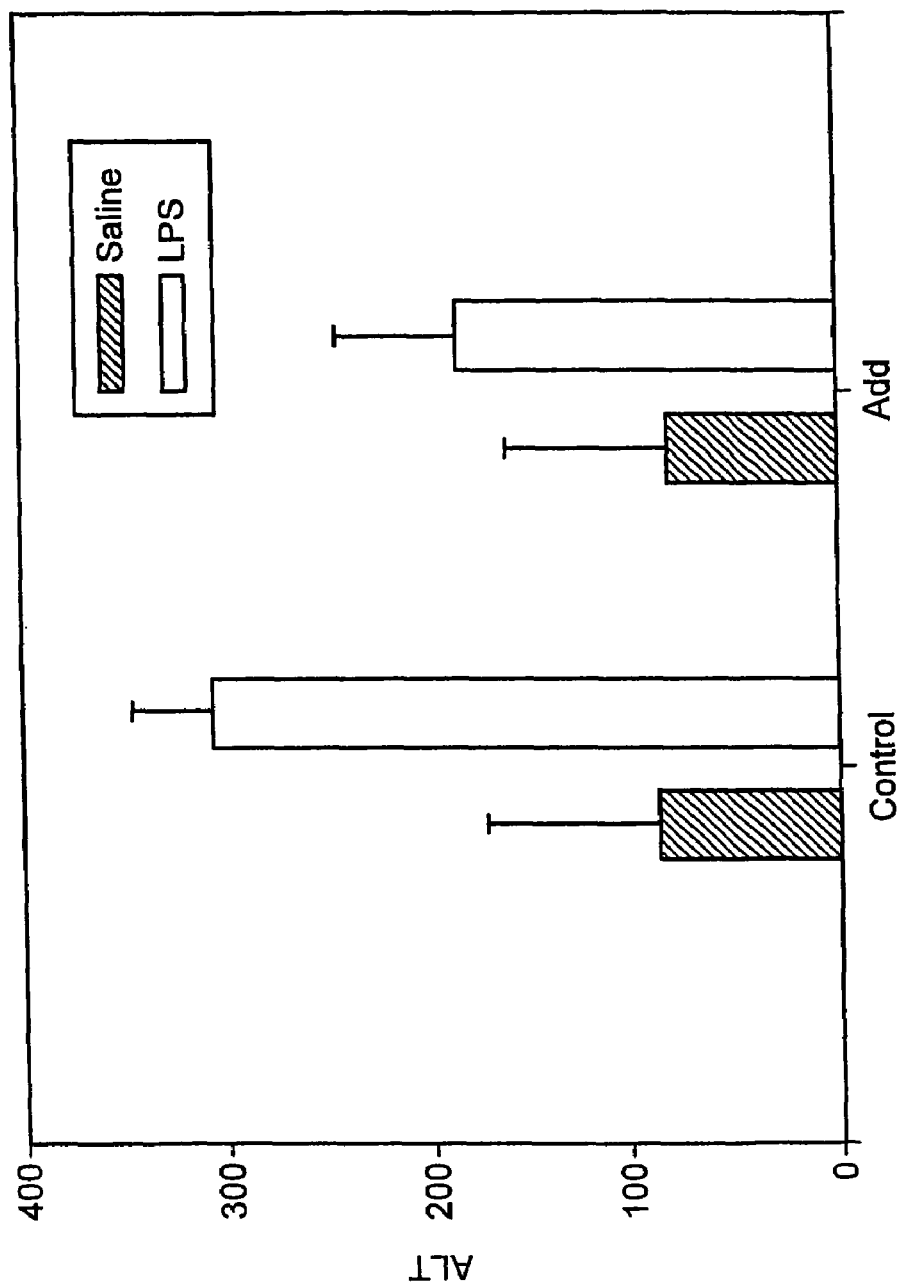
FIG. 24 depicts the effect of the disodium disuccinate astaxanthin derivative at 500 mg/kg by oral gavage on lipopolysaccharide (LPS)-induced liver injury in mice (as measured by elevation in serum alanine aminotransferase, or ALT). Three (3) animals were tested in each group. Control animals received saline alone (sham-treated controls; left portion of figure) or emulsion without disodium disuccinate astaxanthin derivative (vehicle controls). Sham-treated animals receiving the novel derivative demonstrated no effect on background levels of ALT; mice receiving the oral emulsion with the novel derivative at 500 mg/kg showed reduced induced levels of ALT, indicating protection against hepatic necrosis after LPS insult.

In a third experiment, neutrophils were again isolated on a Percoll gradient from whole blood from a second human volunteer. The isolated neutrophils were then re-suspended in phosphate-buffered saline, and maximally stimulated with phorbol ester to induce the respiratory burst and production of superoxide anion. To the solution of activated human neutrophils, the hydrochloride salt dilysinate astaxanthin derivative (XX) was added at four (4) concentrations, and the superoxide signal (as measured with EPR spectroscopy) was subsequently measured. The hydrochloride salt dilysinate astaxanthin derivative XX also reduced the measured superoxide anion signal in a dose-dependent manner (FIG. 21), from approximately 5% reduction at 1 μM to 98% reduction at 3 mM. Once again, near complete suppression of the superoxide anion signal was achieved at 3 mM concentration. This carotenoid derivative XX showed scavenging efficacy at low concentration (1 μM), as well as the ability for increased concentrations of the derivative in this in vitro assay to nearly completely eliminate the superoxide anion signal. The activity of derivative XX in vitro as an aqueous scavenger again suggests that the derivatives (disodium disuccinate astaxanthin XVI, hydrochloride salt dilysine astaxanthin XX) will act as soft drugs (i.e. active as the intact, uncleaved novel derivatives) and not pro-drugs (inactive until cleavage to free astaxanthin) in vivo. The aqueous solubility of this derivative (XX) was greater than 50 mg/mL, demonstrating the utility of the methods of the present invention to increase the water solubility of the parent carotenoids (in this case astaxanthin), from nearly zero inherent water solubility to the high mg/mL range.

Direct Superoxide Anion Scavenging by a
Disodium Disuccinate Astaxanthin Derivative XVI:
Relative Efficacy of Individual Stereoisomers
versus the Statistical Mixture of Stereoisomers by
Electron Paramagnetic Resonance Imaging Materials Non-esterified, all-E astaxanthin 2E [1:2:1 statistical mixture of stereoisomers 3S,3'S, meso (identical 3S,3'R and 3'S,3R), and 3R,3'R] was purchased from Buckton Scott (India) and used as supplied (>95% purity by HPLC). Astaxanthin 2E was dissolved in HPLC grade dimethylsulfoxide (DMSO; Sigma-Aldrich, St. Louis, Mo.). The disodium disuccinate derivatives XVI of astaxanthin 2E were tested separately in nine formulations: statistical mixture of stereoisomers (as for astaxanthin, above, a 1:2:1 mixture of all-E; labeled as "mixture" in all tables and figures); 3S,3'S, and 3R,3'R (optical isomers or enantiomers); and meso (mixture of identical 3S,3'R and 3'S,3R; diastereomers of the enantiomeric pair). All disuccinate derivatives were synthesized at >90% purity by HPLC. The disuccinate derivatives were first tested at the appropriate final concentrations in pure aqueous solution (deionized water) from stock solutions of 10 mM. Each of the four disuccinate derivatives were then tested from stock solutions prepared in a 1:2 mixture of ethanol (final concentration of EtOH in stock solution 33⅓%; final concentration in isolated neutrophil assay 0.3%; HPLC grade ethanol, Sigma-Aldrich, St. Louis, Mo.) at 10 mM. The 3S,3'S derivative was also tested from a 50% EtOH concentration stock solution (final concentration in isolated neutrophil assay 0.5%). Ethanolic formulation of the disuccinate derivatives has been shown to completely disaggregate the supramolecular assemblies which form in pure aqueous solution, providing monomeric solutions of the derivatives immediately before introduction into the test assay. Ethanol alone negative controls (0.3% and 0.5% final EtOH concentrations in isolated neutrophil assay) and superoxide dismutase mimetic positive control (10 μM final concentration; Metaphore® Pharmaceuticals, Inc., St. Louis, Mo.) were also performed.

Figure 17:
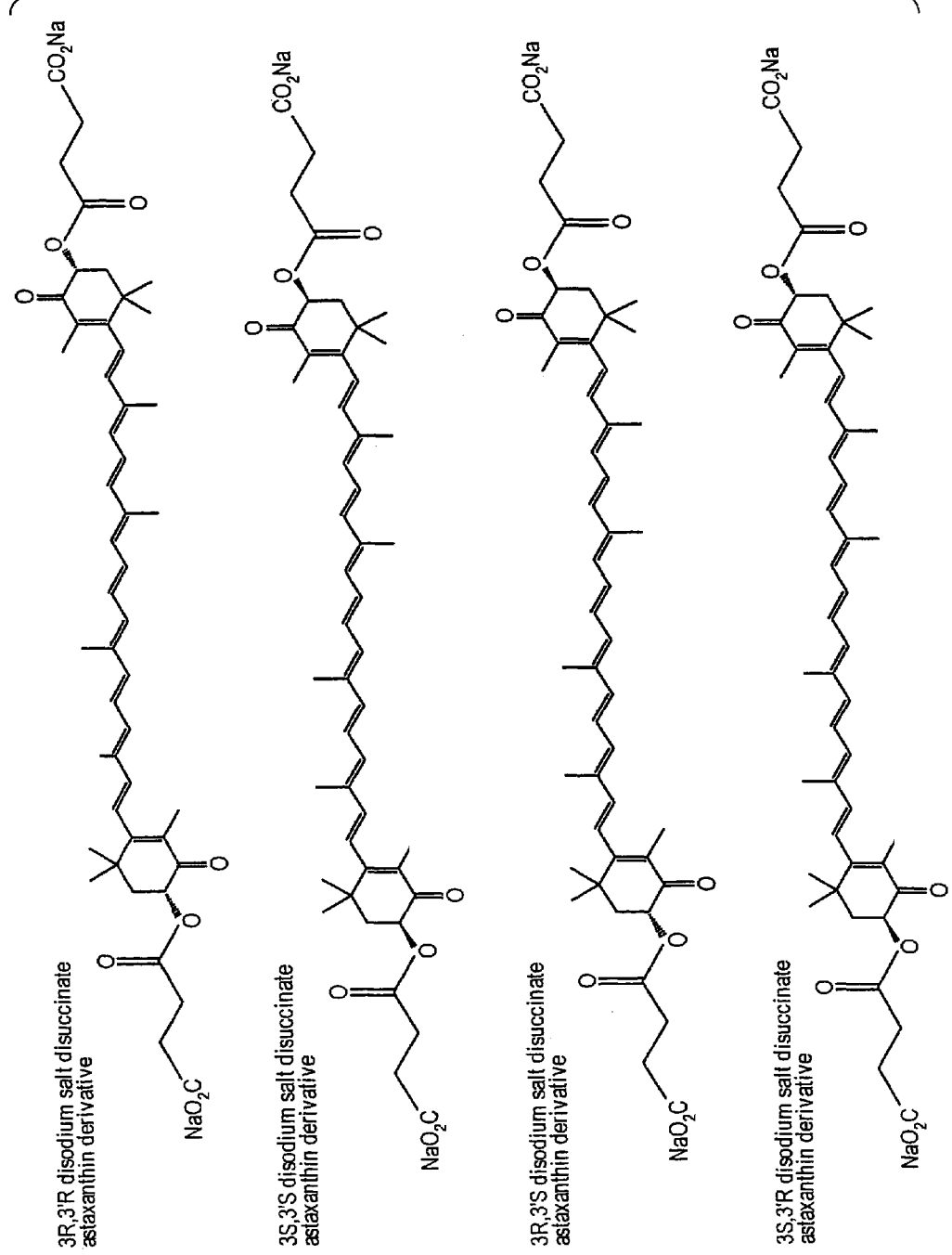
FIG. 17 depicts the 3 stereoisomers of the disodium disuccinate diester of astaxanthin synthesized for the current studies (shown as the all-E geometric isomers); the mixture of stereoisomers, or individual stereoisomers, were used in separate applications (see Figure legends). Note that the meso forms (3R,3'S and 3S,3'R) are identical.

A carotenoid derivative [Succinic acid mono-(4-{18-[4-(3-carboxy-propionyloxy)-2,6,6-trimethyl-3-oxo-cyclohex-1-enyl]-3,7,12,16-tetramethyl-octadeca-1,3,5,7,9,11,13,15,17-nonaenyl}-3,5,5-trimethyl-2-oxo-cyclohex-3-enyl) ester;

FIG. 17] and its stereoisomeric forms were synthesized, disodium disuccinate derivatives XVI of astaxanthin 2E, in all-trans (all-E) form. The derivatives aresymmetric chiral molecules with 2 chiral centers at the 3 and 3' carbon positions, comprising 4 stereoisomers: 3R,3'R and 3S,3'S (optical isomers, or enantiomers), as well as the diastereomeric meso forms (identical 3R,3'S and 3'R,3S). The statistical mixture of stereoisomers synthesized from the commercial source of astaxanthin contains 3R,3'R, meso (identical 3R,3'S and 3'R,3S), and 3S,3'S stereoisomeric forms in a 1:2:1 ratio. All individual stereoisomers and the statistical mixture were synthesized at >90% purity by HPLC, allowing direct comparison of the individual efficacy of these forms as direct radical scavengers. The all-E forms of the stereoisomers used in this study were linear, rigid molecules (bolaamphiphiles) owing to the lack of cis (or Z) configuration(s) in the polyene chain of the spacer material.

The disodium disuccinate diesters XVI of astaxanthin 2E demonstrate increased water "dispersibility" over the parent compound astaxanthin 2E. The water dispersibilities of the individual stereoisomers and the statistical mixture were all greater than 8 mg/mL (approximately 10 mM), allowing them to be introduced into the buffered aqueous test system without a co-solvent. The tendency for the parent carotenoids such as astaxanthin 2E (Salares, 1977), as well as carotenoid derivatives (e.g. capsanthin derivatives) (Zsila, 2001 and Bikadi, 2002) to form supramolecular assemblies in aqueous solution was also observed for the derivatives tested in the current study. Supramolecular self-assembly results in aggregates of significant size in aqueous solution, and prevents maximum direct interaction of aggregated molecules with radical species. Therefore, a comparison of the direct scavenging behavior of the novel astaxanthin derivatives was conducted in both pure aqueous formulation as well as with the co-solvent ethanol. In stock solutions, a 1:2 concentration of EtOH/water was shown to completely disaggregate the statistical mixture, meso, and 3R,3'R derivatives; a 50% ethanolic stock solution was required to completely disaggregate the 3S,3'S isomer. The scavenging ability of the compounds was also tested relative to negative (i.e. ethanol vehicle) and positive [superoxide dismutase (SOD) mimetic, free racemic astaxanthin in DMSO] controls.

Leukocyte Purification and Preparation

Human polymorphonuclear leukocytes (PMNs) were isolated from freshly sampled venous blood of a single volunteer (S.F.L.) by Percoll density gradient centrifugation, which yielded PMNs with a purity of >95%. Each 10 mL of whole blood was mixed with 0.8 mL of 0.1 M EDTA and 25 mL of saline. The diluted blood was layered over 9 mL of Percoll at a specific density of 1.080 g/mL. After centrifugation at 400×g for 20 min at 20° C., the plasma, mononuclear cell, and Percoll layers were removed. Erythrocytes were lysed by addition of 18 mL of ice-cold water for 30 s, followed by 2 mL of 10× PIPES buffer (25 mM PIPES, 110 mM NaCl, and 5 mM KCl, titrated to pH 7.4 with NaOH). Cells were pelleted at 4° C., the supernatant was decanted, and the procedure was repeated. After the second hypotonic lysis, cells were washed twice with PAG buffer (PIPES buffer containing 0.003% human serum albumin and 0.1% glucose). Afterward, PMNs were counted by light microscopy on a hemocytometer. The final pellet was then suspended in PAG-CM buffer (PAG buffer with 1 mM $CaCl_2$ and 1 mM $MgCl_2$).

EPR Measurements

All EPR measurements were performed using a Bruker ER 300 EPR spectrometer operating at X-band with a $TM_{110}$ cavity. The microwave frequency was measured with a Model 575 microwave counter (EIP Microwave, Inc., San Jose, Calif.). To measure $O^-_2$ generation from phorbol-ester (PMA)-stimulated PMNs, EPR spin-trapping studies were performed using DEPMPO (Oxis, Portland, Oreg.) at 10 mM. $1 \times 10^6$ PMNs were stimulated with PMA (1 ng/mL) and loaded into capillary tubes for EPR measurements. To determine the radical scavenging ability of non-esterified, free "racemic" astaxanthin in DMSO and the disodium salt disuccinate derivatives XVI in each of the nine formulations, PMN's were pre-incubated for 5 minutes with compound followed by PMA stimulation as previously described. The instrument settings used in the spin-trapping experiments were as follows: modulation amplitude, 0.32 G; time constant, 0.16 s; scan time, 60 s; modulation frequency, 100 kHz; microwave power, 20 milliwatts; and microwave frequency, 9.76 GHz. The samples were placed in a quartz EPR flat cell, and spectra were recorded. The component signals in the spectra were identified and quantified as reported (Lee, 2000).

Statistical Analysis

Statistical analyses were performed with the NCSS statistical software package (NCSS 2001 and PASS 2002, Kaysville, Utah). All statistical tests were performed at an $\alpha=0.05$.

Brief Discussion of EPR Results:

The potent SOD mimetic produced by Metaphore, Inc. served as a positive control at study outset. As has been observed repeatedly in the Zweier laboratory, the 10 μM dose in water-only vehicle nearly completely eliminated the superoxide anion signal as detected with DEPMPO (97% inhibition; Table 1). An ethanol-alone negative control (final concentration 0.3%) was also evaluated, as ethanol shows minor scavenging activity in these systems; 5.7% inhibition was seen at this concentration. This amount of inhibition was not subtracted from formulations containing ethanol in the descriptive data in Table 1, as the utility of the dosing vehicle itself (disodium disuccinate derivative XVI in EtOH) in direct scavenging was being evaluated in this study. Non-esterified, free astaxanthin in DMSO (100 μM) was evaluated as a reference standard for direct comparison to the novel derivatives synthesized for this study; mean inhibition of the astaxanthin/DMSO vehicle was 28% (Table 1).

Figure 18:
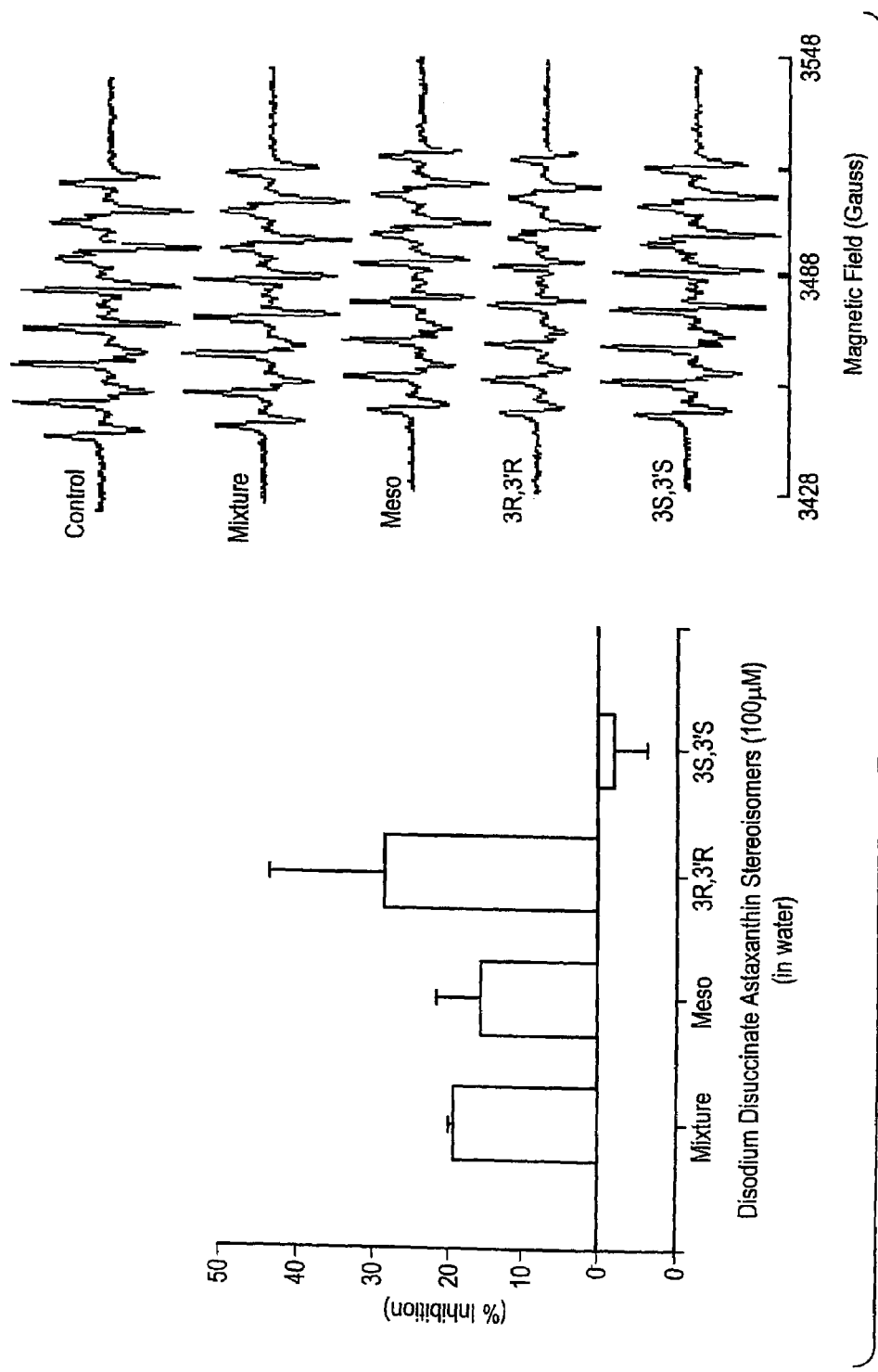
FIG. 18 depicts the mean percent inhibition of superoxide anion signal as detected by DEPMPO spin trap by the disodium disuccinate derivatives of astaxanthin in pure aqueous formulation. Mixture=statistical mixture of stereoisomers [3S,3'S, meso (3R,3'S and 3'R,3S), 3R,3'R in a 1:2:1 ratio]. Each derivative in aqueous formulation was standardized to control EPR signal detected without addition of compound (set at 0% inhibition by convention). Note the absence of superoxide inhibition by 3S,3'S formulation in water. In each case, the aqueous formulation is less potent than the corresponding formulation in EtOH (FIG. 19).
Figure 19:
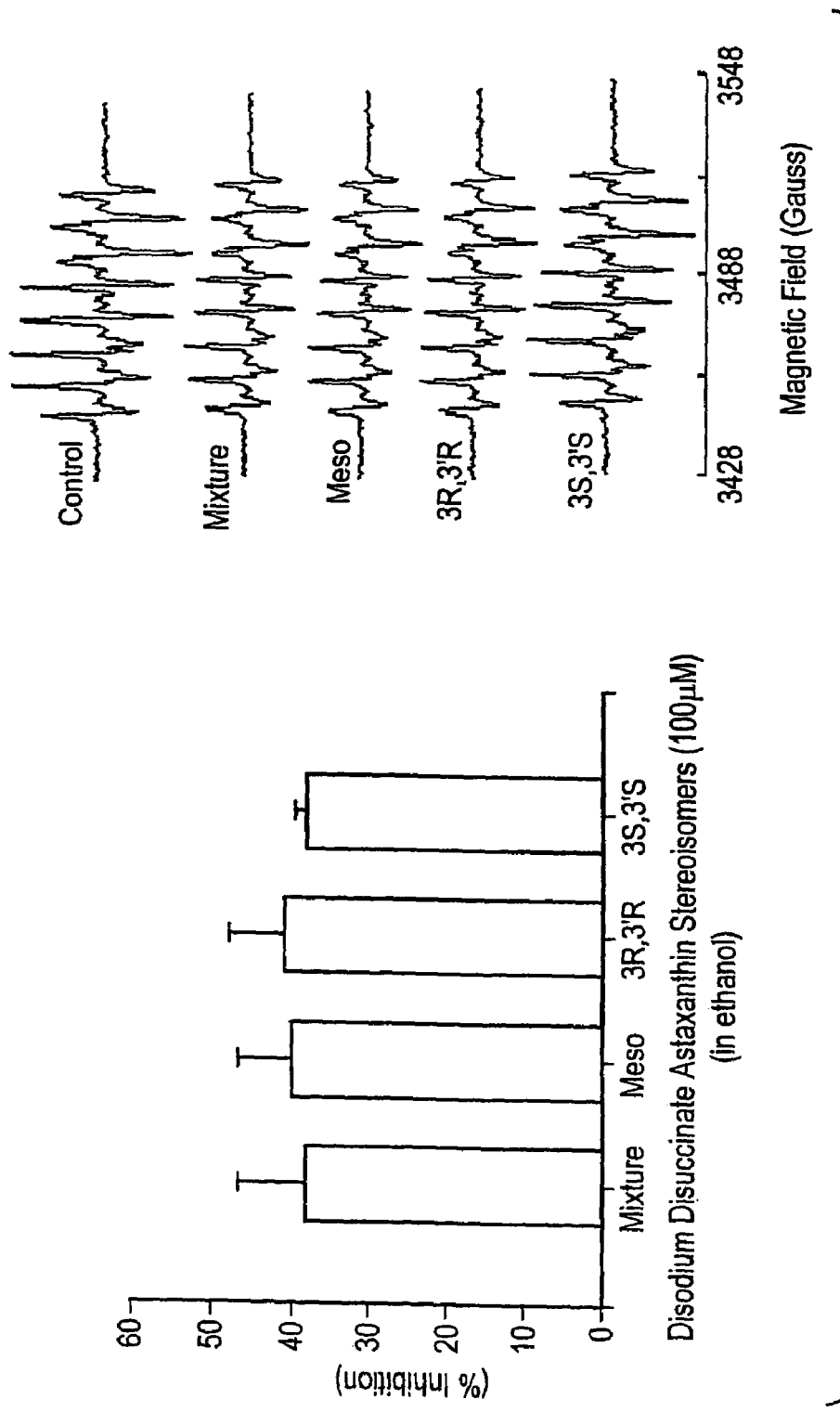
FIG. 19 depicts the mean percent inhibition of superoxide anion signal as detected by DEPMPO spin trap by the disodium disuccinate derivatives of astaxanthin in ethanolic formulation. Mixture=statistical mixture of stereoisomers [3S,3'S, meso (3R,3'S and 3'R,3S), 3R,3'R in a 1:2:1 ratio]. The mixture, meso, and 3R,3'R stock solutions were 1:2 ethanol/water (33⅓% EtOH); the 3S,3'S stock solution was 1:1 ethanol/water (50% EtOH). Final concentration of EtOH in the isolated neutrophil test assay was 0.3% and 0.5%, respectively. Each derivative in ethanolic formulation was standardized to control EPR signal detected without addition of compound (set at 0% inhibition by convention).

FIG. 18 shows the relative scavenging ability of each of the 3 stereoisomers (mixture and 3 individual stereoisomers) in water, at a final concentration of 100 μM. Except for the 3R,3'R enantiomer (28.7% inhibition), all other derivative formulations showed decreased scavenging ability relative to the astaxanthin/DMSO formulation (range −2.0% to 19.3% inhibition; Table 1). As can be seen, the 3S,3'S formulation did not exhibit any mean scavenging activity. When introduced into the isolated neutrophil test system in ethanolic formulation, however, in each case the scavenging ability increased over that of the same derivative formulated in water (FIG. 19; range 38.0% to 42.5%). It is important to note that the 3S,3'S derivative was formulated in 50% EtOH for this comparison. A trend toward increased scavenging capacity over astaxanthin in DMSO was seen for the novel derivatives in ethanolic formulation, but after subtraction of the mean scavenging ability of the ethanol vehicle (final concentration in the test assay 0.3%), the trend was not significant (NS). In addition, no significant differences in mean scavenging ability were observed among the 4 formulations of novel derivatives tested in ethanol (FIG. 19).

Figure 20:
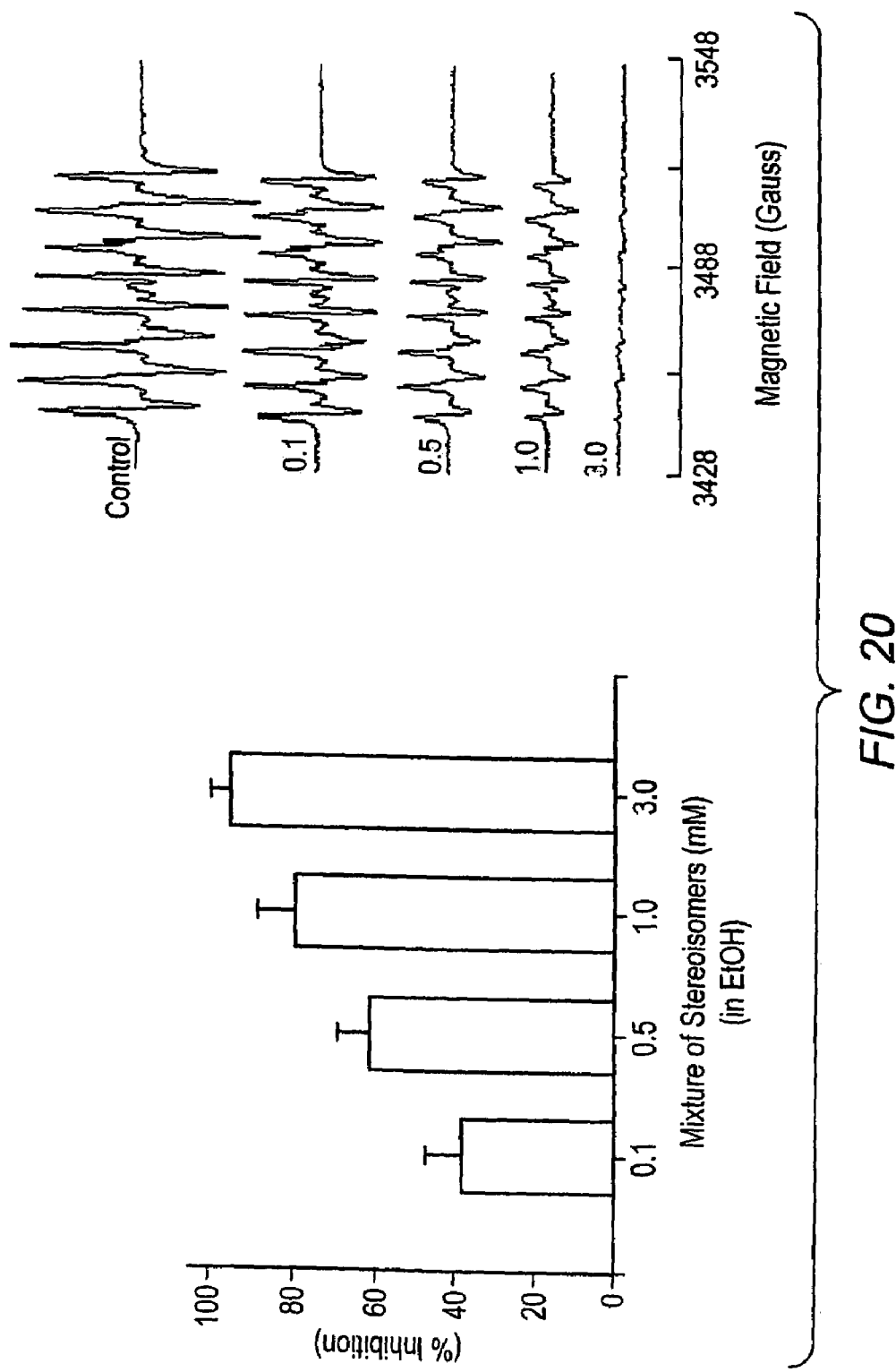
FIG. 20 depicts the mean percent inhibition of superoxide anion signal as detected by DEPMPO spin trap by the mixture of stereoisomers of the disodium disuccinate derivative of astaxanthin (tested in 1:2 EtOH/water formulation; final EtOH concentration in isolated neutrophil assay 0.3%). As the concentration of the derivative increases, inhibition increases in a non-linear, dose-dependent manner. At 3 mM, near-complete inhibition of superoxide anion signal is seen (95.0% inhibition).

FIG. 20 shows the results of titration of superoxide signal inhibition by increasing concentrations of the mixture of stereoisomers of disodium disuccinate astaxanthin XVI in ethanolic formulation. As the concentration was increased from 100 µM to 3 mM, near complete inhibition of superoxide signal was noted (95.0% inhibition at the 3 mM dose; Table 1 and FIG. 18). The dose-response curve was non-linear. Adjusting for percent inhibition and tested dose, the disodium disuccinate derivative was between one and two orders of magnitude less potent than the SOD mimetic used as a positive control in the current study (Table 1). Table 1 depicts descriptive statistics for various formulations of disodium disuccinate derivatives of astaxanthin tested in the current study. Sample sizes of 3 or greater were evaluated for each formulation, with the exception of 3S, 3'S in 50% EtOH stock solution (N=2), and SOD mimetic (positive control, N=1) evaluated at study outset.

radical species. The size of the aggregates must also be taken into account, as aggregates containing as many as $10^6$ molecules and reaching 300 nm or greater in size have been described (Bikadi, 2002).

Titration of the disodium disuccinate astaxanthin derivative XVI dose to 3 mM (as the mixture of stereoisomers in 1:2 EtOH/water) demonstrated near complete suppression of the superoxide anion signal (95% inhibition), as measured with the DEPMPO spin trap (FIG. 20). The dose-response curve was non-linear, requiring increasing doses for near-complete suppression of radical signal (FIG. 20). At the lowest concentration tested (100 µM), nearly 40% of the signal was inhibited. The potency of is the disodium disuccinate astaxanthin derivative at this dose can be compared directly with the superoxide dismutase (SOD) mimetic used as a positive control in the current study (97% inhibition at 10 µM). The results show that as an aqueous-phase radical scavenger, the disodium disuccinate astaxanthin derivative XVI is one to two orders of magnitude less potent than the

TABLE 1

| Sample | Solvent | Concentration | N | Mean (% inhibition) | S.D. | SEM | Min | Max | Range |
|---|---|---|---|---|---|---|---|---|---|
| Astaxanthin 2E | DMSO | 0.1 mM | 4 | 28.0 | 7.6 | 3.8 | 20 | 35 | 15 |
| Mixture | Water | 0.1 mM | 3 | 19.3 | 0.6 | 0.3 | 19 | 20 | 1 |
| Mixture | EtOH | 0.1 mM | 3 | 38.0 | 8.7 | 5.0 | 32 | 48 | 16 |
| Mixture | EtOH | 0.5 mM | 3 | 60.1 | 7.2 | 4.2 | 56 | 69 | 13 |
| Mixture | EtOH | 1.0 mM | 3 | 78.0 | 8.2 | 4.7 | 71 | 87 | 16 |
| Mixture | EtOH | 3.0 mM | 3 | 95.0 | 4.9 | 2.8 | 89 | 98 | 9 |
| Meso | Water | 0.1 mM | 3 | 15.7 | 5.9 | 3.4 | 9 | 20 | 11 |
| Meso | EtOH | 0.1 mM | 4 | 42.5 | 3.4 | 1.7 | 38 | 46 | 8 |
| 3R, 3'R | Water | 0.1 mM | 3 | 28.7 | 15.0 | 8.7 | 13 | 43 | 30 |
| 3R, 3'R | EtOH | 0.1 mM | 5 | 40.8 | 7.5 | 3.3 | 30 | 50 | 20 |
| 3S, 3'S | Water | 0.1 mM | 3 | −2.0 | 4.4 | 2.5 | −7 | 1 | 8 |
| 3S, 3'S | EtOH | 0.1 mM | 6 | 21.3 | 4.9 | 2.0 | 15 | 29 | 14 |
| 3S, 3'S | EtOH (50%) | 0.1 mM | 2 | 38 | 1.4 | 1.0 | 37 | 39 | 2 |
| Control | Water | 0.0 mM | 10 | 0.0 | ND | ND | ND | ND | ND |
| Control | EtOH | 0.3% final | 3 | 5.7 | 2.5 | 1.5 | 3 | 8 | 5 |
| SOD mimetic | Water | 10 µM | 1 | 97.0 | ND | ND | ND | ND | ND |

Brief Discussion of EPR Results.

Astaxanthin 2E is a potent lipophilic antioxidant that normally exerts its antioxidant properties in lipid-rich cellular membranes, lipoproteins, and other tissues (Britton, 1995). Derivatives of astaxanthin—with increased utility as water-dispersible agents—have the ability to directly scavenge aqueous-phase superoxide anion produced by isolated human neutrophils after stimulation of the respiratory burst.

The pure aqueous formulations of the novel derivatives were less potent than the ethanolic formulations in terms of direct scavenging ability. Supramolecular assembly of the water soluble carotenoid derivatives in some solvents (e.g., water) may explain their lack of potency in those solvents. The aggregation is of the helical, "card-pack" type, with aggregates greater than 240 nm in size forming in pure aqueous solution. Increasing ionic strength of buffer solutions may increase both the size and stability of these aggregates. The radical scavenging ability of these aggregates will be diminished over the monomeric solutions of the same compounds; in fact, no scavenging ability was seen for the 3S,3'S stereoisomer dissolved in water (Table 1, FIG. 18). Care must be taken in preparation of formulations for in vitro and in vivo testing, as supramolecular assembly limits the number of molecules available for interaction with SOD mimetic. However, in vivo, these derivatives decay to free astaxanthin, which becomes active in the lipid-rich membranes of cells [including the mitochondrial and nuclear membranes (Goto, 2001)], therefore providing dual protection (aqueous and lipid-phase radical scavenging), not achievable with water-soluble proteins and enzyme mimetics. Non-esterified, free astaxanthin (when provided as a dietary supplement at 0.02% of feed wt/wt) is cardioprotective against the ROS-mediated strenuous exercise insult to both skeletal and cardiac muscle (Aoi et al. 2003).Therefore, this characteristic (i.e. dual-phase radical scavenging) should provide additional utility for this class of compounds as clinical therapeutic agents in those indications for which radical and reactive oxygen species prevention is important (Cross, 1987).

The study demonstrates for the first time direct scavenging of superoxide anion detected by EPR spectroscopy by a group of carotenoid derivatives. The compounds were found to form supramolecular assemblies in pure aqueous solution. Formation of supramolecular assemblies may limit their scavenging potency relative to monomeric solutions of the same compounds. No significant differences in scavenging ability were seen among the 3 stereoisomers of the carotenoid derivatives. Dose-ranging studies revealed that the concentration of derivative could be increased to near-complete suppression of the induced superoxide anion signal. As potential in vivo therapeutic agents, this class of compounds may be used as both an aqueous phase and lipid phase scavenger, which should find wide application in those acute and chronic disease conditions for which potent radical scavengers have demonstrated efficacy.

Figure 33:
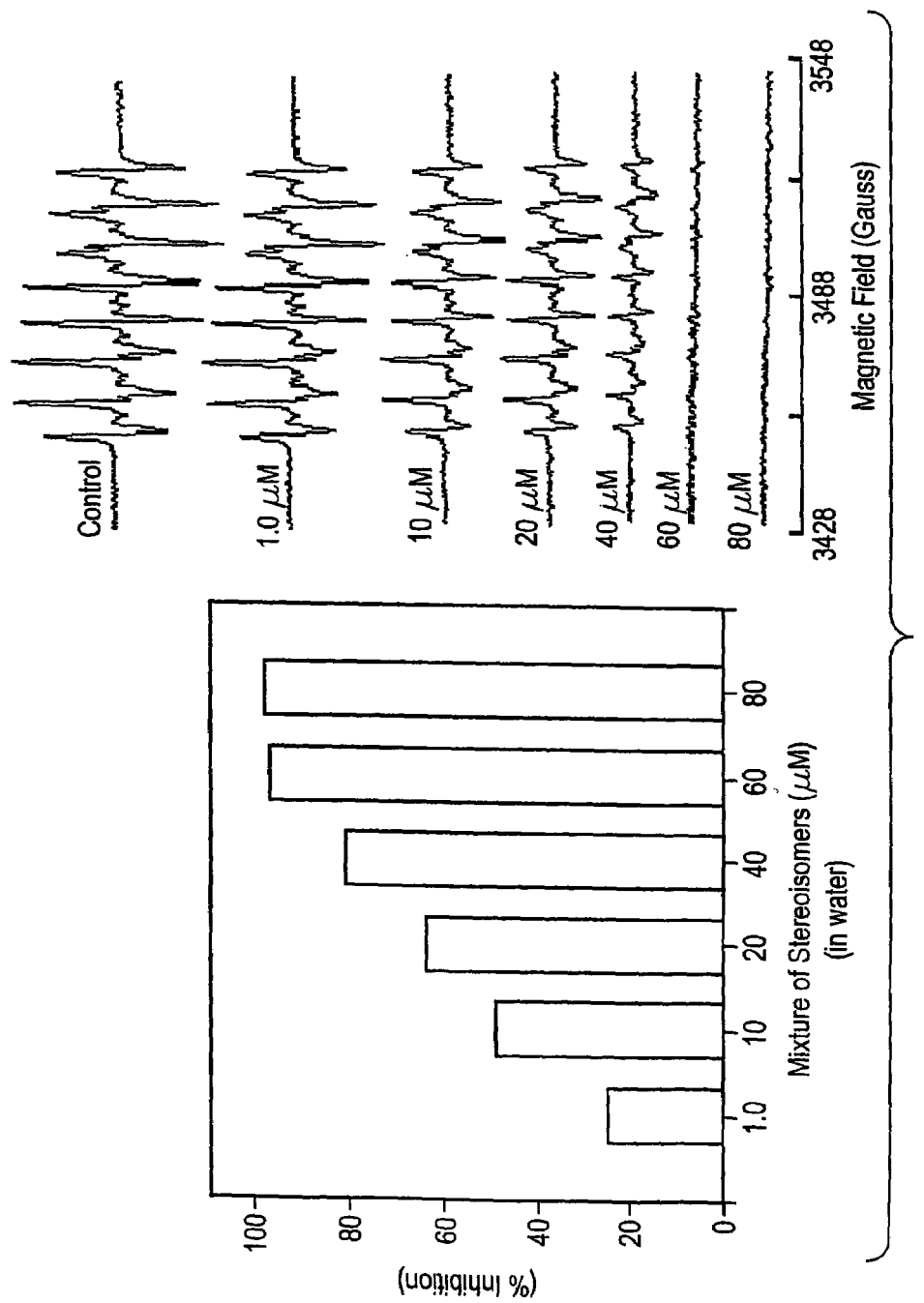
FIG. 33 depicts the mean percent inhibition of superoxide anion signal as detected by DEPMPO spin trap by the disodium salt disuccinate di-vitamin C derivative [derivative (XXIII)]. As the concentration of the derivative increases, inhibition increases in a dose-dependent manner. At 60 µM, nearly complete inhibition of superoxide anion signal is seen. This derivative was also highly water soluble, and was introduced into the test assay without a co-solvent (see FIG. 21). The novel derivative was comparable in radical-quenching efficacy to the formulation of the disodium salt disuccinate astaxanthin derivative in a 1:2 formulation with vitamin C (see FIG. 3), suggesting active, "soft-drug" properties for this derivative. This co-antioxidant derivative strategy increased the relative radical scavenging potency (when compared with the disodium salt disuccinate astaxanthin derivative) by 50-fold.

Direct Superoxide Anion Scavenging by the Disodium Disuccinate Di-vitamin C Astaxanthin Derivative In an electron paramagnetic resonance (EPR) spectroscopy experiment, neutrophils were isolated on a Percoll gradient from whole blood from a human volunteer. The isolated neutrophils were then re-suspended in phosphate-buffered saline, and maximally stimulated with phorbol ester to induce the respiratory burst and production of superoxide anion. To the solution of activated human neutrophils, the disodium disuccinate di-vitamin C astaxanthin derivative (XXIII) (semi-systematic name Succinic acid 4-[18-(4-{3-[2-(3,4-dihydroxy-5-oxo-2,5-dihydrofuran-2-yl)-2-hydroxy-ethoxycarbonyl]-propionyloxy}-2,6,6-trimethyl-2-oxo-cyclohex-1-enyl)-3,7,12,16-tetramethyl-octadeca-1,3,5,7,9,11,13,15,17-nonaenyl]-3,5,5-trimethyl-2-oxo-cyclohex-3-enyl ester 2-(3,4-dihydroxy-5-oxo-2,5-dihydrofuran-2-yl)-2-hydroxy-ethyl ester) was added at various concentrations, and the superoxide signal (as measured with EPR spectroscopy) was subsequently measured. The disodium disuccinate di-vitamin C astaxanthin derivative (XIII) reduced the measured superoxide anion signal in a dose-dependent manner (FIG. 33); complete suppression of the superoxide anion signal was achieved at 60 μM concentration. This represents a 50-fold increase in potency over the disodium disuccinate astaxanthin derivative (XVI) also synthesized for the current series of experiments. The purity of the derivative as tested was 88% (by HPLC area under the curve, or AUC). The carotenoid derivative—designed to be a "soft-drug" by esterification to the 6-OH position of each vitamin C—preserved the antioxidant function of the individual vitamin C molecules. The potency of the derivative (XXIII) approached that of the formulation of disodium disuccinate astaxanthin derivative (XVI) with free vitamin C in a 1:2 molar ratio (which completely suppressed the superoxide anion signal in a 20 μM/40 M disodium disuccinate astaxanthin derivative (XVI)/free vitamin C formulation). Derivative (XXIII), which generates 2 moles of free vitamin C and 1 mole of non-esterified, free astaxanthin for every mole of derivative in vivo may be particularly preferred for certain clinical indications. Derivative (XXIII) will also likely show increased efficacy in those clinical situations in which aqueous-phase scavenging (by the intact parent derivative, as well as free vitamin C) as well as lipid-phase scavenging (by non-esterified, free astaxanthin) are important for reduction in the pathology attributable to ROS and other radical species injury.

Infarct Size Reduction in Male Sprague-Dawley Rats

Figure 4:
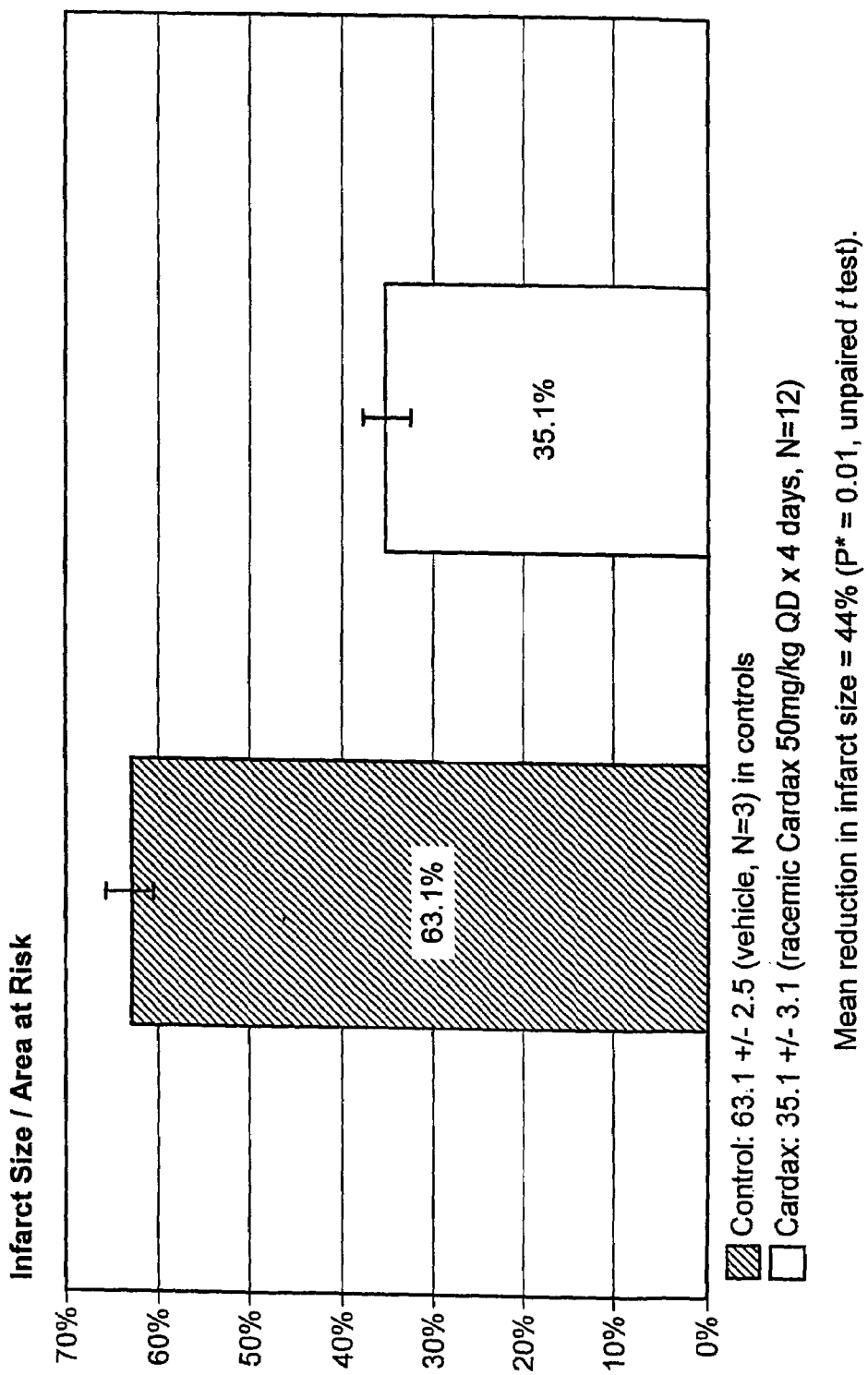
FIG. 4 depicts a graphical representation of a relative reduction of infarct size in male Sprague-Dawley rats with pre-treatment using a disodium salt disuccinate astaxanthin derivative intravenous formulation (Cardax™).
Figure 25:
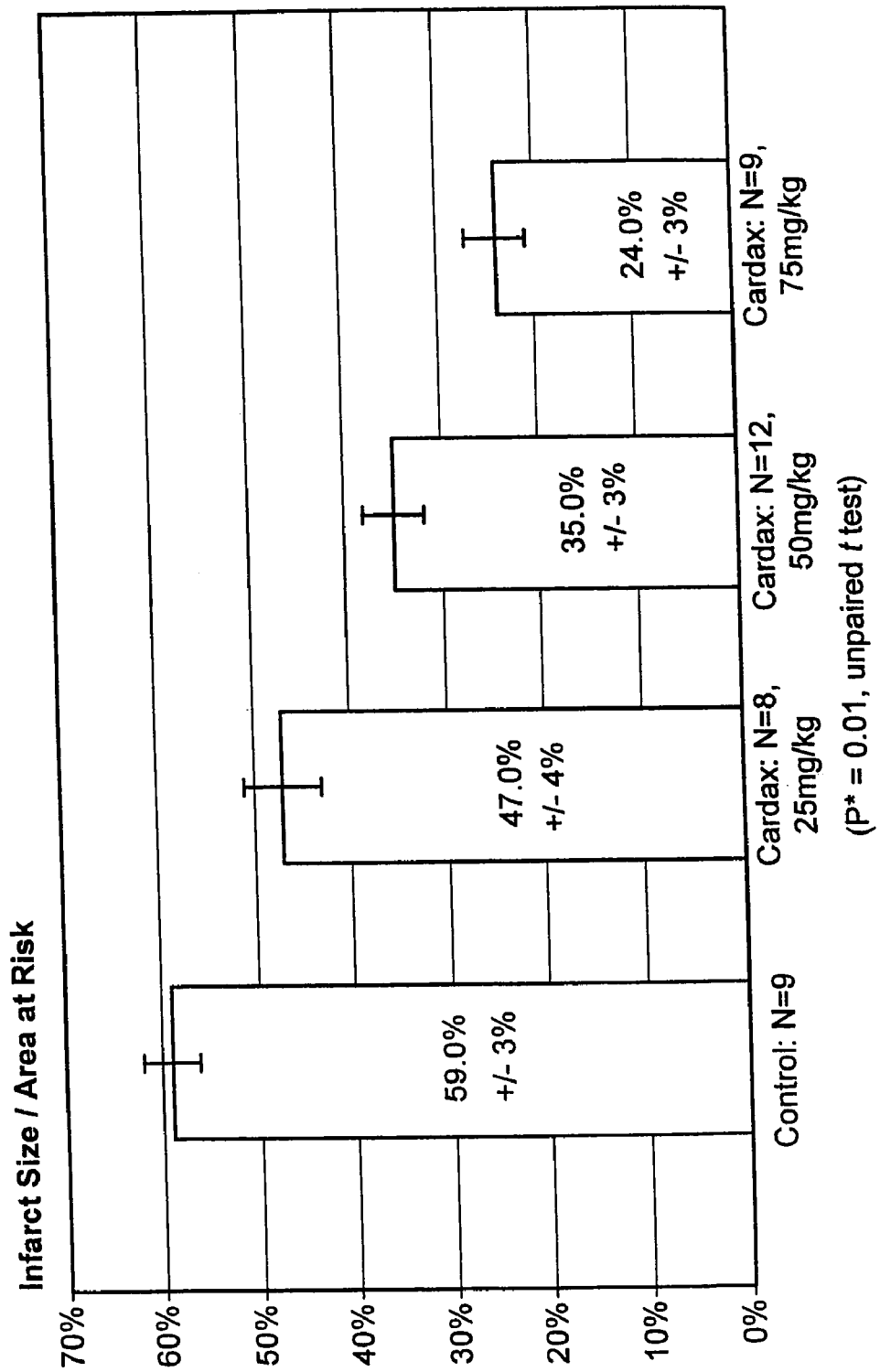
FIG. 25 depicts a graphical representation of a relative reduction of infarct size in male Sprague-Dawley rats with pre-treatment using a disodium salt disuccinate astaxanthin derivative intravenous formulation (Cardax™). A linear relationship between dose and infarct size reduction was seen. The levels of infarct size reduction approach that observed with ischemic pre-conditioning.
Figure 26:
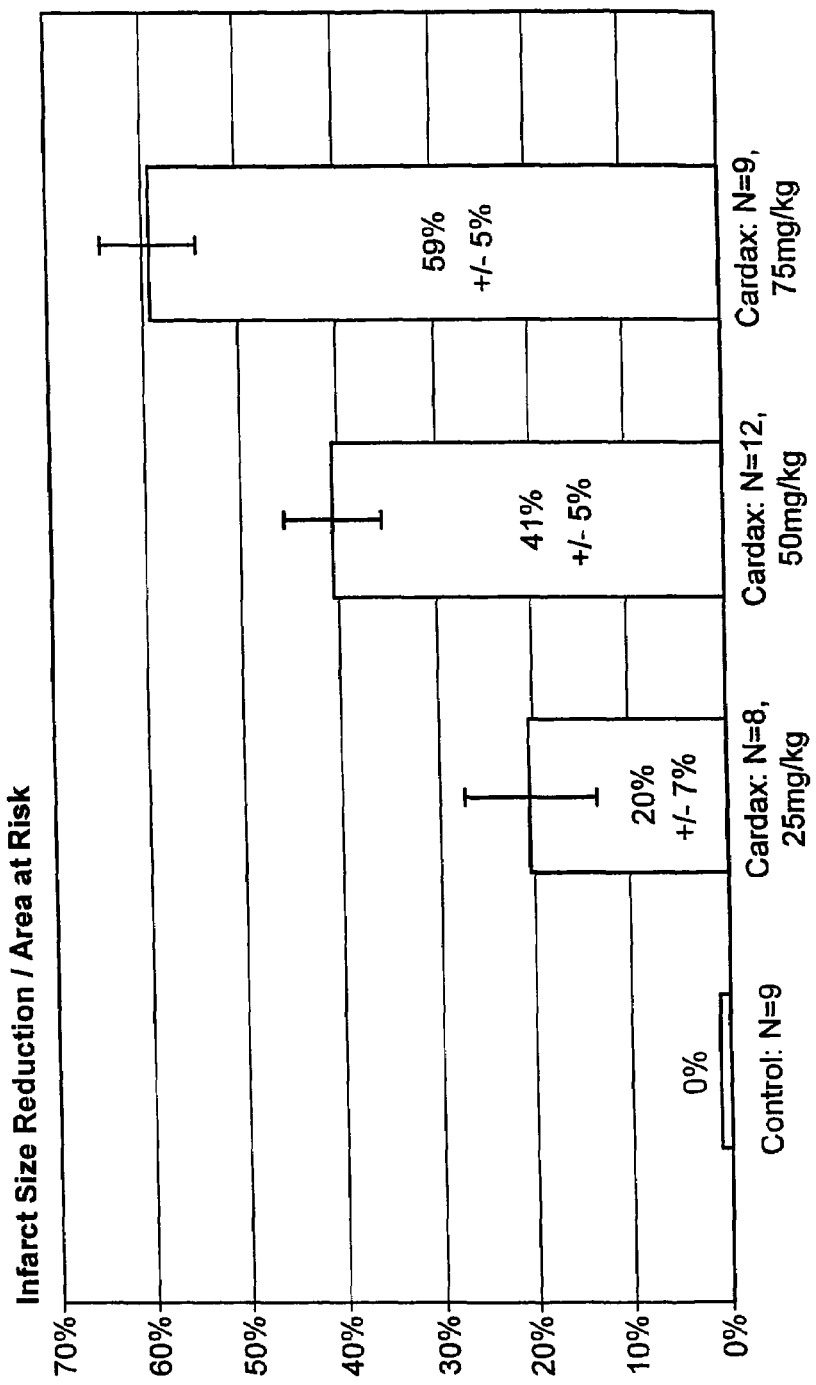
FIG. 26 depicts a graphical representation of a relative reduction of infarct size in male Sprague-Dawley rats with pre-treatment using a disodium salt disuccinate astaxanthin derivative intravenous formulation (Cardax™).

FIG. 4, FIG. 25, and FIG. 26 depict graphical representations of the reduction of infarct size in male Sprague-Dawley rats. Male Sprague-Dawley rats were pre-treated with the disodium salt disuccinate astaxanthin derivative XVI (as the mixture of stereoisomers) in aqueous solution before performing an occlusion and inducing a myocardial infarction. Male Sprague-Dawley rats (175-200 grams) were anaesthetized with 100 mg/kg of Inactin, instrumented, and the heart exposed. The left coronary artery had a suture placed around it and was subjected to 30 minutes of total coronary artery occlusion followed by 2 hours of reperfusion, at which time infarct size was measured in hearts excised from the animal. The hearts were washed in buffer and incubated in triphenyltetrazolium chloride (TTC) staining solution kept at 37° C. in phosphate buffer at pH of 7.40. Infarct size (IS) was expressed as a % of the area at risk (IS/AAR, %). Systemic blood pressure, heart rate, blood gases and body temperature were monitored throughout the experiment, and temperature and blood gases were tightly controlled at normal physiological levels. 25, 50, or 75 mg/kg of the disodium salt disuccinate astaxanthin derivative XVI or sterile saline vehicle was administered I.V. by tail vein injection every day for 4 days prior to the infarct experiment on day 5 and subsequent infarct size determination.

Brief Description of Salvage Results.

Infarct size reduction, and the corresponding myocardial salvage, increased linearly, and significantly, with dose (P=0.001). At the maximum dose tested, 75 mg/kg, mean myocardial salvage was 56%, which approaches that achievable with ischemic pre-conditioning strategies. Volume limitations for single-dose I.V. injection in this rat precluded testing of higher doses; however, the significant linear correlation (P<0.001; $r^2$=0.67) between non-esterified, free plasma levels of astaxanthin 2E and IS/AAR, % suggested that at doses of approximately 120 to 125 mg/kg, 100% salvage might be achieved. This is the first demonstration of cardioprotection by a carotenoid derivative.

Pharmacokinetics, Increased Bioavailability, and Increased Target Tissue Distribution of the Orally Administered Disodium Disuccinate Astaxanthin Derivative Plasma Pharmacokinetics Single dose oral pharmacokinetic parameters (including $C_{max}$, $T_{max}$, $AUC_{(0-72)}$ $V_d$, and clearance) of the disodium disuccinate astaxanthin derivative XVI were determined in male C57BL/6 mice. The animals were administered the derivative orally at a single maximum dose (500 mg/kg) shown in prior studies to likely be efficacious in preventing the injury secondary to $CCl_4$-administration in Sprague-Dawley rats (100 mg/kg body weight in those studies). Samples for HPLC analysis of levels of free astaxanthin in plasma and liver were obtained at the following time points, from at least 3 animals per time point:

Time 0 [Immediately Before Dosing of Test Compound], 2, 4, 6, 8, 12, 16, 24, 48, and 72 Hours After Ingestion.

Additional samples, with N<3, were taken at other intervals (10, 14, and 36 hours; Tables 2 and 3). Non-esterified, free astaxanthin levels were determined in this study as carotenoid esters are completely cleaved in the mammalian gut to free carotenoid, which moves passively across the enterocyte.

Brief Description of Experimental Methods: Plasma Pharmacokinetics

5 Male C57BL/6 mice, approximately 25 g, were housed in cages (three mice/cage) and fed standard mouse chow (Purina Mouse Chow, Ralston Purina, St. Louis) and water ad libitum for at least five days prior to the start of the experiment. The disodium disuccinate astaxanthin derivative XVI was mixed with the following components to make an emulsion suitable for oral gavage:

Sterile filtered (0.2 micron Millipore®) water;
Olive oil (Bertolli USA, Inc., Secaucus, N.J.);
Soybean lecithin, Type IV-S (Sigma-Aldrich Co., St. Louis, Mo.; catalog number P3644).

The disodium disuccinate astaxanthin derivative XVI demonstrates water-solubility of approximately 8.64 mg/mL in pure aqueous formulation. In the emulsion described above, solubility was increased to approximately 50 mg/mL, allowing for dosing up to 500 mg/kg by gavage in these animals. This significant 6-fold increase in solubility in the dosing vehicle greatly facilitated gavage studies in these small mice.

Methods for preparing the Emulsion Were as Follows:

(1) Add 80 mg of soy lecithin (Sigma catalog P3644) to 5.0 mL water. Vortex intermittently for approximately 30 minutes in a 15 mL centrifuge tube until the suspension is uniform;

(2) Add 2.5 mL olive oil at room temperature and vortex. This produces a uniform, thick, cloudy yellow suspension. This emulsion material may be stored either at room temperature or in the refrigerator at 4° C. If stored, vortex immediately before adding the disodium disuccinate derivative XVI in 3 (below);

(3) Add the disodium disuccinate astaxanthin derivative XVI at 50 mg/mL directly to the emulsion. The compound readily enters into a uniform suspension at this concentration. Vortex immediately prior to gavage to assure uniform suspension; and (4) The material has the potential to clog the mouse gavage needle. Rinse the gavage needle after every 2 gavages.

The emulsion was given by oral gavage at 500 mg/kg body weight in a single dose. Food was withdrawn from all cages the evening prior to the experiment. One hour after administration of the emulsion, food and water were restored to all animals.

The methods for whole blood and tissue sampling, sample extraction, and HPLC analysis have been described in detail (Osterlie, 2000). Briefly, whole blood was collected in EDTA-containing Vacutainer® tubes, and plasma subsequently prepared by centrifugation at 4° C., 1500×g for 20 minutes. Plasma samples were then aliquoted and snap frozen in liquid nitrogen prior to transport and HPLC analysis.

Tissue Accumulation

Free astaxanthin concentration was also determined, at the same time points as for plasma samples, in liver. Livers were removed from each animal in the pharmacokinetic study after sacrifice, and snap frozen in liquid nitrogen. Liver tissue was prepared for HPLC analysis as described (Jewell, 1999). Therefore, simultaneous examination of liver accumulation of free astaxanthin was performed at the same time points as the plasma analyses.

Brief Description of Experimental Methods: Liver Accumulation of Free Astaxanthin Up to 300 mg of liver from each animal was snap frozen in liquid nitrogen. Tissue homogenization and extraction were performed with a mixture of chloroform/methanol/water, according to the methods of Jewell (1999). Non-esterified, free astaxanthin accumulation in liver was then evaluated by HPLC as described above for plasma samples.

Brief Discussion of Pharmacokinetic Results

Summary tables of plasma and liver levels of free astaxanthin at the appropriate sampling interval(s) are shown as Tables 2 and 3. Plasma and liver non-esterified free astaxanthin areas under the curve vs. time (AUC's) are also included in Tables 2 and 3. The results demonstrate that for each sampling interval, the levels of free astaxanthin in liver are equal or greater to that in plasma. This improved tissue-specific delivery to the liver is unprecedented in the literature; in fact, liver levels of free astaxanthin are typically lower than the corresponding levels in plasma at equivalent time points post-dose (Kurihara, 2002). Thus, the disodium disuccinate astaxanthin derivative XVI in the emulsion described above is a superior vehicle for delivery of therapeutic concentrations of free carotenoid to tissues of interest after oral dosing.

TABLE 2

Plasma Levels of Non-Esterified, Free Astaxanthin

| Time | Sample | asta nM | asta mg/kg | mean mg/kg | S.D. |
|---|---|---|---|---|---|
| 0 | PK01 | 0.00 | 0.00 | | |
| | PK03 | 0.00 | 0.00 | | |
| | PK06 | 0.00 | 0.00 | | |
| | PK15 | 0.00 | 0.00 | | |
| | PK16 | 0.00 | 0.00 | | |
| | PK20 | | | 0.00 | 0 |
| 2 | PK10 | 38.04 | 0.02 | | |
| | PK12 | 0.00 | 0.00 | | |
| | PK21 | 0 | 0 | | |
| | PK22 | 0 | 0 | | |
| | PK27 | 0 | 0 | | |
| | PK34 | 0 | 0 | | |
| | PK42 | 311.73 | 0.19 | | |
| | PK43 | 74.08 | 0.04 | | |
| | PK48 | 48.41 | 0.03 | | |
| | PK59 | 318.83 | 0.19 | 0.05 | 0.077 |
| 4 | PK07 | 46.18 | 0.03 | | |
| | PK11 | 115.63 | 0.07 | | |
| | PK14 | 20.97 | 0.01 | | |
| | PK17 | 40.57 | 0.02 | | |
| | PK23 | 214.95 | 0.13 | | |
| | PK24 | 179.33 | 0.11 | | |
| | PK28 | | | | |
| | PK44 | 80.48 | 0.05 | | |
| | PK45 | 67.16 | 0.04 | | |
| | PK57 | 119.02 | 0.07 | | |
| | PK58 | 147.85 | 0.09 | 0.062 | 0.039 |
| 6 | PK13 | 40.57 | 0.02 | | |
| | PK18 | 605.01 | 0.36 | | |
| | PK25 | 262.73 | 0.16 | | |
| | PK26 | 377.14 | 0.22 | | |
| | PK32 | | | | |
| | PK46 | 739.91 | 0.44 | | |
| | PK60 | 167.39 | 0.1 | | |
| | PK61 | 131.74 | 0.08 | 0.197 | 0.154 |
| 8 | PK36 | | | | |
| | PK47 | 435.17 | 0.26 | | |
| | PK49 | 371.11 | 0.22 | | |
| | PK62 | 148.98 | 0.09 | | |
| | PK68 | 405 | 0.24 | | |
| | PK69 | 306.86 | 0.18 | | |
| | PK70 | 29.98 | 0.02 | 0.168 | 0.094 |
| 10 | PK31 | | | | |
| 12 | PK37 | | | | |
| | PK63 | 37.19 | 0.02 | | |
| | PK64 | 10.93 | 0.01 | | |
| | PK67 | 8.12 | 0 | | |
| | PK71 | 53.19 | 0.03 | | |
| | PK72 | 7.66 | 0 | | |
| | PK73 | 8.46 | 0.01 | 0.012 | 0.012 |
| 14 | PK51 | 0 | 0 | | |
| | PK52 | 3.14 | 0 | 0 | 0 |

TABLE 2-continued

Plasma Levels of Non-Esterified, Free Astaxanthin

| Time | Sample | asta nM | asta mg/kg | mean mg/kg | S.D. |
|---|---|---|---|---|---|
| 16 | PK65 | 8.44 | 0.01 | | |
| | PK66 | 10.47 | 0.01 | | |
| | PK75 | 28.24 | 0.02 | | |
| | PK76 | 4.51 | 0 | 0.010 | 0.008 |
| 24 | PK29 | 0 | 0 | | |
| | PK35 | 18.03 | 0.01 | | |
| | PK39 | 13.93 | 0.01 | | |
| | PK50 | 1.51 | 0 | | |
| | PK53 | 0 | 0 | 0.004 | 0.005 |
| 36 | PK38 | 21.37 | 0.01 | 0.01 | |
| 48 | PK30 | 0 | 0 | | |
| | PK33 | 0 | 0 | | |
| | PK54 | 22.71 | 0.01 | | |
| | PK55 | 0 | 0 | 0.003 | 0.005 |
| 72 | PK40 | 1.7 | 0 | | |
| | PK41 | | | | |
| | PK56 | 0 | 0 | | |
| | PK74 | 1.92 | 0 | 0 | 0 |

TABLE 3

Liver Levels of Non-Esterified, Free Astaxanthin

| Time | Sample | asta nM | asta mg/kg | mean mg/kg | S.D. |
|---|---|---|---|---|---|
| 0 | PK01 | 0.00 | 0.00 | | |
| | PK03 | 0.00 | 0.00 | | |
| | PK06 | 0.00 | 0.00 | | |
| | PK15 | 0.00 | 0.00 | | |
| | PK16 | 7.67 | 0.00 | | |
| | PK20 | 8.18 | 0.00 | 0.00 | 0 |
| 2 | PK10 | 139.37 | 0.08 | | |
| | PK12 | 30.66 | 0.02 | | |
| | PK21 | 414.34 | 0.25 | | |
| | PK22 | 725.87 | 0.43 | | |
| | PK27 | 294.07 | 0.18 | | |
| | PK34 | 165.32 | 0.1 | | |
| | PK42 | 689.36 | 0.41 | | |
| | PK43 | 129.66 | 0.08 | | |
| | PK48 | 244.5 | 0.15 | | |
| | PK59 | 564.28 | 0.34 | 0.20 | 0.146 |
| 4 | PK07 | 103.07 | 0.06 | | |
| | PK11 | 243.4 | 0.15 | | |
| | PK14 | 89.18 | 0.05 | | |
| | PK17 | 1565.15 | 0.93 | | |
| | PK19 | 1373.34 | 0.82 | | |
| | PK23 | 2558.63 | 1.52 | | |
| | PK24 | 4701.95 | 2.8 | | |
| | PK28 | 1023.78 | 0.61 | | |
| | PK44 | 359.73 | 0.21 | | |
| | PK45 | 211.35 | 0.13 | | |
| | PK57 | 322.06 | 0.19 | | |
| | PK58 | 500.82 | 0.3 | 0.648 | 0.812 |
| 6 | PK13 | 374.28 | 0.22 | | |
| | PK18 | 2970.44 | 1.77 | | |
| | PK25 | 3515.52 | 2.1 | | |
| | PK26 | 2087.8 | 1.24 | | |
| | PK32 | 687.99 | 0.41 | | |
| | PK46 | 1070.13 | 0.64 | | |
| | PK60 | 974.69 | 0.58 | | |
| | PK61 | 841.37 | 0.5 | 0.933 | 0.690 |
| 8 | PK36 | 1290.15 | 0.77 | | |
| | PK47 | 230.88 | 0.14 | | |
| | PK49 | 1115.86 | 0.67 | | |
| | PK62 | 1247 | 0.74 | | |
| | PK68 | 1263.31 | 0.75 | | |
| | PK69 | 1036.29 | 0.62 | | |
| | PK70 | 1518.27 | 0.9 | 0.637 | 0.244 |
| 10 | PK31 | 1303.06 | 0.78 | 0.780 | |
| 12 | PK37 | 3225.35 | 1.92 | | |
| | PK63 | 921.74 | 0.55 | | |
| | PK64 | 713.97 | 0.43 | | |
| | PK67 | 410.93 | 0.24 | | |
| | PK71 | 1382.45 | 0.82 | | |
| | PK72 | 567.95 | 0.34 | | |
| | PK73 | 716.89 | 0.43 | 0.468 | 0.579 |
| 14 | PK51 | 141.9 | 0.08 | | |
| | PK52 | 179.51 | 0.09 | 0.085 | 0.007 |
| 16 | PK65 | 240.6 | 0.14 | | |
| | PK66 | 340.38 | 0.2 | | |
| | PK75 | 788.66 | 0.47 | | |
| | PK76 | 499.84 | 0.3 | 0.278 | 0.144 |
| 24 | PK29 | 440.72 | 0.26 | | |
| | PK35 | 321.14 | 0.19 | | |
| | PK39 | 155.42 | 0.09 | | |
| | PK50 | 156.61 | 0.09 | | |
| | PK53 | 89.18 | 0.05 | 0.136 | 0.086 |
| 36 | PK38 | 658.41 | 0.39 | 0.39 | |
| 48 | PK30 | 106.07 | 0.06 | | |
| | PK33 | 116.79 | 0.07 | | |
| | PK54 | 17.81 | 0.01 | | |
| | PK55 | 28.79 | 0.02 | 0.04 | 0.029 |
| 72 | PK40 | 33.52 | 0.02 | | |
| | PK41 | 11.66 | 0.01 | | |
| | PK56 | 9.21 | 0.01 | | |
| | PK74 | 19.31 | 0.01 | 0.013 | 0.005 |

Pretreatment (15 days to 6 weeks) is often required when carotenoids such as astaxanthin are provided in oral vehicle or in feed to achieve efficacious levels in liver-injury studies (Kang, 2001; Kim, 1997; Aoi et al. 1993). In this case, therapeutic levels (200 nM or above) were achieved with a single dose.

The $C_{max}$ (Table 4) of 0.9 mg/L is also unprecedented in rodents, animals which absorb only small percentage of the oral dose of carotenoids. It is significant that these plasma and liver levels of free carotenoid were obtained after just a single dose of compound in the emulsion vehicle. In humans, Osterlie et al. (2000) have described $C_{max}$, plasma levels of 1.3 mg/L after a single dose of 100 mg (approximately 1.1 mg/kg oral dose) of esterified, free astaxanthin in olive oil vehicle. Humans typically absorb 40 to 50% of the oral dose of carotenoid when provided in fatty vehicle, as opposed to a few percentage points for rodents. Therefore, the current study demonstrates achievement of nearly 70% of the $C_{max}$ in humans with the emulsion vehicle developed for rodents, greatly increasing the utility of this derivative for hepato-protection studies.

TABLE 4 pK Parameters

| Parameter | Liver | Plasma |
|---|---|---|
| *$C_{max}$ (mg/L) | 0.9 | 0.2 |
| **$T_{max}$ (hr) | 6 | 6 |
| Elimination half-life (hr) | 11.655 | 3.938 |
| Elimination rate (1/hr) | 0.059 | 0.176 |
| ***AUC$_{(0-72)}$ (mg hr/L) | 15.8 | 1.2 |
| ***AUC∞ (mg hr/L) | 15.9 | 1.2 |
| Oral clearance (L/hr) | 15.856 | 216.822 |
| Volume of distribution (L/kg) | 263.9 | 1232.1 |

*Maximal concentration
**Time at maximum concentration
***Area under the curve

Reduction of Experimental Infarct Size and
Circulating Levels of C-reactive Protein in Rabbits
After Parenteral Administration Of Cardax™
(Disodium Disuccinate Astaxanthin Derivative)

The influence of parenteral administration of the disodium disuccinate astaxanthin derivative (XVI) on induced infarct size and induced levels of circulating C-reactive protein (CRP) in rabbits was investigated using the methods of Barrett et al. (2002) with slight modifications. The purpose of the current study was to investigate the ability of the disodium disuccinate astaxanthin derivative (XVI) to reduce inflammation as measured by CRP in the setting of experimental myocardial ischemia-reperfusion injury in the rabbit heart. It has been suggested that CRP, commonly used as a marker for the acute inflammatory ("acute-phase") response, may actually have a pro-inflammatory effect mediated through the activation of the complement cascade. Myocardial ischemia-reperfusion injury, which is accompanied by an increase in the formation of oxygen radicals (ROS), has also been shown to activate the complement system. It has been demonstrated that (1) the endogenous increase in plasma CRP secondary to a remote inflammatory lesion was associated with an increase in myocardial tissue injury secondary to regional ischemia and reperfusion; (2) this increase in injury (manifested as increased infarct size) was mediated by complement activity; and (3) CRP was an "effector", and not merely an indirect measure of systemic inflammation, in this system. Therefore, reduction of circulating CRP levels, together with the reduction(s) in infarct size previously noted with Cardax™ in rodents, would form a powerful anti-inflammatory therapeutic modality in the acute coronary syndrome setting.

In brief, male New Zealand white rabbits (2.25-2.5 kg) were used for the study. The acute phase inflammatory response was induced by subcutaneous injection of four aliquots (0.5 mL each) of 1% croton oil in corn oil beginning on the second day of pre-treatment with Cardax™. Either Cardax™ (at 50 mg/kg IV by ear vein injection) in water or equal volumes of sterile saline were given once per day for 4 days prior to experimental infarction on day 5. The time course of increases in circulating CRP levels were obtained as described previously (Barret et al. 2002), using an ELISA-based method with anti-rabbit CRP antibodies. On the final day of the experiment (day 5: approximately 24 hours after the last drug infusion), the rabbits were anesthetized with a mixture of xylazine (3 mg/kg) and ketamine (35 mg/kg) followed by pentobarbital (90 mg/kg) intramuscularly. Additional pentobarbital was administered as necessary to maintain anesthesia. After tracheotomy, the rabbits were ventilated with room air, and the heart was exposed via a left thoracotomy. The heart was then supported in a pericardial cradle and a 3-0 silk ligature was placed around the left anterior descending coronary artery. The artery was occluded for 30 minutes by exerting traction on the ligature and subsequently reperfused for 180 minutes. Shortly before completing the protocol, a venous blood sample was obtained for determination of plasma CRP.

At the completion of the reperfusion phase of the protocol, the hearts were removed and cannulated by the aorta on the Langendorff perfusion apparatus. The hearts were then perfused with a modified Krebs-Henseleit buffer for 10 to 15 minutes (20-25 mL/minute). At the conclusion of this period, the hearts were perfused with 80 mL of 0.4% 2,3,5-triphenyltetrazolium chloride (TTC) at 37° C. for determination of the area-at-risk (AAR). The left circumflex coronary artery was then ligated in the same area as it was during the surgical preparation/experimental infarction. At this time, the perfusion pump was stopped, and 3.0 mL of Evan's blue dye was injected slowly into the hearts through a sidearm port connected to the aortic cannula. The solution was allowed to distribute through the heart for approximately 30 seconds. The hearts were then cut into six transverse sections at right angles to the vertical axis. The right ventricle, apex, and atrial tissue were discarded. Tissue demarcated by a purple/blue color represented the region perfused by the noninfarct-related coronary artery distribution. Both surfaces of each transverse section were traced onto clear acetate sheets that were scanned and subsequently digitized to calculate infarct area. Total area at risk was expressed as a percentage of the left ventricle. Infarct size was then expressed as a percentage of area at risk.

Figure 37:
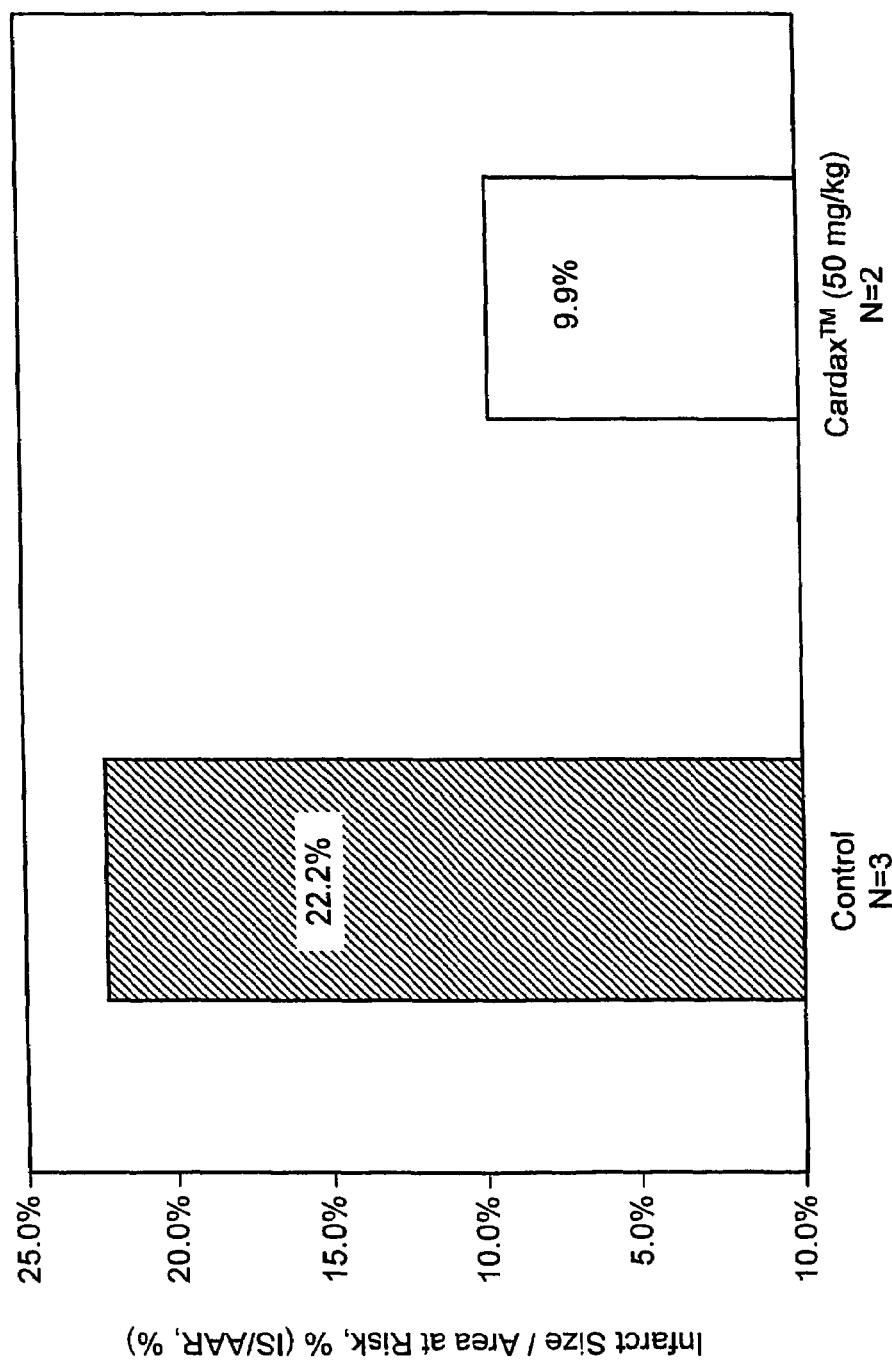
FIG. 37 depicts a graphical representation of a relative reduction of infarct size in male New Zealand rabbits with pre-treatment using a disodium salt disuccinate astaxanthin derivative intravenous formulation (Cardax™). When compared with the infarct size reduction seen at the same dose and identical pre-treatment schedule in rodents, a 38% increase in infarct size reduction was observed in the rabbit model.
Figure 38:
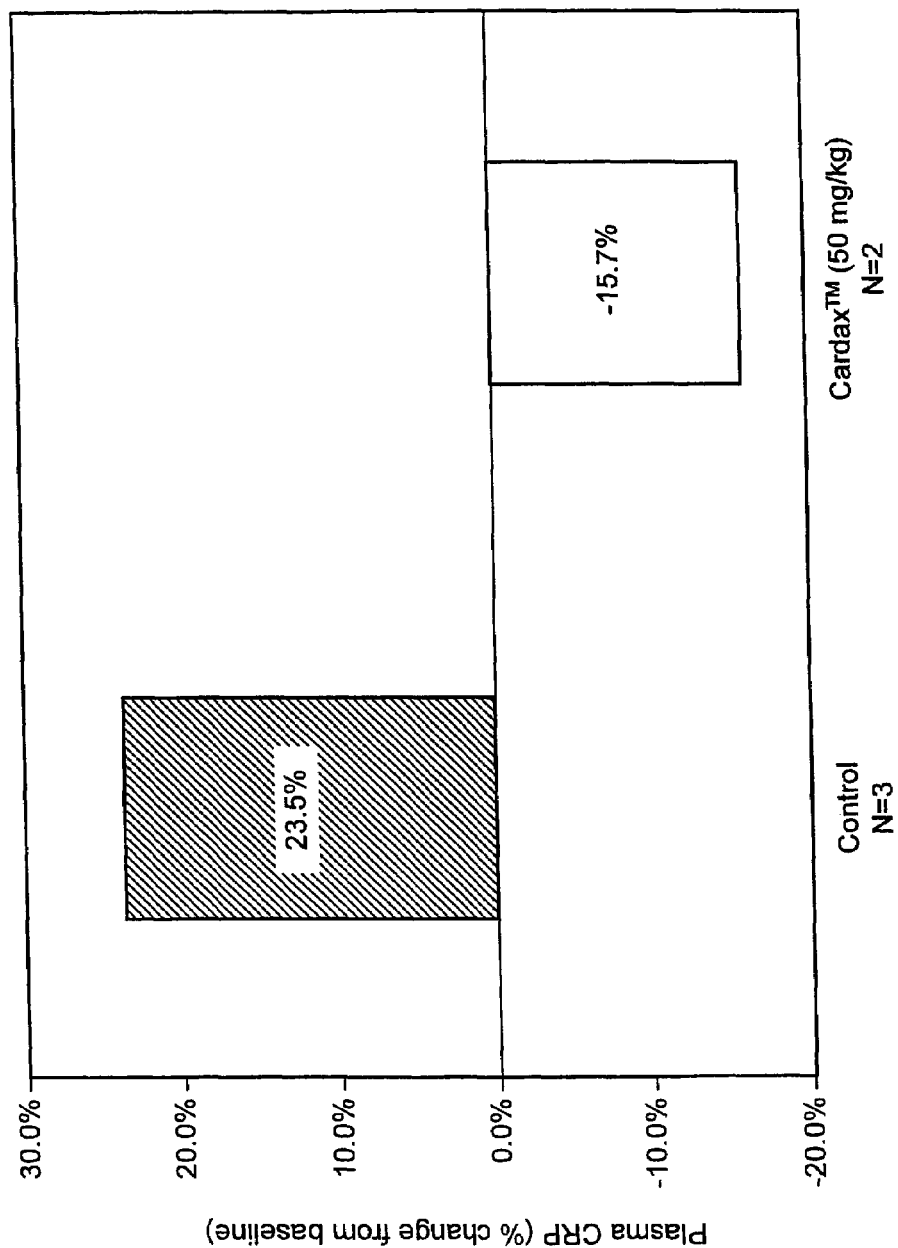
FIG. 38 depicts a graphical representation of a relative reduction of circulating levels of plasma C-reactive protein (CRP) in male New Zealand rabbits with pre-treatment using a disodium disuccinate astaxanthin derivative intravenous formulation (Cardax™). Control rabbits (saline injection alone) stimulated for the acute-phase response with 1% croton oil by subcutaneous injection showed a mean increase of 23.5% in circulating CRP levels from baseline (venous sample taken at the time of reperfusion). In contrast, Cardax™—treated animals (50 mg/kg) demonstrated a mean reduction in circulating CRP levels from baseline (−15.7%), demonstrating the potent anti-inflammatory effects of Cardax™.

Mean infarct size in control animals and Cardax™—treated animals is shown in FIG. 37. Levels of circulating CRP in control animals and Cardax™—treated animals (shown as the mean difference between baseline levels and induced levels at the time of reperfusion) is shown in FIG. 38. Reductions in infarct size of approximately 55.4% percent were seen in Cardax™—treated rabbits; ischemic area-at-risk was similar in both groups. Similarly, the mean increase in circulating CRP levels in controls (+23.5%) over baseline was completely abrogated in the Cardax™—treated animals, to mean levels below those observed at baseline (−15.7%). As CRP is both an effector in the acute coronary syndrome—resulting in an increased infarct size in the presence of elevated levels of this acute phase reactant—and a strong independent predictor of cardiovascular risk in primary and secondary prevention cardiac patients—reductions in the levels of this circulating protein forms a strong therapeutic modality.

Oral Administration of Disodium Disuccinate
Astaxanthin Reduces Alanine Aminotransferase
(ALT) Elevations Produced by Lipopolysaccharide
(LPS) in Mice The following study evaluates the utility of oral administration of the disodium disuccinate astaxanthin derivative XVI for hepatoprotective effects in a model of LPS-induced liver injury in mice.

Brief Description of Experimental Methods:

Three-month old male ICR mice were treated with LPS and galactosamine in order to induce liver injury (Leist, 1995). Mice were first orally gavaged with either an olive oil/water/lecithin emulsion (10 mL/kg, or 0.3 mL for a 30 gram mouse), or the same emulsion containing the disodium disuccinate astaxanthin derivative XVI (50 mg/mL) for a final disodium disuccinate astaxanthin dose of 500 mg/kg. Two hours later mice were injected intraperitoneally (IP) with either saline (10 mL/kg) or a solution of E. coli LPS (3 mg/kg, Sigma catalog number L-3755) and D-galactosamine (700 mg/kg). Animals were sacrificed by carbon dioxide ($CO_2$) asphyxiation 5 hours after the IP injection, and plasma was then collected for ALT determination.

Brief Description of LPS-Induced Injury Results.

These initial results demonstrated that the disodium disuccinate astaxanthin derivative had no effect on plasma ALT in the saline injected (liver-injury sham-treated control) animals. In control animals gavaged with emulsion only (without the derivative), there was a greater than 3-fold increase in ALT. In animals that received the emulsion with disodium disuccinate astaxanthin derivative XVI at 500 mg/kg included, the ALT elevation was substantially reduced (N=3 animals per group), demonstrating the efficacy of the compound in reducing ALT, a serum marker of hepatocyte necrosis in these animals. As LPS-induced liver injury is mediated by ROS (including the radical nitric oxide NO.), and substantial systemic inflammation occurs after LPS insult, for which non-esterified, free astaxanthin is protective (Ohgami et al. 2003), the utility of the novel derivative for clinical indications in which such inflammation is promoted represents a particularly useful embodiment.

Accumulation of Free Astaxanthin in Plasma and Liver After Multiple Dose Oral Administration in Black Mice In this pharmacokinetic study, with methods as described herein, eleven (11) individual daily oral doses of the disodium disuccinate astaxanthin derivative XVI (500 mg/kg) were given by oral gavage in the emulsion vehicle to black mice, and the accumulation of free astaxanthin in plasma and liver was measured in three (3) animals at the probable $C_{max}$ and $T_{max}$ (6 hours). Probable $C_{max}$ and $T_{max}$ (6 hours) was deduced from plasma and liver samples in the prior single dose oral pharmacokinetic study. Accumulation of non-esterified, free astaxanthin in plasma and liver after single emulsion doses was assessed. The mean plasma concentration for all animals tested was 381 nM. Mean liver concentration for all animals tested was 1735 nM. In the single dose study, on average, a protective level (set at the antioxidant $ED_{50}$ for non-esterified, free astaxanthin of 200 nM) was achieved in both plasma and liver; the mean liver concentration achieved was almost 9 times the protective level.

Figure 32:
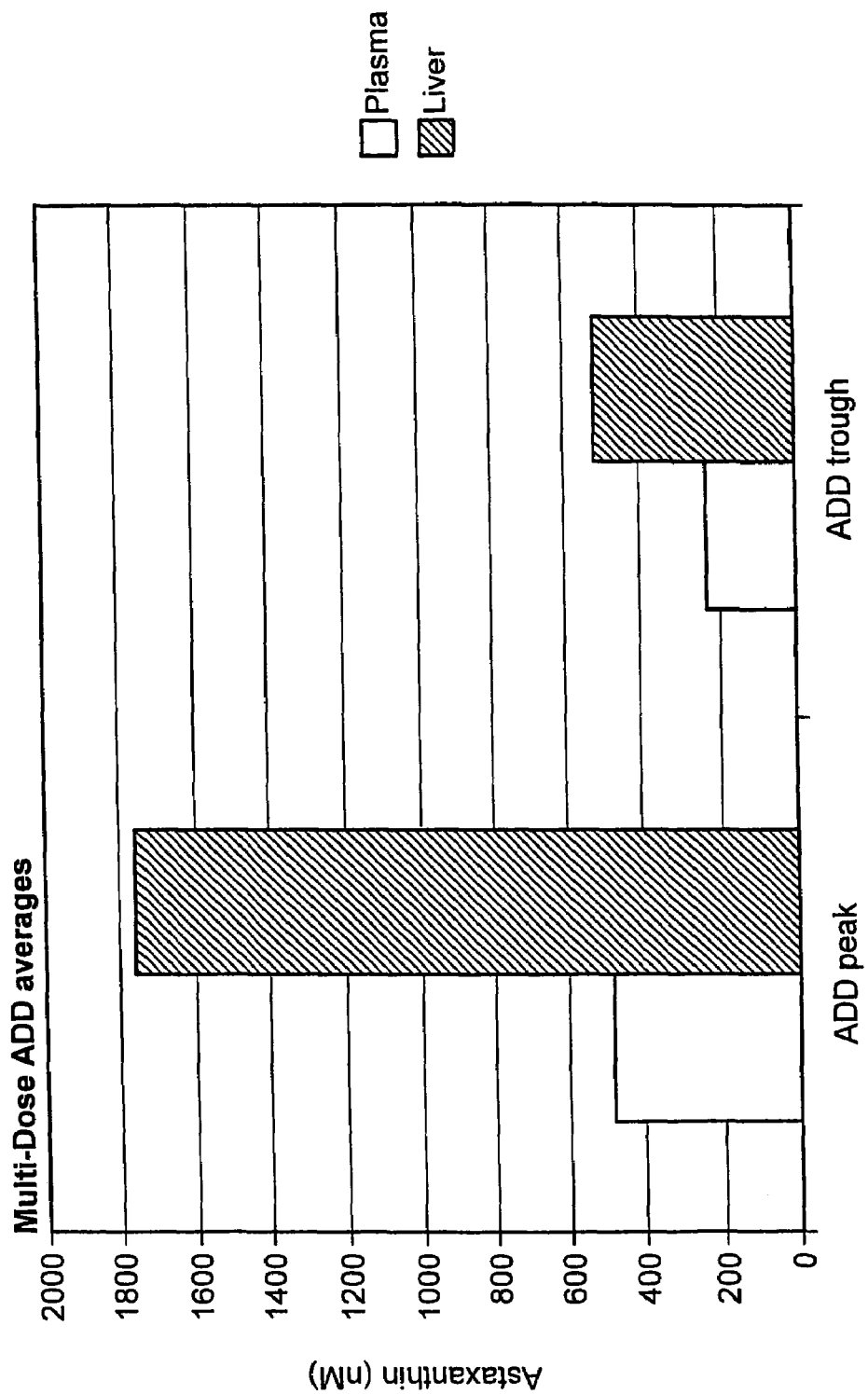
FIG. 32 depicts a graph of mean levels of non-esterified, free astaxanthin in plasma and liver after eleven (11) days of oral gavage of 500 mg/kg disodium disuccinate astaxanthin derivative (ADD) in emulsion vehicle to black mice. Both peak and trough levels in plasma and liver achieved were >200 nM, considered to be protective against oxidative stress and hepatic injury in vivo. The peak levels obtained in liver at 6 hours post-$11^{th}$ dose were nearly 9 times the protective levels necessary (1760 nM).

In the multiple dose study, both peak and trough levels were taken (peak levels taken 6 hours after dosing at the probable $C_{max}$; trough levels obtained 6 hours after $C_{max}$, or 12 hours post-dose). Mean peak levels in plasma at peak and trough, respectively, were 485 nM and 231 nM; mean peak levels in liver at peak and trough, respectively, were 1760 nM and 519 nM. Again, in each case protective levels were achieved and maintained to 11 days post-multiple dosing; in the case of liver, levels almost 9 times the protective level were achieved. Again, at each time point after multiple dosing, the accumulation in liver was greater than that observed in plasma, demonstrating the increased utility of this dosing vehicle for targeting to this solid organ (FIG. 32). It is also apparent from this data set that chronic administration of the disodium disuccinate astaxanthin derivative XVI will be efficacious in hepatoprotection.

Accumulation of Free Astaxanthin in Myocardium (Heart) and Brain after Single Dose Oral Administration in Black Mice:

A single maximum dose of the disodium disuccinate astaxanthin derivative XVI (500 mg/kg) was given by oral gavage in the emulsion vehicle to black mice, and the accumulation of non-esterified, free astaxanthin was measured in four (4) animals at the probable $C_{max}$ and $T_{max}$ (6 hours), as deduced from plasma and liver samples in the prior study. Accumulation of non-esterified, free astaxanthin in heart after a single dose (mean+/−SEM of 4 animals=693.25+/−272 nM) paralleled that seen with accumulation of non-esterified, free astaxanthin in liver. At each time point, the accumulation in heart was greater than that observed in plasma, demonstrating the increased utility of this dosing vehicle for targeting to solid organs. Accumulation of non-esterified, free astaxanthin in the CNS (brain) was less striking (mean+/−SEM of 4 animals=3.6+/−1.7 nM), suggesting that penetration of the blood-brain barrier (BBB) was possible, but that chronic, multiple-dose administration may be necessary to achieve protective levels for those CNS applications (Alzheimer's disease, stroke, etc.).

Interaction of the Disodium Salt Disuccinate Derivative of meso-Astaxanthin with Human Serum Albumin (HSA):

Poor aqueous solubility of most carotene carotenoids, and the vast majority of xanthophylls limits their use as aqueous-phase singlet oxygen quenchers and radical scavengers. Chemical modifications which increase the apparent solubility and/or dispersibility of the carotenoids have found application in basic science as well as clinical research. However, the tendency for the parent carotenoids and novel derivatives to form supramolecular assemblies in aqueous solution warrants comprehensive evaluation of such behavior prior to moving into in vitro and in vivo assays of the efficacy of such compounds.

Figure 5:
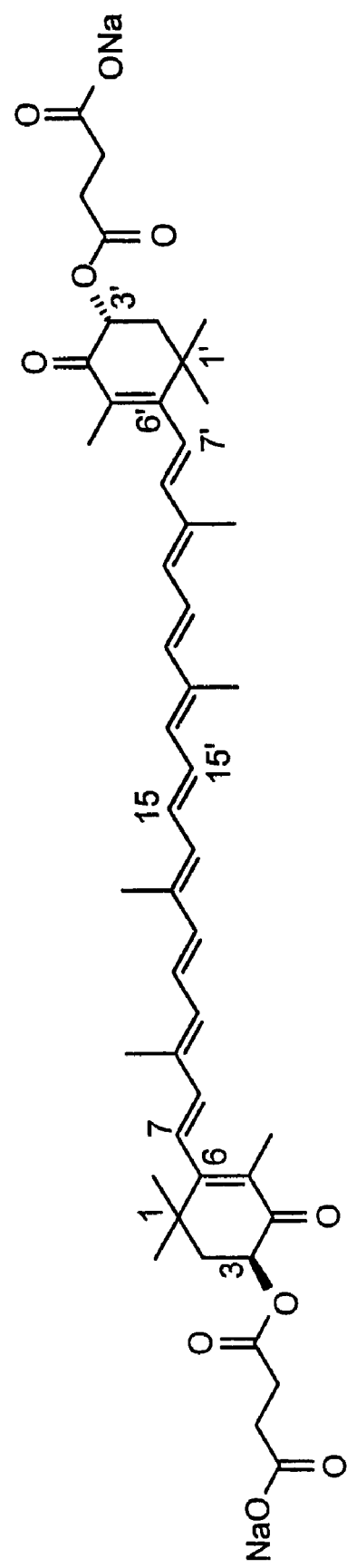
FIG. 5 depicts the chemical structure of the all-trans (all-E) disodium salt disuccinate ester derivative of meso-astaxanthin (3R,3'S- or 3S,3'R-dihydroxy-β,β-carotene-4,4'-dione; dAST) synthesized for the current study (shown as the all-E dianionic bolamphiphile).

FIG. 5 depicts a carotenoid derivative, the disodium salt disuccinate derivative XVI (dAST) of synthetic meso-astaxanthin (3R,3'S-dihydroxy-β,β-carotene-4,4'-dione), in all-trans (all-E) form. The symmetric $C_{40}$-xanthophyll used to generate the new derivative has two chiral centers at the 3 and 3' positions. In aqueous solution $C_{40}$-xanthophyll exhibits no optical activity, as these stereocenters have opposite absolute configurations and internally compensate each other. Natural carotenoid molecules possessing carboxylic functionality bind preferentially to human serum albumin (HSA), the most abundant protein in the blood. Since albumin binding strongly influences the potential in vivo biochemical activities of a given compound, circular dichroism (CD), ultraviolet-visible (UV/Vis) and fluorescence spectroscopy were used to characterize the interaction of this novel carotenoid derivative with fatty acid-free HSA. The protein binding and aggregation properties were investigated of this symmetric carotenoid attached through direct esterification to a moiety with carboxylate end groups, forming a rigid, long-chain, highly unsaturated dianionic bolamphiphile. It was verified that in buffer solution in the absence of protein, the meso-carotenoid formed closely-packed H-type (card-pack) aggregates exhibiting no CD Cotton effects (CE). At low ligand/protein (L/P) molar ratios, however, the meso-carotenoid immediately and preferentially associated with HSA in monomeric fashion, suggesting that the secondary chemical interactions (van der Waals forces, hydrogen bonding) that permit supramolecular assembly in aqueous solution were overcome in a biologically relevant environment. Above 1:1 ligand/protein molar ratio the meso-carotenoid molecules again began to aggregate; the aggregation observed at these ratios was chiral, resulting in a supramolecular structure showing intense, exciton-type CD activity.

Brief Description of Experimental Methods

The novel derivative dAST XVI was synthesized from crystalline astaxanthin 2E [3R,3'R, 3R,3'S, 3S,3'S (25:50:25)], a statistical mixture of stereoisomers obtained commercially (Buckton Scott, India). The astaxanthin stereoisomers were separated by high-pressure liquid chromatography (HPLC), allowing for the synthesis of the purified meso-disodium salt disuccinate derivative XVI for testing in the current study. The all-trans (all-E) form of the meso stereoisomer used was a linear, rigid molecule owing to the lack of cis (or Z) configuration(s) in the polyene chain of the spacer material (FIG. 5). The disodium salt disuccinate derivative XVI of synthetic meso-astaxanthin was successfully synthesized at >99% purity by HPLC.

Materials

Essentially fatty acid-free human serum albumin (catalog No. A-1887, lot No. 14H9319) were obtained from Sigma and used as supplied. Double-distilled water and spectroscopy grade dimethyl sulfoxide (DMSO, Scharlau Chemie S.A., Barcelona, Spain) and ethanol (Chemolab, Budapest, Hungary) were used. All other chemicals were of analytical grade.

Preparation of Stock Solution of dAST XVI

After dissolution of the meso-carotenoid in DMSO, 100 µl of DMSO solution was added to 2 mL ethanol in a rectangular cuvette with 1 cm pathlength. The absorption spectrum was registered between 260 and 650 nm. Concentration was calculated from the light absorption value at the $\lambda_{max}$ ($\epsilon_{478\ nm}$=116,570 $M^{-1}$ $cm^{-1}$).

Preparation of HSA Solutions

For spectroscopic sample preparation, HSA was dissolved in pH 7.4 Ringer or 0.1 M pH 7.4 phosphate buffer solutions. Albumin concentration was calculated with the value of $E_{1cm}^{1\%}$=5.31, using experimentally obtained absorbance data at 279 nm. The molecular weight of HSA was defined as 66500 Da.

Circular Dichroism and UV/Vis Absorption Spectroscopy

CD and UV spectra were recorded on a Jasco J-715 spectropolarimeter at 25±0.2 and 37±0.2° C. in a rectangular cuvette with 1 cm pathlength. Temperature control was provided by a Peltier thermostat equipped with magnetic stirring. All spectra were accumulated three times with a bandwidth of 1.0 nm and a resolution of 0.5 nm at a scan speed of 100 nm/min. Induced CD was defined as the CD of the dAST XVI-HSA mixture minus the CD of HSA alone at the same wavelengths, and is expressed as ellipticity in millidegrees (mdeg).

CD/UV/Vis Titration of HSA with dAST XVI in pH 7.4 Ringer and 0.1 M Phosphate Buffer Solutions at 37° C.

Ringer buffer, I/P values from 0.007 to 0.10: 2 mL of $1.6 \times 10^{-4}$ M HSA solution was placed in the cuvette with 1 cm optical pathlength and small amounts of the ligand stock solution (c=$2.2 \times 10^{-4}$) were added with an automatic pipette in 10 µL aliquots. Ringer buffer, L/P values from 0.82 to 13.13: 2 ml of $2.3 \times 10^{-6}$ M HSA solution was placed in the cuvette with 1 cm optical pathlength and µL volumes of the ligand stock solution (c=$3.9 \times 10^{-4}$) were added with an automatic pipette. Phosphate buffer, L/P values from 0.82 to 13.10: 2 mL of $2.2 \times 10^{-6}$ M HSA solution was placed in the cuvette with 1 cm optical pathlength and µL volumes of the ligand stock solution (c=$3.6 \times 10^{-4}$) were added with an automatic pipette.

Measurement of the Intrinsic Fluorescence of HSA in the Presence of dAST XVI 2 mL of $4.2 \times 10^{-6}$ M HSA solution was prepared in a 1 cm rectangular cell in 0.1 M pH 7.4 phosphate buffer. $1.3 \times 10^{-4}$ and $3.3 \times 10^{-4}$ M meso-carotenoid DMSO solutions were consecutively added in µL volumes to the cuvette in the sample chamber of the Jasco J-715 spectropolarimeter. The resulting sample solution was excited between 240 and 360 nm in 0.5 nm wavelength increments. Total fluorescence intensity was collected at each wavelength with a Hamamatsu H5784-type photomultiplier detector mounted on a right angle to the light source. In the sample solution, initial and final concentrations of HSA and dAST were $4.2 \times 10^{-6}$ M–$4.0 \times 10^{-6}$ M and $1.3 \times 10^{-7}$ M–$1.4 \times 10^{-5}$ M, respectively. The meso-carotenoid/HSA molar ratio was varied between 0.03 and 3.53. During the fluorescence measurements, final DMSO concentration did not exceed 5 v/v%. A control experiment was also performed, in which the fluorescence of HSA during addition of 20, 50 and 100 µL DMSO to the solution was measured.

Brief Discussion of UV/Vis and CD Spectroscopy Results

Figure 6:
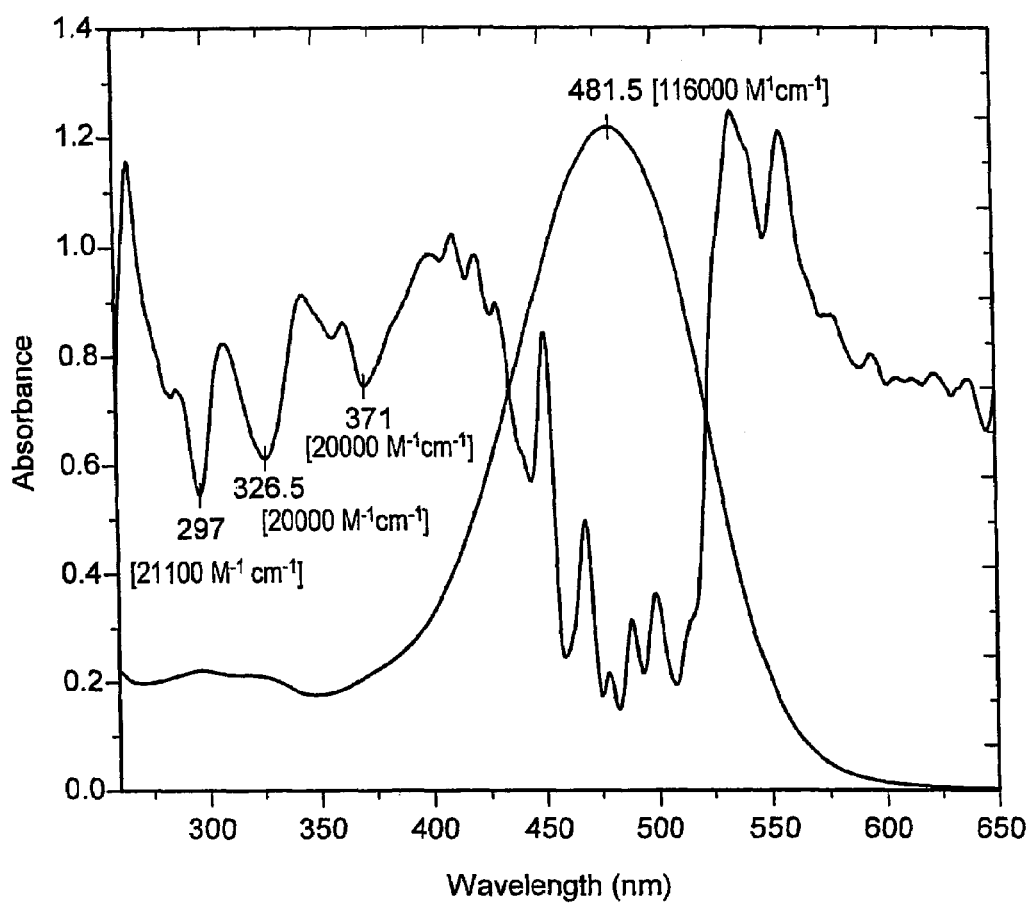
FIG. 6 depicts the ultraviolet-visible absorption spectrum of dAST in ethanol at 25° C. (cell length 1 cm, $c=1.05\times10^{-5}$ M). Molar absorption coefficients are shown in parentheses. The second derivative curve of the absorption spectrum indicates the exact position of peaks in the near-UV region and the hidden vibrational fine structure of the main band.

UV/Vis and CD Spectral Properties of dAST XVI in Ethanol and Aqueous Buffer Solution Because of its extended π-system, dAST XVI exhibited intense light absorption in the visible spectrum (FIG. 6). The main bell-shaped absorption band centered at 481.5 nm was due to the lowest energy electronic dipole allowed, a π→π*1 transition polarized along the long axis of the polyene chain. At room temperature, lack of fine structure is typical for carotenoids containing one or more conjugated carbonyl groups. However, the vibrational sub-bands were indeed present beneath this curve, as revealed by the second derivative of the spectrum (FIG. 6). Additionally, in the near-UV region, further transitions were present. According to theoretical calculations performed on polyene models, the electronic transition moment (µ) of the moderately intense band around 300 nm is polarized parallel to the long axis of the dAST XVI molecule. At the same time, the band at 371 nm µ is oriented along the twofold, $C_2$ symmetry axis of the conjugated system. The weak n→π* transitions of the carbonyl groups were obscured by the other bands. As expected, the meso-carotenoid compound did not show any CD bands in ethanol since the effects of the two opposite chiral centers (3R,3'S) canceled each other (data not shown).

Figure 7:
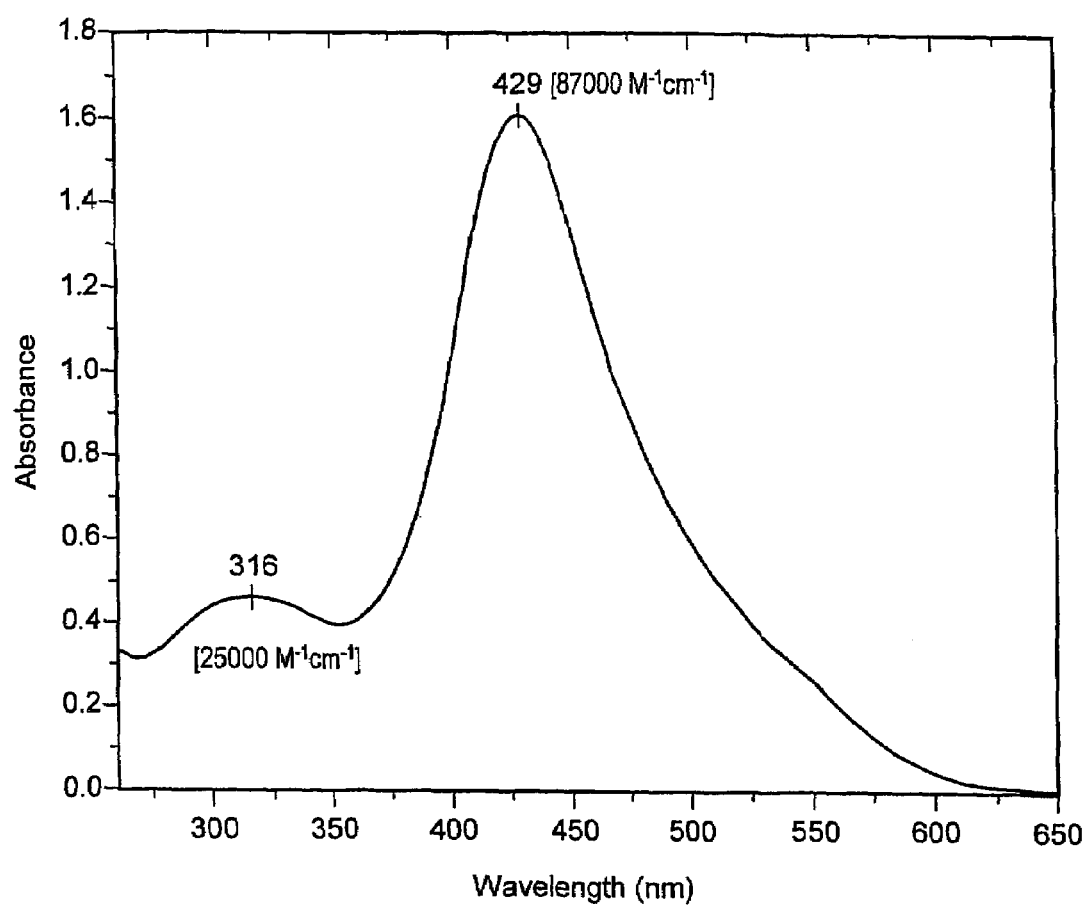
FIG. 7 depicts the absorption spectrum of dAST in Ringer buffer (pH 7.4, cell length 1 cm, $c=1.85\times10^{-5}$ M, $t=37°$ C.). Molar absorption coefficients are indicated.

In Ringer buffer solution, the principal absorption band of dAST XVI changed, exhibiting a large blue-shift (2541.6 $cm^{-1}$) as well as bandwidth narrowing (FIG. 7). These spectral changes indicated the formation of so-called "cardpack" aggregates, in which the molecules were held together in close proximity (within a few angstroms) by both exclusion from the aqueous environment and H-bonding interactions. As a result, the excited-state wave functions of the polyene chains were delocalized inter-molecularly, allowing exciton resonance interaction to occur between neighboring molecules. This interaction resulted in a high-energy exciton peak in the UV/Vis spectrum. Due to unfavorable steric interactions arising among the bulky end-groups, parallel alignment of the polyene chains is not allowed; the long axes of the separate molecules instead close a definite intermolecular overlay angle. In such cases, carotenoid aggregates built up by chiral monomers also exhibit induced Cotton effects (CE) due to the chiral intermolecular arrangement determined by asymmetric centers. In contrast, the meso-carotenoid compound demonstrated no optical activity in the aggregated state in solution (data not shown) due to the lack of net chirality of the molecules.

Figure 8:
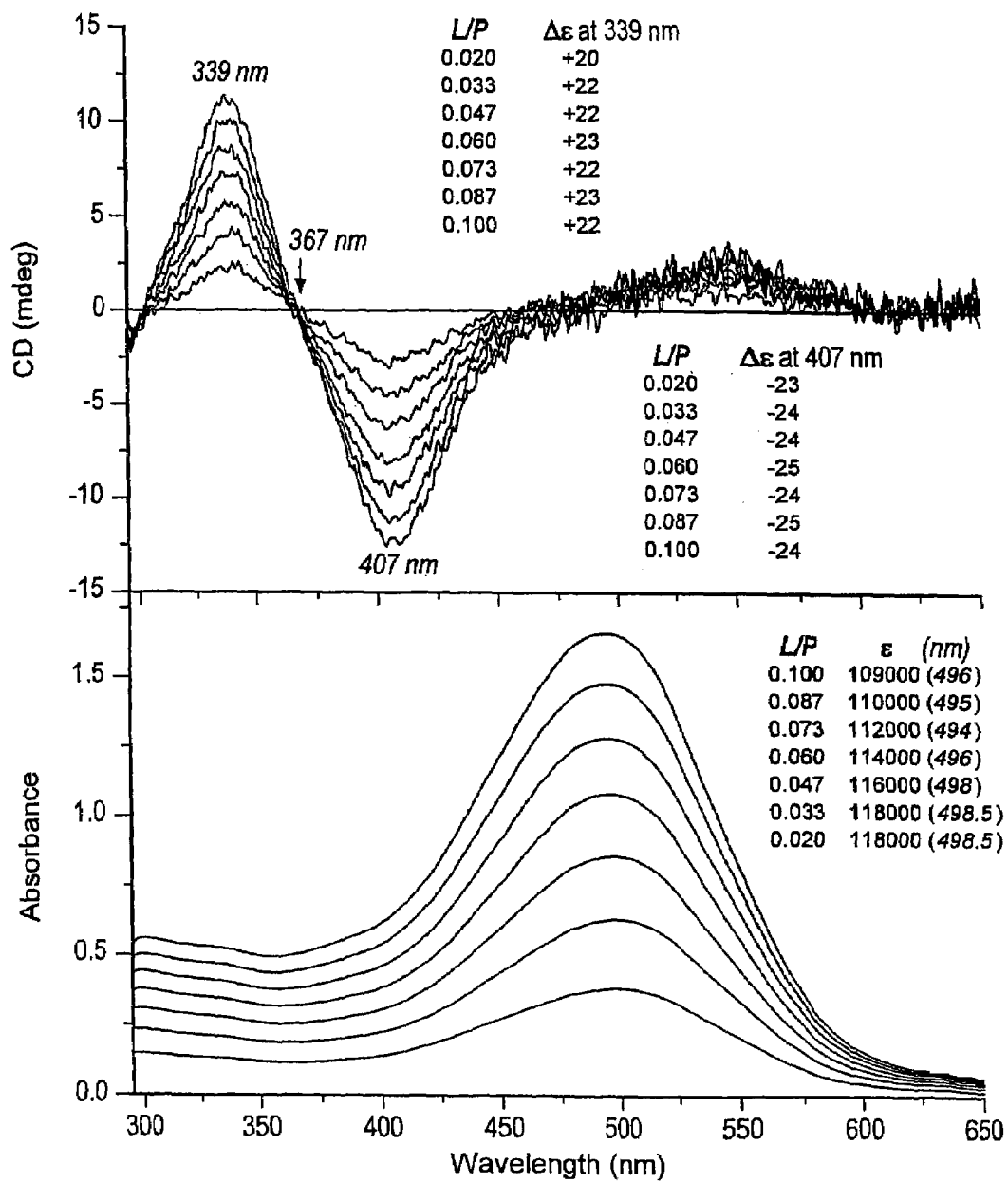
FIG. 8 depicts the induced CD and UV/Vis spectra obtained by titration of human serum albumin (HSA) with dAST in Ringer buffer solution (pH 7.4) at low L/P ratios. Concentration of HSA was $1.6\times10^{-4}$ M and the ligand was added as aliquots of DMSO stock solution (cell length 1 cm, $t=37°$ C.). Curves measured at different L/P values are shown. Insets: molar circular dichroic absorption coefficients ($\Delta\epsilon$ in $M^{-1}$ $cm^{-1}$) and molar absorption coefficients ($\epsilon$ in $M^{-1}$ $cm^{-1}$) of the induced CD and absorption bands calculated on the basis of total meso-carotenoid concentration in the solution.

Optical Properties of dAST XVI in the Presence of Human Serum Albumin at Low Ligand/protein Molar Ratios Upon addition of dAST to the HSA solution prepared in pH 7.4 Ringer buffer, two definite, oppositely-signed induced CD bands appeared between 300 and 450 nm with a zero cross-over point at 367 nm (FIG. 8). The figure inserts show the intensities of the induced Cotton effects and the main absorption band at different L/P ratios (Δε and ε values are calculated with respect to the total meso-carotenoid concentration). Magnitudes of the CEs increased with increasing concentration of the ligand, however, their shape and wavelength positions remain unchanged. As mentioned above, there are two transitions below 450 nm which might be responsible for the observed optical activity. The absorption band around 300 nm has transition symmetry B, and the corresponding electric and magnetic transition moments are perpendicular to the twofold symmetry axis along the polyene chain. The electric and magnetic transition moments of the band at 372.5 nm are polarized parallel to the $C_2$ axis, its transition symmetry is A. It is reasonable to assume that upon protein binding, these bands shift to longer wavelengths due to the changing microenvironment surrounding the polyene chain. It has been well established that CD spectra of carotenoids in which the chromophoric portions belong to the $C_2$ point group conform to the $C_2$-rule: if the overall conjugated system acquires right-handed chirality (i.e. dihedral angles around bonds 6-7 and 6'-7' are negative), then transitions of symmetry A lead to negative CE, and transitions of symmetry B lead to positive CE (FIG. 8). Therefore, the meso-carotenoid binds to HSA in such a manner that the protein environment fixes the terminal rings in a well-defined chiral conformation that results in the observed negative- and positive-induced CD bands. The absolute configurations of the chiral 3 and 3' centers do not determine the chiroptical property of the molecule; rather, the asymmetric protein environment of the albumin molecule (via non-covalent chemical interactions) determines the observed activity. In contrast to the aggregate behavior in the aqueous solutions described above, the dAST molecules do not aggregate in HSA solution at these L/P ratios, as demonstrated by the retention of the bell-shaped and slightly red-shifted visible absorption band (FIG. 8). Thus, both the UV/Vis absorption and CD spectra indicate that the binding of the meso-carotenoid molecules to HSA occurs in monomeric form.

Optical Properties of dAST XVI in the Presence of HSA above 1:1 L/P Ratios

Figure 9:
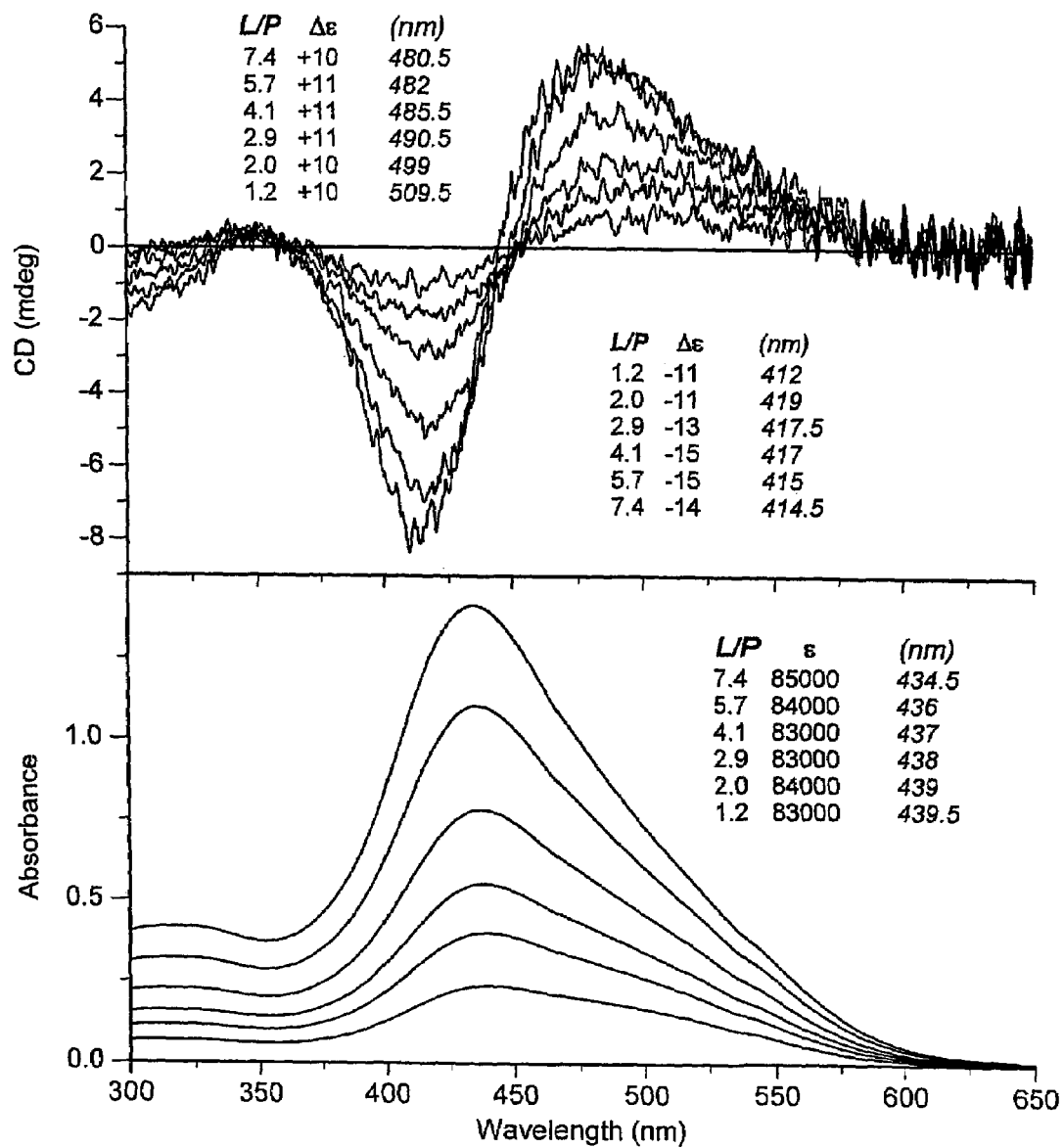
FIG. 9 depicts the induced CD and UV/Vis spectra obtained by titration of HSA with dAST in Ringer buffer solution (pH 7.4) above L/P ratio of 1. Concentration of HSA was $2.3\times10^{-4}$ M and the ligand was added as aliquots of DMSO stock solution (cell length 1 cm, $t=37°$ C.). Curves measured at L/P values of 1.2, 2.0, 2.9, 4.1, 5.7 and 7.4 are shown. CD intensities increase in parallel with the ligand concentration.
Figure 10:
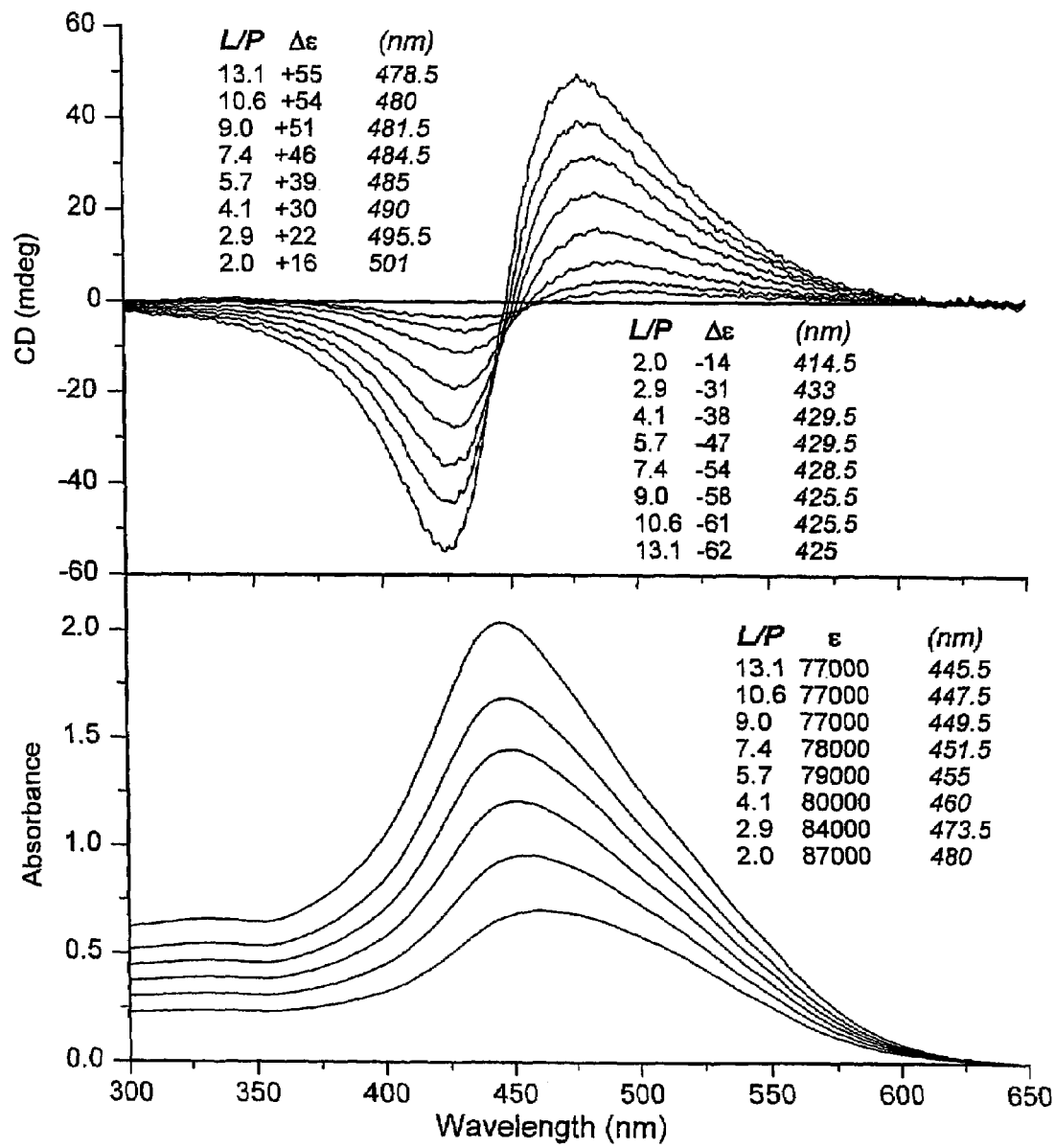
FIG. 10 depicts the induced CD and UV/Vis spectra obtained by titration of HSA with dAST in 0.1 M pH 7.4 phosphate buffer solution above L/P ratio of 1. Concentration of HSA was $2.2\times10^{-4}$ M and the ligand was added as aliquots of DMSO stock solution (cell length 1 cm, $t=37°$ C.). Curves measured at L/P values of 1.2, 2.0, 2.9, 4.1, 5.7, 9.0, 10.6 and 13.1 are shown. CD intensities increase in parallel with the ligand concentration.

An increasing amount of dAST XVI was added to solutions of HSA prepared either with pH 7.4 Ringer or 0.1 M pH 7.4 phosphate buffer to achieve L/P ratios higher than 1. Both CD and UV/Vis absorption spectra exhibited profound changes during addition of the ligand (FIG. 9 and FIG. 10). In addition to the blue-shifted visible absorption band a new, positive-negative CD band pair appeared around 480 and 420 nm, respectively. These CE's exhibited no vibrational fine structure and their amplitudes grew with increasing concentration of the ligand. However, there were some notable differences between the spectra obtained in the Ringer and phosphate buffer solutions:
a) The main absorption band shifted to lower wavelength (434.5 nm) in Ringer buffer. The corresponding value was 451.5 nm in phosphate buffer.
b) Deviation of the zero cross-over point of CEs from the maximum of the absorption band was three times larger in Ringer (441.6 $cm^{-1}$) than phosphate buffer solution (148.4 $cm^{-1}$).
c) Above an L/P value of 8, the intensities of the CD bands no longer increased in Ringer solution. In contrast, the amplitude(s) of the CD bands continued to increase with increasing L/P ratio in phosphate buffer, even at an L/P value of 13.
d) At the same L/P ratios, more intense CD bands were measured in phosphate buffer (FIG. 9 and FIG. 10).

Figure 11A:
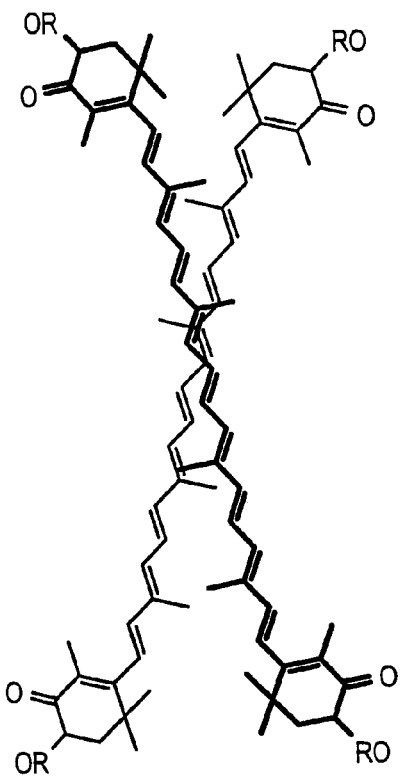
FIG. 11A-FIG. 11C depicts an illustration of right-handed chiral arrangements of two meso-carotenoid molecules for which excitonic interactions produce long-wavelength positive and short-wavelength negative Cotton effects in the CD spectrum. Gray-colored molecules lie behind the plane of the paper.
Figure 11B:
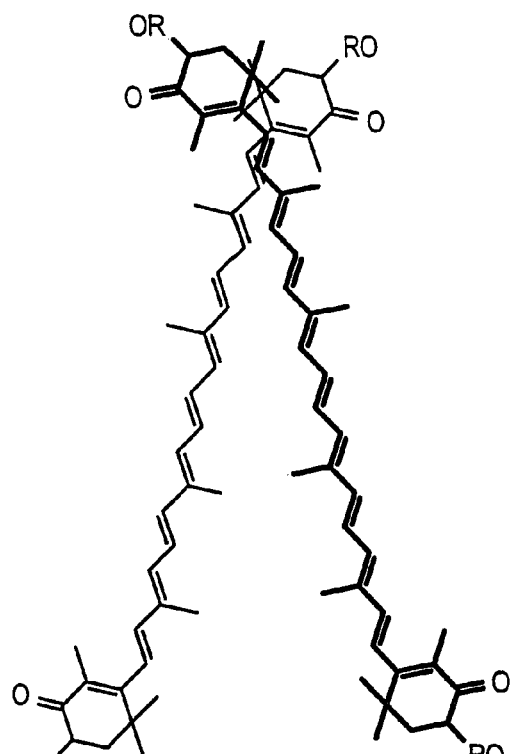
Figure 11C:
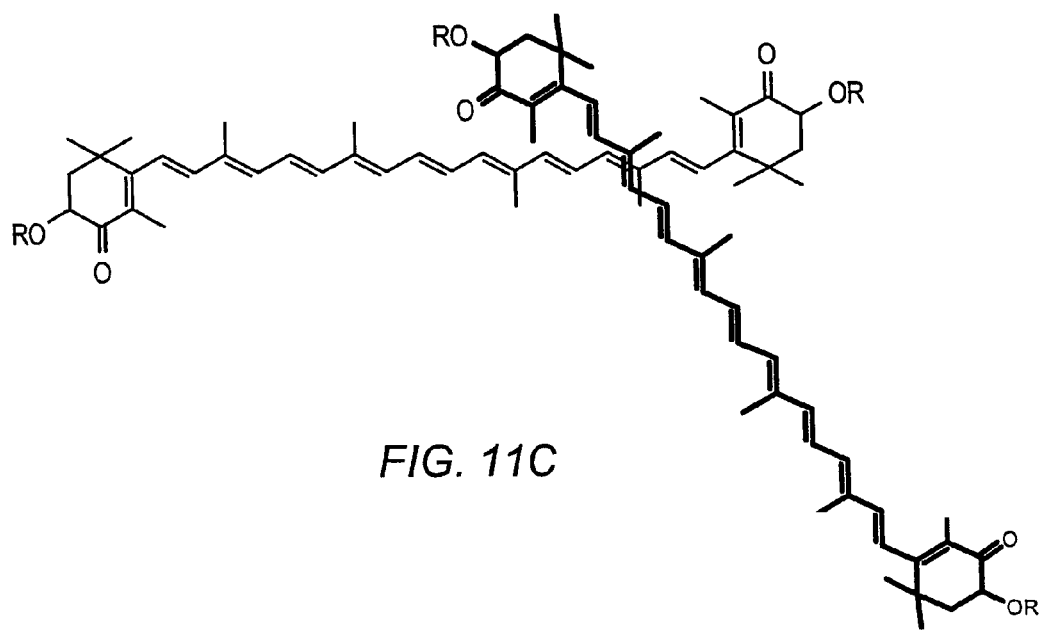

The fact that these oppositely-signed CD bands appear only above 1:1 L/P ratio strongly suggests that they stemmed from chiral intermolecular interactions between adjacent meso-carotenoid molecules. When two electric transition dipole moments are similar in energy, lie close to each other in space, and form a chiral array, their interaction is manifested as chiral exciton coupling: the CD spectrum shows a bisignate couplet matched with the spectral position of the corresponding absorption band, whose sign is determined by the absolute sense of twist between the two dipoles. According to the exciton chirality rule, a positive twist corresponds to a positive long-wavelength CE and a negative CE at shorter wavelength, and vice versa. In this case, the direction of the transition dipole moment is known; it is polarized along the long axis of the polyene chain. Thus, the neighboring meso-carotenoid molecules are arranged in such a manner that their long axes form a positive (clockwise) intermolecular overlay angle. Chiral arrangements of two conjugated chains shown in FIG. 11 satisfy the former condition; in these cases, a long-wavelength positive and a short wavelength negative band would appear in the CD spectrum. However, the spectroscopic behavior of the absorption band helps to differentiate between these spatial arrangements. Due to unfavourable Coulombic interactions between the transition dipole moments of neighbouring meso-carotenoid molecules in the case of a and b (FIG. 11), the absorption maximum shifts to higher energies; if the c form exists, then the absorption band widens and its maximum shifts to lower energies. Consequently, dAST XVI molecules form a right-handed chiral array in which the long axes of meso-carotenoid monomers form an acute, positive angle (FIGS. 11, a and b).

The following scenario is proposed for the origin of the chiral ordering of the ligand molecules. Albumin appears necessary for the induced optical activity and, at first, it is tempting to assume that there is a large binding site on HSA able to accommodate two meso-carotenoid molecules. At low L/P values albumin would bind only a single ligand; at higher L/P concentrations, a second meso-carotenoid monomer would be complexed. As stated above, however, the magnitudes of CEs continue to increase at quite high L/P values (FIG. 10), in which case a single binding site should already be saturated. One resolution to this issue assumes that HSA is an asymmetric template on which the chiral self-assembly is started. The first few meso-carotenoid molecules bind to HSA in right-handed arrangement, and subsequent meso-carotenoid monomers build upon this chiral architecture. In this scenario, HSA provides the first essential step, the chiral initiation ("chiral seeding"); after this the self-assembly continues automatically. It is very important to note, however, that without their chiral end-groups only a few dAST XVI molecules would be held in right-handed arrangement at the binding site of HSA. The 3 and 3' chiral centers play a decisive role in allowing the aggregates to form the chiral self-assembly on the HSA molecules. In the absence of protein, the meso-carotenoid molecules form right- and left-handed assemblies to an equal extent, due to the lack of chiral discrimination.

As listed above, the spectral differences between the CD curves measured in phosphate buffer and Ringer solutions suggested the influence of the salt concentration on the stability of the aggregates (FIG. 9 and FIG. 10). The osmolarity and ionic strength of the Ringer buffer was higher than that of phosphate buffer. The succinic moieties were ionized at pH 7.4 in both buffer solutions and electrostatic repulsion arose both within and among the aggregates. Positively-charged salt ions are able to decrease this repulsion, and therefore contribute to an increasing stability and size of the aggregates in the presence of these cations. During the titration of HSA with dAST XVI above the 1:1 LP ratio, both chiral and achiral aggregates were simultaneously formed; however, only chiral aggregates were associated with HSA, while achiral aggregates were not. CD spectra obtained in Ringer buffer solution (FIG. 9) suggested that the achiral aggregates were better stabilized in this higher osmolarity buffer due to the screening effect of the salt ions. The added ligand molecules preferentially associated with existing aggregates, which resulted in the amplitudes of the CD bands reaching a plateau and becoming constant in contrast with the phosphate buffer.

Fluorescence Quenching of HSA upon Addition of dAST

Figure 12:
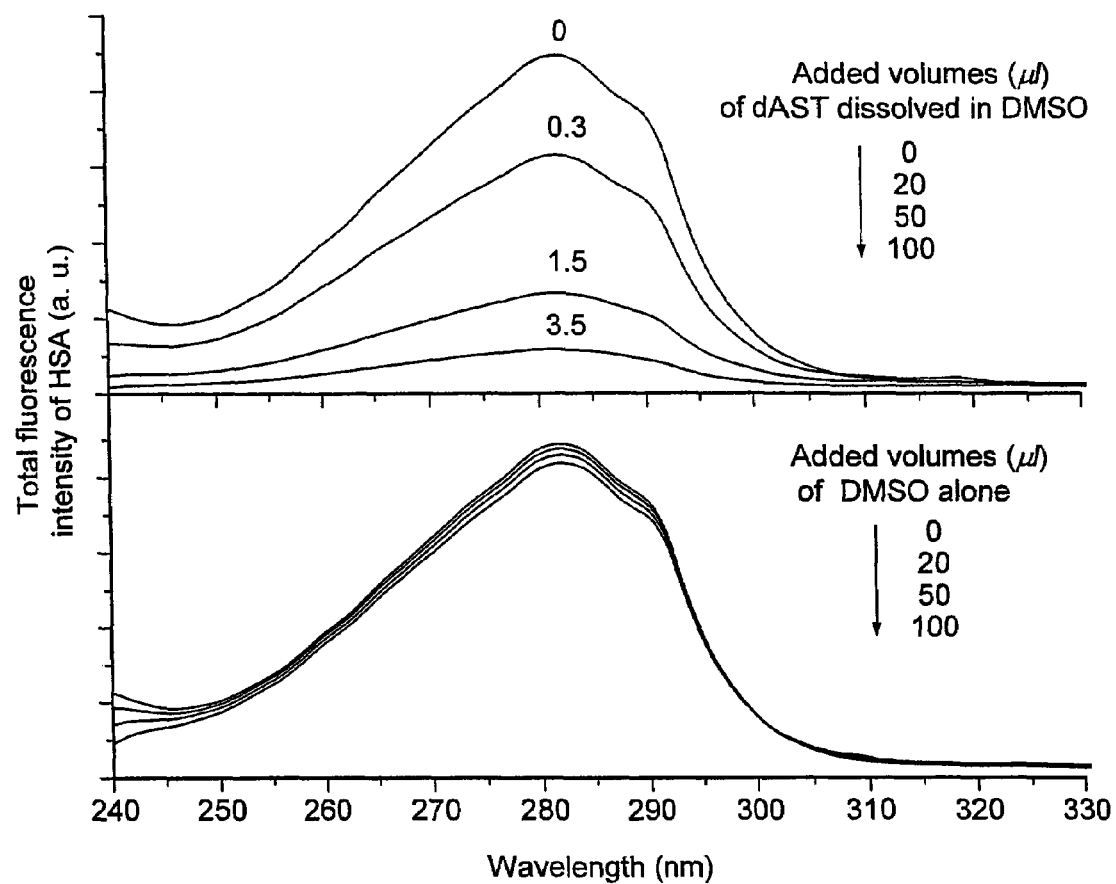
FIG. 12 depicts (upper figure): fluorescence quenching of HSA by dAST measured in 0.1 M pH 7.4 phosphate buffer solution at 37° C. Initial and final concentrations of HSA and the ligand were varied between $4.2\times10^{-6}$ M–$4.0\times10^{-6}$ M and $1.3\times10^{6}$ M–$1.4\times10^{-5}$ M, respectively. L/P ratios are noted on curves. The lower figure depicts an effect of DMSO alone on the intrinsic fluorescence of HSA.
Figure 13:
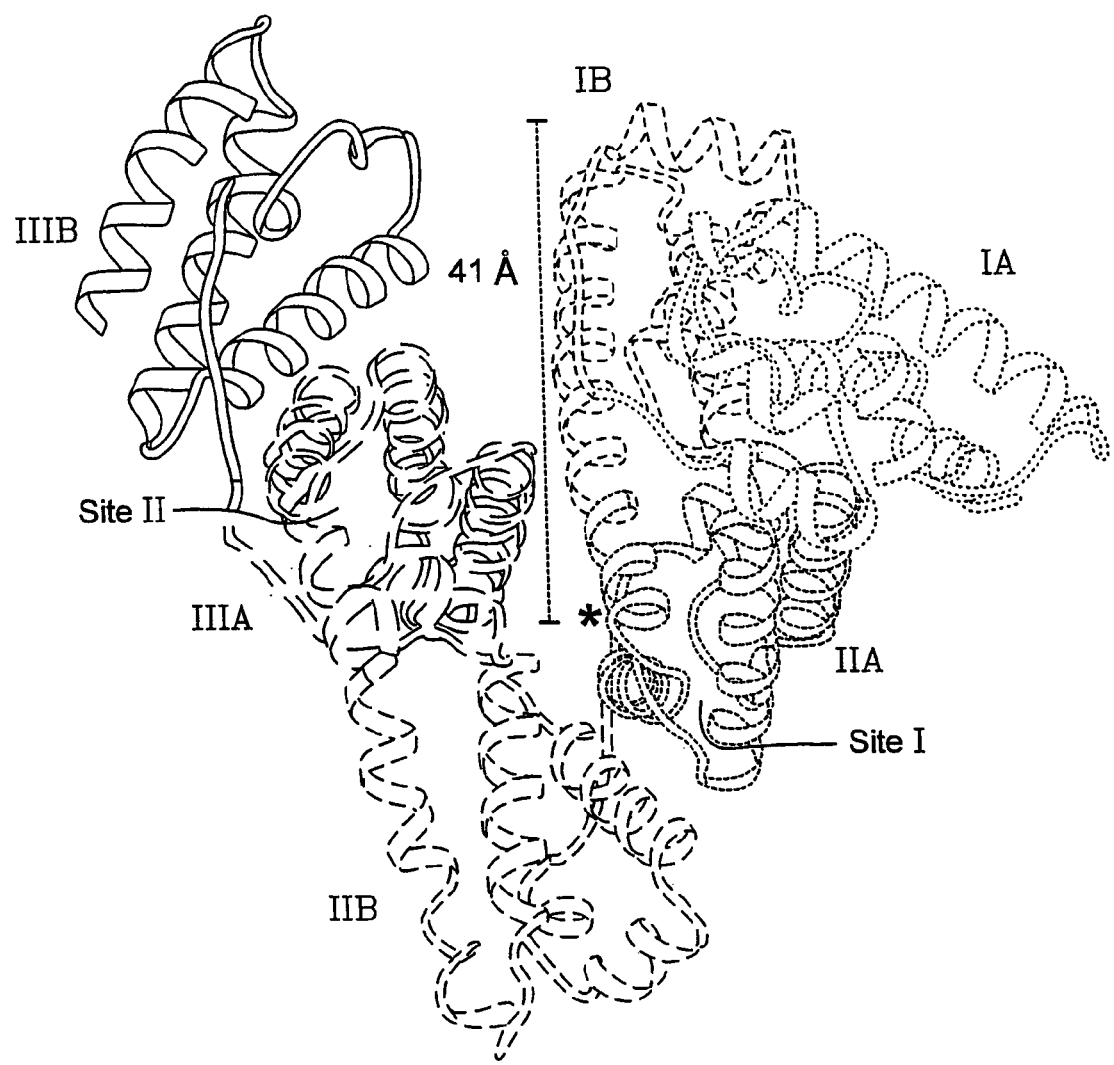
FIG. 13 depicts the X-ray crystallographic structure of fatty acid-free HSA. Subdomains and the two primary drug-binding sites of HSA are indicated. Dotted bar represents spatial dimension of the interdomain cleft, and asterisk indicates the position of Trp214. The inter-atomic distance between the 3 and 3' chiral carbon atoms of the dAST molecule is 28 Å.
Figure 14A:
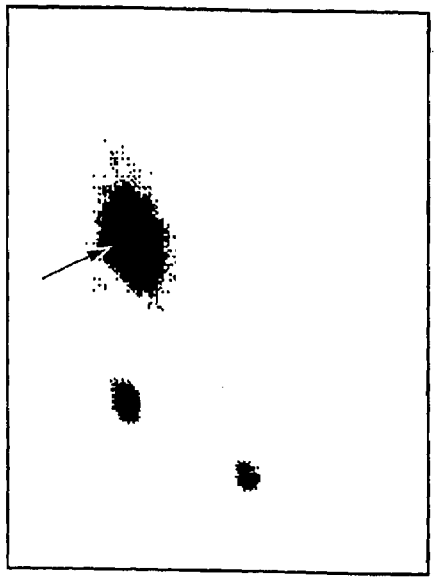
FIG. 14A-FIG. 14F depicts that the statistical mixture of stereoisomers of the disodium salt disuccinate astaxanthin derivative ("rac" in Figure Legends) induces functional gap junctional communication in murine embryonic fibroblast (10T1/2) cells. Confluent cultures were treated for 4 days as described in text, then assayed for the ability to transfer the fluorescent dye Lucifer Yellow. Arrows indicate the cell injected with Lucifer Yellow.
Figure 14B:
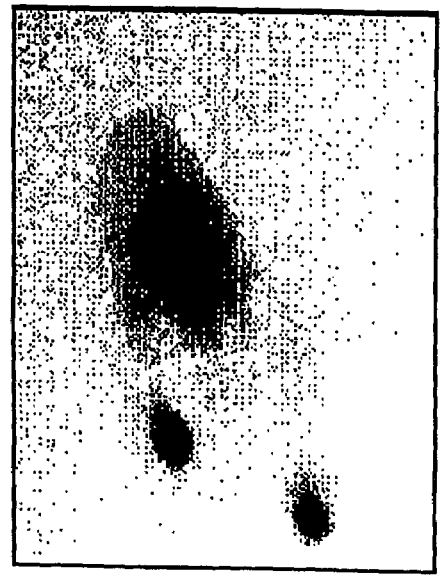
Figure 14C:
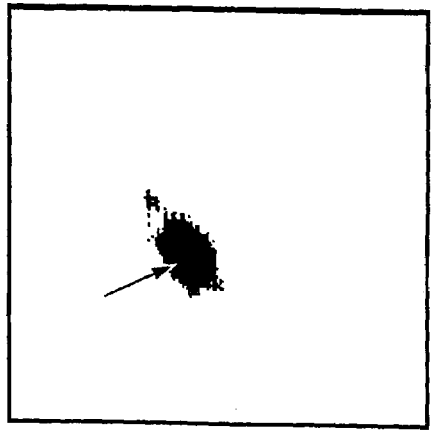
Figure 14D:
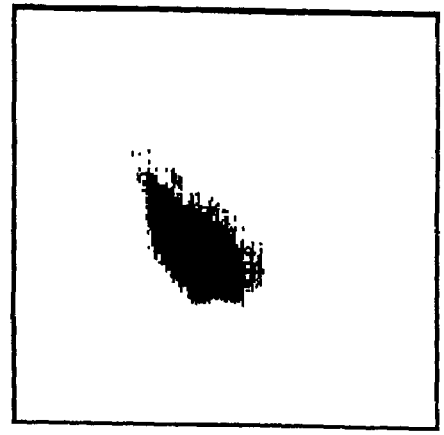
Figure 14E:
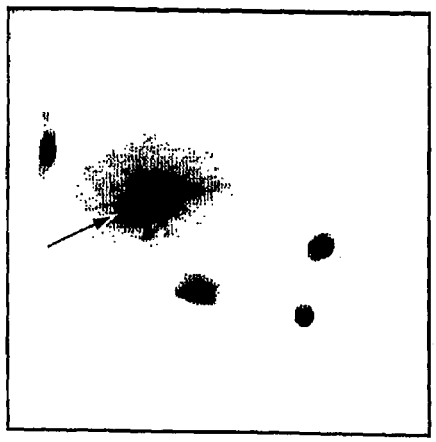
Figure 14F:
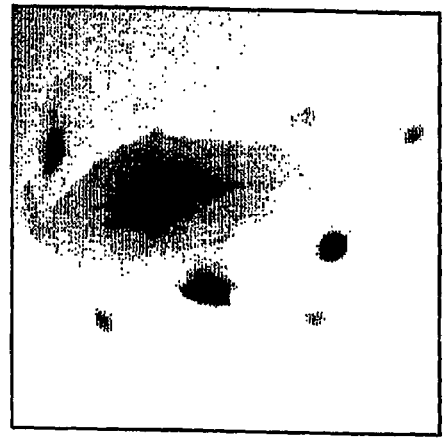

The single tryptophan residue (Trp214) located in the depth of subdomain IIA is largely responsible for the intrinsic fluorescence of HSA. The fluorescence emission spectrum of HSA overlaps with the absorption spectrum of the meso-carotenoid. Therefore, fluorescence spectroscopic measurements were obtained after incremental addition of dAST XVI in DMSO to a solution of HSA. The results clearly demonstrated that the meso-carotenoid molecules were able to effectively quench the intrinsic fluorescence of HSA (FIG. 12). The DMSO used to prepare the stock solution of dAST XVI exhibited a negligible effect on the intrinsic HSA fluorescence (FIG. 12). At an L/P ratio of 0.7, the baseline fluorescence intensity decreased by 50%. The observed phenomenon suggested that a meso-carotenoid molecule was bound in the vicinity of Trp214, which forms part of the wall in one of the two main binding cavities of HSA (site I, subdomain IIA; FIG. 13). However, neither site I nor site II (subdomain IIIA)—both hydrophobic fatty acid binding tunnels—are capable of accommodating the long, rigid dAST XVI molecule (FIG. 13). Based on structural similarity, a second possibility is that dAST XVI binds to other long-chain (C18, C20) fatty acid binding sites of HSA, which have been well-characterized by high resolution X-ray crystallography. In the case of shorter, open-chain carotenoids having no bulky end-groups, this possibility may be likely. However, the polyene chain of the meso-carotenoid derivative itself measures 28 Å (between the 3 and 3' chiral carbon atoms). Despite their conformational mobility, the succinate moieties require additional space, increasing the effective length of the molecule to 48 Å. Careful inspection of the crystal structure of HSA suggests that the long, narrow cleft between domains I and III may be suitable for the binding of a meso-carotenoid molecule (FIG. 13). The interdomain cleft is wide, and its narrow end is close to the tryptophan (Trp214;* on FIG. 13) residue which would provide a structural explanation for the observed fluorescence quenching upon binding of the meso-carotenoid molecule to the interdomain cleft of HSA. Furthermore, it may be assumed that association of additional dAST XVI molecules to the single one in the interdomain cleft induces significant conformational changes of HSA resulting in the widening of the central crevice. This might be the reason why the fluorescence quenching did not stop at an L/P=1 ratio but keeps on strengthening as the CEs increase (FIG. 13).

Discussion of UV/Vis and CD Spectroscopy Results

As a consequence of exclusion from the aqueous environment and intermolecular hydrogen bonding, the disodium salt disuccinate derivative XVI of synthetic, achiral meso-astaxanthin formed optically inactive, card-pack type aggregates in aqueous buffer solutions, as indicated by the large blue-shift of the main visible absorption band versus the band observed in ethanolic solution. In the presence of an excess of fatty acid-free HSA, the meso-carotenoid appears to be preferentially associated with HSA in monomeric fashion. These results suggest that the weak van der Waal's forces and hydrogen bonding that permits supramolecular assembly in aqueous solution will be rapidly overcome in a biologically relevant environment. The concentration of albumin in human blood in vivo is approximately 0.6 mM, suggesting that at doses of up to 500 mg, the meso-carotenoid (molecular weight 841 Da) will associate with the albumin in monomeric fashion (excluding additional potential non-specific binding to circulating blood cells and lipoproteins, which would increase the potential non-aggregating dose). Bound meso-carotenoid molecules exhibited induced CD bands which were adequately explained by a right-handed helical conformation of the conjugated system. Graded fluorescence quenching of HSA in the presence of increasing concentrations of dAST XVI reinforced the notion that formation of carotenoid-albumin complexes were responsible for this quenching, and suggested spatial proximity between the bound ligand and the tryptophan 214 residue of HSA. Based on the spectroscopic data, the molecular length of the dAST XVI molecule, and the well-characterized crystal structure of HSA, the binding site was tentatively assigned to the interdomain cleft located between domains I and III.

There appears to be a positive-negative band pair in the CD spectrum above 1:1 L/P ratio of meso-carotenoid to HSA. This finding was attributed to intermolacular chiral exciton coupling between meso-carotenoid polyene chains arranged in right-handed assembly. The experimental data suggested that HSA acts as a chiral template on which the self-assembly begins, and subsequently continues governed by the chirality of the end-groups of the meso-carotenoid molecules. The differences between bisignate CD spectra obtained in pH 7.4 phosphate buffer and Ringer solutions indicate that the self-assembly is influenced by the osmolarity and ionic strength of the solution. With increasing osmolarity, the stability of the aggregates is enhanced presumably due to the electrostatic screening of the negatively-charged succinic carboxylate functions by salt cations.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

REFERENCES

The following references are specifically incorporated herein by reference:

| U.S. Patent Documents | | |
|---|---|---|
| 5871766 | February 1999 | Hennekens |

Other References

Axford-Gatley, R. A, and Wilson, J. G. (1991). Reduction of experimental myocardial infarct size by oral administration of alpha-tocopherol. Cardiovasc Res 25: 89-92.

Baxter, G. F., and Yellon, D. M. (1993). Attenuation of reperfusion-induced ventricular fibrillation in the rat isolated hypertrophied heart by preischemic diltiazem treatment. Cardiovasc Drugs Ther 7: 225-231.

Blaustein, A. S., Schine, L., Brooks, W. W., Franburg, B. L, and Bing, O. H. (1986). Influence of exogenously generated oxidant species on myocardial function. Am J Physiol 250: H595-H599.

Bolli, R., Patel, B. S., Zhu, W. X., et al. (1987). The iron chelator desferioxamine attenuates postischemic ventricular dysfunction. Am J Physiol 253: H1372-H1380.

Bolli, R., Zhu, W. X., and Hartley, C. J. (1987). Attenuation of dysfunction in the postischemic "stunned" myocardium by dimethylurea. Circulation 76: 458-468.

Bolli, R., Jeroudi, M. O., Patel, B. S., et al. (1989). Direct evidence that oxygen-derived free radicals contribute to post-ischemic myocardial dysfunction in the intact dog. Proc Natl Acad Sci USA 86: 4695-4699.

Chopra, M., McMurray, J., Stewart, J., Dargie, H. J., and Smith, W. E. (1990). Free radical scavenging: potentially beneficial action of thiol-containing angiotensin-converting enzyme inhibitors. Biochem Soc Trans 18: 1184-1185.

Conorev, E. A., Sharov, V. G., and Saks, V. A. (1991). Improvement of contractile recovery of isolated rat heart after cardioplegic ischemic arrest with endogenous phosphocreatine: involvement of antiperoxidative effect? Cardiovasc Res 25: 164-171.

Duilio, C., Ambrosio, G., Kuppusamy, P., Dipaula, A., Becker, L. C., and Zweier, J. L. (2001). Neutrophils are primary source of $O_2$ radicals during reperfusion after prolonged myocardial ischemia. Am J Physiol Heart Circ Physiol 280: H2649-H2657.

Goto, S., Kogure, K., Abe, K., Kimata, Y., Kitahama, K., Yamashita, E., and Terada, H. (2001). Efficient radical trapping at the surface and inside the phospholipids membrane is responsible for highly potent antiperoxidative activity of the carotenoid astaxanthin. Biochimica et Biophysica Acta 1512: 251-258.

Hearse, D. J., Manning, A. S., Downey, J. M., and Yellon, D. M. (1986). Xanthine oxidase: a critical mediator of myocardial injury during ischemia and reperfusion. Acta Physiol Scand 548: 65-74.

Horwitz, L. D., Kong, Y., and Robertson, A. D. (1999). Timing of treatment for myocardial reperfusion injury. J Cardiovasc Pharmacol 33 (1): 19-29.

Johansson, M. H., Deinum, J., Marklund, S. L., and Sjodquist, P. O. (1990). Recombinant human extracellular superoxide dismutase reduces concentration of oxygen free radicals in the reperfused rat heart. Cardiovasc Res 24: 500-503.

Kimura, Y., Engelman, R. M., Rousou, J., Flack, J., Iyengar, J., and Das, D. K. (1992). Moderation of myocardial ischemia reperfusion injury by calcium channel and calmodulin receptor inhibition. Heart Vessels 7: 189-195.

Levy, Y., Bartha, P., Ben-Amotz, A., Brook, J. G., Dankner, G., Lin, S., and Hammerman, H. (1998). Plasma antioxidants and lipid peroxidation in acute myocardial infarction and thrombolysis. J Am Coll Nutr 17 (4): 337-341.

Mahaffey, K. W., Puma, J. A., Barbagelata, N. A., DiCarli, M. F., Leesar, M. A., Browne, K. F., Eisenberg, P. R., Bolli, R., Casas, C., Molina-Viamonte, V., Orlandi, C., Blevins, R., Gibbons, R. J., Califf, R. M., Granger, C. B. (1999). Adenosine as an adjunct to thrombolytic therapy for acute myocardial infarction. J Am Coll Cardiol 34(6): 1711-1720.

McMurray, J., and Chopra, M. (1991). Influence of ACE inhibitors on free radicals and reperfusion injury: pharmacological curiosity or therapeutic hope? Br J Pharmacol 31: 373-379.

Petty, M. A., Dow, J., Grisar, J. M., and De-Jong, W. Effect of a cardioselective alpha-tocopherol analogue on reperfusion injury in rats induced by myocardial ischemia. Eur J Pharmacol 192: 383-388.

Sajkowska, A., Wykretowicz, A., Szczepanik, A., Kempa, M., Minczykowski, A., and Wysocki, H. (1999). Fibrinolytic therapy and n-acetylcysteine in the treatment of patients with acute myocardial infarction: its influence on authentic plasma hydroperoxide levels and polymorphonuclear neutrophil oxygen metabolism. Cardiology 91: 60-65.

Schaer, G. L., Spaccavento, L. J., Browne, K. F., Krueger, K. A., Krichbau, D., Phelan, J. M., Fletcher, W. O., Grines, C. L., Edwards, S., Jolly, M. K, and Gibbons, R. J. (1996). Beneficial effects of RheothRx injection in patients receiving thrombolytic therapy for acute myocardial infarction. Results of a randomized, double-blind, placebo-controlled trial. Circulation 94(3): 298-307.

Sethi, R., Takeda, N., Nagano, M., and Dhalla, N. S. (2000). Beneficial effects of vitamin E treatment in acute myocardial infarction. J Cardiovasc Pharmacol Ther 5: 51-58.

Shuter, S. L., Davies, M. J., Garlick, P. B, Hearse, D. J., and Slater, T. F. (1990). Studies on the effects of of antioxidants and inhibitors of radical generation on free radical production in the reperfused rat heart using electron spin resonance spectroscopy. Free Radic Res Commun 9: 223-232.

Simpson, P. J., and Lucchesi, B. R. (1987). Free radicals and myocardial ischemia and reperfusion injury. J Lab Clin Med 110: 13-30.

Singh, R. B., Niaz, M. A., Sharma, J. P., Kumar, R., Bishnoi, I., and Begom, R. (1994). Plasma levels of antioxidant vitamins and oxidative stress in patients with acute myocardial infarction. Acta Cardiologica Vol. XLIX 5: 441-452.

Such, L., Morcillo, E., Chorro, F. J., et al. Beneficial effects of N-acetylcysteine on acute myocardial infarction in open chest dogs. Arch Pharmacol Toxicol 12: 37-40.

Rogers, M., Berestecky, J. M., Hossain, M. Z., Guo, H., Kadle, R., Nicholson, B. J., and Bertram, J. S. (1990). Retinoid-enhanced gap junctional communication is achieved by increased levels of connexin 43 mRNA and protein. Molecular Carcinogenesis 3: 335-343.

Bertram, J. S. (1999). Carotenoids and gene regulation. Nutrition Reviews 57(6): 182-191.

Gutstein, D. E., Morley, G. E., Tamaddon, H., Vaidya, D., Schneider, M. D., Chen, J., Chien, K. R., Stuhlmann, H., Fishman, G. I. (2001). Conduction slowing and sudden arrhythmic death in mice with cardiac-restricted inactivation of connexin 43. Circulation Research: 333-339.

Dulio, C., Ambrosio, G., Kuppusamy, P., Dipaula, A., Becker, L. C., Zweier, J. L. (2001). Neutrophils are primary source of $O_2$ radicals during reperfusion after prolonged myocardial ischemia. Am J Physiol Heart Circ Physiol 280: H2649-H2657.

Liao, M.-L., Wang, S. Y., Chung, C., Liang, Y.-T., Sejb, P. A., (1988). Synthesis of L-Ascorbate 6-Phosphate. Carbohydrate Research 176: 73-77.

Bock, K., Lundt, I., Pedersen, C., (1979). Preparation of Some Bromodeoxyaldonic Acids. Carbohydrate Research 68: 313-319.

Stuber, H. A., Tolbert, B. M., (1978). A New Synthesis of L-threo-Hex-2-Enaro-1,4-Lactone ("Saccharoascorbic" Acid): A Method for the Protection of the Enediol of Ascorbic Acid. Carbohydrate Research 60: 251-258.

G. Britton, Structure and properties of carotenoids in relation to function, FASEB J. 9 (1995) 1551-1558.

A.M. Papas, Antioxidant status: diet, health and disease; Part I: Factors affecting antioxidant status and its role, Mature Medicine (1999) 315-319.

W. Miki, Biological functions and activities of animal carotenoids, Pure Appl. Chemistry 63 (1991) 141-146.

S.F. Lockwood, S. O'Malley, G. L. Mosher, Improved aqueous solubility of crystalline astaxanthin (3,3'-dihydroxy-beta, beta-carotene-4,4'-dione) by Captisol(R) (sulfobutyl ether beta-cyclodextrin), J. Pharm. Sci. 92 (2003) 922-926.

M. Buchwaldt, W. P. Jencks, Optical properties of astaxanthin solutions and aggregates, Biochemistry 7 (1968) 834-843.

V. Salares, N. Young, P. Carey, H. Bernstein, Excited state (exciton) interactions in polyene aggregates, J. Raman Spectr. 6 (1977) 282-288.

F. Zsila, Z. Bikádi, J. Deli, M. Simonyi, Chiral detection of carotenoid assemblies, Chirality 13 (2001) 446-453.

R. K. Müller, K. Bernhard, H. Mayer, A. Ruttimann, M. Vecchi, Contribution to the analytical separation and the synthesis of 3-hydroxy-4-oxocarotenoids, Helv. Chim. Acta 63 (1980) 1654-1664.

F. Zsila, Z. Bikádi, M. Simonyi, Induced chirality upon crocetin binding to human serum albumin: origin and nature, Tetrahedron: Assymmetry 12 (2001) 3125-3137.

T. Peters, All About Albumin, Academic Press, San Diego (Calif.), 1996.

H. Watanabe, S. Tanase, K. Nakajou, T. Maruyama, U. Kragh-Hansen, M. Otagiri, Role of Arg-410 and Tyr-411 in human serum albumin for ligand binding and esterase-like activity, Biochem. J. 349 (2000) 813-819.

U. Kragh-Hansen, V. Chuang, M. Otagiri, Practical aspects of the ligand-binding and enzymatic properties of human serum albumin, Biol. Pharm. Bull. 25 (2002) 695-704.

F. Zsila, Z. Bikádi, Z. Keresztes, J. Deli, M. Simonyi, Investigation of the self-organization of lutein and lutein diacetate by electronic absorption, circular dichroism spectroscopy, and atomic force microscopy, J. Phys. Chem. B 105 (2001) 9413-9421.

K. Bernhard, G. Englert, H. Mayer, R. K. Muller, A. Ruttimann, M. Vecchi, E. Widmer E, R. Zell, Synthesis of optically-active natural carotenoids and structurally related-compounds. 9. Synthesis of (3R)-hydroxyechinenone, (3R,3'R)-adonixanthin and (3R,3'S)-adonixanthin, (3R)-adonirubin, their optical antipodes and related-compounds, Helv. Chim. Acta 64 (1981) 2469-2484.

V. Sturzenegger, R. Buchecker, G. Wagniere, Classification of the CD spectra of carotenoids, Helv. Chim. Acta 63 (1980) 1074-1092.

A. G. Andrewes, G. Borch, S. Liaaen-Jensen, G. Snatzke, Animal carotenoids. 9. On the absolute configuration of astaxanthin and actinioerythrin, Acta Chem. Scand. B 28 (1974) 730-736.

B. F. Lutnaes, O. R. Gautun, S. Liaaen-Jensen, Is (9Z)-"meso"-zeaxanthin optically active? Chirality 13 (2001) 224-229.

Z. Bikádi, F. Zsila, J. Deli, G. Mády, M. Simonyi, The supramolecular structure of self-assembly formed by capsanthin derivatives, Enantiomer 7 (2002) 67-76.

K. Noack, A. J. Thomson, Conformation and optical-activity of all-trans, mono-cis, and di-cis carotenoids—temperature-dependent circular-dichroism, Helv. Chim. Acta 62 (1979) 1902-1921.

K. Noack, A. J. Thomson, Temperature and concentration dependent circular-dichroism of mono-cis and di-cis isomers of (3R,3'S)-astaxanthin diacetate, Helv. Chim. Acta 64 (1981) 2383-2392.

N. Harada, K. Nakanishi, Circular Dichroic Spectroscopy—Exciton Coupling in Organic Stereochemistry, University Science Books, Mill Valley (CA), 1983.

N. Harada, Y. Takuma, H. Uda, Circular dichroic power due to chiral exciton coupling between two polyacene chromophores, J. Am. Chem. Soc. 100 (1978) 4029-4036.

J-K. Choi, J. Ho, S. Curry, D. Qin, R. Bittman, J. Hamilton, Interactions of very long-chain saturated fatty acids with serum albumin, J. Lipid Res. 43 (2002) 1000-1010.

S. Curry, P. Brick, N. P. Franks, Fatty acid binding to human serum albumin: new insights from crystallographic studies, Biochim. Biophys. Acta 1441 (1999) 131-140.

I. Petitpas, T. Grüne, A. Bhattacharya, S. Curry, Crystal structures of human serum albumin complexed with monounsaturated and polyunsaturated fatty acids, J. Mol. Biol. 314 (2001) 955-960.

A. A. Bhattacharya, T. Grüne, S. Curry, Crystallographic analysis reveals common modes of binding of medium and long-chain fatty acids to human serum albumin, J. Mol. Biol. 303 (2000) 721-732.

Cross, C. E., B. Halliwell, E. T. Borish, W. A. Pryor, B. N. Ames, R. L. Saul, J. M. McCord, and D. Harman. (1987) Oxygen radicals and human disease. Ann. Intern. Med., 107:526-545.

Zhang, L.-X., Cooney, R. V., and Bertram, J. S. (1992) Carotenoids up-regulate connexin 43 gene expression independent of their pro-vitamin A or antioxidant properties. Cancer Res., 52, 5707-5712.

Peters, N. S. (1995) Myocardial gap junction organization in ischemia and infarction. Microsc. Res. Tech., 31, 375-386.

Zhang, L.-X. and Bertram, J. S. (1994) Assays for Regulation of Gap Junctional Communication and Connexin expression by Carotenoids. In Packer, L. (ed.) Oxygen radicals in biological systems, Part C. In: Methods in Enzymology: Vol 234. Academic Press, Orlando, pp 235-44.

Hossain, M. Z., Zhang, L.-X., and Bertram, J. S. (1993) Retinoids and carotenoids upregulate gap junctional communication: correlation with enhanced growth control and cancer prevention. In Hall, J. E., Zampighi, G. A., and Davies, R. M. (eds.) Progress in Cell Research Vol. 3: Gap Junctions. Elsiever, Amsterdam, pp 301-9.

Perkins, G., Goodenough, D., and Sosinsky, G. (1997) Three-dimensional structure of the gap junction connexon. Biophysical Journal, 72, 533-544.

Saez, J. C., Martinez, A. D., Branes, M. C., and Gonzalez, H. E. (1998) Regulation of gap junctions by protein phosphorylation. *Braz.J.Med.Biol.Res.*, 31, 593-600.

A. S. Moore, and A. M. Papas, Biochemistry and health significance of Vitamin E, J. Adv. Med. 9 (1996) 11-29.

P. Di Mascio, T. P. Devasagayam, S. Kaiser, and H. Sies, Carotenoids, tocopherols and thiols as biological singlet molecular oxygen quenchers, Biochem. Soc. Trans. 18 (1990) 1054-1056.

P. Di Mascio, M. E. Murphy, and H. Sies, Antioxidant defense systems: the role of carotenoids, tocopherols, and thiols, Am. J. Clin. Nutr. 53 (1991) 194S-200S.

J. H. Tinkler, F. Böhm, W. Schalch, and T. G. Truscott, Dietary carotenoids protect human cells from damage, J. Photochem. Photobiol. B. 26 (1994) 283-285.

H. Jyonouchi, S. Sun, K. Iijima, and M. D. Gross, Antitumor activity of astaxanthin and its mode of action, Nutr. Cancer 36 (2000) 59-65.

A. Kistler, H. Liechti, L. Pichard, E. Wolz, G. Oesterhelt, A. Hayes, and P. Maurel, Metabolism and CYP-inducer properties of astaxanthin in man and primary human hepatocytes, Arch. Toxicol. 75 (2002) 665-675.

A. Mortensen, L. H. Skibsted, J. Sampson, C. Rice-Evans, and S. A. Everett, Comparative mechanisms and rates of free radical scavenging by carotenoid antioxidants, FEBS Lett. 418 (1997) 91-97.

J. Terao, Antioxidant activity of beta-carotene-related carotenoids in solution., Lipids 24 (1989) 659-661.

P. Palozza, and N. I. Krinsky, Astaxanthin and canthaxanthin are potent antioxidants in a membrane model, Arch. Biochem. Biophys. 297 (1992) 291-295.

B. P. Lim, A. Nagao, J. Terao, K. Tanaka, T. Suzuki, and K. Takama, Antioxidant activity of xanthophylls on peroxyl radical-mediated phospholipid peroxidation, Biochim. Biophys. Acta 1126 (1992) 178-184.

B. N. Ames, M. K. Shigenaga, and T. M. Hagen, Oxidants, antioxidants, and the degenerative diseases of aging, Proc. Natl. Acad. Sci. U. S. A. 90 (1993) 7915-7922.

S. Mayne, Beta-carotene, carotenoids, and disease prevention in humans., FASEB J. 10 (1996) 690-701.

V. R. Salares, N. M. Young, H. J. Bernstein, and P. R. Carey, Resonance Raman spectra of lobster shell carotenoproteins and a model astaxanthin aggregate. A possible photobiological function for the yellow protein, Biochemistry 16 (1977) 4751-4756.

F. Zsila, J. Deli, Z. Bikadi, and M. Simonyi, Supramolecular assemblies of carotenoids, Chirality 13 (2001) 739-744.

Z. Bikadi, F. Zsila, J. Deli, G. Mady, and M. Simonyi, The supramolecular structure of self-assembly formed by capsanthin derivatives, Enantiomer 7 (2002) 67-76.

C. V. Serrano, Jr., E. A. Mikhail, P. Wang, B. Noble, P. Kuppusamy, and J. L. Zweier, Superoxide and hydrogen peroxide induce CD18-mediated adhesion in the postischemic heart, Biochim. Biophys. Acta 1316 (1996) 191-202.

E. W. Gabrielson, P. Kuppusamy, A. C. Povey, J. L. Zweier, and C. C. Harris, Measurement of neutrophil activation and epidermal cell toxicity by palytoxin and 12-O-tetradecanoylphorbol-13-acetate, Carcinogenesis 13 (1992) 1671-1674.

C. Lee, K. Miura, X. Liu, and J. L. Zweier, Biphasic regulation of leukocyte superoxide generation by nitric oxide and peroxynitrite, J. Biol. Chem. 275 (2000) 38965-38972.

M. Kurashige, E. Okimasu, M. Inoue, and K. Utsumi, Inhibition of oxidative injury of biological membranes by astaxanthin., Physiol. Chem. Phys. Med. NMR 22 (1990) 27-38.

E. Oliveros, A. M. Braun, T. Aminian-Saghafi, and H. R. Sliwka, Quenching of singlet oxygen by carotenoid derivatives: kinetic analysis by near-infrared luminescence, New J. Chem. 18 (1994) 535-539.

F. Zsila, J. Deli, and M. Simonyi, Color and chirality: carotenoid self-assemblies in flower petals, Planta 213 (2001) 937-942.

Osterlie M, Bjerkeng B, Liaaen-Jensen S. 2000. Plasma appearance and distribution of astaxanthin E/Z and R/S isomers in plasma lipoproteins of men after single dose administration of astaxanthin. J. Nutr. Biochem. 10: 482-490.

Jewell C, O'Brien N M. 1999. Effect of dietary supplementation with carotenoids on xenobiotic metabolizing enzymes in the liver, lung, kidney and small intestine of the rat. Br. J. Nutr. 81(3): 235-42.

Kurihara H, Koda H, Asami S, Kiso Y, Tanaka T. 2002. Contribution of the antioxidative property of astaxanthin to its protective effect on the promotion of cancer metastasis in mice treated with restraint stress. Life Sci. (21): 2509-20.

Kang J O, Kim S J, Kim H. 2001. Effect of astaxanthin on the hepatotoxicity, lipid peroxidation and antioxidative enzymes in the liver of CCl4-treated rats. Methods Find Exp Clin Pharmacol. 23(2): 79-84.

Kim H P, Kim S Y, Lee E J, Kim Y C, Kim Y C. 1997. Zeaxanthin dipalmitate from *Lycium chinense* has hepatoprotective activity. Res. Comm. Mol. Path. Pharm. 97: 301-314.

Leist M, Gantner F, Bohlinger I, Tiegs G, Germann P G, Wendel A. 1995. Tumor necrosis factor-induced hepatocyte apoptosis precedes liver failure in experimental murine shock models. Am. J. Pathol. 146: 1220-1234.

Ding, Y. *J. Chem. Soc., Perkin Trans.* 1, 2000, 1651-1655.

Bertram, J. S., Pung, A., Churley, M., Kappock, T. J. I., Wilkins, L. R., and Cooney, R. V. (1991) Diverse carotenoids protect against chemically induced neoplastic transformation. *Carcinogenesis*, 12, 671-678.

Pung, A., Rundhaug, J. E., Yoshizawa, C. N., and Bertram, J. S. (1988) b-Carotene and canthaxanthin inhibit chemically- and physically-induced neoplastic transformation in 10T1/2 cells. *Carcinogenesis*, 9, 1533-1539.

Reznikoff, C.A., Bertram, J. S., Brankow, D. W., and Heidelberger, C. (1973) Quantitative and Qualitative Studies of Chemical Transformation of Cloned C3H Mouse Embryo Cells Sensitive to Postconfluence Inhibition of Cell Division. *Cancer Research*, 33, 2339-2349.

R. Merriman and J. S. Bertram. Reversible inhibition by retinoids of 3-methylcholanthrene-induced neoplastic transformation in C3H10T1/2 cells. *Cancer Res.* 39:1661-1666, 1979.

J. S. Bertram. Neoplastic Transformation in Cell Cultures: In Vitro/In-Vivo Correlations. *IARC Sci.Pub.* 67:77-91, 1985.

J. S. Bertram, M. Z. Hossain, A. Pung, and J. E. Rundhaug. Development of in vitro systems for chemoprevention research. *Prev.Med.* 18:562-575, 1989.

W. Aoi, Y. Naito, K. Sakuma, M. Kuchide, H. Tokuda, T. Maoka, S. Toyokuni, S. Oka, M. Yasuhura, and T. Toshikawa. Astaxanthin limits exercise-induced skeletal and cardiac muscle damage in mice. *Antioxidants & Redox Signaling* 5(1):139-144, 2003.

K. Ohgami, K. Shiratori, S. Kotake, T. Nishida, N. Mizuki, K. Yazawa, and S. Ohno. Effects of astaxanthin on lipopolysaccharide-induced inflammation in vitro and in vivo. *Investigative Ophthalmology & Visual Science* 44(6):2694-2701, 2003.

Barrett, T. D., Herman, J. K., Marks, R. M., and Lucchesi, B. R. (2002). C-reactive protein associated increase in myocardial infarct size after ischemia/reperfusion. Journal of Pharmacology and Experimental Therapeutics 303 (3): 1007-1013.

What is claimed is:

1. A composition comprising a chemical compound having the structure

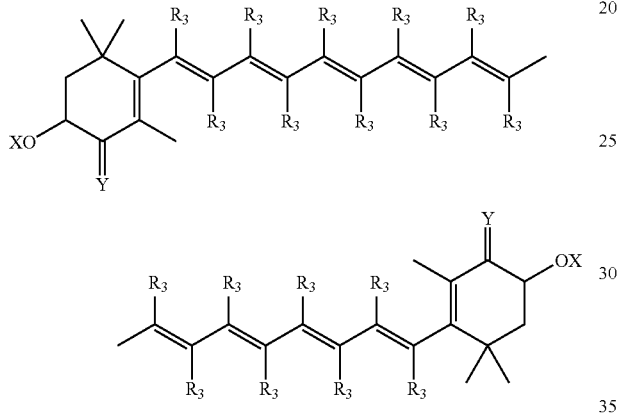

where each $R^3$ is independently hydrogen or methyl;
where each Y is independently O or $H_2$;
where each X is independently

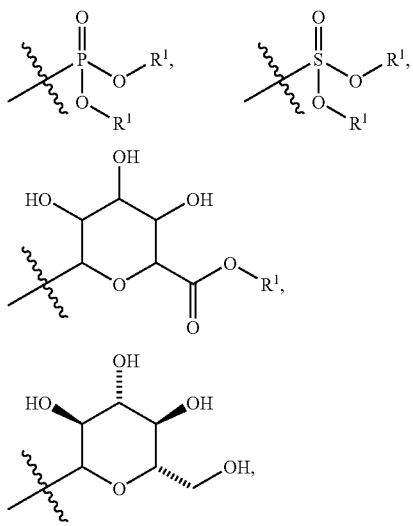

-alkyl-$NR^2_3{}^+$, -aryl-$NR^2_3{}^+$, -alkyl-$CO_2{}^-$, -aryl-$CO_2{}^-$, -amino acid-$NH_3{}^+$, -phosphorylated amino acid-$NH_3{}^+$, polyethylene glycol, dextran, alkyl, or benzyl,

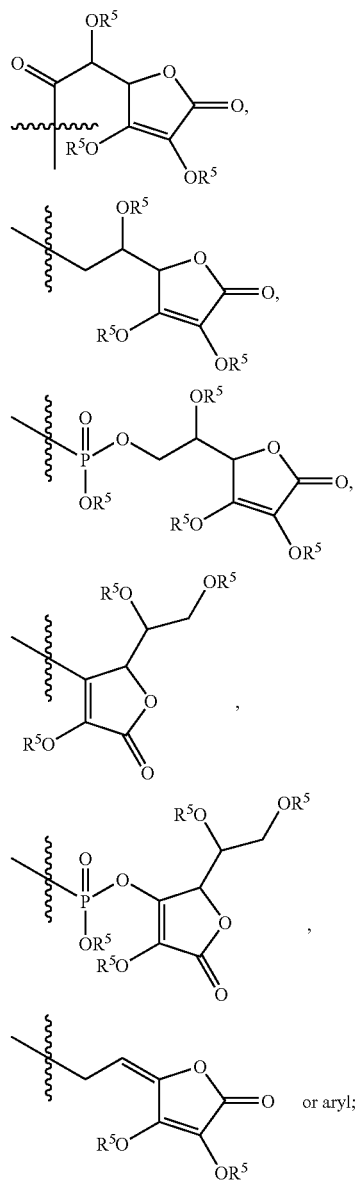

where each $R^1$ is independently -alkyl-$NR^2_3{}^+$, -aryl-$NR^2_3{}^+$, -alkyl-$CO_2{}^-$, -aryl-$CO_2{}^-$, -alkyl-$CO_2H$; -alkyl-$CO_2R^6$; amino acid-$NH_2$, -amino acid-$NH_3{}^+$, -phosphorylated amino acid-$NH_3{}^+$, polyethylene glycol, dextran, H, alkyl, aryl, or alkali salt;

where each $R^2$ is independently H, alkyl, or aryl; and
where each $R^5$ is independently H, alkyl, benzyl, or alkali salt.

2. The composition of claim 1, wherein each X is independently

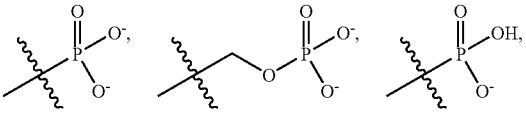

163

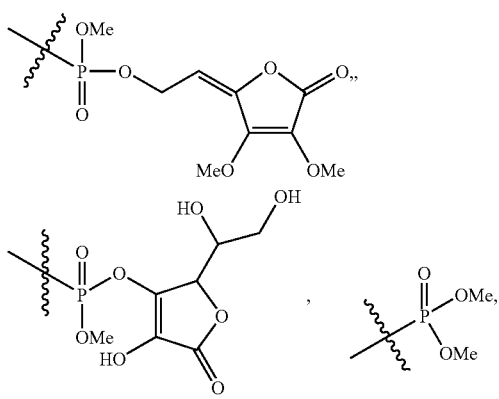

164

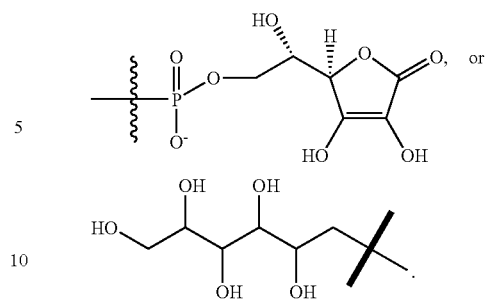

3. The composition of claim 1, wherein the chemical compound has the structure

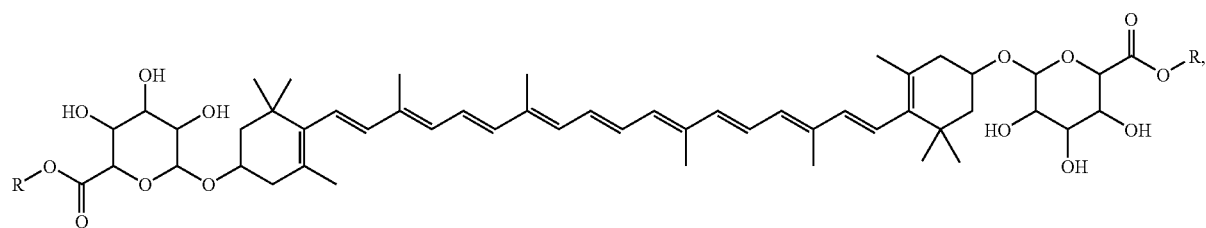

where each R is independently -alkyl-$NR^4_3{}^+$, -aryl-$NR^4_3{}^+$, -alkyl-$CO_2{}^-$, amino acid-$NH_3{}^+$, -phosphorylated amino acid-$NH_3{}^+$, polyethylene glycol, dextran, H, alkyl, or aryl, and where each $R^4$ is independently H, alkyl, or aryl.

4. The composition of claim 1, wherein the chemical compound has the structure

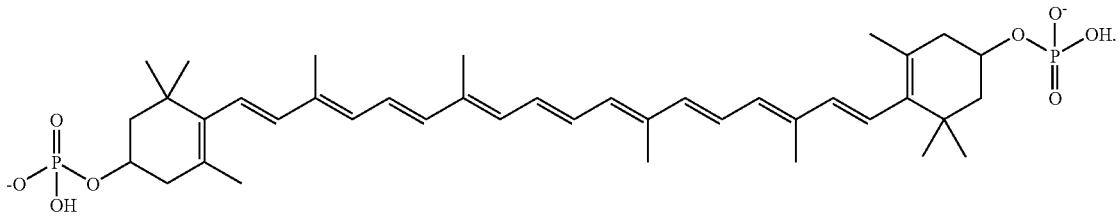

5. The composition of claim 1, wherein the chemical compound has the structure

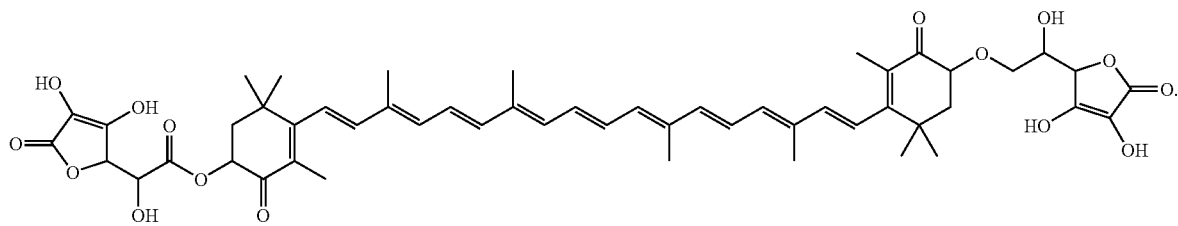

6. The composition of claim 1, wherein the chemical compound has the structure
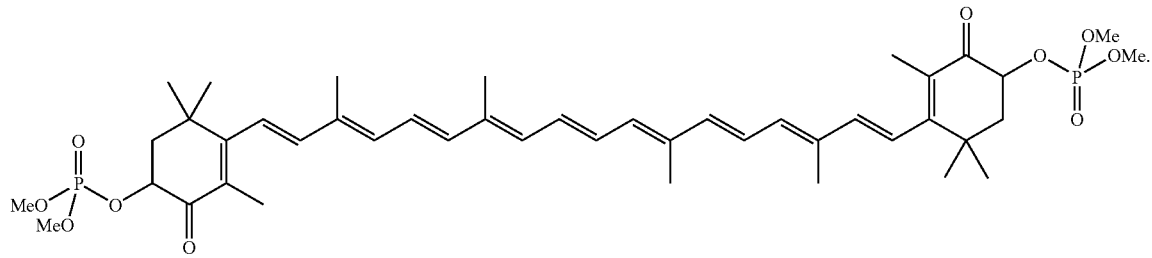
7. The composition of claim 1, wherein the chemical compound has the structure
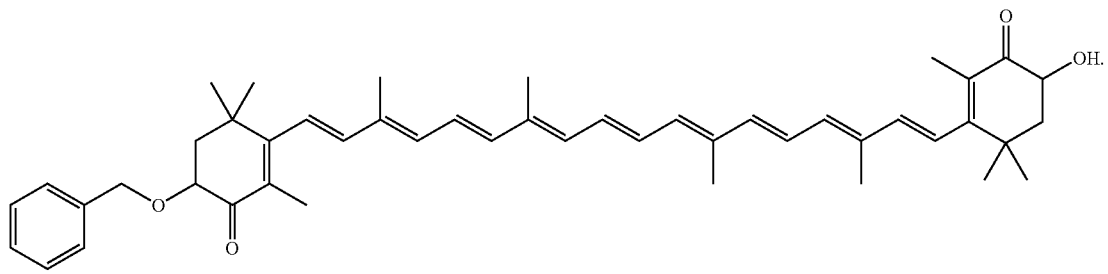
8. The composition of claim 1, wherein the chemical compound has the structure
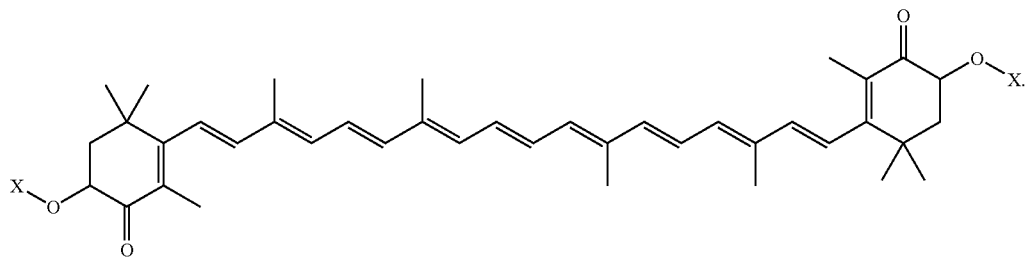
9. The composition of claim 1, wherein the chemical compound has the structure
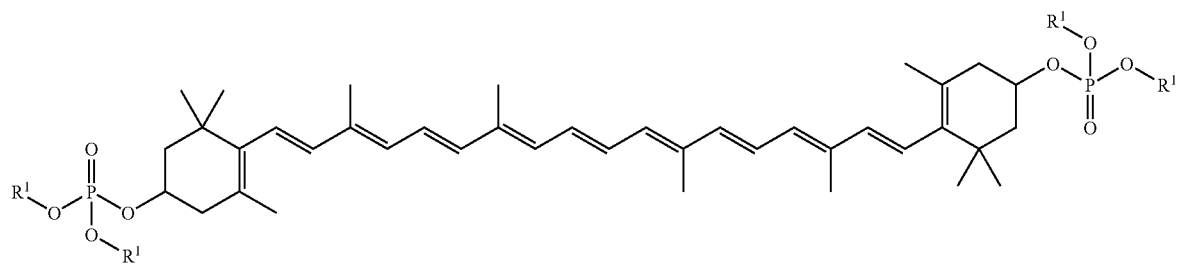

where R¹ is hydrogen, alkyl,

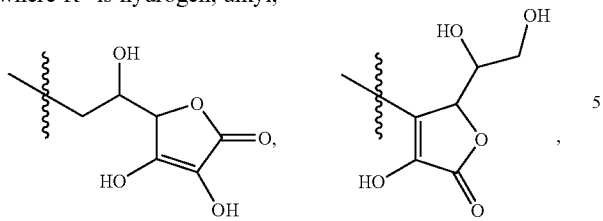

or alkali salt.

10. The composition of claim 1, wherein the chemical compound has the structure:

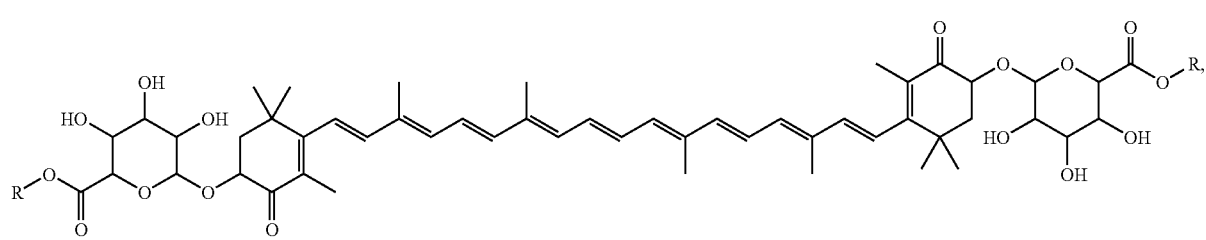

where each R is independently -alkyl-$NR^4_3{}^+$, -aryl-$NR^4_3{}^+$, -alkyl-$CO_2{}^-$, -aryl-$CO_2{}^-$, -amino acid-$NH_3{}^+$, -phosphorylated amino acid-$NH_3{}^+$, polyethylene glycol, dextran, H, alkyl, or aryl, and where each $R^4$ is independently H, alkyl, or aryl.

11. The composition of claim 1, wherein the chemical compound has the structure

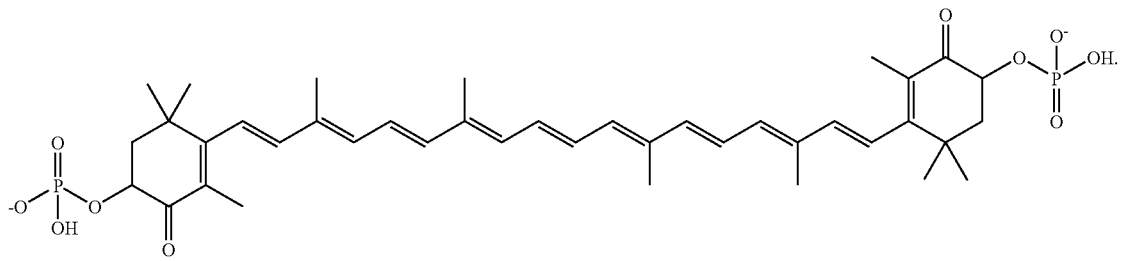

12. The composition of claim 1, wherein the chemical compound has the structure

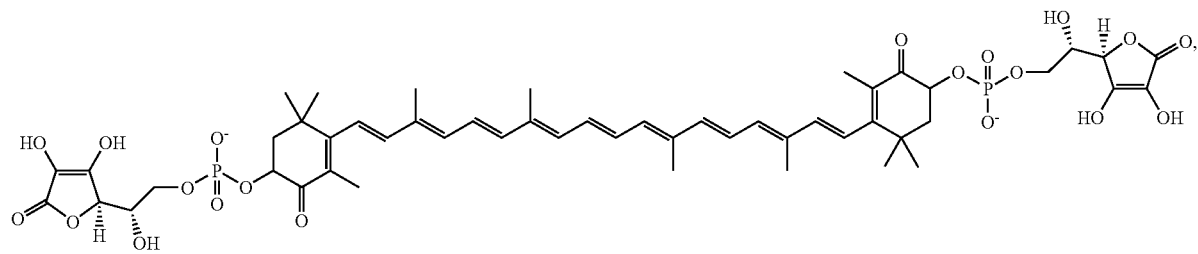

13. The composition of claim 1, wherein the chemical compound has the structure:
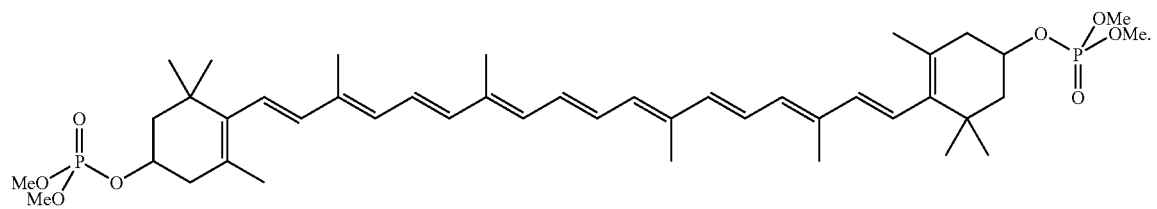
14. The composition of claim 1, wherein the chemical compound has the structure
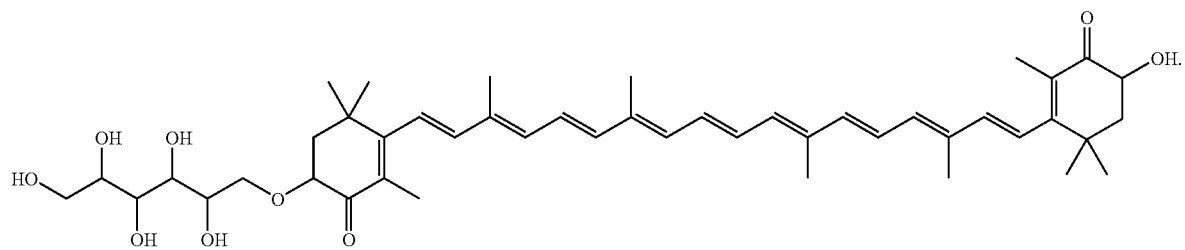
15. The composition of claim 1, wherein the chemical compound has the structure:
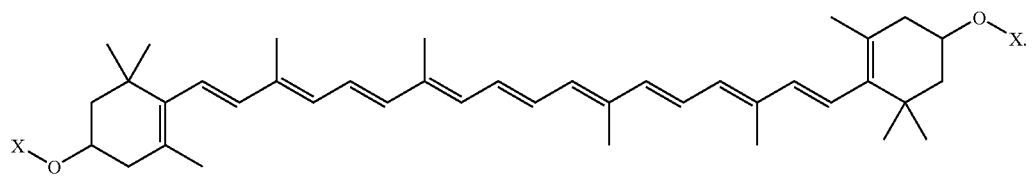
16. The composition of claim 1, wherein the chemical compound has the structure
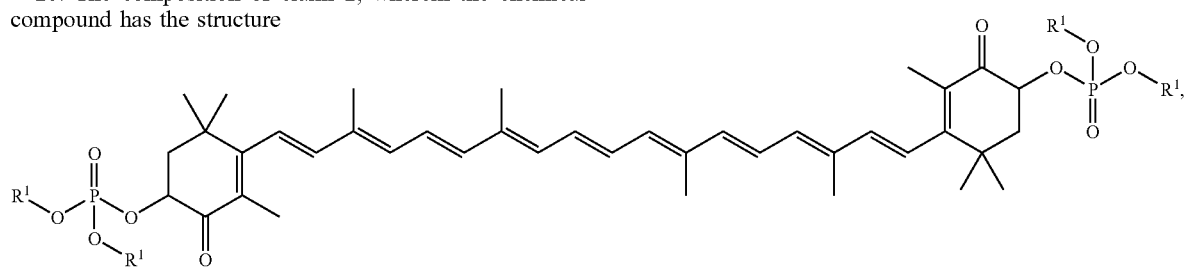
where $R^1$ is hydrogen, alkyl,
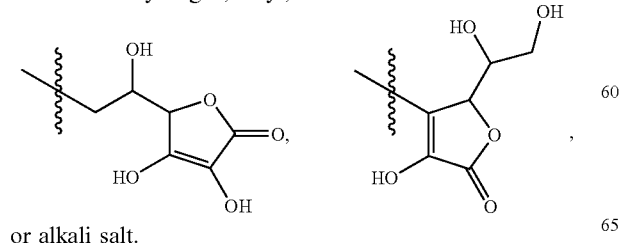
or alkali salt.
* * * * *

UNITED STATES PATENT AND TRADEMARK OFFICE
CERTIFICATE OF CORRECTION

PATENT NO. : 7,345,091 B2
APPLICATION NO. : 10/793671
DATED : March 18, 2008
INVENTOR(S) : Lockwood et al.

It is certified that error appears in the above-identified patent and that said Letters Patent is hereby corrected as shown below:

In the Claims:

Claim 2, col. 163, please add the following structures before structures on Line 1:

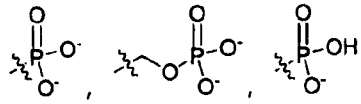

--

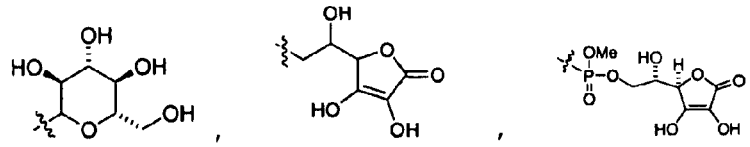 --.

Signed and Sealed this

Fifth Day of August, 2008

JON W. DUDAS
*Director of the United States Patent and Trademark Office*